(12) United States Patent
Parham et al.

(10) Patent No.: US 11,588,117 B2
(45) Date of Patent: *Feb. 21, 2023

(54) MATERIALS FOR ELECTRONIC DEVICES

(71) Applicant: Merck Patent GmbH, Darmstadt (DE)

(72) Inventors: Amir Hossain Parham, Frankfurt am Main (DE); Irina Martynova, Griesheim (DE); Anja Jatsch, Frankfurt am Main (DE); Thomas Eberle, Landau (DE); Jonas Valentin Kroeber, Frankfurt am Main (DE); Christof Pflumm, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/908,375

(22) PCT Filed: Jul. 7, 2014

(86) PCT No.: PCT/EP2014/001860
§ 371 (c)(1),
(2) Date: Jan. 28, 2016

(87) PCT Pub. No.: WO2015/014434
PCT Pub. Date: Feb. 5, 2015

(65) Prior Publication Data
US 2016/0181548 A1    Jun. 23, 2016

(30) Foreign Application Priority Data
Jul. 30, 2013 (EP) .................................... 13003800

(51) Int. Cl.
| *H01L 51/00* | (2006.01) |
| *C07D 487/04* | (2006.01) |
| *C09K 11/06* | (2006.01) |
| *C07D 405/14* | (2006.01) |
| *C07D 405/04* | (2006.01) |
| *C07D 405/10* | (2006.01) |
| *C07D 417/10* | (2006.01) |
| *C07D 307/91* | (2006.01) |
| *H05B 33/10* | (2006.01) |
| *C07D 498/04* | (2006.01) |
| *C07D 209/88* | (2006.01) |

(Continued)

(52) U.S. Cl.
CPC ........ *H01L 51/0073* (2013.01); *C07D 209/86* (2013.01); *C07D 209/88* (2013.01); *C07D 239/26* (2013.01); *C07D 251/24* (2013.01); *C07D 307/91* (2013.01); *C07D 403/10* (2013.01); *C07D 403/14* (2013.01); *C07D 405/04* (2013.01); *C07D 405/10* (2013.01); *C07D 405/14* (2013.01); *C07D 409/14* (2013.01); *C07D 417/10* (2013.01); *C07D 487/04* (2013.01); *C07D 495/14* (2013.01); *C07D 498/04* (2013.01); *C07F 5/025* (2013.01); *C07F 7/0812* (2013.01); *C09K 11/025* (2013.01); *C09K 11/06* (2013.01); *H01L 51/008* (2013.01); *H01L 51/0052* (2013.01); *H01L 51/0061* (2013.01); *H01L 51/0067* (2013.01); *H01L 51/0071* (2013.01); *H01L 51/0072* (2013.01); *H01L 51/0085* (2013.01); *H01L 51/0087* (2013.01); *H01L 51/0094* (2013.01); *H05B 33/10* (2013.01); *C09K 2211/1007* (2013.01); *C09K 2211/1011* (2013.01); *C09K 2211/1014* (2013.01); *C09K 2211/1029* (2013.01); *C09K 2211/1037* (2013.01); *C09K 2211/1044* (2013.01); *C09K 2211/1059* (2013.01); *C09K 2211/1088* (2013.01); *C09K 2211/1092* (2013.01); *C09K 2211/1096* (2013.01); *C09K 2211/185* (2013.01); *H01L 51/0002* (2013.01); *H01L 51/5012* (2013.01); *H01L 51/5056* (2013.01); *Y02E 10/549* (2013.01)

(58) Field of Classification Search
CPC ............ H01L 51/0073; H01L 51/0072; H01L 51/0061; H01L 51/0071; H01L 51/0067; H01L 51/0094; H01L 51/008; H01L 51/0052; H01L 51/0085; H01L 51/0087; H01L 51/5012; C07D 405/041; C07D 307/91; C07D 405/10; C07D 417/10; C07D 405/14; C07D 487/04; C07F 7/0812; C07F 5/025; C09K 11/025; C09K 11/06
See application file for complete search history.

(56) References Cited

U.S. PATENT DOCUMENTS

| 7,993,760 B2 | 8/2011 | Komori et al. |
| 9,006,379 B2 | 4/2015 | Yu et al. |

(Continued)

FOREIGN PATENT DOCUMENTS

| CN | 101321755 A | 12/2008 |
| CN | 102850334 A | 1/2013 |

(Continued)

OTHER PUBLICATIONS

JP2011-084531, Katakura, Machine Translation, Apr. 2011.*
International Search Report for PCT/EP2014/001860 dated Sep. 3, 2014.

*Primary Examiner* — Devina Pillay
(74) *Attorney, Agent, or Firm* — Faegre Drinker Biddle & Reath LLP

(57) ABSTRACT

The invention relates to compounds comprising functional substituents in a specific spatial arrangement, devices containing same, and the preparation and use thereof.

13 Claims, No Drawings

(51) Int. Cl.
  *C07D 239/26* (2006.01)
  *C07D 209/86* (2006.01)
  *C07D 403/14* (2006.01)
  *C07D 409/14* (2006.01)
  *C07D 251/24* (2006.01)
  *C07D 403/10* (2006.01)
  *C07D 495/14* (2006.01)
  *C07F 5/02* (2006.01)
  *C07F 7/08* (2006.01)
  *C09K 11/02* (2006.01)
  *H01L 51/50* (2006.01)

(56) References Cited

U.S. PATENT DOCUMENTS

| | | | |
|---|---|---|---|
| 9,269,911 | B2 | 2/2016 | Horiuchi et al. |
| 9,391,281 | B2 | 7/2016 | Lee et al. |
| 9,882,145 | B2 | 1/2018 | Lee et al. |
| 9,882,146 | B2 | 1/2018 | Lee et al. |
| 2001/0006670 | A1 | 7/2001 | Karg |
| 2003/0198831 | A1* | 10/2003 | Oshiyama .......... H01L 51/0084 428/690 |
| 2006/0231843 | A1* | 10/2006 | Qin .................... H01L 51/5016 257/79 |
| 2009/0284138 | A1* | 11/2009 | Yasukawa .............. C09K 11/06 313/504 |
| 2011/0006670 | A1 | 1/2011 | Katakura et al. |
| 2012/0085997 | A1* | 4/2012 | Sugita ................. C07D 471/04 257/40 |
| 2012/0223276 | A1* | 9/2012 | Parham ............... C07D 403/10 252/500 |
| 2012/0261654 | A1 | 10/2012 | Yasukawa et al. |
| 2012/0273766 | A1 | 11/2012 | Kato et al. |
| 2012/0319052 | A1 | 12/2012 | Brocke et al. |
| 2013/0049576 | A1 | 2/2013 | Katakura et al. |
| 2013/0317475 | A1 | 11/2013 | Eberle et al. |
| 2014/0158992 | A1* | 6/2014 | Xia .................... H01L 51/0067 257/40 |
| 2014/0272398 | A1 | 9/2014 | Hakii et al. |
| 2014/0299192 | A1 | 10/2014 | Lee et al. |
| 2014/0374724 | A1 | 12/2014 | Kim et al. |
| 2015/0061942 | A1 | 3/2015 | Koyama |
| 2015/0104636 | A1 | 4/2015 | Takemura |
| 2015/0123089 | A1 | 5/2015 | Lee et al. |
| 2015/0280133 | A1 | 10/2015 | Parham et al. |
| 2015/0340621 | A1 | 11/2015 | Parham et al. |
| 2016/0172598 | A1 | 6/2016 | Lee et al. |
| 2016/0218298 | A1 | 7/2016 | Lee et al. |
| 2016/0251472 | A1 | 9/2016 | Spyrou et al. |
| 2016/0296957 | A1 | 10/2016 | Baillet et al. |

FOREIGN PATENT DOCUMENTS

| | | | | |
|---|---|---|---|---|
| CN | 103848822 | A | 6/2014 | |
| EP | 1956022 | A1 | 8/2008 | |
| EP | 2123733 | A2 | 11/2009 | |
| EP | 2873667 | A1 | 5/2015 | |
| JP | 2009263579 | A | 11/2009 | |
| JP | 2009267257 | A | 11/2009 | |
| JP | 2010251675 | A | 11/2010 | |
| JP | 2011-084531 | * | 4/2011 | ......... C07D 491/048 |
| JP | 2011249754 | A | 12/2011 | |
| JP | 2012049518 | A | 3/2012 | |
| JP | 2013-510803 | A | 3/2013 | |
| JP | 2013045923 | A | 3/2013 | |
| JP | 2013521238 | A | 6/2013 | |
| JP | 2013154378 | A | 8/2013 | |
| JP | 2013206649 | A | 10/2013 | |
| JP | 2013242988 | A | 12/2013 | |
| JP | 2015520125 | A | 7/2015 | |
| JP | 2015-524797 | A | 8/2015 | |
| JP | 2015536567 | A | 12/2015 | |
| JP | 2016-523647 | A | 8/2016 | |
| JP | 2016529211 | A | 9/2016 | |
| JP | 2016530230 | A | 9/2016 | |
| JP | 2016530366 | A | 9/2016 | |
| JP | 2016530367 | A | 9/2016 | |
| JP | 2016-534095 | A | 11/2016 | |
| JP | 2016540063 | A | 12/2016 | |
| KR | 2011011209 | | 10/2011 | |
| KR | 20120129733 | A | 11/2012 | |
| KR | 20130007390 | A | 1/2013 | |
| KR | 20130010633 | A | 1/2013 | |
| KR | 20140009919 | A | 1/2014 | |
| KR | 20150002417 | A | 1/2015 | |
| KR | 20150006758 | A | 1/2015 | |
| WO | WO-07/063754 | A1 | 6/2007 | |
| WO | WO-2009/069442 | A1 | 6/2009 | |
| WO | WO-2010150593 | A1 | 12/2010 | |
| WO | WO-2011004639 | A1 | 1/2011 | |
| WO | WO-2011057706 | A2 * | 5/2011 | ........... C07D 403/10 |
| WO | WO-2011136156 | A1 | 11/2011 | |
| WO | WO-2011157790 | A1 | 12/2011 | |
| WO | WO-2012049828 | A1 | 4/2012 | |
| WO | WO-2012099038 | A1 | 7/2012 | |
| WO | WO-2012105310 | A1 | 8/2012 | |
| WO | WO-2012107163 | A1 | 8/2012 | |
| WO | WO-2013073356 | A1 | 5/2013 | |
| WO | WO-2013085339 | A2 | 6/2013 | |
| WO | | 2013/109045 A1 | 7/2013 | |
| WO | WO-2013157420 | A1 | 10/2013 | |
| WO | WO-2013157515 | A1 | 10/2013 | |
| WO | WO-2014010823 | A1 | 1/2014 | |
| WO | WO-2014010824 | A1 | 1/2014 | |
| WO | WO-2014094964 | A1 | 6/2014 | |
| WO | | 2014/208829 A1 | 12/2014 | |

* cited by examiner

MATERIALS FOR ELECTRONIC DEVICES

CROSS-REFERENCE TO RELATED APPLICATIONS

This application is a national stage application (under 35 U.S.C. § 371) of PCT/EP2014/001860, filed Jul. 7, 2014, which claims benefit of European Application No. 13003800.3, filed Jul. 30, 2013, both of which are incorporated herein by reference in their entirety.

The present invention relates to cyclic compounds having a specific arrangement of electron-conducting and hole-conducting groups, to the use thereof in electronic devices, to the production thereof and to electronic devices.

The structure of organic electroluminescent devices (e.g. OLEDs—organic light-emitting diodes or OLECs—organic light-emitting electrochemical cells) in which organic semiconductors are used as functional materials is described, for example, in U.S. Pat. Nos. 4,539,507, 5,151,629, EP 0676461 and WO 98/27136. Emitting materials used here, as well as fluorescent emitters, are increasingly organometallic complexes which exhibit phosphorescence (M. A. Baldo et al., Appl. Phys. Lett. 1999, 75, 4-6). For quantum-mechanical reasons, up to four times the energy efficiency and power efficiency is possible using organometallic compounds as phosphorescent emitters. In general terms, both in the case of OLEDs which exhibit singlet emission and in the case of OLEDs which exhibit triplet emission, there is still a need for improvement, especially with regard to efficiency, operating voltage and lifetime. This is especially true of OLEDs which emit in the shorter-wave range, i.e. green and especially blue.

The properties of organic electroluminescent devices are not only determined by the emitters used. Also of particular significance here are especially the other materials used, such as host and matrix materials, hole blocker materials, electron transport materials, hole transport materials and electron or exciton blocker materials. Improvements to these materials can lead to distinct improvements to electroluminescent devices.

According to the prior art, ketones (for example according to WO 2004/093207 or WO 2010/006680) or phosphine oxides (for example according to WO 2005/003253) are among the matrix materials used for phosphorescent emitters. Further matrix materials according to the prior art are represented by triazines (for example WO 2008/056746, EP 0906947, EP 0908787, EP 0906948).

For fluorescent OLEDs, according to the prior art, fused aromatics in particular, especially anthracene derivatives, are used as host materials for blue-emitting electroluminescent devices in particular, for example 9,10-bis(2-naphthyl)anthracene (U.S. Pat. No. 5,935,721). WO 03/095445 and CN 1362464 disclose 9,10-bis(1-naphthyl)anthracene derivatives for use in OLEDs. Further anthracene derivatives are disclosed in WO 01/076323, in WO 01/021729, in WO 2004/013073, in WO 2004/018588, in WO 2003/087023 or in WO 2004/018587. Host materials based on aryl-substituted pyrenes and chrysenes are disclosed in WO 2004/016575. Host materials based on benzanthracene derivatives are disclosed in WO 2008/145239. It is desirable for high-value applications to have improved host materials available.

The prior art discloses the use of compounds containing one or more carbazole groups in electronic devices, known, for example, in WO 2005/039246, US 2005/0069729, JP 2004/288381, EP 1205527 or WO 2008/086851.

The prior art further discloses the use of compounds containing one or more indenocarbazole groups in electronic devices, known, for example, in WO 2010/136109 and WO 2011/000455.

The prior art further discloses the use of compounds containing one or more electron-deficient heteroaromatic six-membered rings in electronic devices, known, for example, in WO 2010/015306, WO 2007/063754 and WO 2008/056746.

WO 2009/069442 discloses tricyclic systems such as carbazole, dibenzofuran or dibenzothiophene having a high level of substitution by electron-deficient heteroaromatics (e.g. pyridine, pyrimidine or triazine). The tricyclic systems are not substituted by hole-conducting groups, i.e. electron-rich groups.

JP 2009-21336 discloses substituted carbazoles as matrix materials, where the carbazoles are substituted by an electron-conducting group and by a hole-conducting group. However, the compounds do not have any face-to-face substitution.

WO 2011/057706 discloses substituted carbazoles as matrix materials, where the carbazoles are substituted by an electron-conducting group and by a hole-conducting group. However, most of the carbazoles disclosed do not have any face-to-face substitution. In the individual face-to-face arrangements disclosed, however, the hole- or electron-conducting group is bonded directly to the tricyclic system.

However, there is still a need for improvement in the case of use of these materials, and likewise of other materials, especially in relation to the efficiency and lifetime of the device.

It is therefore an object of the present invention to provide compounds suitable for use in a fluorescent or phosphorescent OLED, for example as host and/or matrix material or as hole transport/electron blocker material or exciton blocker material, or as electron transport or hole blocker material, and which lead to good device properties when used in an OLED, and to provide the corresponding electronic device.

It has been found that, surprisingly, particular compounds described in detail below achieve these objects and lead to good properties of the organic electroluminescent device, especially with regard to lifetime, efficiency and operating voltage. Electronic devices, especially organic electroluminescent devices, containing such compounds, and the corresponding preferred compounds, are therefore provided by the present invention. The surprising effects are achieved through a specific arrangement ("face-to-face", i.e. mutually opposite arrangement of groups) of electron-conducting and hole-conducting groups in compounds of the formulae adduced below. Without being bound to a theory, the rapid charge transport could be because of the relatively well-defined (highly ordered) parallel alignment of the molecules (face-to-face arrangement), in which there is a certain short-range order of the molecules. Because of the short distances between the groups, intermolecular interactions, for example direct $\pi$-$\pi$ interaction, could be one of the causes of the rapid charge transfer.

The compounds of the invention also have a high glass transition temperature ($T_g$), which is advantageous in terms of the processing of the compounds in the production of electronic devices. The high glass transition temperature of the compounds also permits the use of the compounds in thin amorphous organic layers.

Moreover, the compounds of the invention allow stabilization of the charge carriers in the excited state and have sufficiently high triplet energy, which is an important prerequisite for phosphorescent devices. Furthermore, the compounds of the invention have improved performance data in OLEDs compared to the compounds from the prior art.

The present invention therefore provides compounds of the general formula (1)

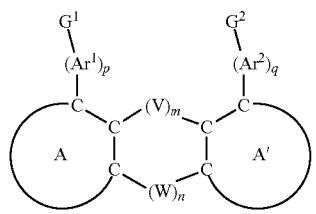

Formula (1)

where the symbols and indices used are as follows:

A and A' are the same or different and are an aromatic or heteroaromatic ring which has 5 or 6 ring atoms and may be substituted by one or more $R^1$ radicals which may be independent of one another;

$G^1$, $G^2$ are the same or different at each instance and are an organic electron-transporting group (ETG) from the group of the electron-deficient heteroaromatic groups, the ETGs preferably being a heteroaryl group having 5 to 60 aromatic ring atoms, N-containing heteroaryl groups being very preferred heteroaryl groups, and most preferred ETGs being selected from the group of the triazines, pyrimidines, pyrazines and pyridines;

or an electron-rich organic group which conducts holes (LTG), the LTGs preferably being selected from the group of the arylamines, triarylamines, bridged amines, preferred bridged amines being dihydroacridines, dihydrophenazines, phenoxazines and phenothiazines, carbazoles, bridged carbazoles, biscarbazoles, indenocarbazoles and indolocarbazoles, where at least one of the two $G^1$ and $G^2$ groups must be an electron-transporting group (ETG) and where the $G^1$ and $G^2$ groups may be substituted by one or more independent $R^1$ radicals;

$Ar^1$ is, when $G^1$ is an electron-transporting group, a bivalent aromatic or heteroaromatic, preferably aromatic, ring or ring system having 5 to 60 ring atoms, where the ring or ring system is bridged neither with the ring system comprising the A and A' rings nor with the ETG, it being preferable when $Ar^1$ is a pyridylene, pyrimidylene, phenylene, biphenylene or fluorene, spiro, terphenylene, thiophene or furan group, preference being given particularly to a phenylene, biphenylene or terphenylene group and very particularly to a phenylene group, or, when $G^1$ is a hole-transporting group, an aromatic ring or ring system having 5 to 60 ring atoms, where the ring or ring system is bridged neither with the ring system comprising the A and A' rings nor with the LTG, it being preferable when $Ar^1$ is a phenylene, biphenylene or terphenylene group and particular preference being given to a phenylene group;

$Ar^2$ is, when $G^2$ is an electron-transporting group, a bivalent aromatic or heteroaromatic ring or ring system having 5 to 60 ring atoms, where the ring or ring system is bridged neither with the ring system comprising the A and A' rings nor with the ETG, it being preferable when $Ar^2$ is a pyridylene, pyrimidylene, phenylene, biphenylene or fluorene, spiro, terphenylene, thiophene or furan group, preference being given particularly to a phenylene, biphenylene or terphenylene group and very particularly to a phenylene group, or, when $G^2$ is a hole-transporting group, an aromatic ring or ring system having 5 to 60 ring atoms, where the ring or ring system is bridged neither with the ring system comprising the A and A' rings nor with the LTG, it being preferable when $Ar^2$ is a phenylene, biphenylene or terphenylene group and particular preference being given to a phenylene group;

V is a single bond, $C=O$, $C(R^1)_2$, $NAr^3$, O, S, $Si(R^1)_2$, $BR^1$, $PR^1$, $P(=O)R^1$, SO or $SO_2$, where, in the case of a single bond, the carbon atoms of the A and A' rings are joined directly to one another by a single bond, preference being given to a single bond, $C(R^1)_2$, $NAr^3$, O and S, particular preference being given to a single bond, $C(R^1)_2$, O and S, very particular preference to O and S and especial preference to O;

W is a single bond, $C=O$, $C(R^1)_2$, $NR^1$, O, S, $Si(R^1)_2$, $BR^1$, $PR^1$, $P(=O)R^1$, SO or $SO_2$, where, in the case of a single bond, the carbon atoms of the A and A' rings are joined directly to one another by a single bond, preference being given to a single bond, $C(R^1)_2$, $NR^1$, O and S, particular preference being given to a single bond, $C(R^1)_2$, O and S, very particular preference to O and S and especial preference to O;

where it is further preferable that V is a single bond if W is not a single bond or that W is a single bond if V is not a single bond;

where it is further very preferable that V is a single bond if W is O or S or that W is a single bond if V is O or S; where it is further very particularly preferable that V is a single bond if W is O or that W is a single bond if V is O;

m is either 0 or 1;

n is either 0 or 1, where m=n;

p is either 0 or 1;

q is either 0 or 1, where p+q is either 1 or 2, it being preferable when p+q=1;

$Ar^3$ is an aromatic or heteroaromatic ring or ring system having 5 to 30 ring atoms, where the ring or the may each be substituted by one or more $R^2$ radicals which may be substituted by one or more $R^3$ radicals, where two or more $R^2$ radicals together may form a ring;

$R^1$ is the same or different at each instance and is H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 carbon atoms or a straight-chain alkenyl or alkynyl group having 2 to 40 carbon atoms or a branched or cyclic alkyl, alkenyl, alkynyl, alkoxy, alkylalkoxy or thioalkoxy group having 3 to 40 carbon atoms, each of which may be substituted by one or more $R^2$ radicals, where one or more nonadjacent $CH_2$ groups may be replaced by $R^2C=CR^2$, $C≡C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^2$ radicals, or an aryloxy, arylalkoxy or heteroaryloxy group which has 5 to 60 aromatic ring atoms and may be substituted by one or more $R^2$ radicals, or a diarylamino group, diheteroarylamino group or arylheteroarylamino group which has 10 to 40 aromatic ring atoms and may be substituted by one or more $R^2$ radicals, or a combination of two or more of these groups or a crosslinkable Q group;

$R^2$ is the same or different at each instance and is H, D, F, Cl, Br, I, $N(R^3)_2$, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy or thioalkoxy group having 1 to 40 carbon atoms or a straight-chain alkenyl or alkynyl group having 2 to 40 carbon atoms or a branched or cyclic alkyl, alkenyl, alkynyl, alkoxy, alkylalkoxy or thioalkoxy group having 3 to 40 carbon atoms, each of which may be substituted by one or more $R^3$ radicals, where one or more nonadjacent $CH_2$ groups may be replaced by $R^3C=CR^3$, $C\equiv C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^3$ radicals, or an aryloxy, arylalkoxy or heteroaryloxy group which has 5 to 60 aromatic ring atoms and may be substituted by one or more $R^3$ radicals, or a diarylamino group, diheteroarylamino group or arylheteroarylamino group which has 10 to 40 aromatic ring atoms and may be substituted by one or more $R^3$ radicals, or a combination of two or more of these groups; at the same time, two or more adjacent $R^2$ radicals together may form a mono- or polycyclic, aliphatic or aromatic ring system;

$R^3$ is the same or different at each instance and is H, D, F or an aliphatic, aromatic and/or heteroaromatic hydrocarbyl radical having 1 to 20 carbon atoms, in which one or more hydrogen atoms may also be replaced by F; at the same time, two or more $R^3$ substituents together may also form a mono- or polycyclic aliphatic or aromatic ring system;

with the proviso that not more than one $R^1$ substituent in the A ring and not more than one $R^1$ substituent in the A' ring contains an aromatic or heteroaromatic group having 5 to 30 ring atoms.

Accordingly, for example, for the compounds of the general formula (1), in the case that m=n=1 and V=W=single bond, the general formula is as follows:

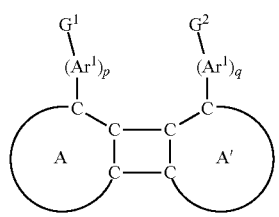

In addition, for example, for the compounds of the general formula (1), in the case that m=n=1 and V=N—$Ar^3$ and W=single bond, the general formula is as follows:

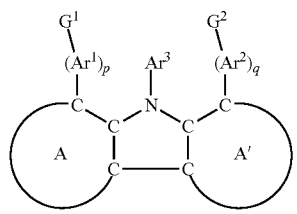

In addition, for example, for the compounds of the general formula (1), in the case that m=n=0, the general formula is as follows:

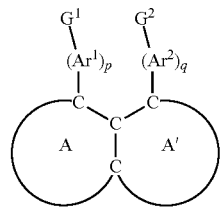

In a preferred embodiment of the present invention, the $G^1$ and $G^2$ groups contain exclusively one kind of charge-transporting units. This means that, for example, if $G^1$ is an ETG, $G^1$ cannot contain any groups that are hole-conducting.

If triazines are used as ETGs, in a further preferred embodiment, the triazines are in substituted form, meaning that none of the triazines in an ETG may have hydrogen atoms bonded directly to the triazine. If the triazines still have hydrogen atoms bonded directly to the triazine, this leads to worse performance data of electronic, especially electroluminescent, devices compared to triazines that do not have any hydrogen atoms bonded directly to the triazine.

In a preferred embodiment, the compound is selected from the general formula (2)

Formula (2)

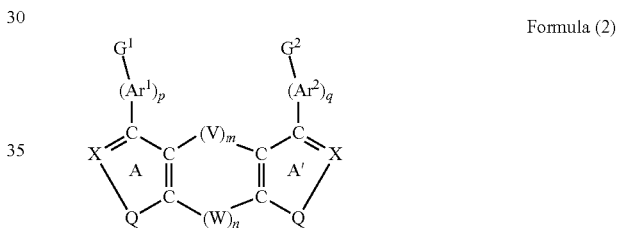

where the symbols additionally used are as follows:

X is the same or different at each instance and is N or $CR^1$;

Q is the same or different at each instance and is X=X, S, O or $NR^1$, preferably X=X, S and O, very preferably X=X and S and most preferably X=X.

A very preferred compound is accordingly of the general formulae (3) to (11)

Formula (3)

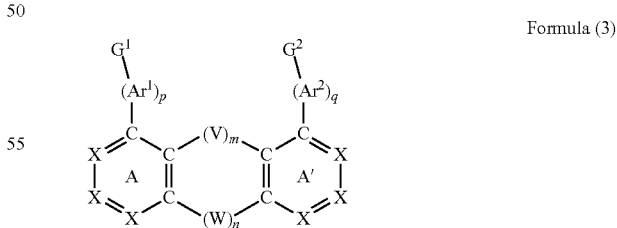

Formula (4)

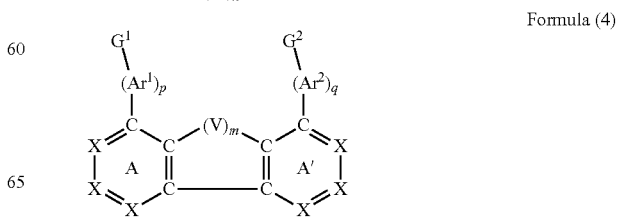

-continued

Formula (5)
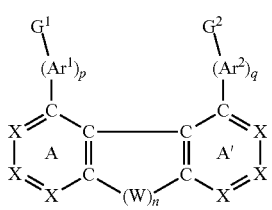

Formula (6)
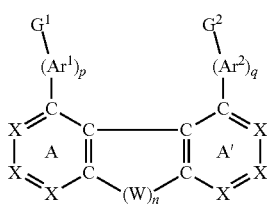

Formula (7)
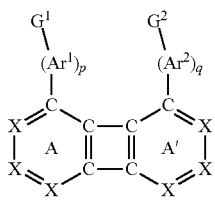

Formula (8)
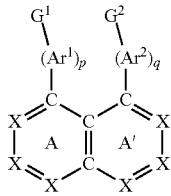

Formula (9)
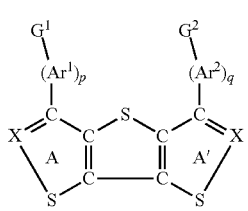

Formula (10)
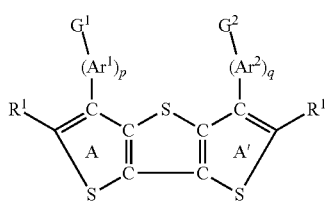

Formula (11)
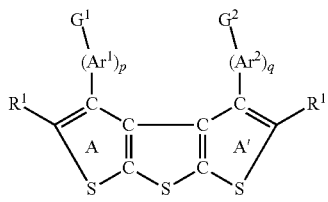

with very particular preference for a compound of the general formulae (3) to (8) and especial preference for a compound of the general formula (4).

It is further very particularly preferable when X in the formulae (1) to (11) is $CR^1$.

In a preferred embodiment, the present invention relates to a compound of the formula (4), preferably a compound of the formula (4) where X is $CR^1$ and m=1, very preferably a compound of the formula (4) where X is $CR^1$, n=1 and V is O, where the above definitions and preferred embodiments apply to the other symbols and indices.

In a further preferred embodiment, the present invention relates to a compound of the formula (4) where X is $CR^1$, m=1 and V is N—$Ar^3$, where the above definitions and preferred embodiments apply to the other symbols and indices.

In a further preferred embodiment, the present invention relates to a compound of the general formula (12)

Formula (12)
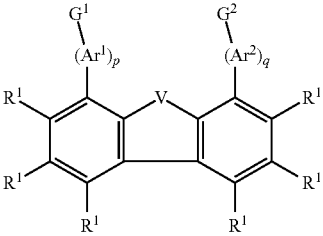

where V is O or S and where the definitions and preferred embodiments adduced herein apply to the indices and symbols used. It is very preferable when V in the compound of the formula (12) is O.

In a further preferred embodiment, the present invention relates to a compound of the general formula (13)

Formula (13)
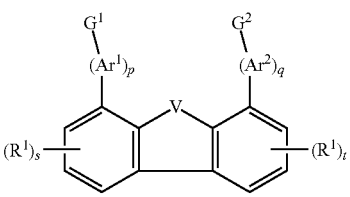

where V is O or S and where the definitions and preferred embodiments adduced herein apply to the indices and symbols used and where the aromatic rings A and A' each have not more than one $R^1$ substituent, i.e. s is 0 or 1 and t is 0 or 1, where s+t may be 0, 1 or 2. It is very preferable when V in the compound of the formula (13) is O.

In a very preferred embodiment, the present invention relates to a compound of the general formula (14)

Formula (14)
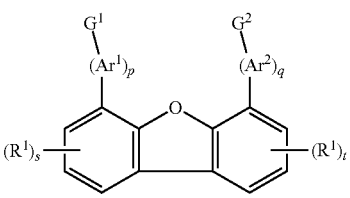

where the definitions and preferred embodiments adduced herein apply to the indices and symbols used and where the aromatic rings A and A' each have not more than one $R^1$ substituent.

In a very particularly preferred embodiment, the present invention relates to a compound of the general formula (15)

Formula (15)

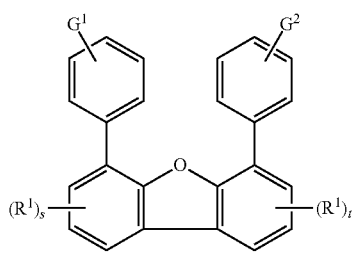

where the definitions and preferred embodiments adduced herein apply to the symbols used and where the aromatic rings each have not more than one R¹ substituent.

In a further very particularly preferred embodiment, the present invention relates to a compound of the general formula (16)

Formula (16)

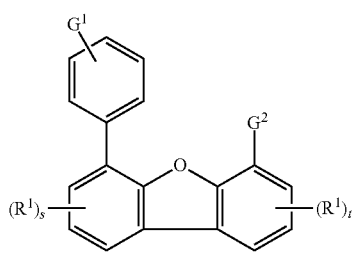

where the definitions and preferred embodiments adduced herein apply to the symbols used and where the aromatic rings each have not more than one R¹ substituent.

It is further especially preferable when R¹ in the rings A and A' in the compounds of the formulae (12) to (16) is H.

In a preferred embodiment, the sum total of the two indices p and q in the formulae (12) to (16) is 1.

In another preferred embodiment, the sum total of the two indices p and q in the formulae (12) to (16) is 2.

The wording that two or more radicals together may form a ring, in the context of the present application, shall be understood to mean, inter alia, that the two radicals are joined to one another by a chemical bond. This is illustrated by the following scheme:

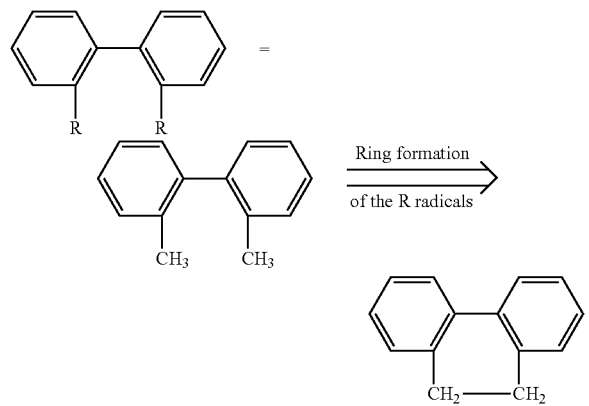

In addition, however, the abovementioned wording shall also be understood to mean that, if one of the two radicals is hydrogen, the second radical binds to the position to which the hydrogen atom was bonded, forming a ring. This shall be illustrated by the following scheme:

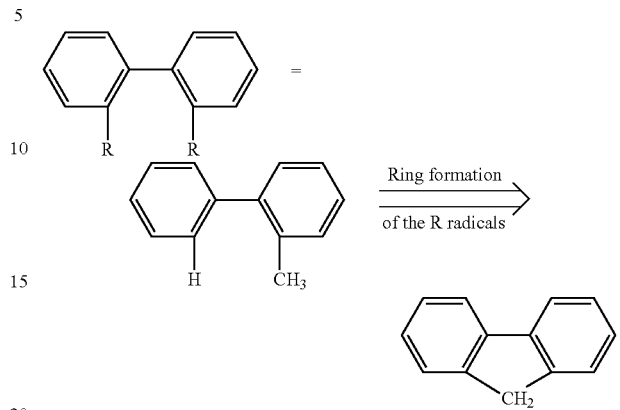

A fused aryl group is understood to mean an aryl group containing two or more aromatic rings fused to one another, meaning that they share one or more aromatic bonds. A corresponding definition applies to heteroaryl groups. Examples of fused aryl groups, regardless of the number of ring atoms therein, are naphthyl, anthracenyl, pyrenyl, phenanthrenyl and perylenyl. Examples of fused heteroaryl groups are quinolinyl, indolyl, carbazolyl and acridinyl.

There follow general definitions of chemical groups in the context of the present application:

An aryl group in the context of this invention contains 6 to 60 aromatic ring atoms, a heteroaryl group in the context of this invention contains 5 to 60 aromatic ring atoms, at least one of which is a heteroatom. The heteroatoms are preferably selected from N, O and S. This is the fundamental definition. If other preferences are stated in the description of the present invention, for example with regard to the number of aromatic ring atoms or of heteroatoms present, these are applicable.

An aryl group or heteroaryl group is understood here to mean either a simple aromatic cycle, i.e. benzene, or a simple heteroaromatic cycle, for example pyridine, pyrimidine or thiophene, or a fused (annelated) aromatic or heteroaromatic polycycle, for example naphthalene, phenanthrene, quinoline or carbazole. A fused (annelated) aromatic or heteroaromatic polycycle, in the context of the present application, consists of two or more simple aromatic or heteroaromatic cycles fused to one another.

An electron-deficient heteroaryl group in the context of the present invention is defined as a 5-membered heteroaryl group having at least two heteroatoms, for example imidazole, oxazole, oxadiazole, etc., or as a 6-membered heteroaryl group having at least one heteroatom, for example pyridine, pyrimidine, pyrazine, triazine, etc. It is also possible for further 6-membered aryl or 6-membered heteroaryl groups to be fused onto these groups, as is the case, for example, in benzimidazole, quinoline or phenanthroline.

An aryl or heteroaryl group, each of which may be substituted by the abovementioned radicals and which may be joined to the aromatic or heteroaromatic system via any desired positions, is especially understood to mean groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2, 3-triazine, tetrazole, 1,2,4,5-tetrazine, 1,2,3,4-tetrazine, 1,2, 3,5-tetrazine, purine, pteridine, indolizine and benzothiadiazole.

An aryloxy group as defined in the present invention is understood to mean an aryl group as defined above bonded via an oxygen atom. An analogous definition applies to heteroaryloxy groups.

An aromatic ring system in the context of this invention contains 6 to 60 carbon atoms in the ring system. A heteroaromatic ring system in the context of this invention contains 5 to 60 aromatic ring atoms, at least one of which is a heteroatom. The heteroatoms are preferably selected from N, O and/or S. An aromatic or heteroaromatic ring system in the context of this invention is understood to mean a system which does not necessarily contain only aryl or heteroaryl groups, but in which it is also possible for two or more aryl or heteroaryl groups to be bonded by a nonaromatic unit (preferably less than 10% of the atoms other than H), for example an sp$^3$-hybridized carbon, silicon, nitrogen or oxygen atom, an sp$^2$-hybridized carbon or nitrogen atom or an sp-hybridized carbon atom. For example, systems such as 9,9'-spirobifluorene, 9,9'-diarylfluorene, triarylamine, diaryl ethers, stilbene, etc. are also to be regarded as aromatic ring systems in the context of this invention, and likewise systems in which two or more aryl groups are joined, for example, by a linear or cyclic alkyl, alkenyl or alkynyl group or by a silyl group. In addition, systems in which two or more aryl or heteroaryl groups are joined to one another via single bonds are also to be regarded as aromatic or heteroaromatic ring systems in the context of this invention, for example systems such as biphenyl, terphenyl or diphenyltriazine.

An aromatic or heteroaromatic ring system which has 5-60 aromatic ring atoms and may also be substituted in each case by radicals as defined above and which may be joined to the aromatic or heteroaromatic system via any desired positions is especially understood to mean groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazine, 1,2,4, 5-tetrazine, 1,2,3,4-tetrazine, 1,2,3,5-tetrazine, purine, pteridine, indolizine and benzothiadiazole or combinations of these groups.

In the context of the present invention, a straight-chain alkyl group having 1 to 40 carbon atoms and a branched or cyclic alkyl group having 3 to 40 carbon atoms and an alkenyl or alkynyl group having 2 to 40 carbon atoms in which individual hydrogen atoms or $CH_2$ groups may also be replaced by the groups mentioned above in the definition of the radicals are preferably understood to mean the methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl radicals. An alkoxy or thioalkyl group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

When $G^1$ or $G^2$ is an electron-transporting group (ETG), the group is preferably an electron-deficient heteroaromatic group which may be substituted by one or more $R^1$ radicals. Even more preferred are accordingly heteroaromatic groups having 6 aromatic ring atoms of which at least one is a nitrogen atom, or heteroaromatic groups having 5 aromatic ring atoms of which at least 2 are heteroatoms, and preferably at least one of them a nitrogen atom which may be substituted by $R^1$, where further aryl or heteroaryl groups may also be fused onto each of these groups.

Preferred electron-deficient heteroaromatic groups are selected from the following groups:

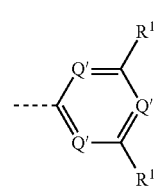

Formula (E-1)

-continued

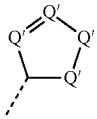
Formula (E-2)

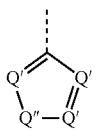
Formula (E-3)

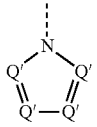
Formula (E-4)

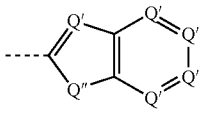
Formula (E-5)

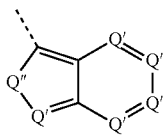
Formula (E-6)

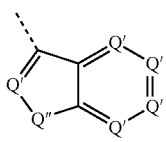
Formula (E-7)

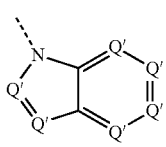
Formula (E-8)

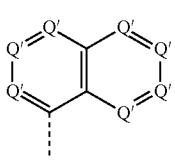
Formula (E-9)

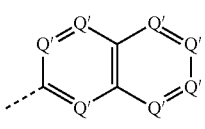
Formula (E-10)

where the dotted bond marks the attachment position, $R^1$ is as defined above and Q' is the same or different at each instance and is $CR^1$ or N, and Q" is $NR^1$, O or S;

where at least one Q' is N and/or at least one Q" is $NR^1$.

Preferred examples of electron-deficient heteroaromatic groups are: pyridines, pyrazines, pyrimidines, pyridazines, 1,2,4-triazines, 1,3,5-triazines, quinolines, isoquinolines, quinoxalines, pyrazoles, imidazoles, benzimidazoles, thiazoles, benzothiazoles, oxazoles or benzoxazoles, each of which may be substituted by $R^1$. Even more preferably, the electron-transporting group is a pyridine, pyrazine, pyrimidine, pyridazine and 1,3,5-triazine substituted by one or more $R^1$ radicals.

Very preferred electron-deficient heteroaromatic groups are selected from the following groups:

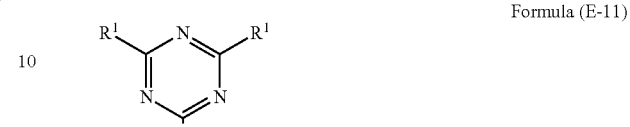
Formula (E-11)

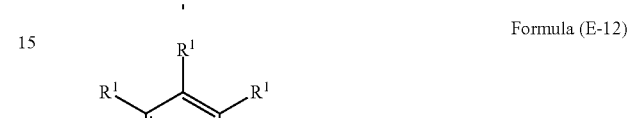
Formula (E-12)

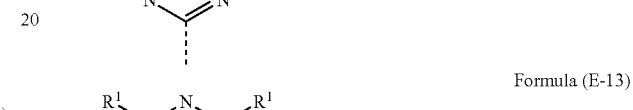
Formula (E-13)

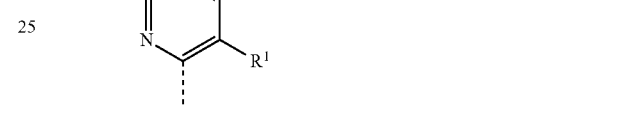
Formula (E-14)

Formula (E-15)

Formula (E-16)

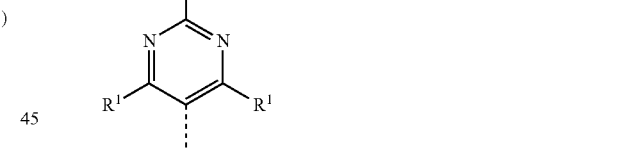

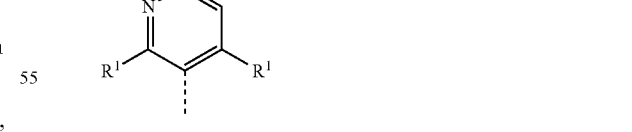

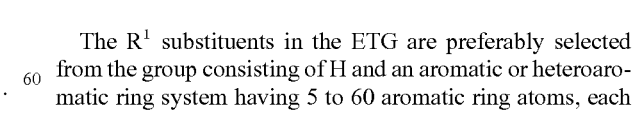

The $R^1$ substituents in the ETG are preferably selected from the group consisting of H and an aromatic or heteroaromatic ring system having 5 to 60 aromatic ring atoms, each of which may be substituted by one or more $R^2$ radicals.

Examples of very particularly preferred ETGs having $R^1$ radicals are the following groups which may be substituted by one or more independent $R^2$ radicals, where the dotted bonds indicate the binding positions to the $Ar^1$ and $Ar^2$ groups.

Formula (E-17)
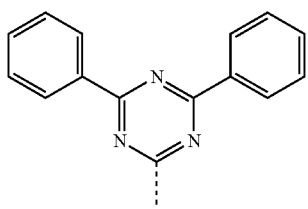
Formula (E-18)
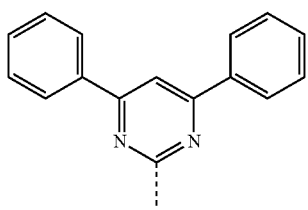
Formula (E-19)
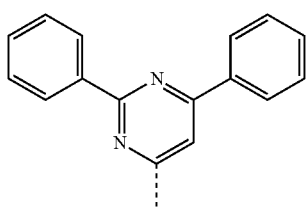
Formula (E-20)
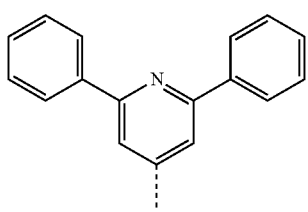
Formula (E-21)
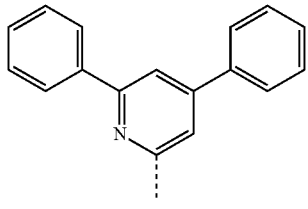
Formula (E-22)
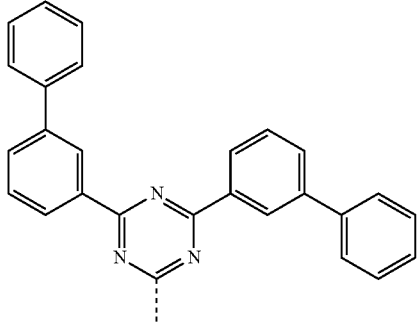
Formula (E-23)
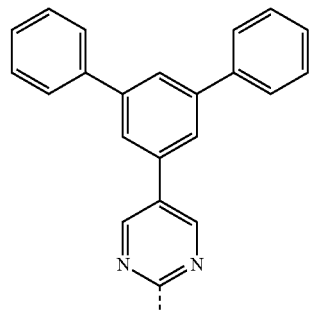
Formula (E-24)
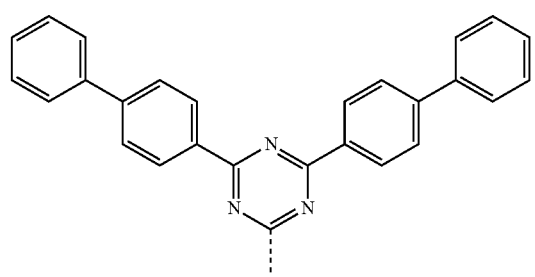
Formula (E-25)
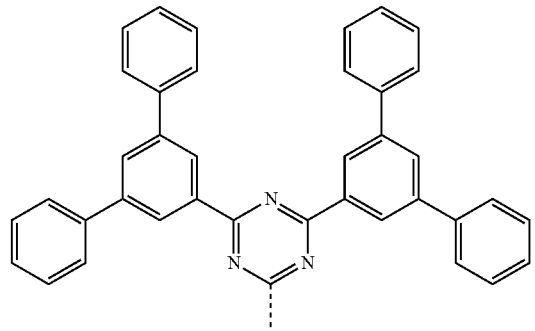
Formula (E-26)
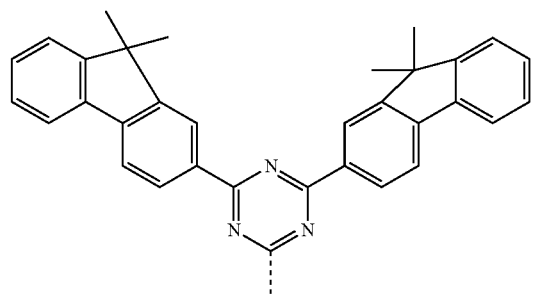
Formula (E-27)
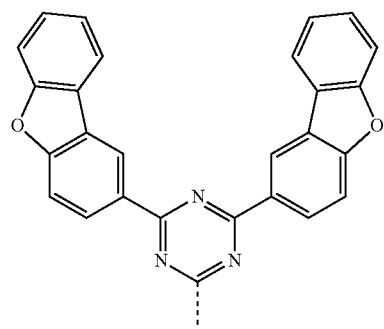

Formula (E-28)

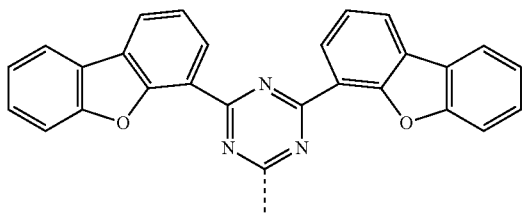

Formula (E-29)

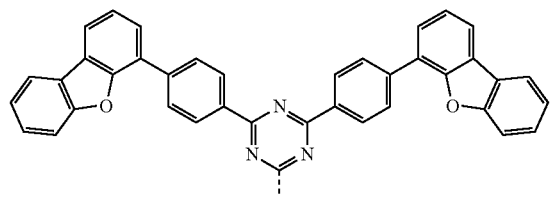

Formula (E-30)

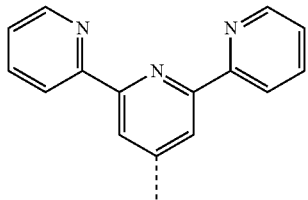

The electron transport group preferably has a LUMO (lowest unoccupied molecular orbital) energy of less than −1.3 eV, very preferably less than −2.5 eV and most preferably less than −2.7 eV.

HOMO (highest occupied molecular orbital) and LUMO (lowest unoccupied molecular orbital) energy levels and the energy of the lowest triplet state $T_1$ and that of the lowest excited singlet state $S_1$ of the materials are determined via quantum-chemical calculations. For this purpose, the "Gaussian09 W" (Gaussian Inc.) software package is used. For calculation of organic substances, an optimization of geometry is first conducted by the "Ground State/Semi-empirical/Default Spin/AM1/Charge 0/Spin Singlet" method. Subsequently, an energy calculation is effected on the basis of the optimized geometry. This is done using the "TD-SFC/DFT/Default Spin/B3PW91" method with the "6-31G(d)" basis set (charge 0, spin singlet). The HOMO energy level HEh or LUMO energy level LEh is obtained from the energy calculation in Hartree units. This is used to determine the HOMO and LUMO energy levels in electron volts, calibrated by cyclic voltammetry measurements, as follows:

HOMO(eV)=((HEh*27.212)−0.9899)/1.1206

LUMO(eV)=((LEh*27.212)−2.0041)/1.385

These values are to be regarded as HOMO and LUMO energy levels of the materials in the context of this application.

The lowest triplet state Ti is defined as the energy of the triplet state having the lowest energy, which is apparent from the quantum-chemical calculation described.

The lowest excited singlet state $S_1$ is defined as the energy of the excited singlet state having the lowest energy, which is apparent from the quantum-chemical calculation described.

Further preferably, the electron transport group is characterized in that the electron mobility $\mu_-$ is $10^{-6}$ cm$^2$/(Vs) or more, very preferably $10^{-5}$ cm$^2$/(Vs) or more and most preferably $10^{-4}$ cm$^2$/(Vs) or more.

In the compounds of formula (1), the LUMO is preferably localized to the electron transport group. It is very preferable when the LUMO is more than 80% localized on the electron-transporting group, and even more preferable when the LUMO is not localized on the LTG (for example an amine or carbazole group) at all. It is especially preferred when the HOMO and LUMO of the compound of the invention do not overlap at all. The person skilled in the art has no difficulties at all in determining the overlap of the orbitals. For this purpose, the calculation method specified herein is used and orbitals having a probability density of 90% are assumed. The overlap can be calculated by determining overlap integrals.

The hole transport group preferably has a HOMO energy (HOMO$_{LTG}$) within the range of the electron work function of the anode used (φanode) plus +1.5 eV or less, i.e.:

HOMO$_{LTG}$≤(φ$_{anode}$+1.5 eV)

When the anode used has an electron work function of −5 eV, the HOMO energy of the hole transport group is −3.5 eV or less (i.e. more negative than −3.5 eV). It is very preferable when the hole transport group has a HOMO energy equal to or less than the electron work function of the anode, most preferably less.

Further preferably, the hole transport group is characterized in that the hole mobility $\mu_+$ is $10^{-6}$ cm$^2$/(Vs) or more, very preferably $10^{-5}$ cm$^2$/(Vs) or more and most preferably $10^{-4}$ cm$^2$/(Vs) or more.

In the compounds of formula (1), the HOMO is significantly localized on the hole transport group. "Significantly" means here that the HOMO is localized on the hole-conducting group to an extent of 80% or more or is not localized on the electron-deficient electron-transporting group.

Preferably, the LTG is a group of the following general formulae, where the positions indicated by the dotted bond are the joining positions to Ar$^1$ or Ar$^2$ and where the groups may be substituted by one or more R$^1$ radicals which may be the same or different at each instance:

Formula (L-1)

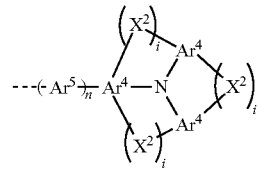

Formula (L-2)

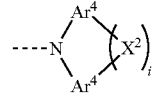

Formula (L-3)

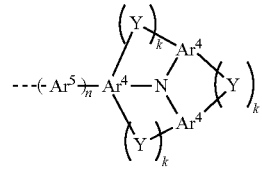

Formula (L-4)

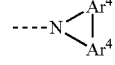

Ar⁴ is the same or different at each instance and is selected from aryl or heteroaryl groups which have 6 to 13 aromatic ring atoms and may be substituted by one or more R¹ radicals;

Ar⁵ is the same or different at each instance and is selected from aryl or heteroaryl groups which have 6 to 13 aromatic ring atoms and may be substituted by one or more R¹ radicals;

X² is the same or different at each instance and is selected from C(R²)₂, Si(R²)₂, C=O, 0, S, S=O, SO₂ and NR²

Y is a single bond;

n is the same or different at each instance and is 0, 1, 2, 3 or 4;

i is the same or different at each instance and is 0 or 1;

k is the same or different at each instance and is 0 or 1, where at least one index k per group has to be 1;

and where the above definitions otherwise apply.

Particularly preferred groups of the formula (L-1) are those of the following formulae (L-5) to (L-10):

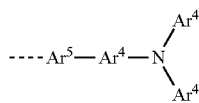

Formula (L-5)

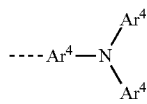

Formula (L-6)

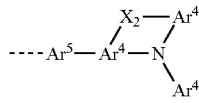

Formula (L-7)

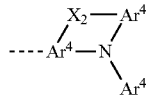

Formual (L-8)

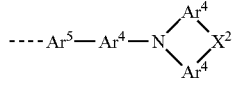

Formula (L-9)

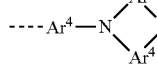

Formula (L-10)

where the symbols that occur are defined as specified above. The preferred embodiments of groups specified in the application are likewise considered to be preferred.

Particularly preferred groups of the formula (L-2) are those of the following formulae (L-11) to (L-12):

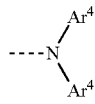

Formula (L-11)

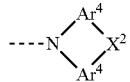

Formula (L-12)

where the symbols that occur are defined as specified above. The preferred embodiments of groups specified in the application are likewise considered to be preferred.

It is especially preferable that, in the formulae (L-11) to (L-12), Ar⁴ is the same or different and is selected from phenyl, naphthyl, pyridyl, pyrimidyl, pyridazyl, pyrazinyl and triazinyl, each of which may be substituted by one or more R² radicals. It is further preferable that the X group is the same or different at each instance and is selected from C(R²)₂, C=O, O, S and NR².

Particular preference is given to the formula (L-11).

Particularly preferred groups of the formula (L-3) are those of the following formulae:

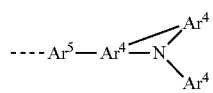

Formual (L-13)

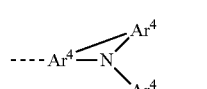

Formula (L-14)

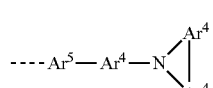

Formula (L-15)

Formula (L-16)

where the symbols that occur are as defined above. The preferred embodiments of groups specified in the application are likewise considered to be preferred.

It is especially preferable that, in the formulae (L-13) to (L-16), Ar⁴ and Ar⁵ are the same or different and are selected from phenyl, naphthyl, pyridyl, pyrimidyl, pyridazyl, pyrazinyl and triazinyl, each of which may be substituted by one or more R² radicals.

Particularly preferred groups of the formula (L-4) are those of the following formula:

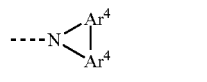

Formula (L-17)

where Ar⁴ is the same or different and is selected from phenyl, naphthyl, pyridyl, pyrimidyl, pyridazyl, pyrazinyl and triazinyl, each of which may be substituted by one or more R² radicals.

It is especially preferable that, in the formulae (L-5) to (L-10), Ar⁴ and Ar⁵ are the same or different and are selected from phenyl, naphthyl, pyridyl, pyrimidyl, pyridazyl, pyrazinyl and triazinyl, each of which may be substituted by one or more R² radicals. It is further preferable that the X² group is the same or different at each instance and is selected from C(R²)₂, C=O, O, S and NR².

Particular preference is given to the formulae (L-5) and (L-6).

Examples of very particularly preferred LTGs having R¹ radicals are the following groups which may be substituted by one or more independent R² radicals, where the dotted bonds indicate the binding positions to the Ar¹ and Ar² groups.

Formula (L-18)
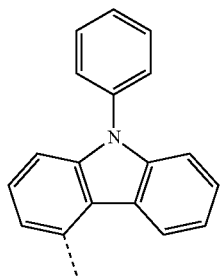
Formula (L-19)
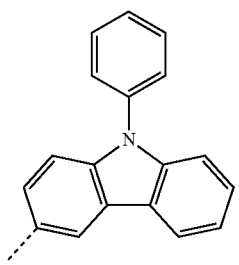
Formula (L-20)
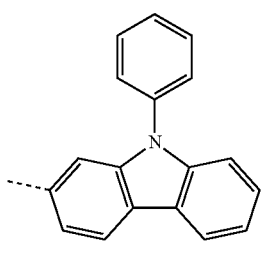
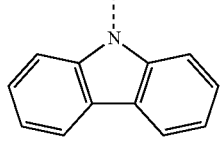
Formula (L-22)
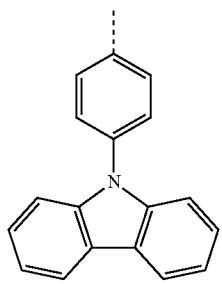
Formula (L-23)
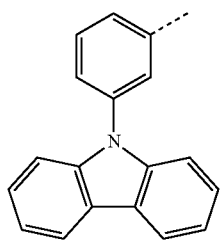
Formula (L-24)
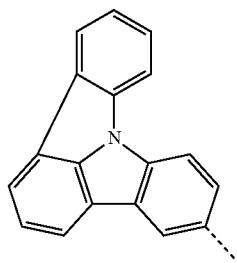
Formula (L-25)
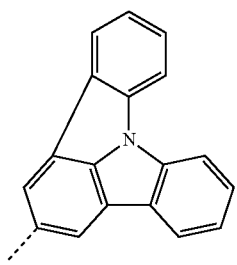
Formula (L-26)
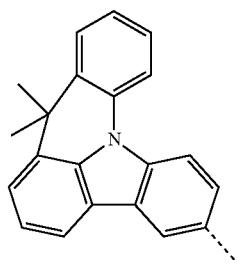
Formula (L-27)
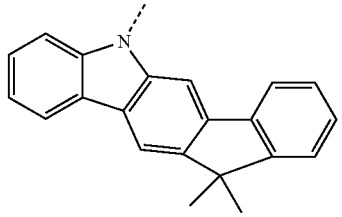
Formula (L-28)
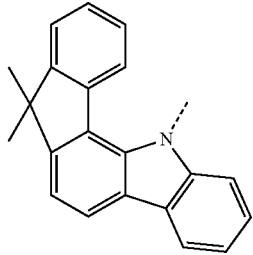
Formula (L-29)
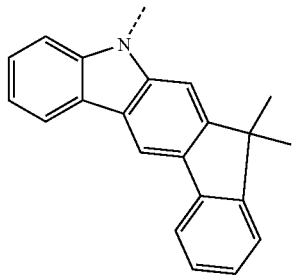

Formula (L-30)
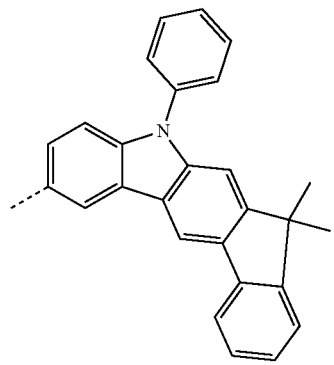
Formula (L-31)
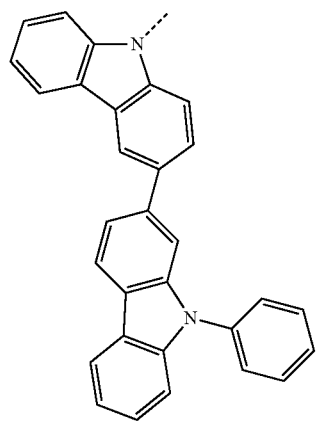
Formula (L-32)
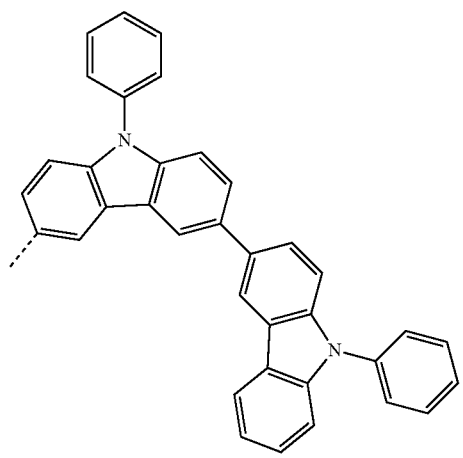
Formula (L-33)
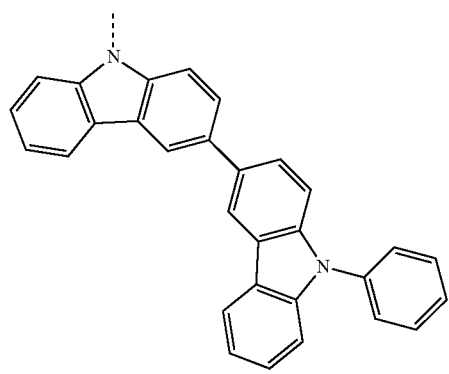
Formula (L-34)
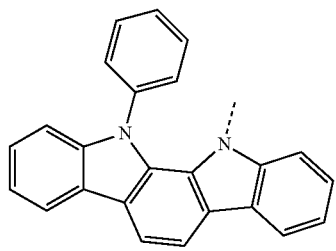
Formula (L-35)
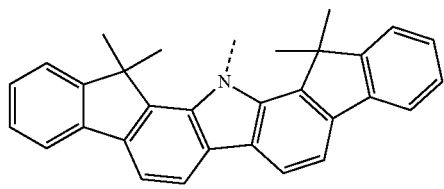
Formula (L-36)
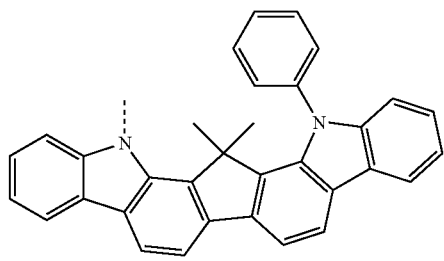
Formula (L-37)
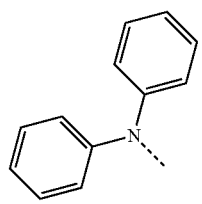
Formula (L-38)
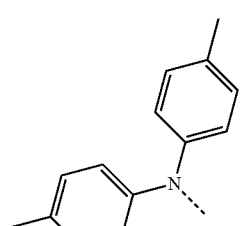
Formula (L-39)
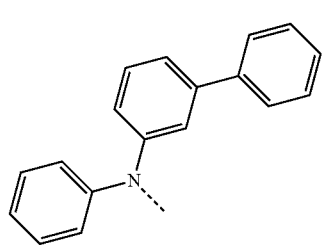

Formula (L-40)
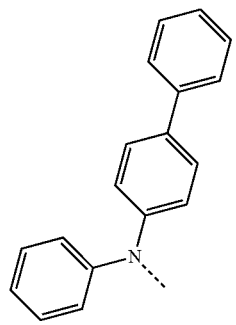
Formula (L-41)
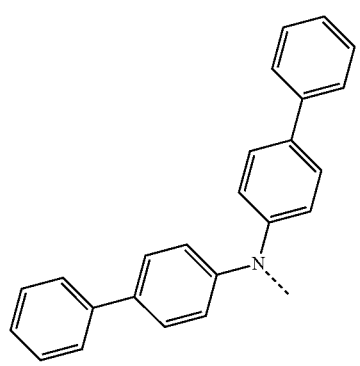
Formula (L-42)
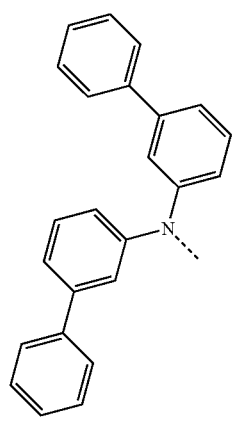
Formula (L-43)
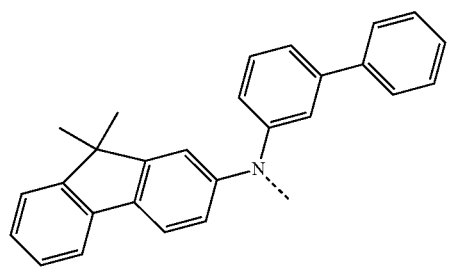
Formula (L-44)
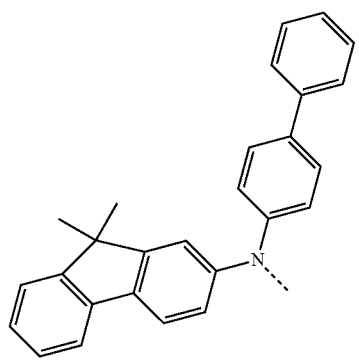
Formula (L-45)
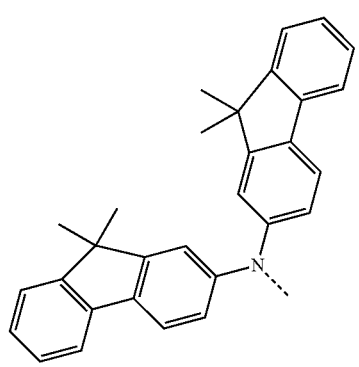
Formula (L-46)
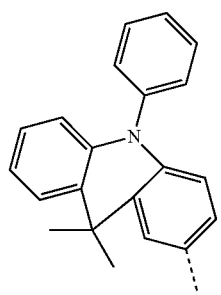
Formula (L-47)
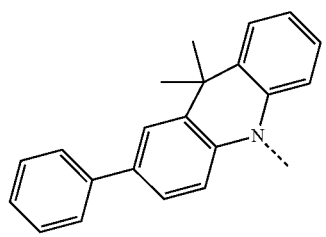
Formula (L-48)
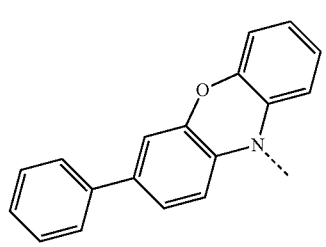

Formula (L-49)
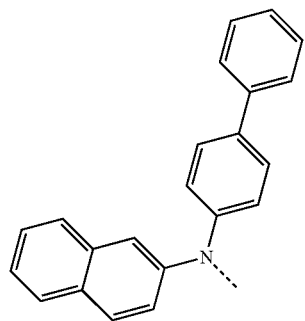
Formula (L-50)
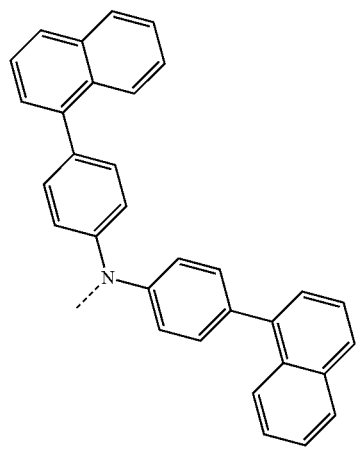
Formula (L-51)
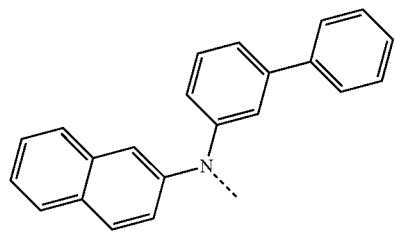
Formula (L-52)
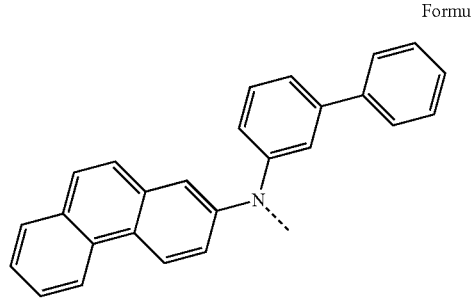
Formula (L-53)
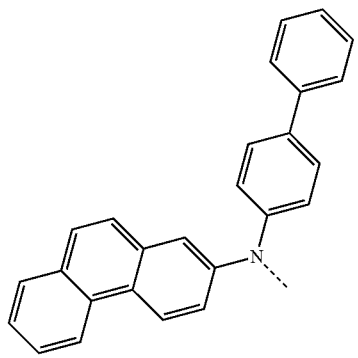
Formula (L-54)
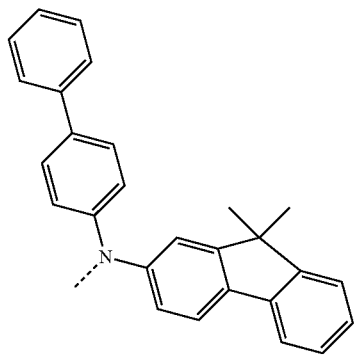
Formula (L-55)
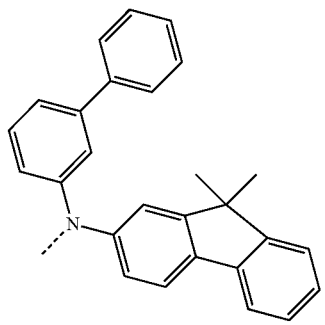
Formula (L-56)
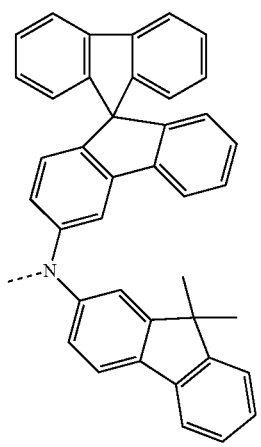

-continued

Formula (L-57)

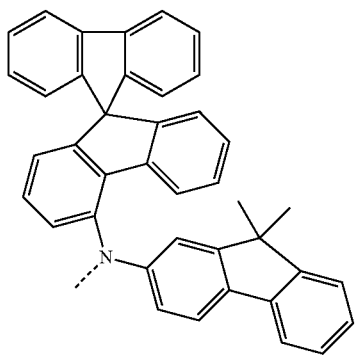

Formula (L-58)

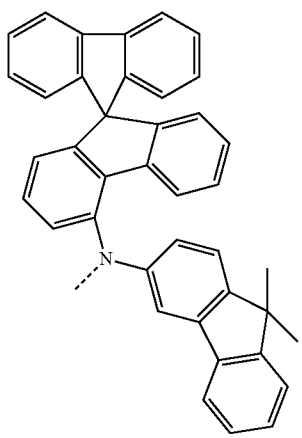

Formula (L-59)

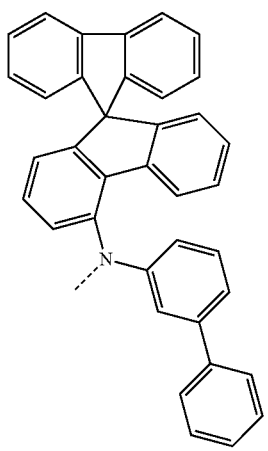

Formula (L-60)

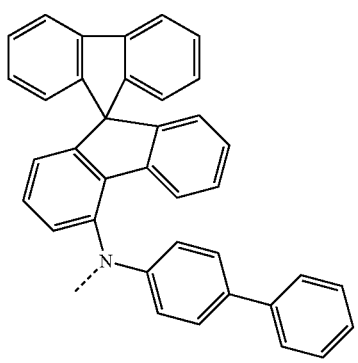

The compounds of the invention may be prepared according to schemes 1 and 2.

The corresponding monoboronic acids (a) can be prepared by Suzuki coupling and subsequent silylation (scheme 1). A further option is to prepare the corresponding monoboronic acids proceeding from the monobromides by Buchwald coupling and subsequent silylation (scheme 2). The reaction of these monoboronic acids via Suzuki coupling with appropriate aryl bromides or aryl chlorides leads to the target compounds.

Scheme 1

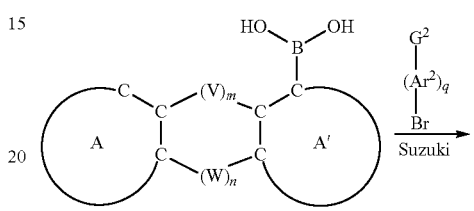

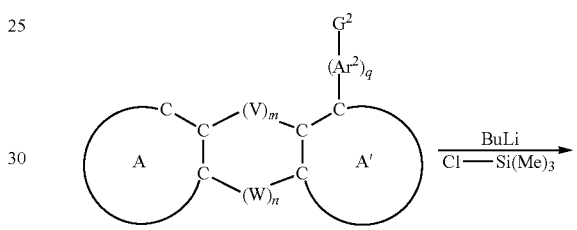

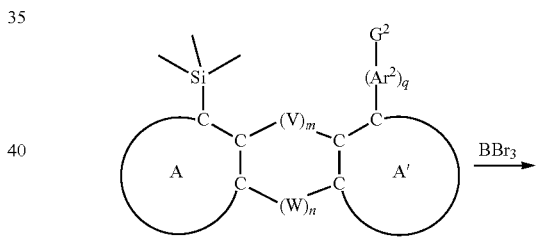

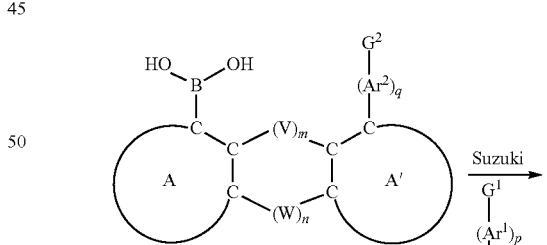

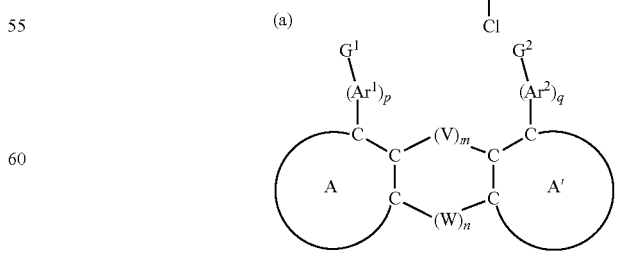

where the above-specified definitions and the preferred embodiments thereof apply to the indices and symbols used.

Scheme 2

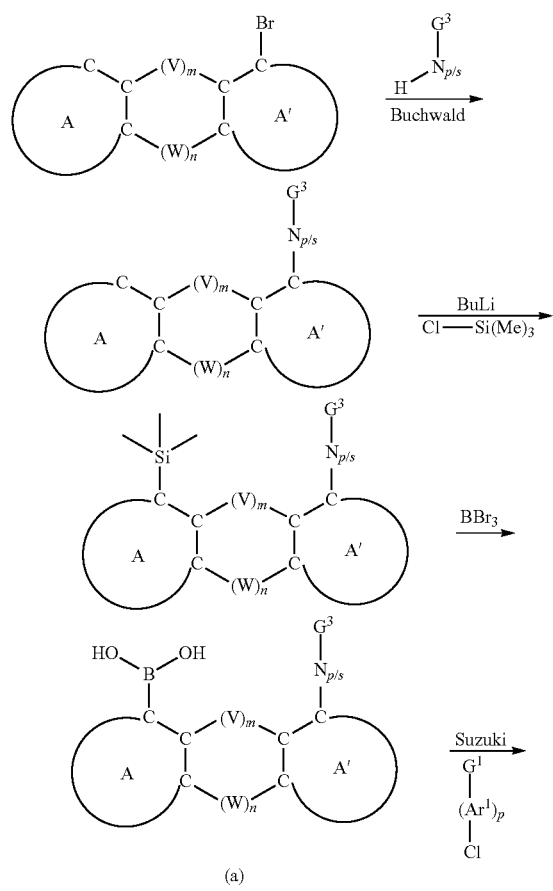

(a)

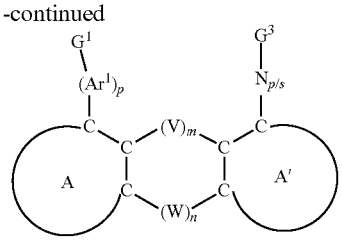

where the $G^3$-$N_{p/s}$—H group is the $G^2$ group and where the $G^2$ group contains a primary (p) or secondary (s) amine and is an LTG. The $G^1$ group in this case is an ETG. In addition, p is 1. The above-specified definitions and the preferred embodiments thereof apply to the other indices and symbols used.

The Suzuki and Buchwald reactions are well-known to those skilled in the art, who will not have any difficulties in applying the reactions and known variations thereof to the compounds of the invention, in order to prepare them in the range claimed, taking account of common knowledge in the art. Furthermore, both in the Suzuki reaction and in the Buchwald reaction, the chemical functionalities can be exchanged between the substituent and the structure containing the A and A' rings. This means that the substituent containing $G^1$ or $G^2$ may also contain the boronic acid, whereas the structure containing the rings A and A' contains the halide. The schemes which follow illustrate the application of the processes mentioned by way of example using more specific cases, where the above definitions apply to the symbols and indices used. The Ar groups in the schemes which follow are the same or different at each instance and represent aromatic or heteroaromatic groups which may be selected in such a way that the above definitions for ETG, LTG and generally those of formula (1) are satisfied. Hal represents halides is preferably Br or I.

Scheme 3

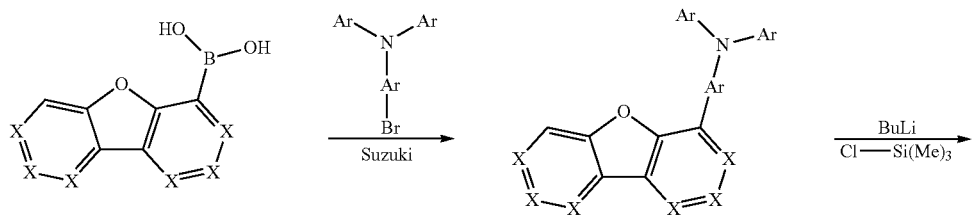

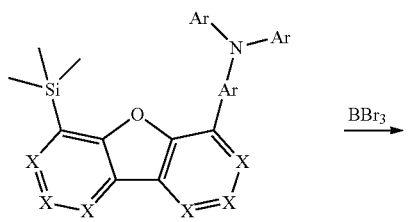

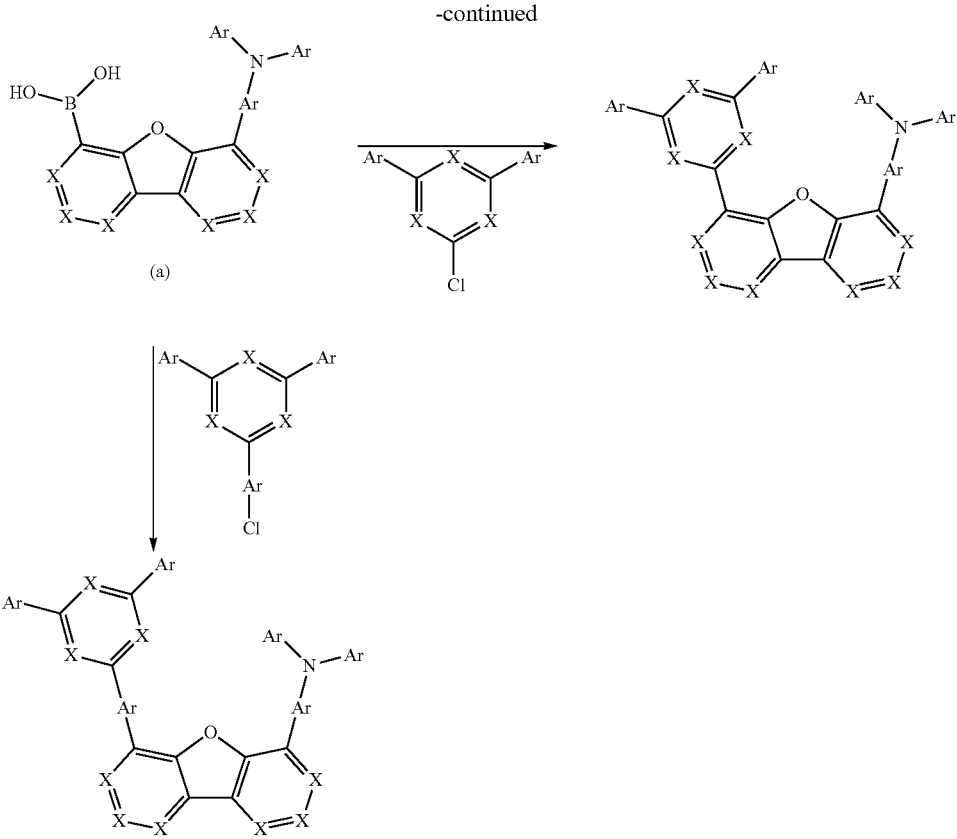

where the group containing the N(Ar₃) unit is the LTG and the other group is the ETG.

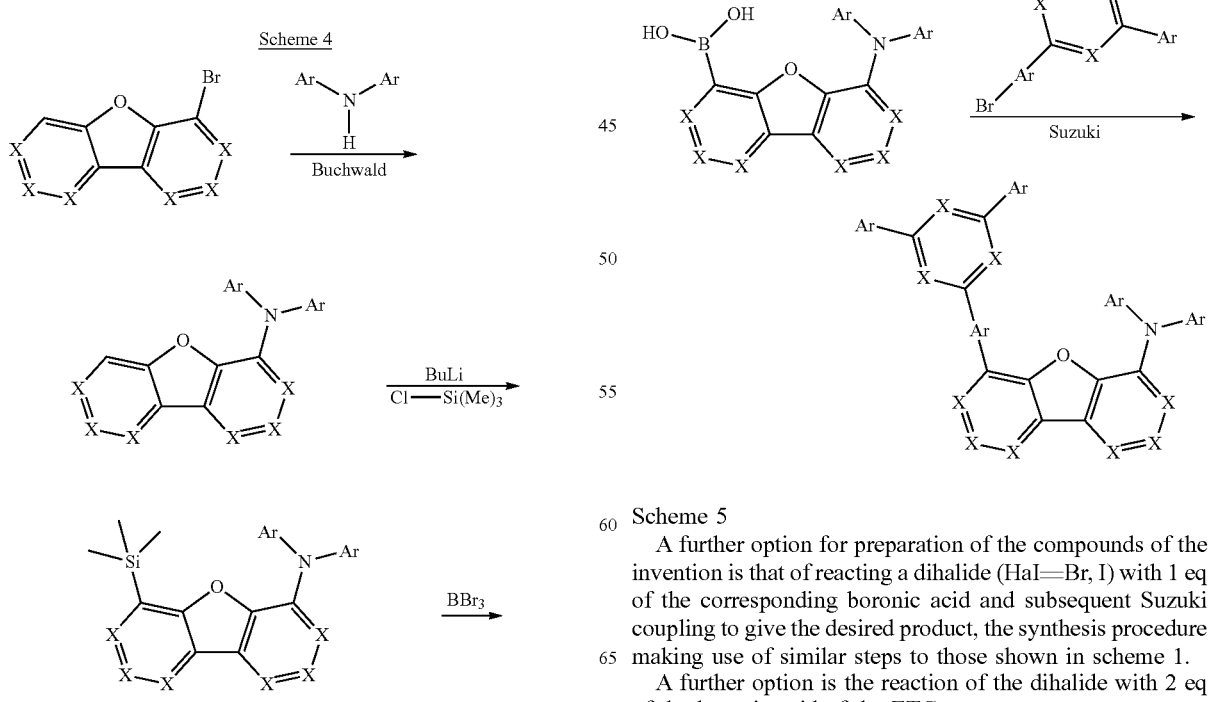

Scheme 5

A further option for preparation of the compounds of the invention is that of reacting a dihalide (Hal=Br, I) with 1 eq of the corresponding boronic acid and subsequent Suzuki coupling to give the desired product, the synthesis procedure making use of similar steps to those shown in scheme 1.

A further option is the reaction of the dihalide with 2 eq of the boronic acid of the ETG.

Scheme 6
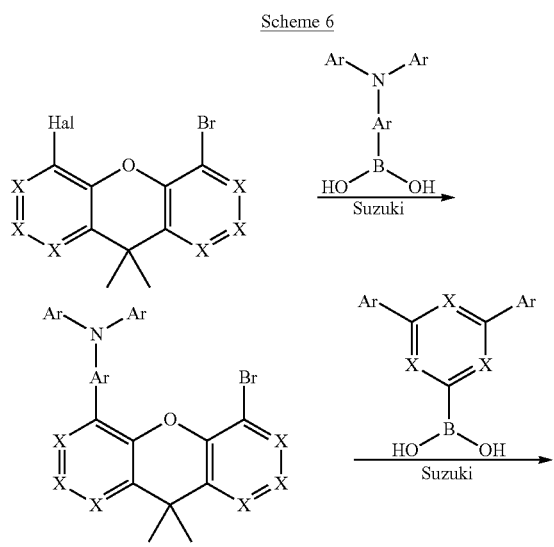
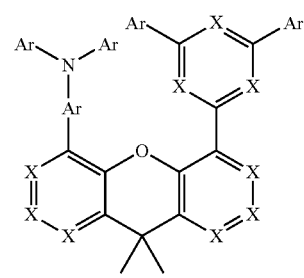
Many of the dihalides (a) or diboronic acids (b) are commercially available or can be synthesized as specified in scheme 6. They can subsequently be converted to the desired products via Suzuki couplings.
Scheme 7
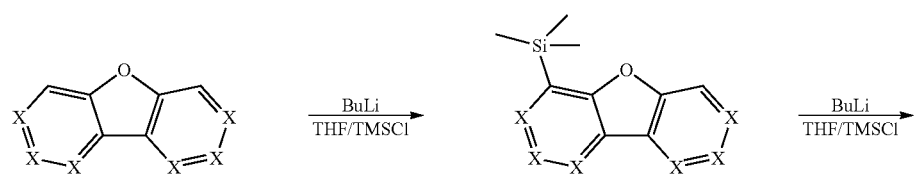
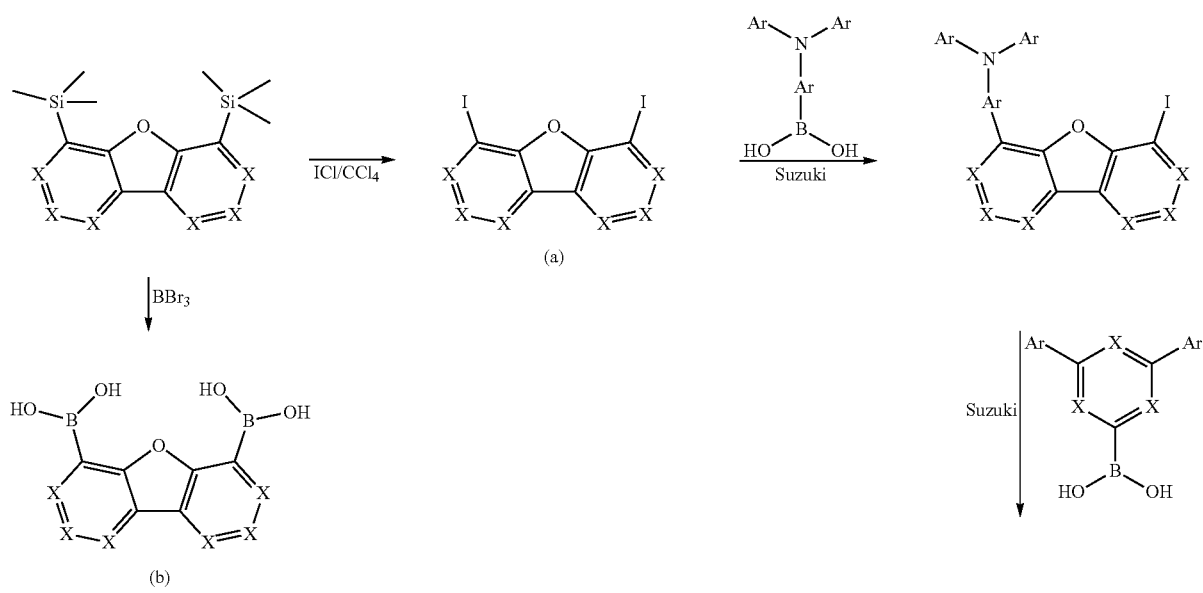

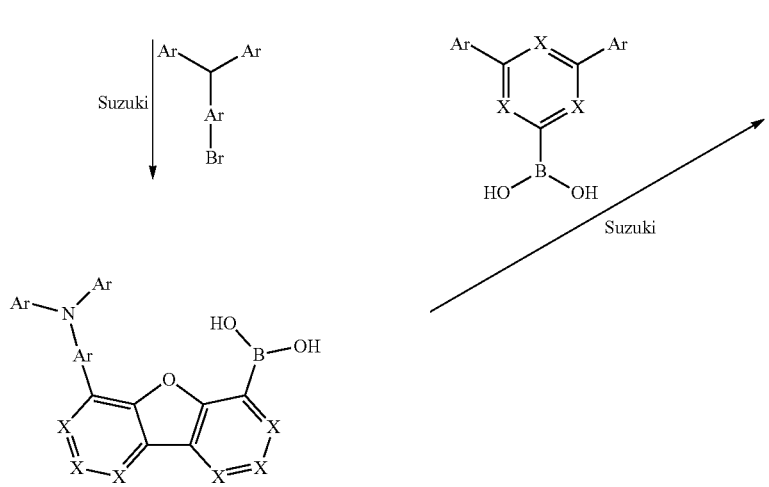
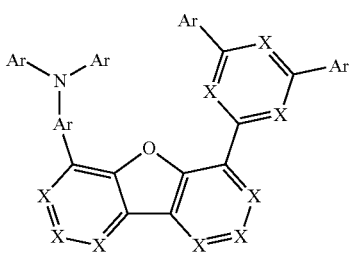

A further option for preparation of compounds of the invention is that of converting carbazole derivatives, followed by an Ullmann or Buchwald coupling.

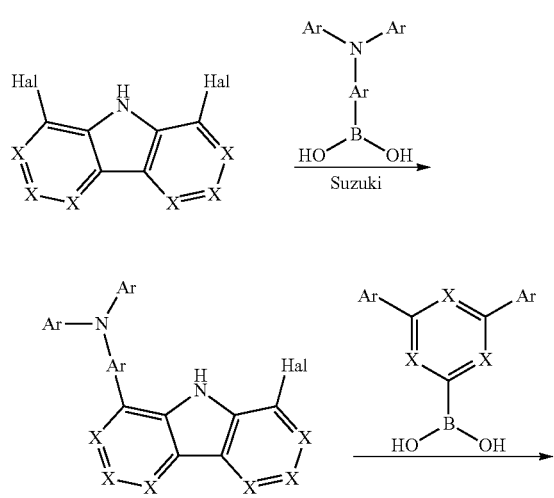

The processes shown for synthesis of the compounds of the invention should be understood by way of example. The person skilled in the art will be able to develop alternative synthesis routes within the scope of his common knowledge in the art.

The overview which follows contains an illustration of compounds of the invention which can be prepared by one of the processes described herein.

Formula (17)

Formula (18)

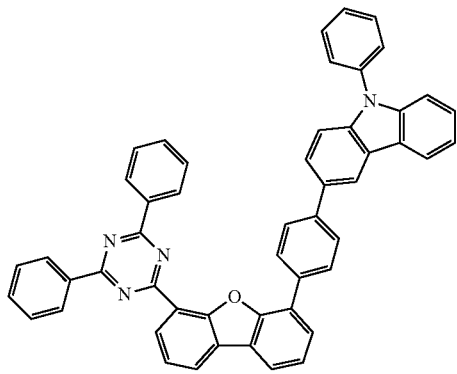
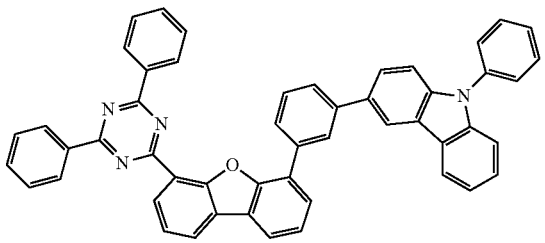

Formula (19)
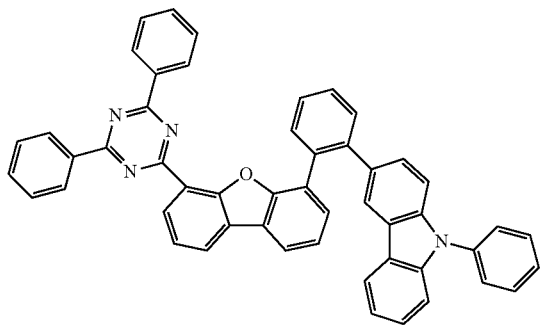
Formula (20)
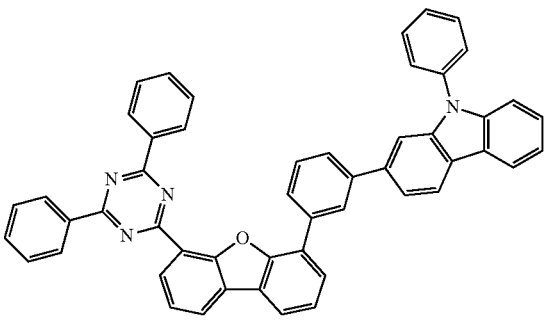
Formula (21)
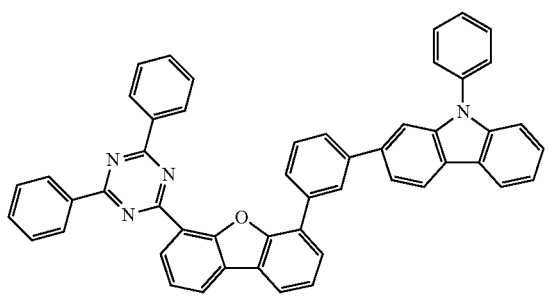
Formula (22)
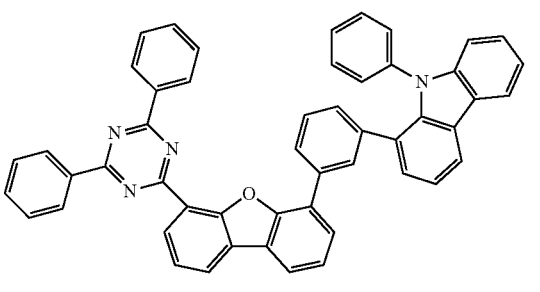
Formula (23)
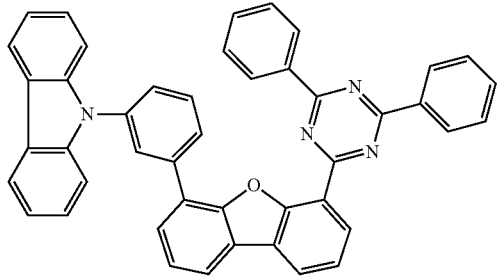
Formula (24)
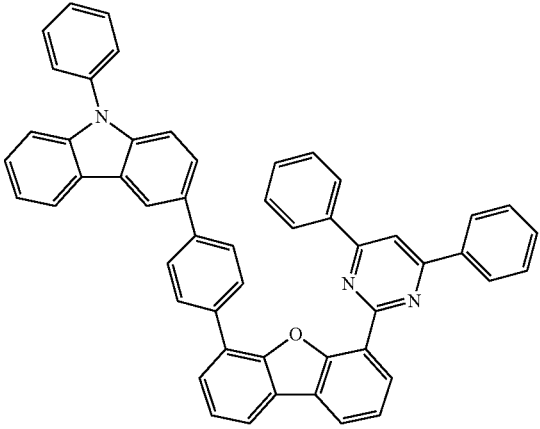
Formula (25)
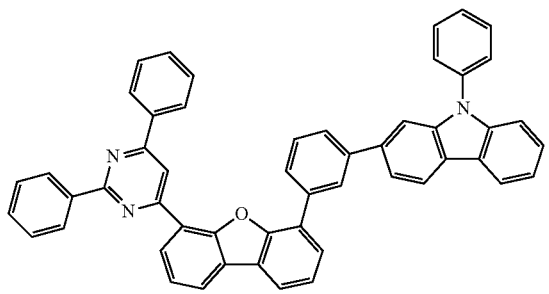
Formula (26)
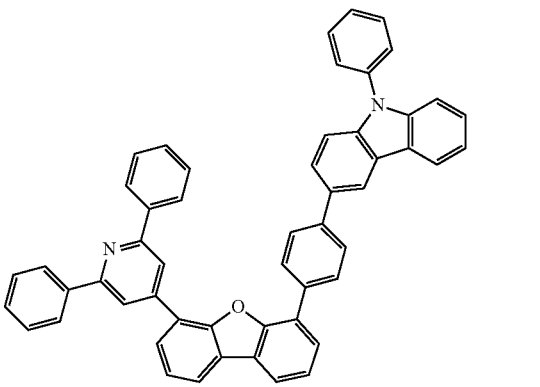

Formula (27)
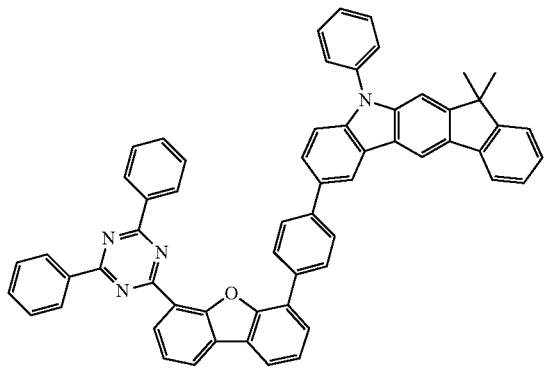
Formula (28)
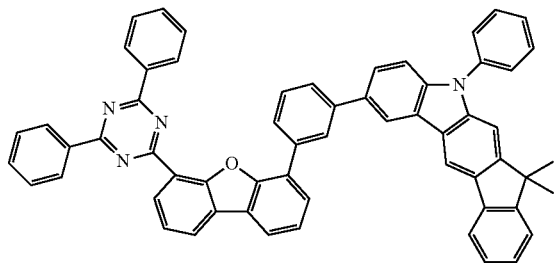
Formula (29)
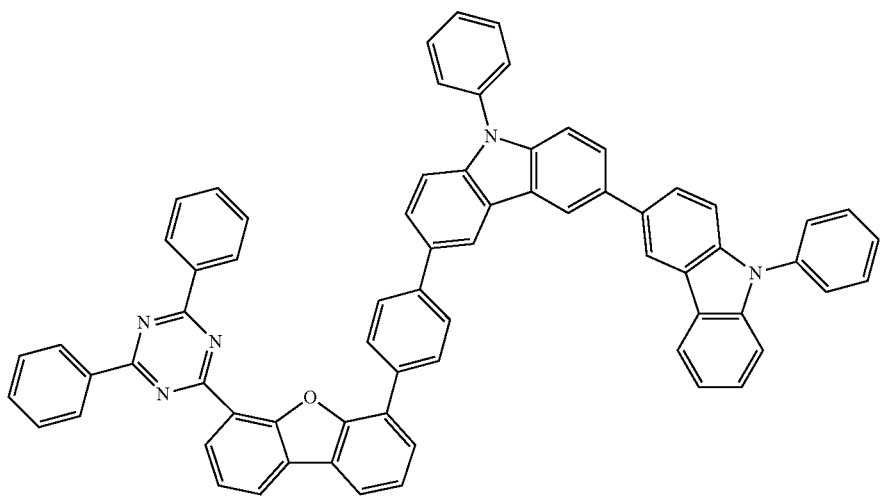
Formula (30)
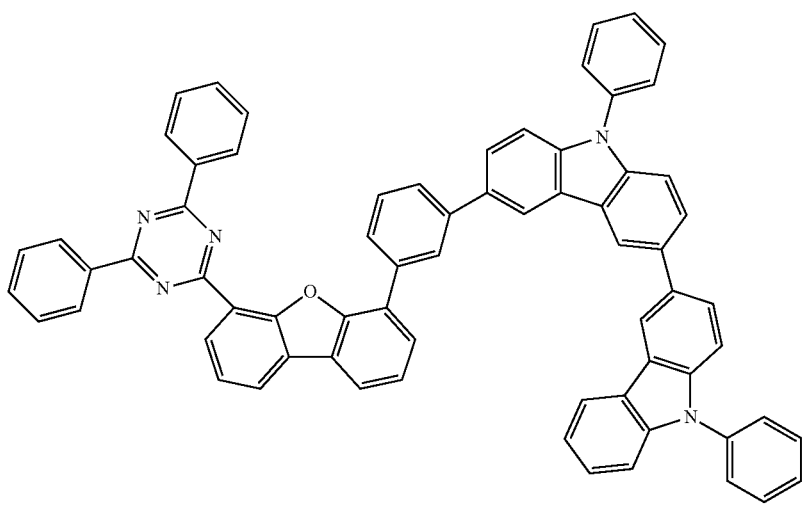

Formula (31)
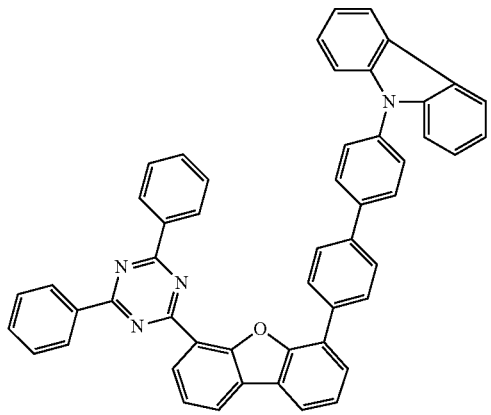
Formula (32)
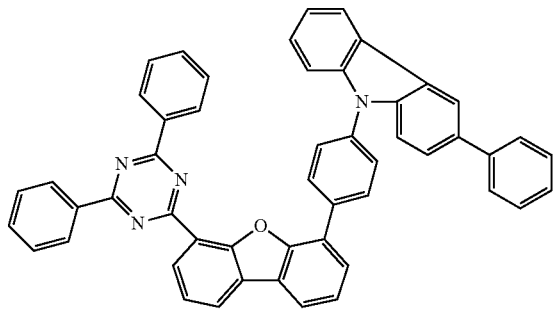
Formula (33)
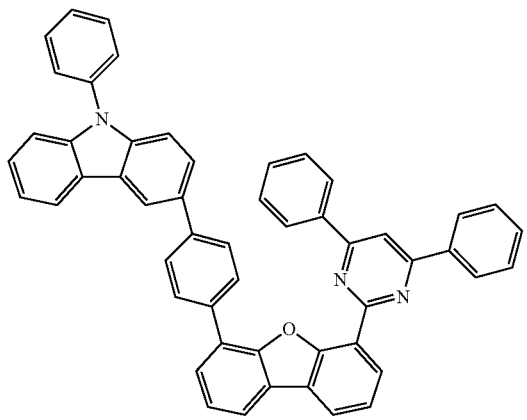
Formula (34)
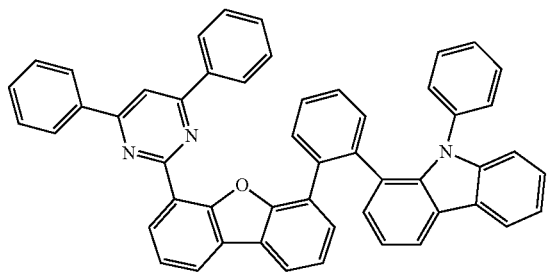
Formula (35)
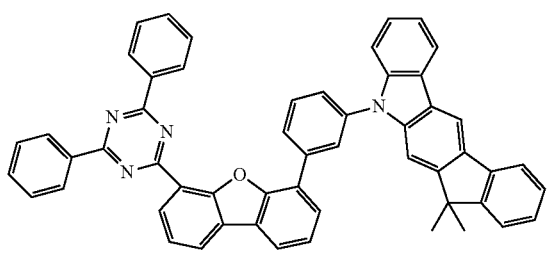
Formula (36)
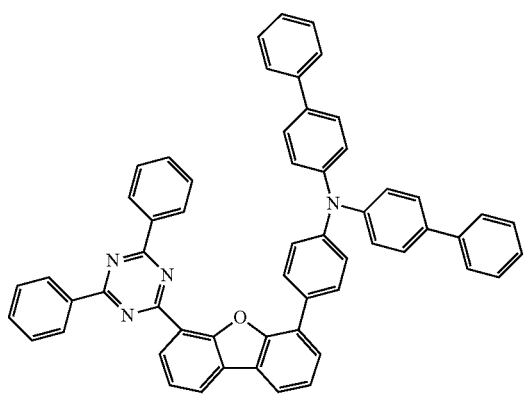

-continued
Formula (37)
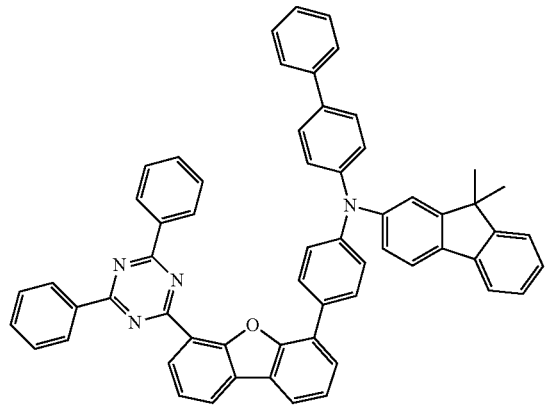
Formula (38)
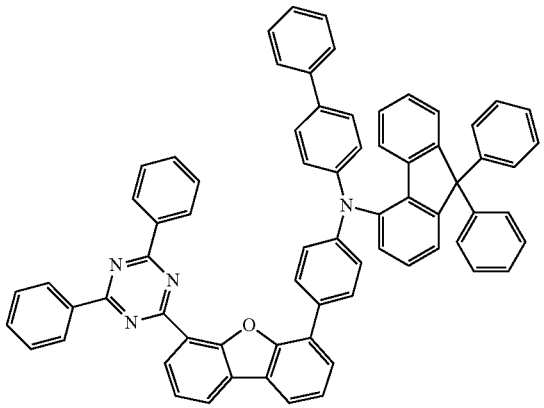
Formula (39)
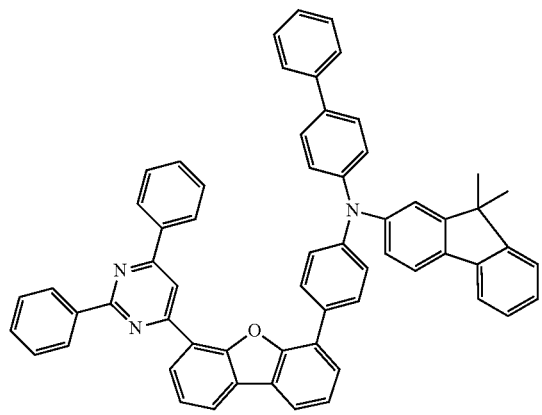
Formula (40)
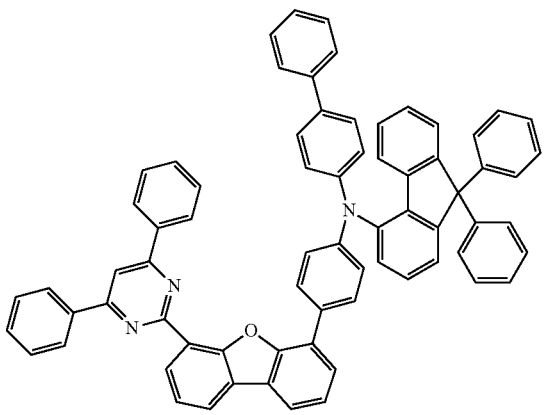
Formula (41)
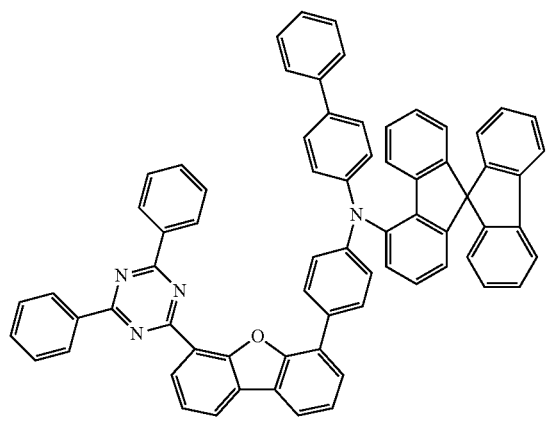
Formula (42)
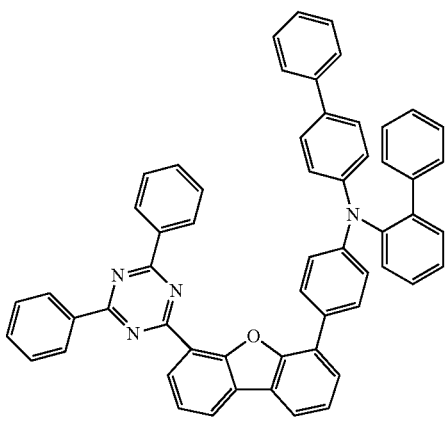

-continued
Formula (43)
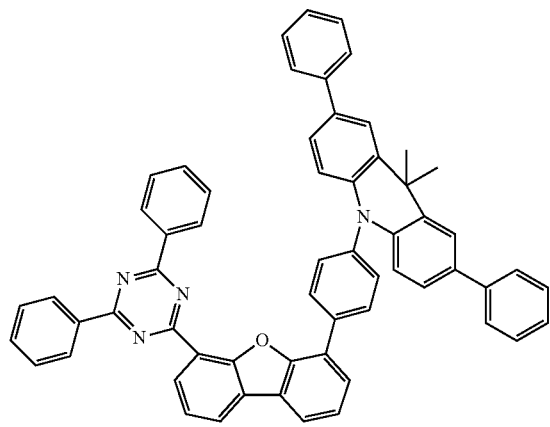
Formula (44)
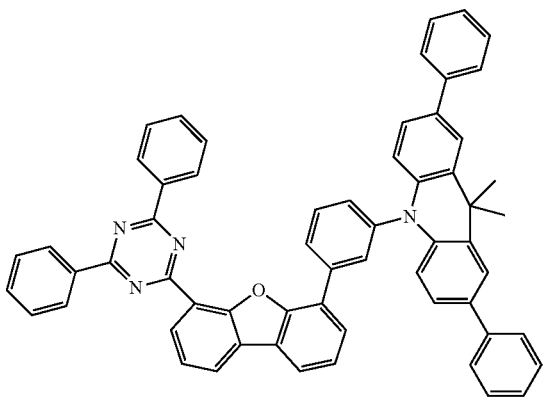
Formula (45)
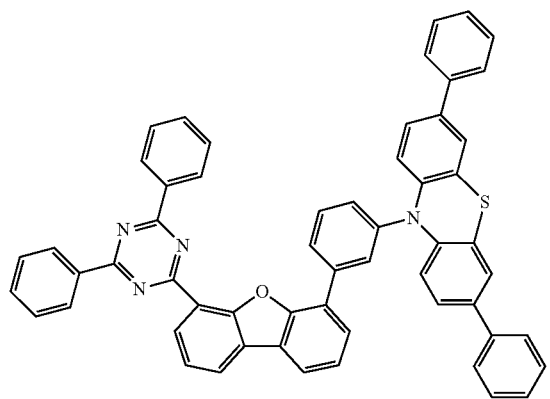
Formula (46)
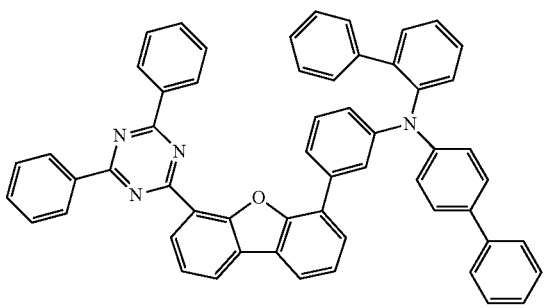
Formula (47)
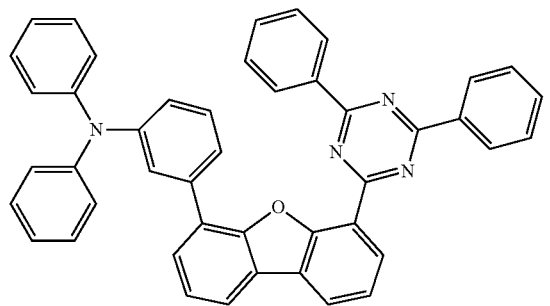
Formula (48)
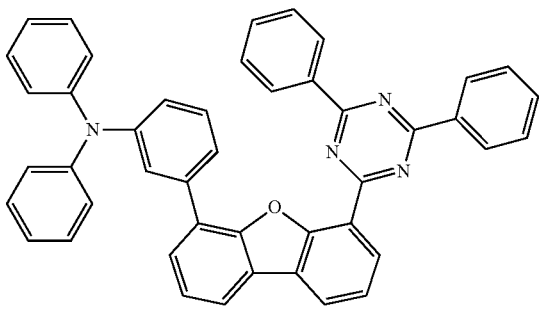
Formula (49)
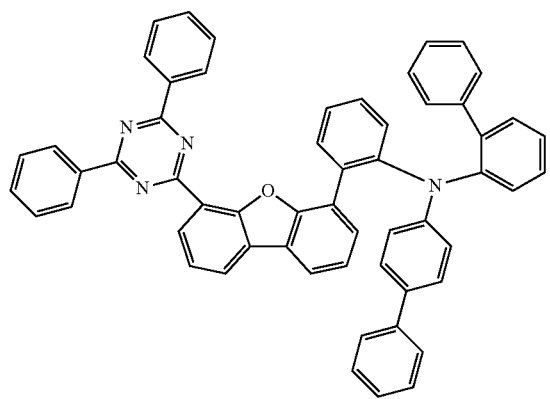
Formula (50)
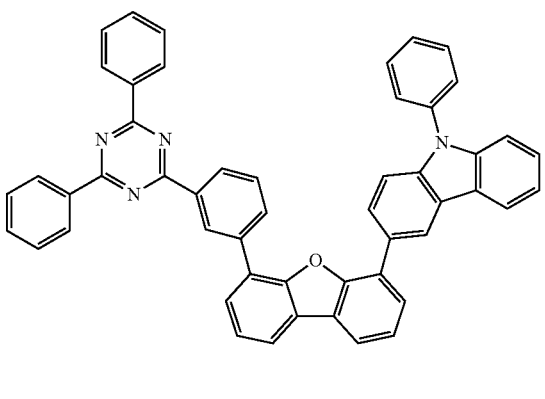

Formula (51)
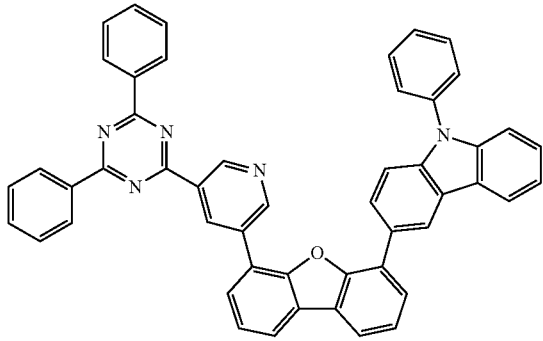
Formula (52)
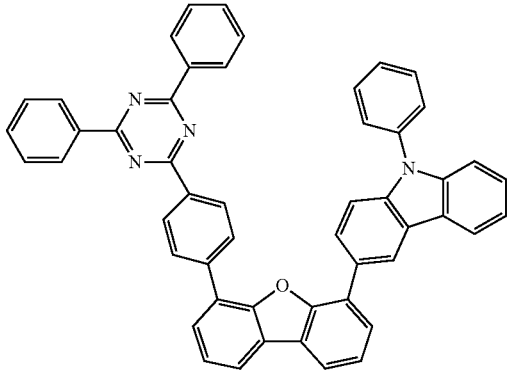
Formula (53)
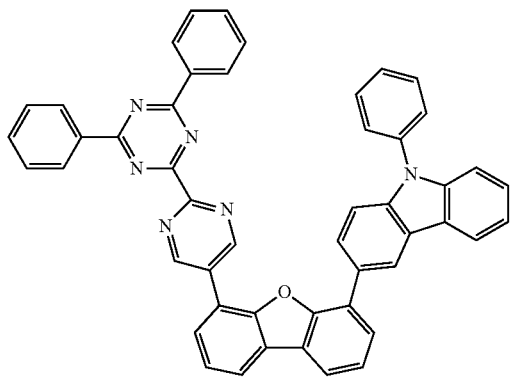
Formula (54)
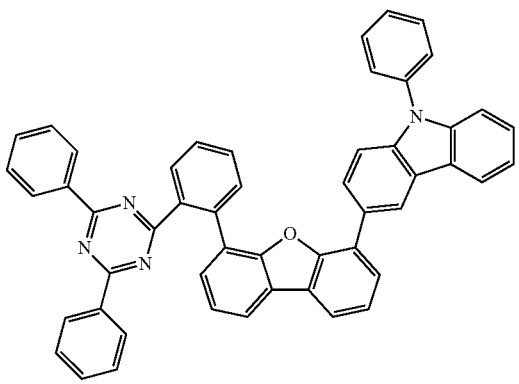
Formula (55)
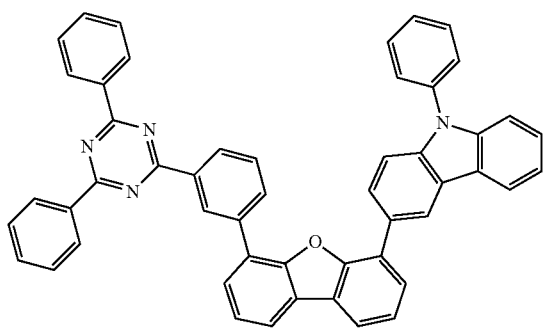
Formula (56)
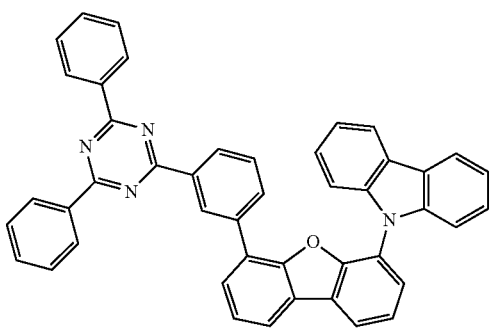
Formula (57)
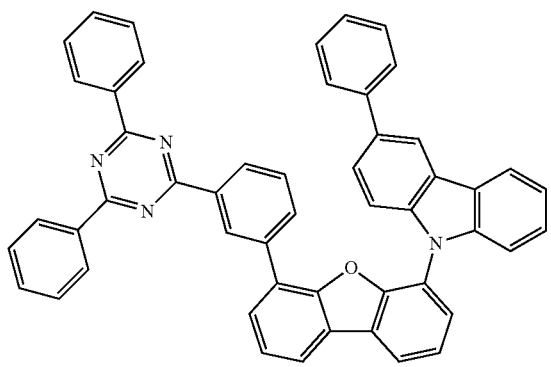
Formula (58)
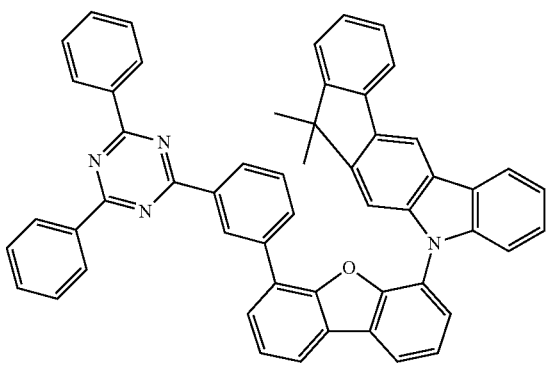

Formula (59)
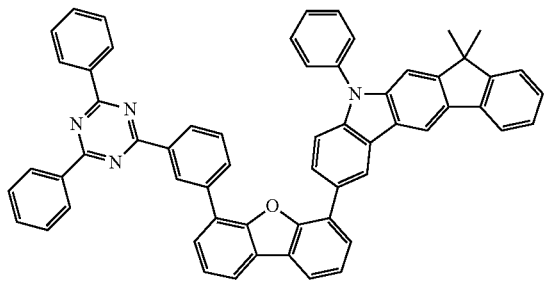
Formula (60)
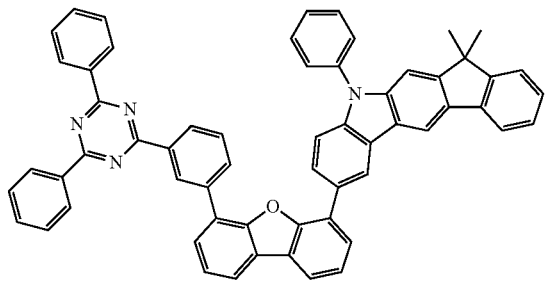
Formula (61)
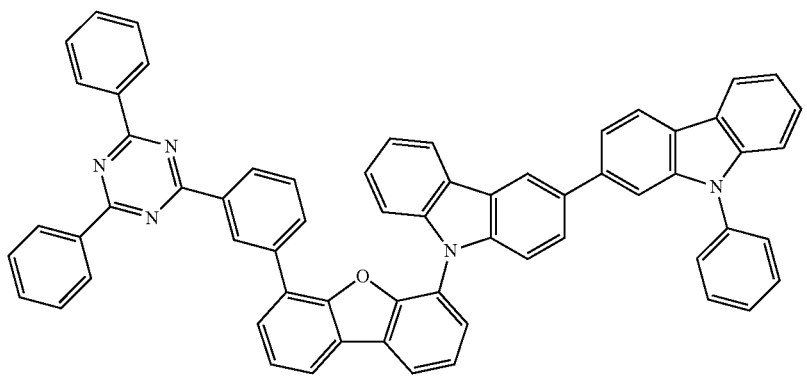
Formula (62)
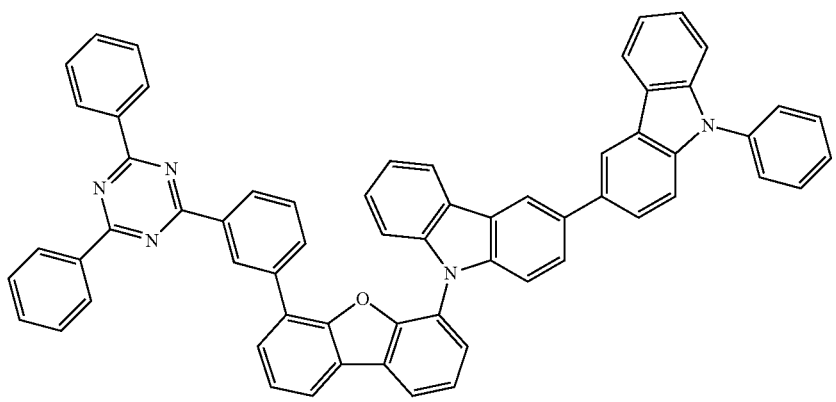
Formula (63)
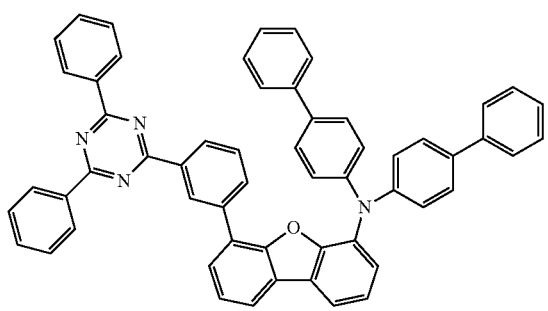
Formula (64)
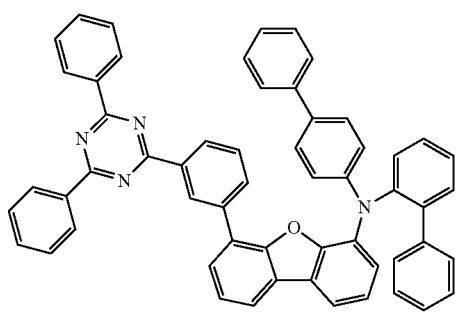

Formula (65)
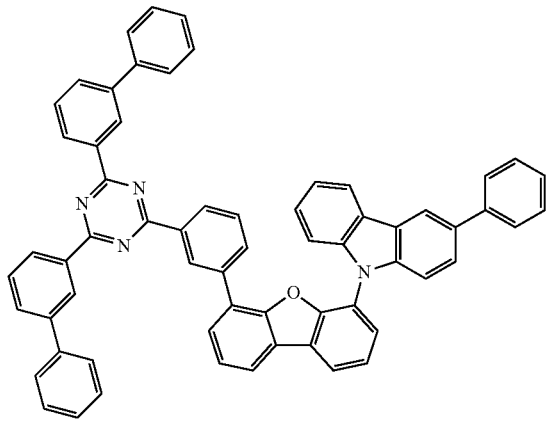
Formula (66)
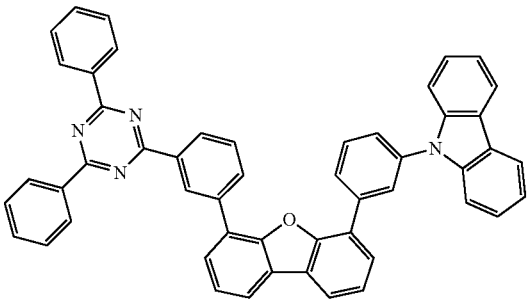
Formula (67)
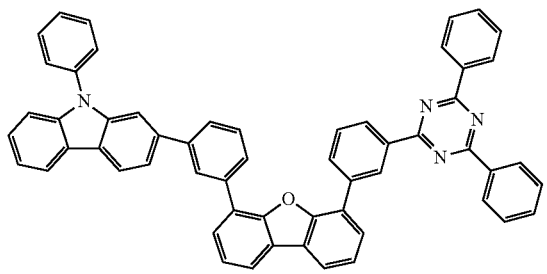
Formula (68)
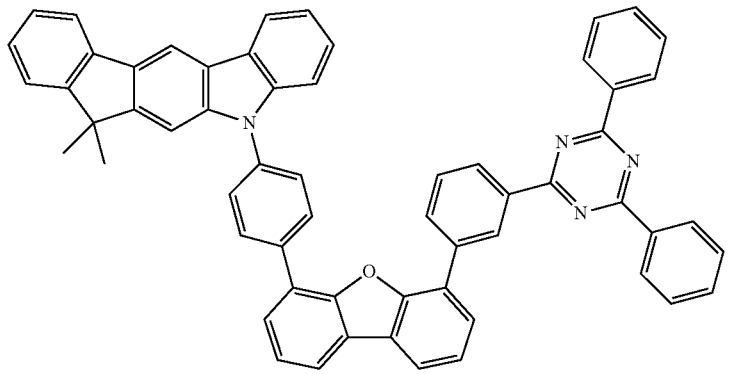
Formula (69)
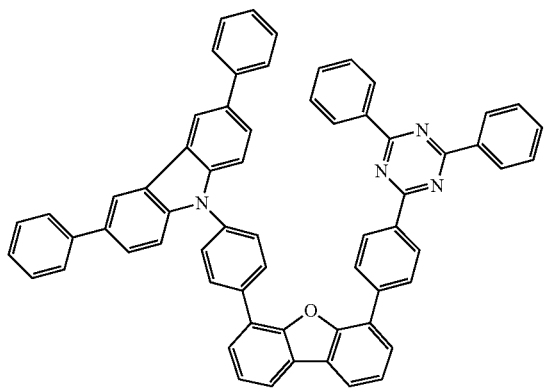
Formula (70)
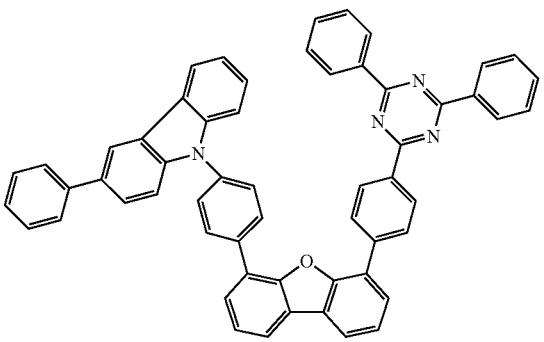

Formula (71)
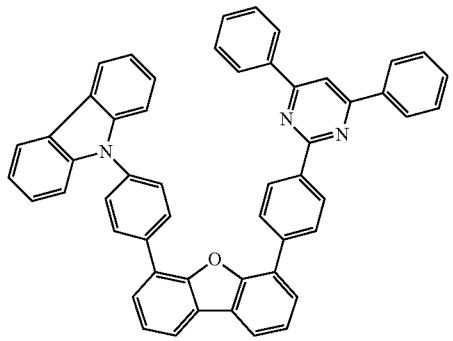
Formula (72)
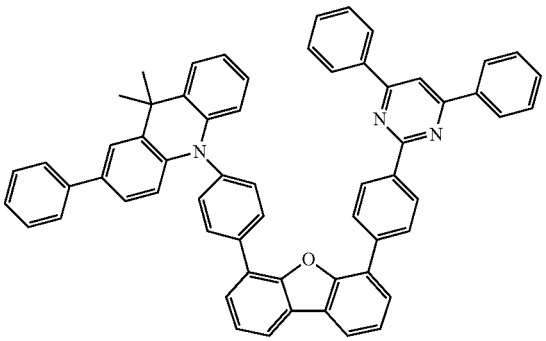
Formula (73)
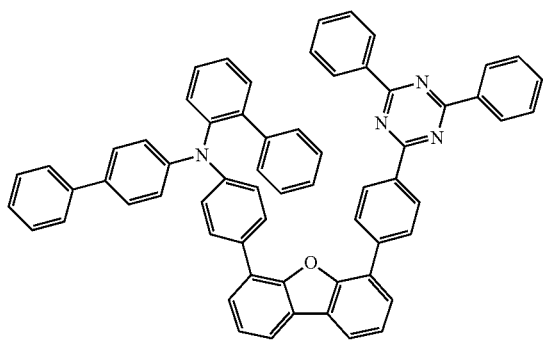
Formula (74)
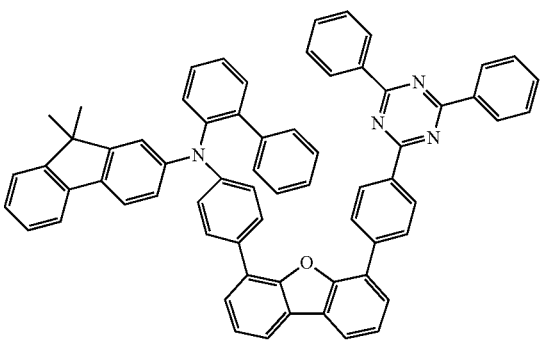
Formula (75)
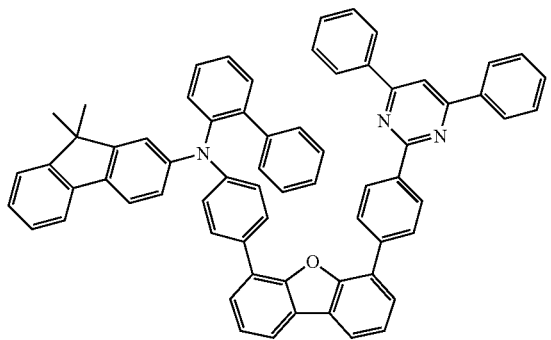
Formula (76)
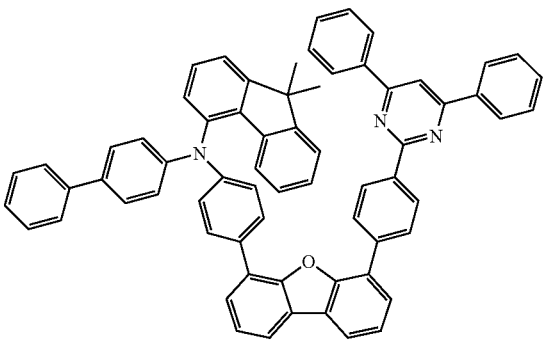
Formula (77)
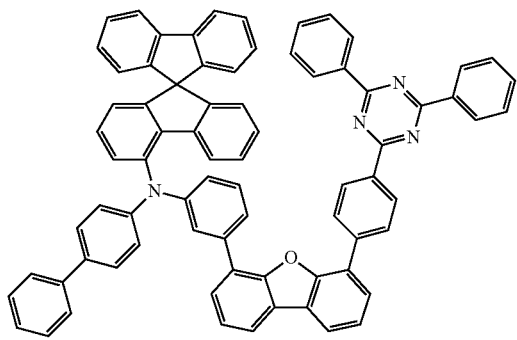
Formula (78)
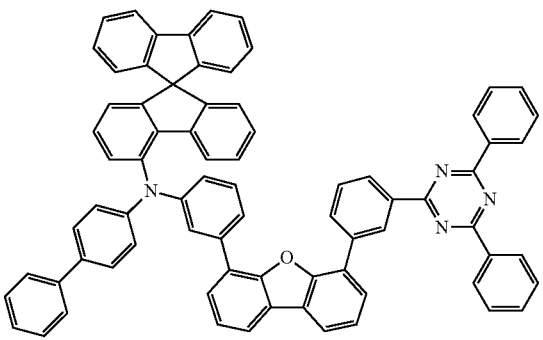

-continued
Formula (79)
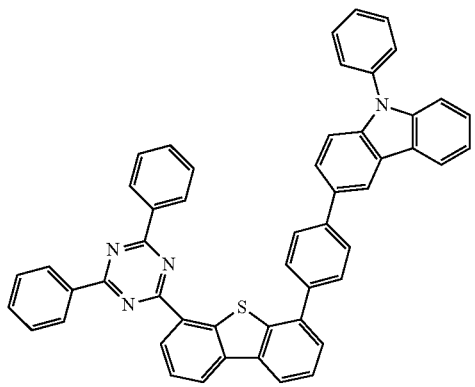
Formula (80)
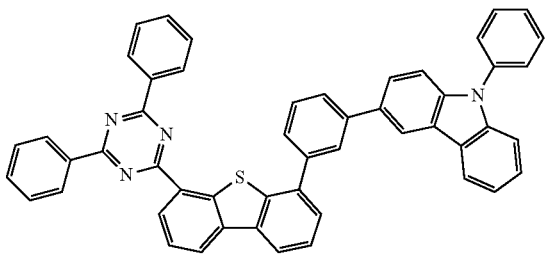
Formula (81)
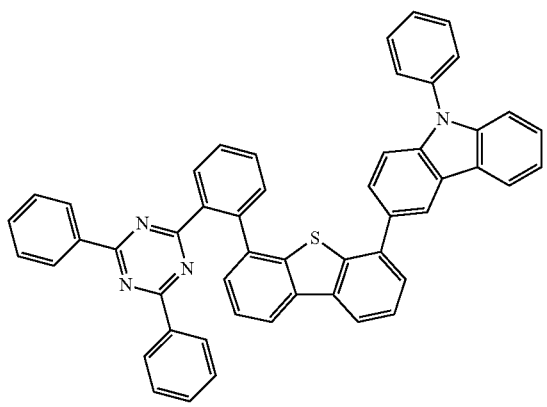
Formula (82)
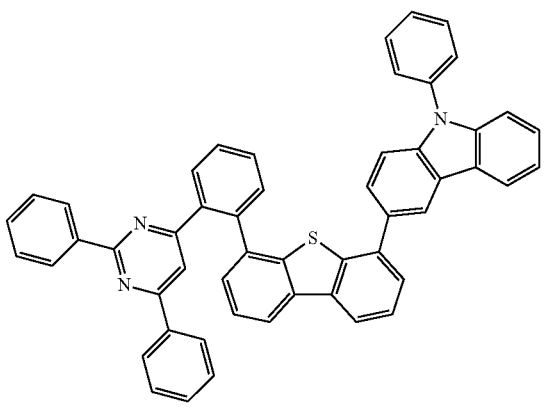
Formula (83)
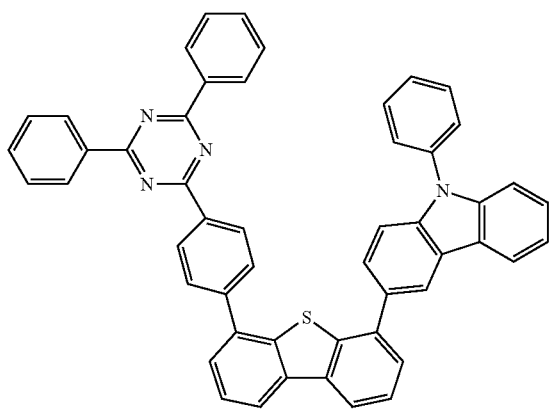
Formula (84)
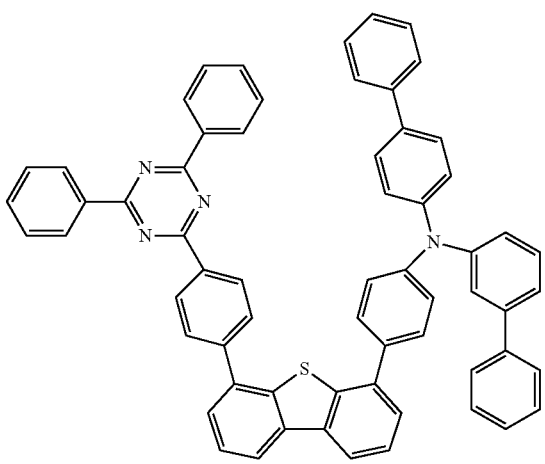

Formula (85)
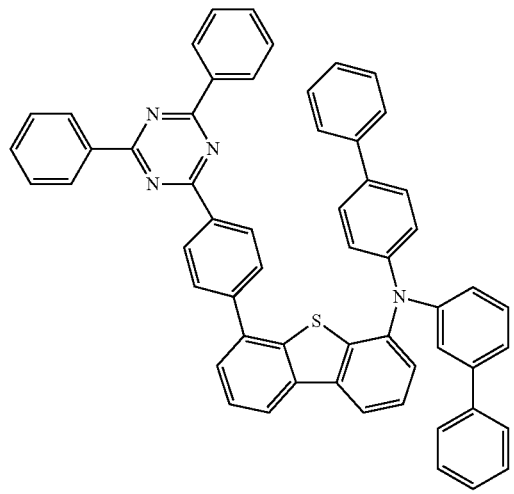
Formula (86)
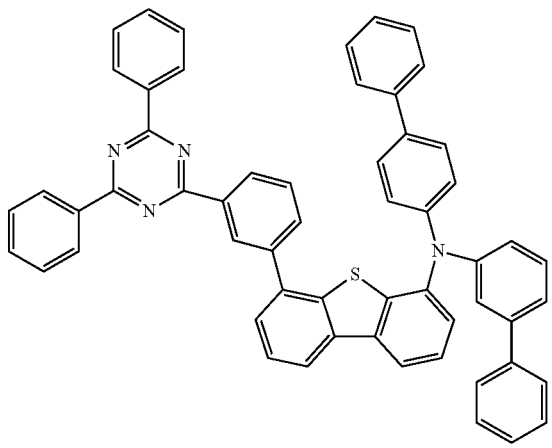
Formula (87)
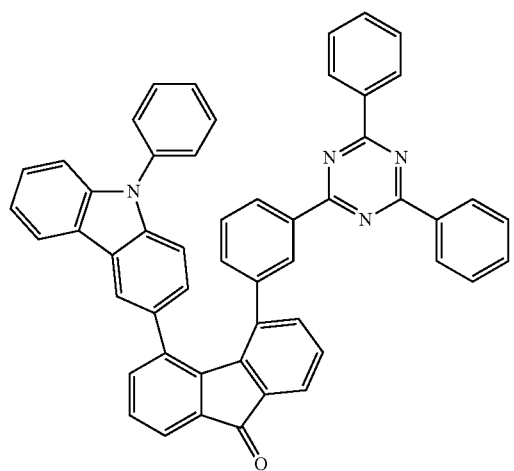
Formula (88)
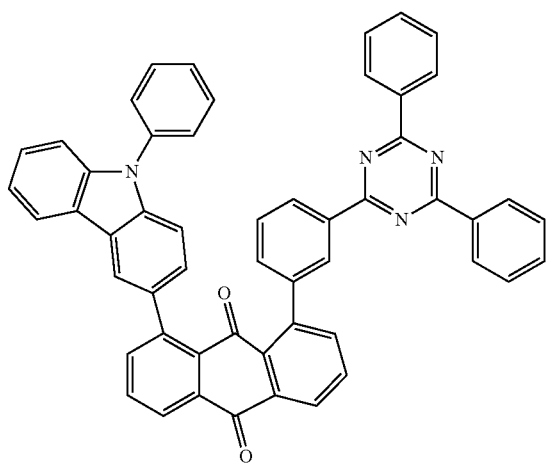
Formula (89)
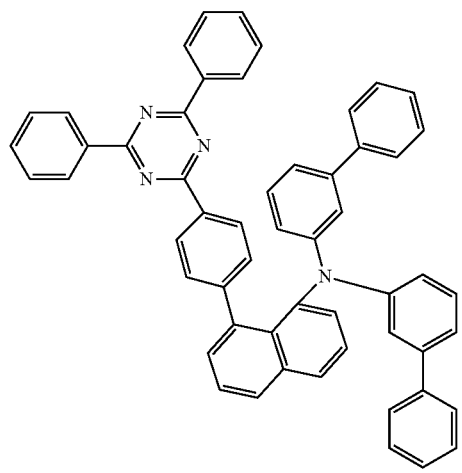
Formula (90)
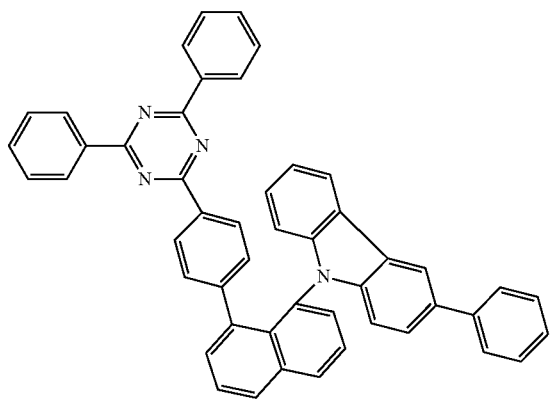

Formula (91)
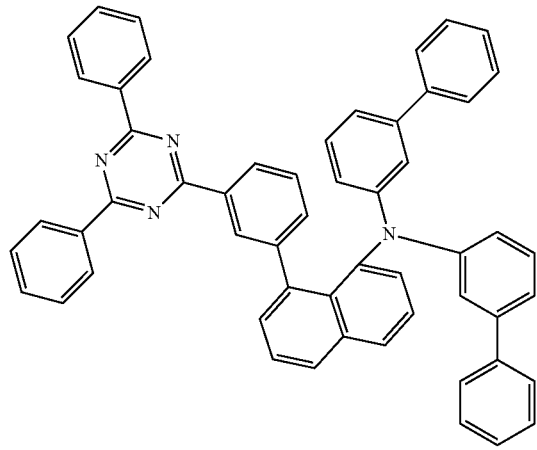
Formula (92)
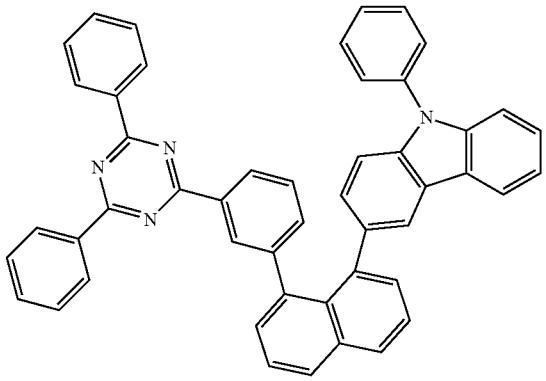
Formula (93)
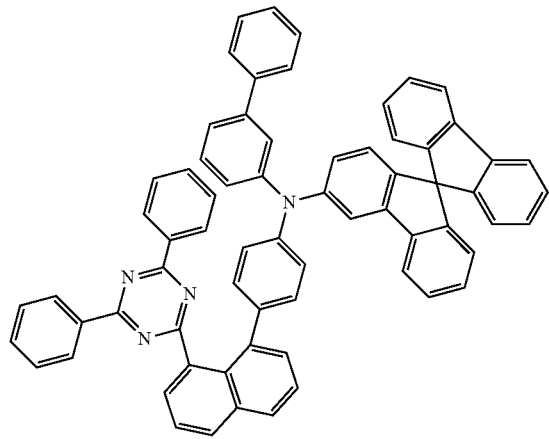
Formula (94)
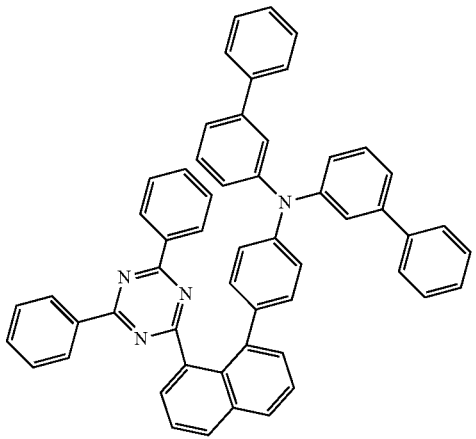
Formula (95)
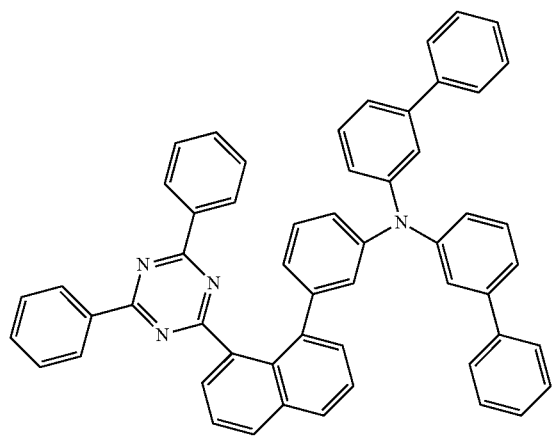
Formula (96)
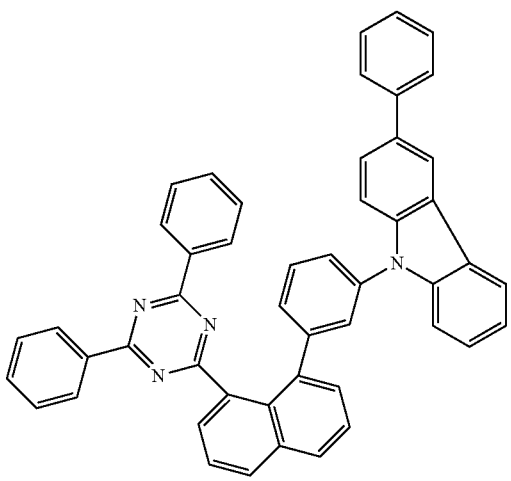

-continued
Formula (97)
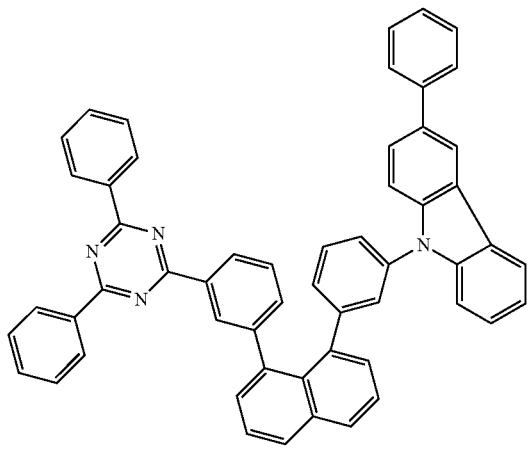
Formula (98)
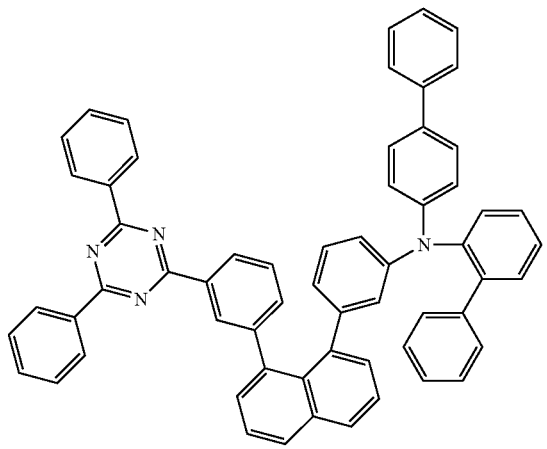
Formula (99)
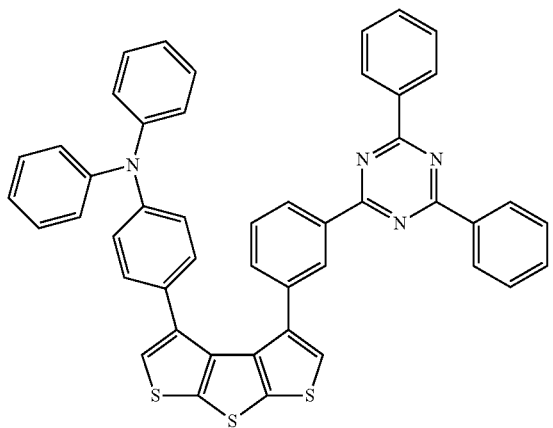
Formula (100)
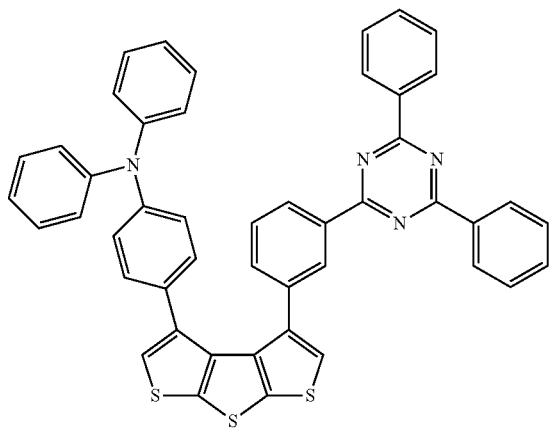
Formula (101)
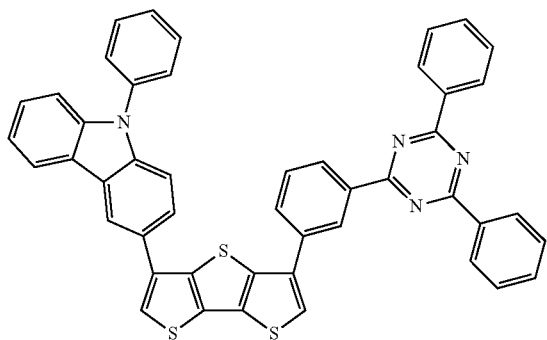
Formula (102)
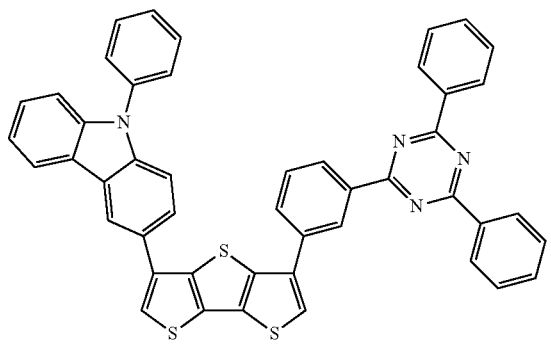

-continued
Formula (103)
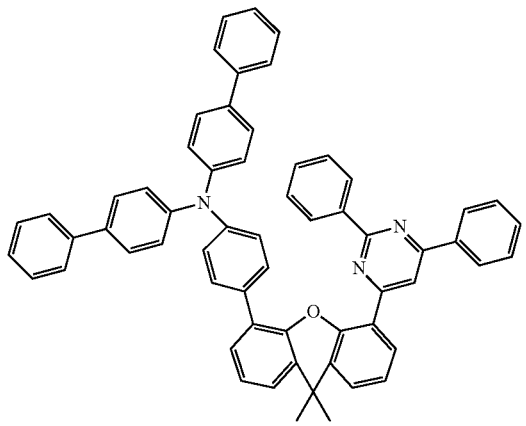
Formula (104)
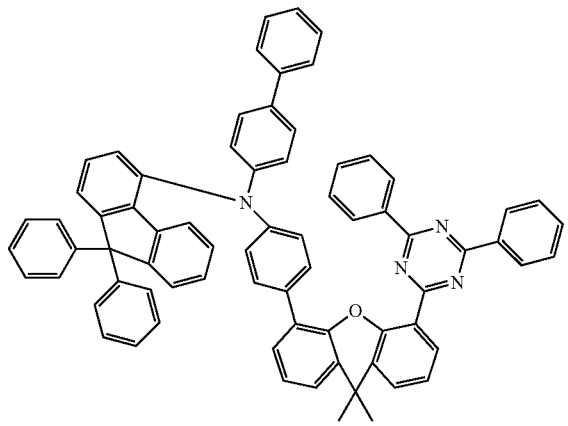
Formula (105)
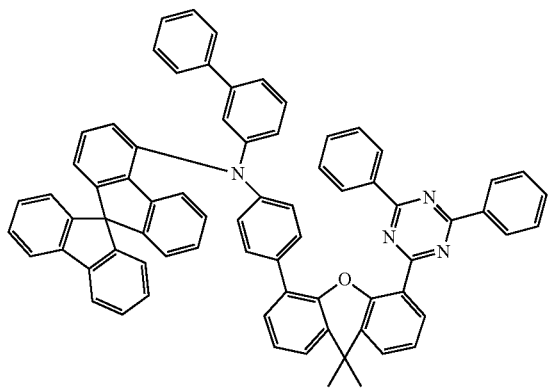
Formula (106)
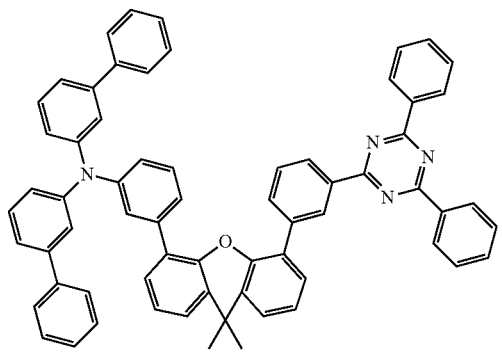
Formula (107)
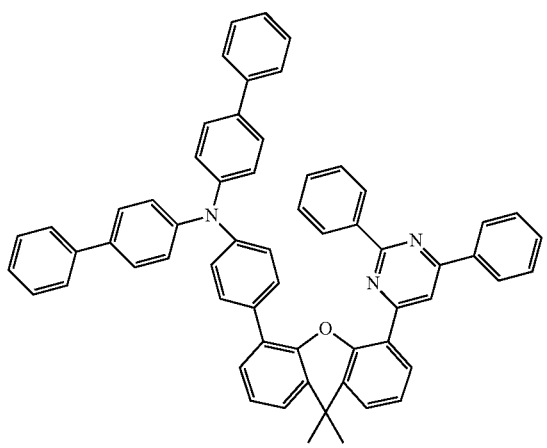
Formula (108)
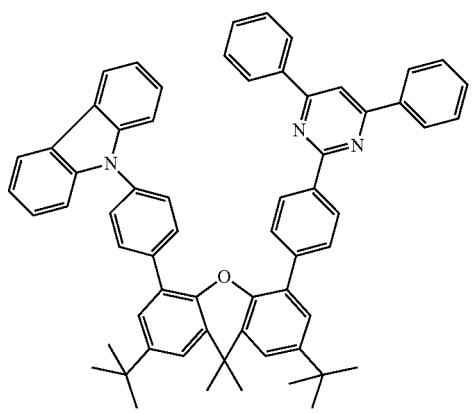

Formula (109)
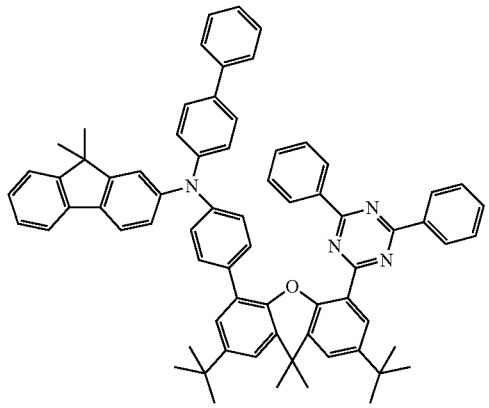
Formula (110)
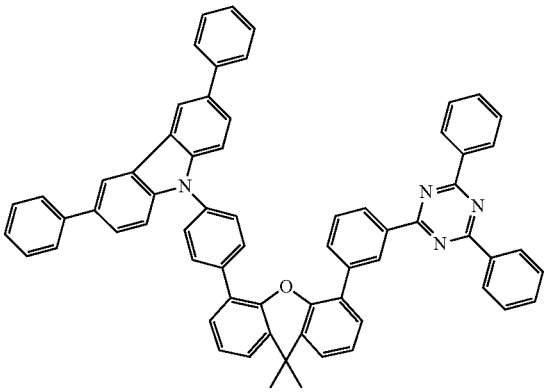
Formula (111)
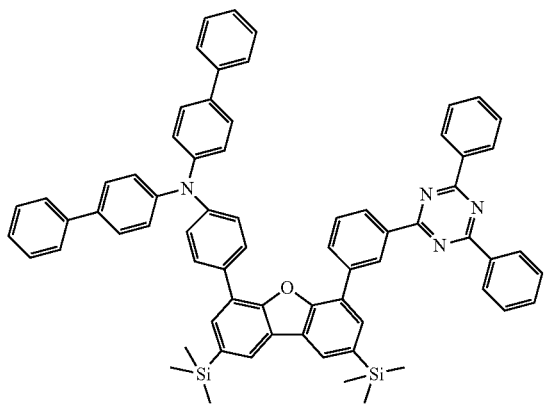
Formula (112)
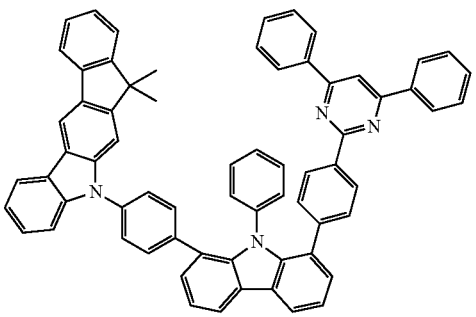
Formula (113)
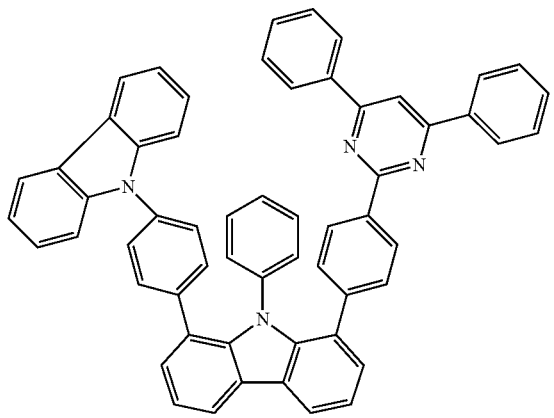
Formula (114)
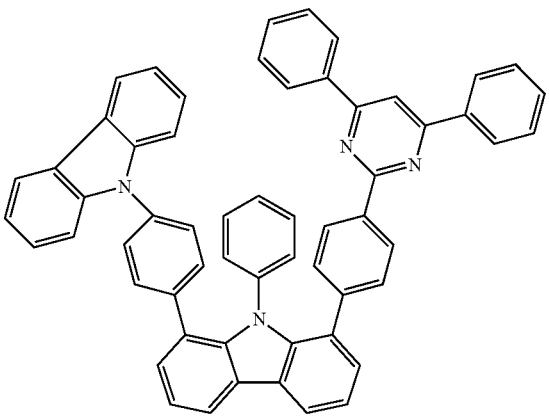
Formula (115)
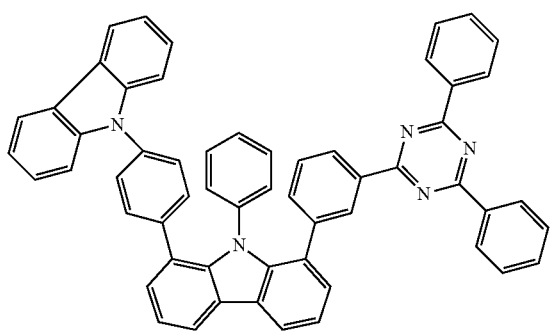
Formula (116)
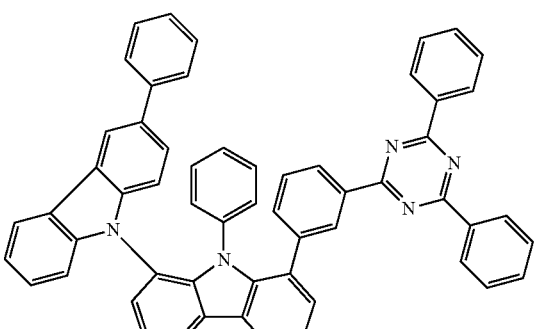

-continued
Formula (117)
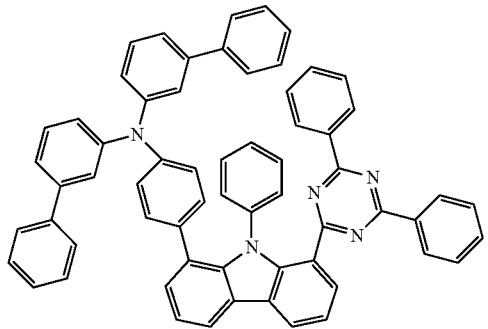
Formula (118)
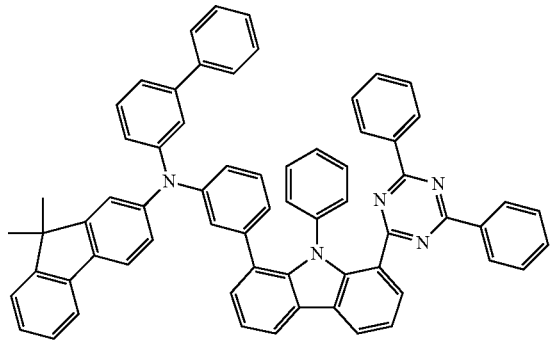
Formula (119)
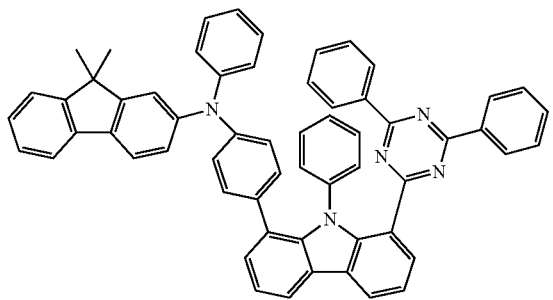
Formula (120)
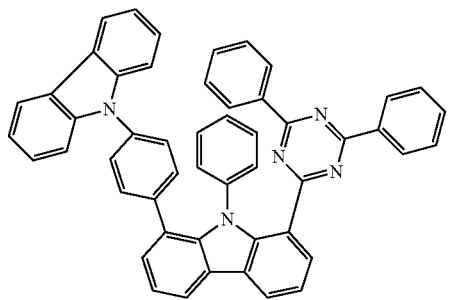
Formula (121)
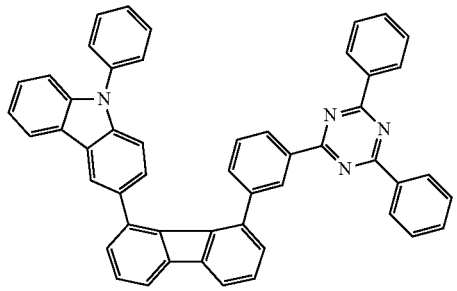
Formula (122)
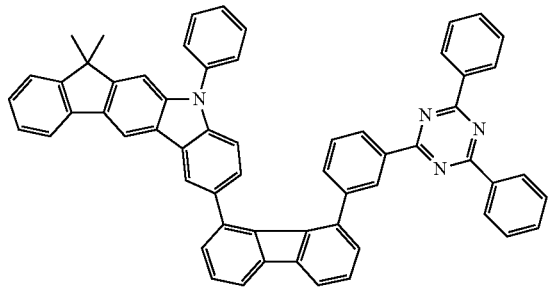
Formula (123)
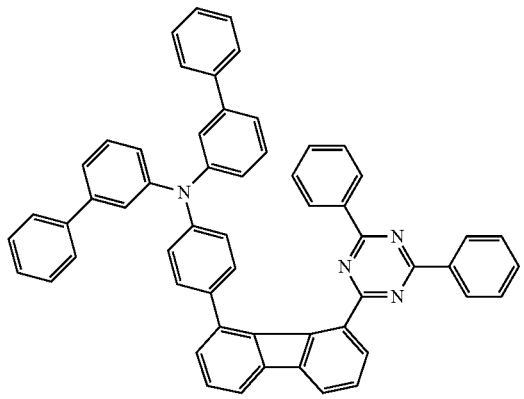
Formula (124)
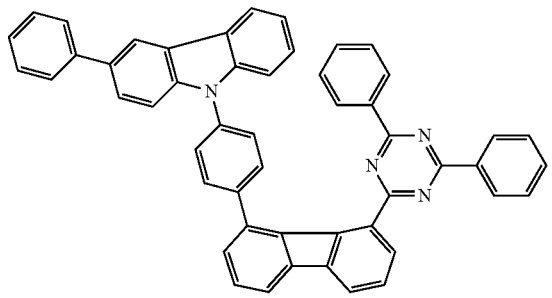

-continued
Formula (125)
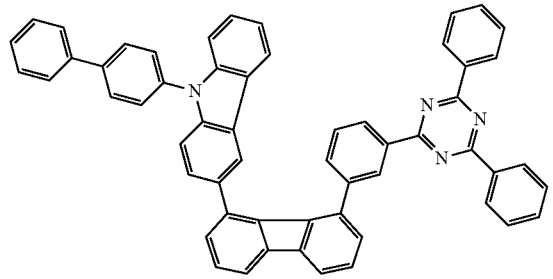
Formula (126)
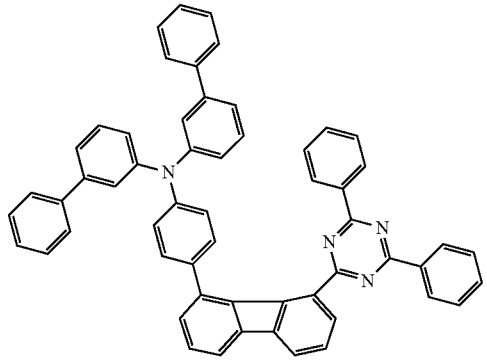
Formula (127)
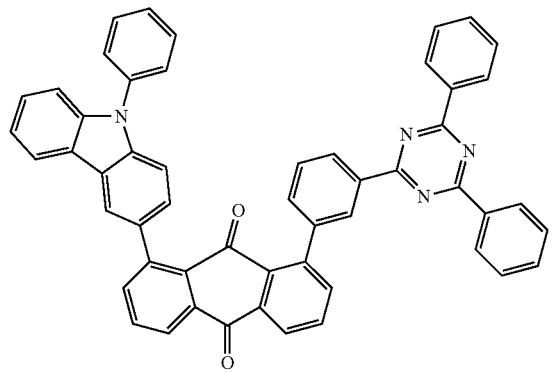
Formula (128)
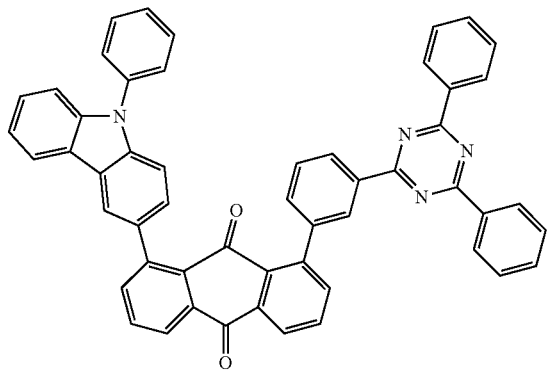
Formula (129)
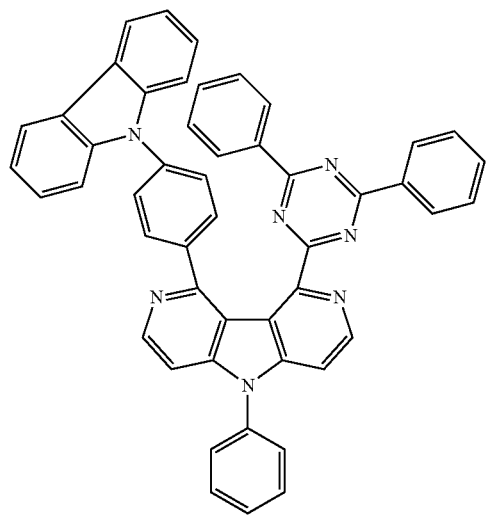
Formula (130)
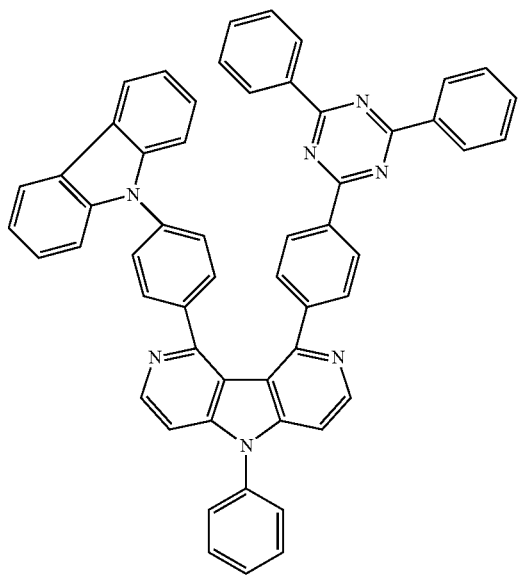

Formula (131)
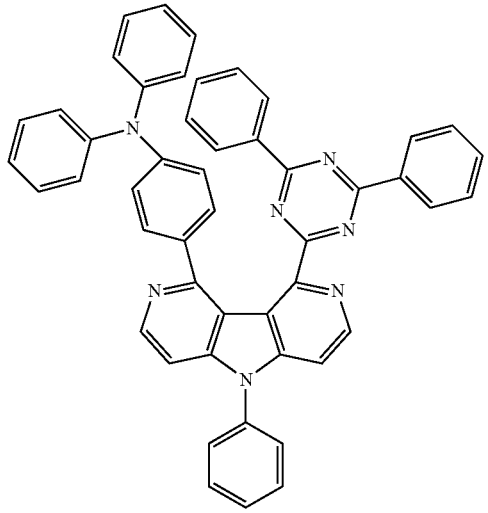
Formula (132)
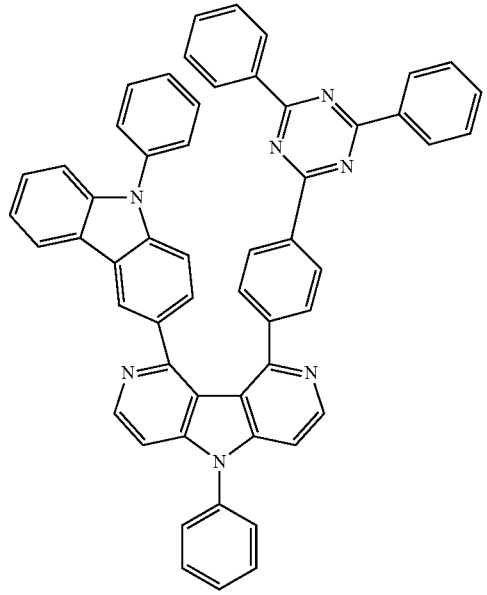
Formula (133)
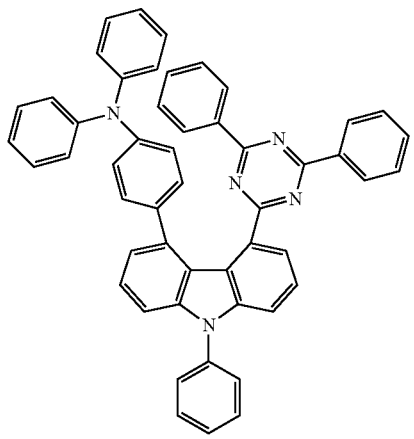
Formula (134)
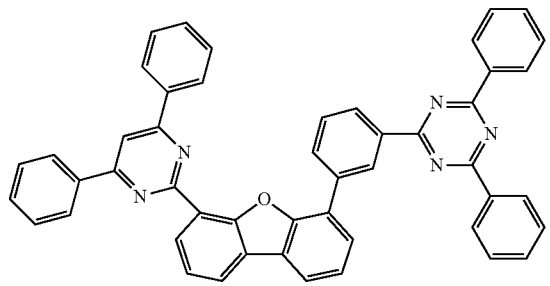
Formula (135)
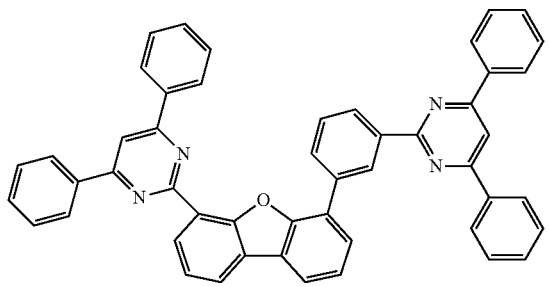
Formula (136)
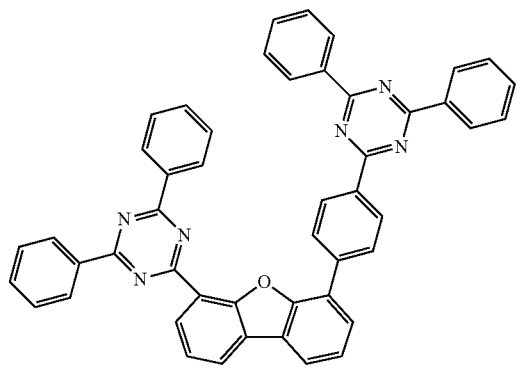

Formula (137)
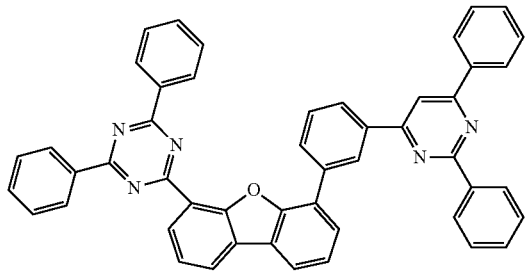
Formula (138)
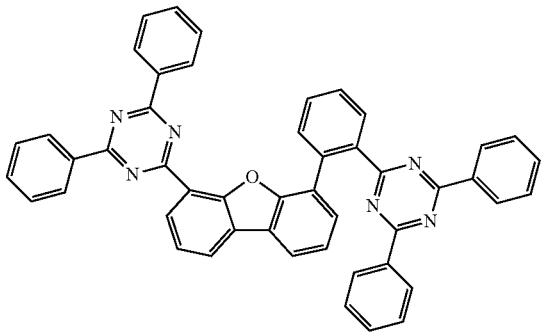
Formula (139)
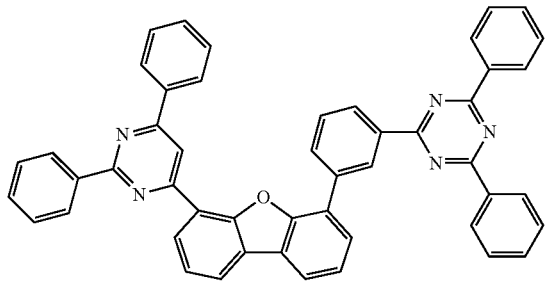
Formula (140)
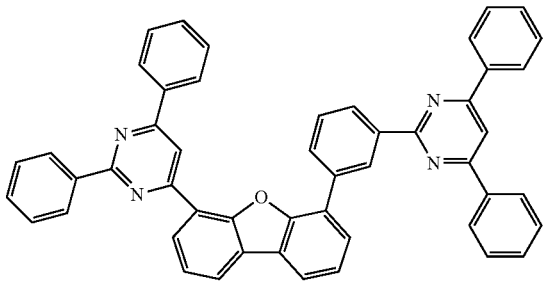
Formula (141)
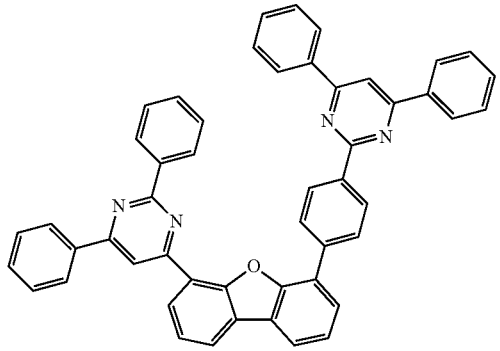
Formula (142)
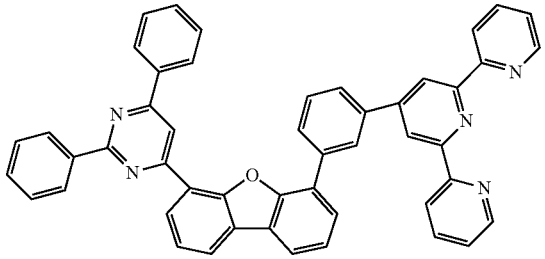
Formula (143)
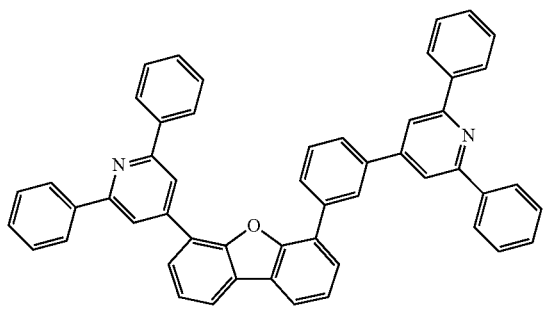
Formula (144)
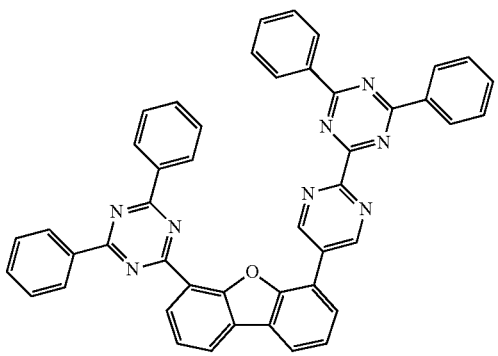

Formula (145)
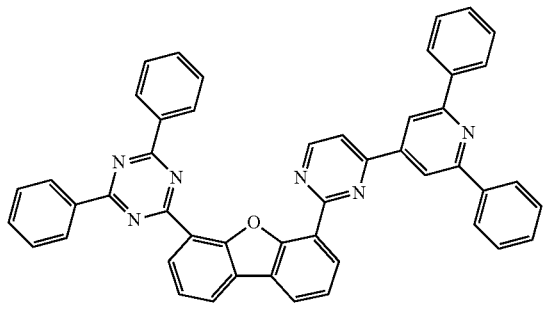
Formula (146)
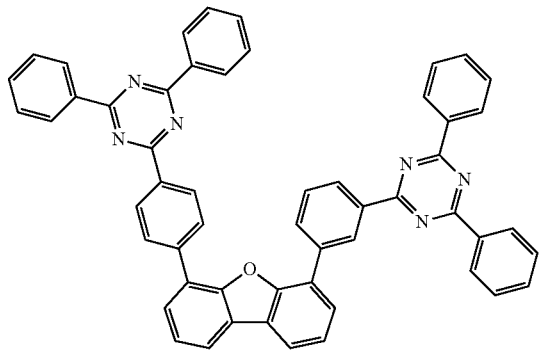
Formula (147)
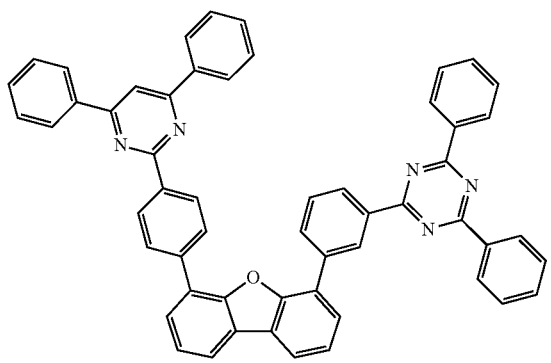
Formula (148)
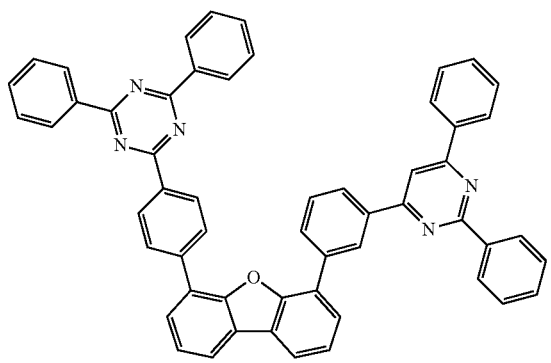
Formula (149)
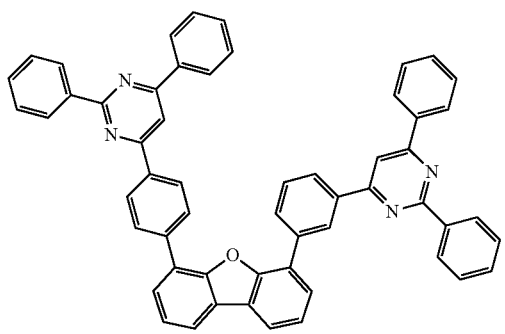
Formula (150)
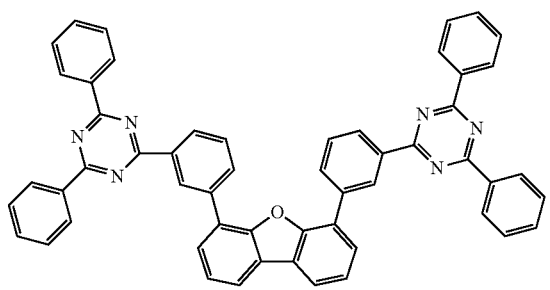
Formula (151)
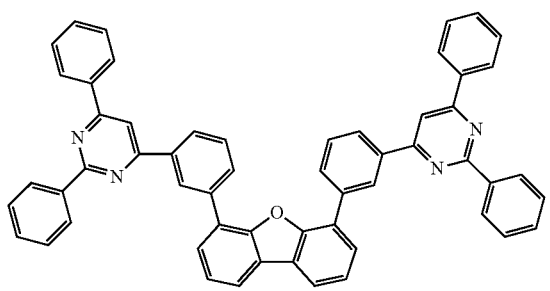
Formula (152)
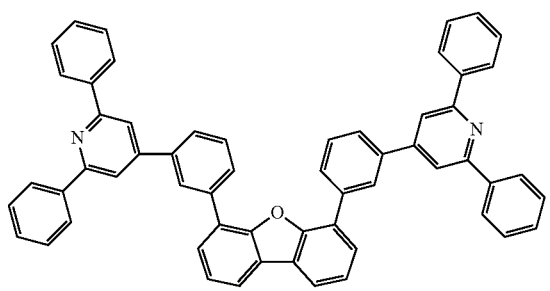

Formula (153)
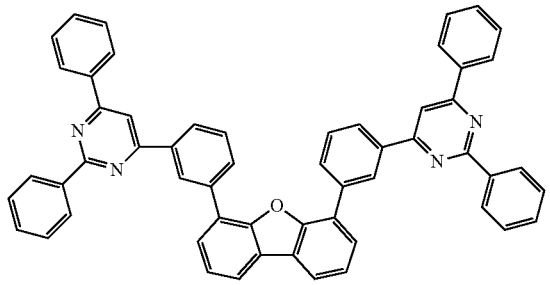
Formula (154)
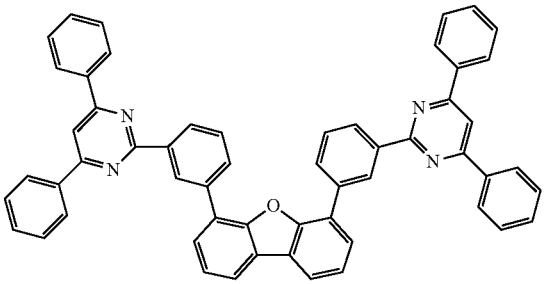
Formula (155)
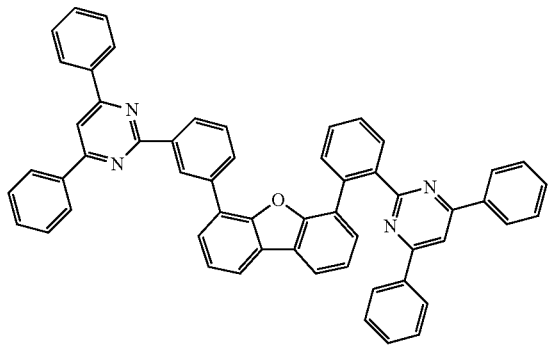
Formula (156)
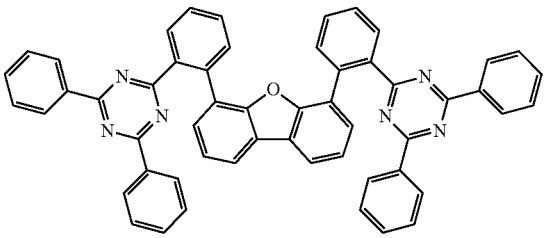
Formula (157)
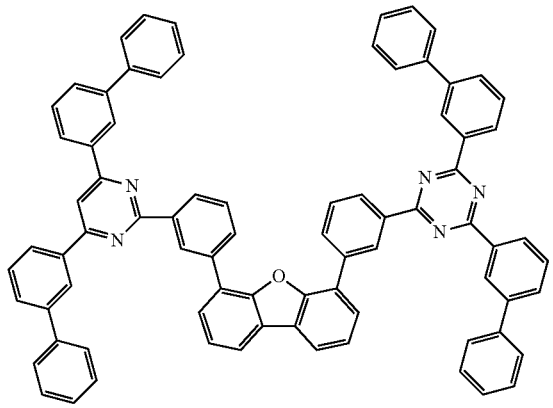
Formula (158)
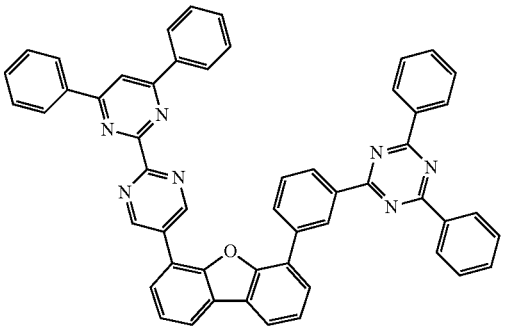
Formula (159)
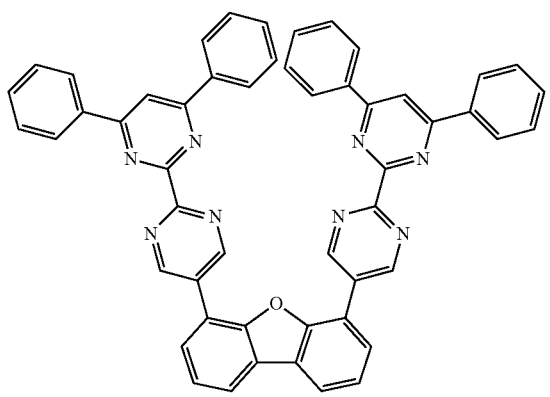
Formula (160)
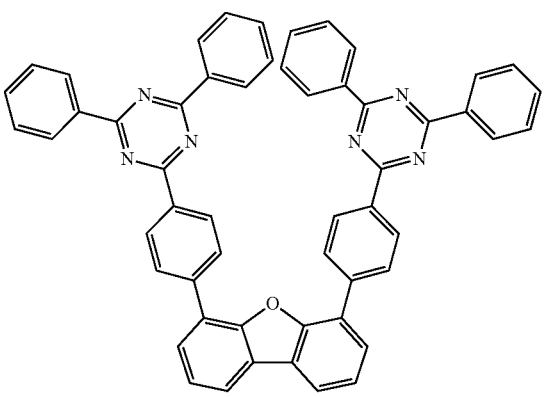

Formula (161)
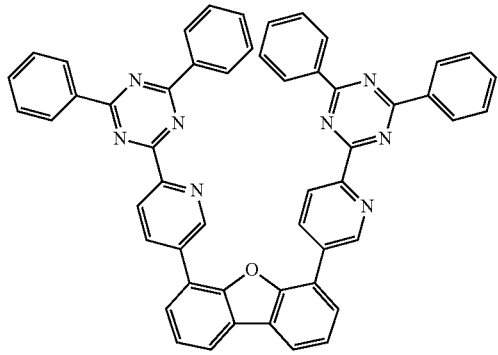
Formula (162)
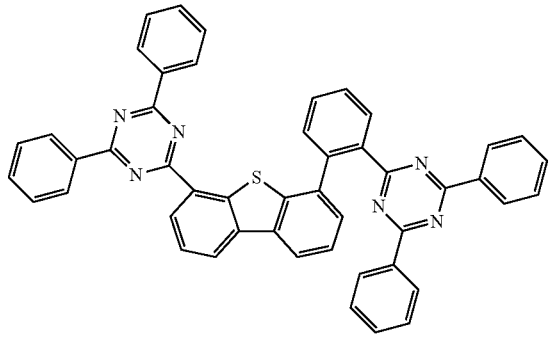
Formula (163)
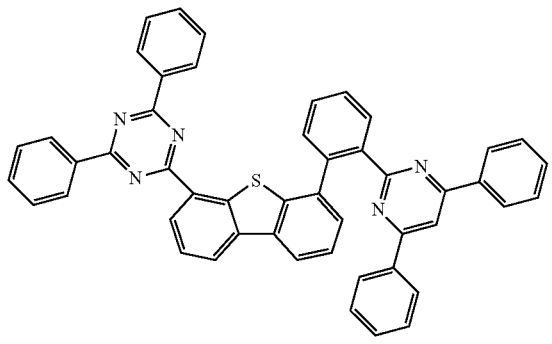
Formula (164)
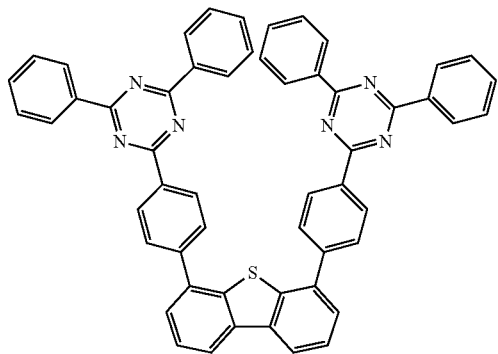
Formula (165)
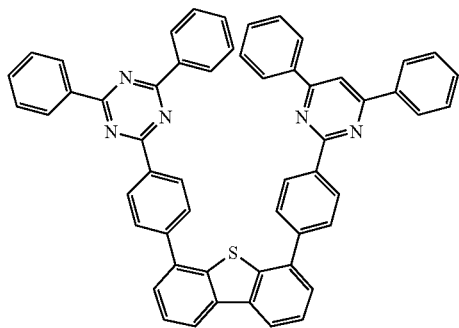
Formula (166)
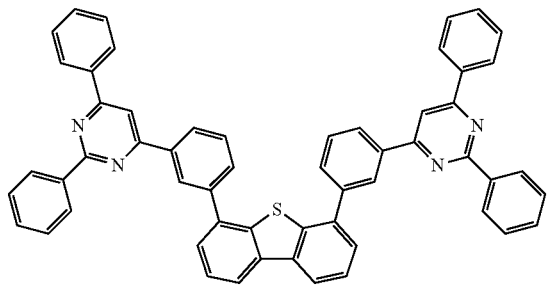
Formula (167)
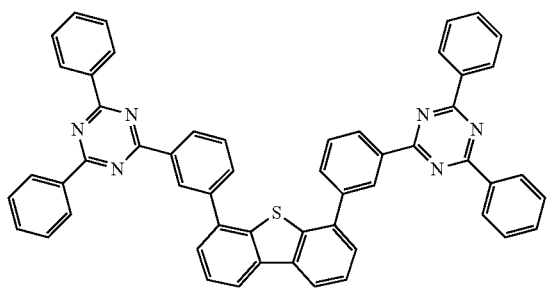
Formula (168)
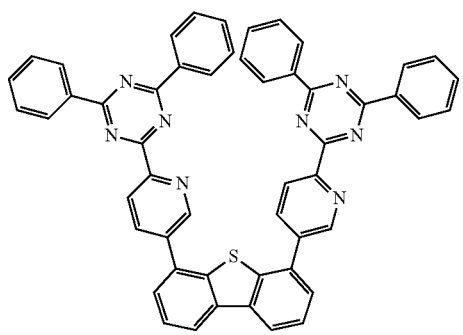

Formula (169)
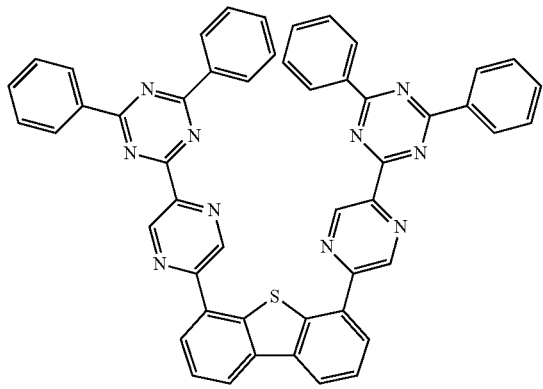
Formula (170)
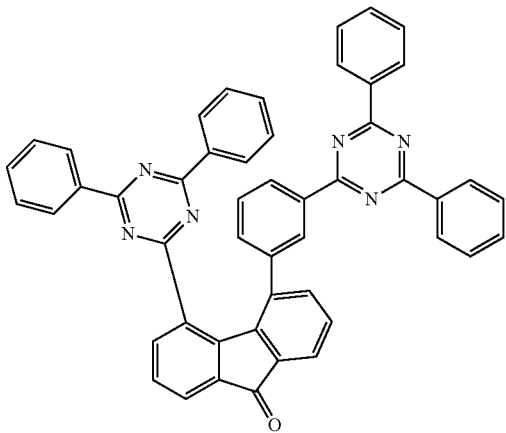
Formula (171)
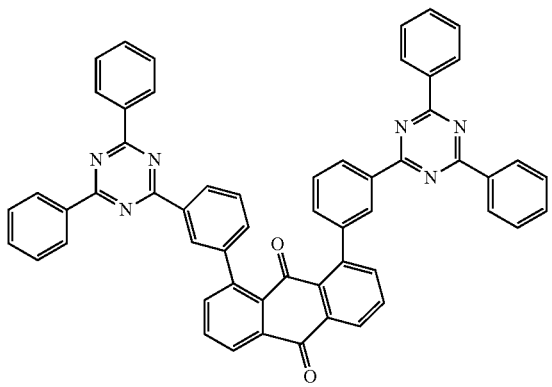
Formula (172)
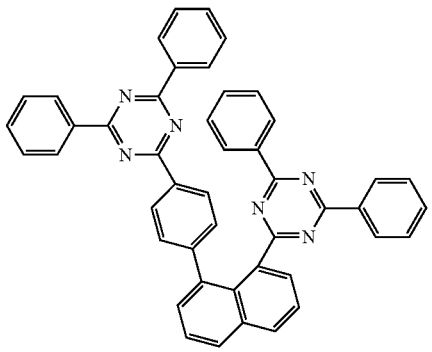
Formula (173)
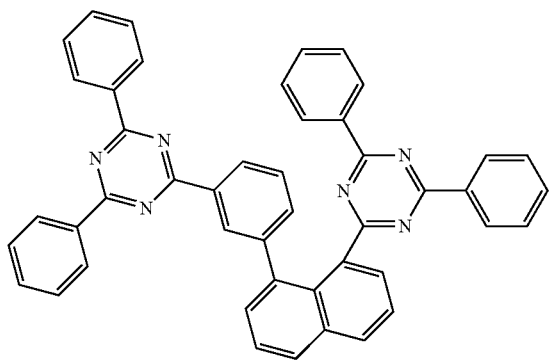
Formula (174)
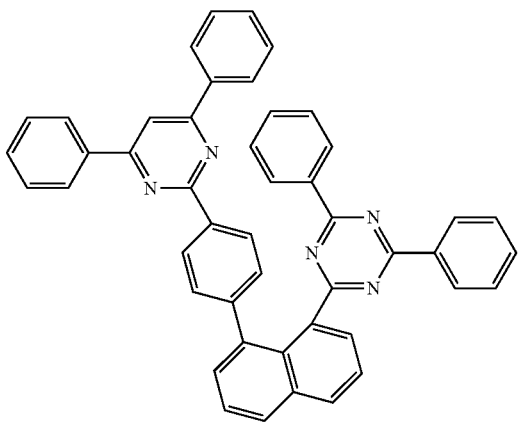

Formula (175)
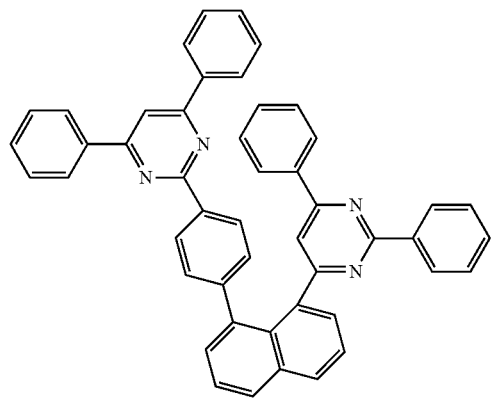
Formula (176)
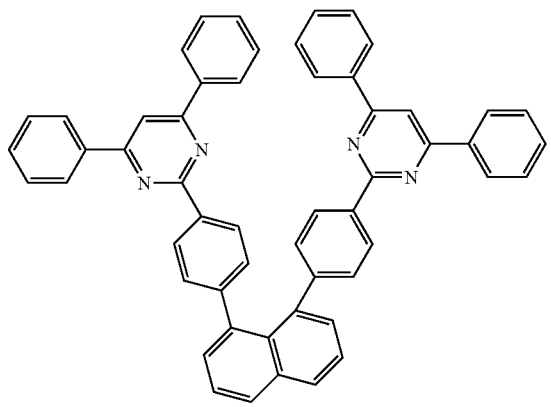
Formula (177)
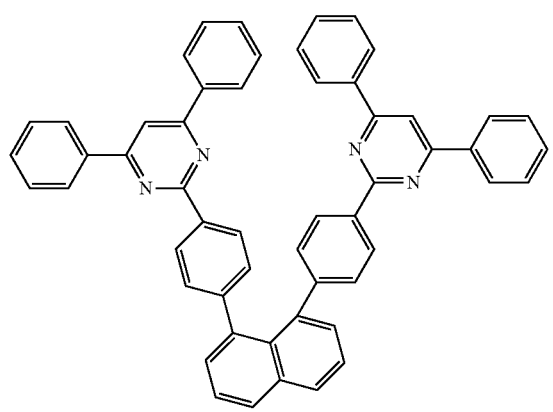
Formula (178)
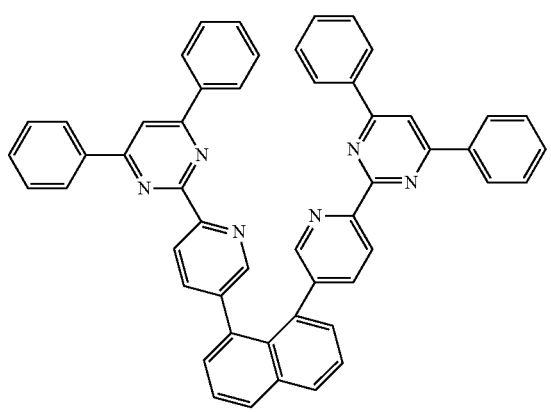
Formula (179)
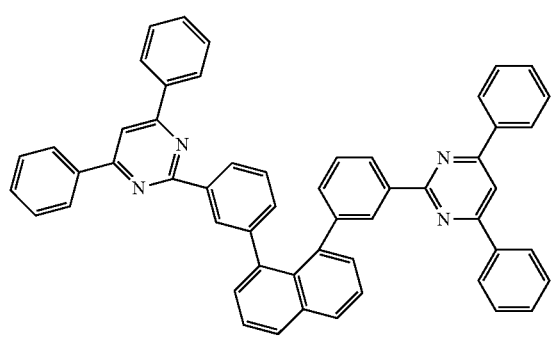
Formula (180)
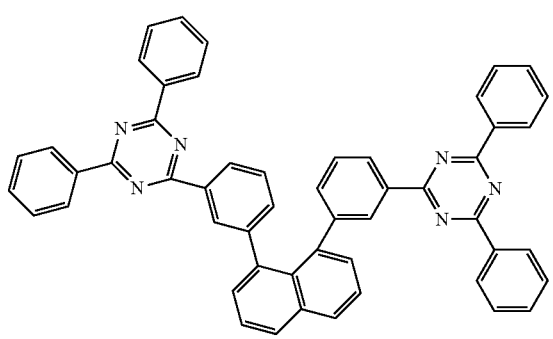
Formula (181)
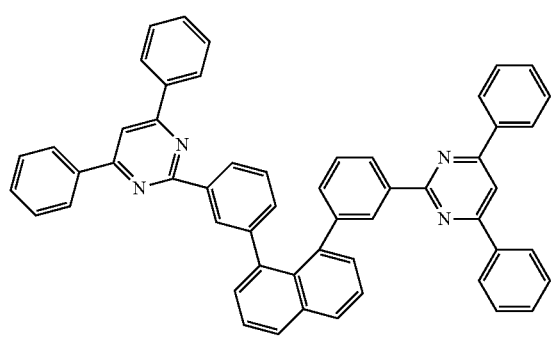
Formula (182)
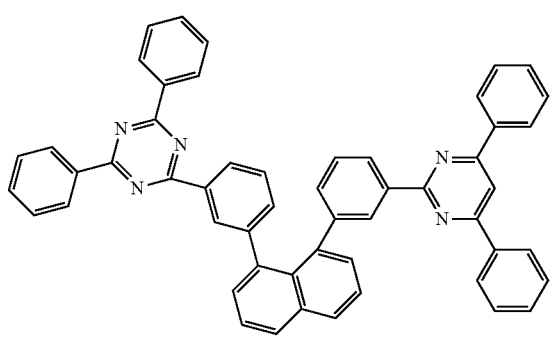

Formula (183)
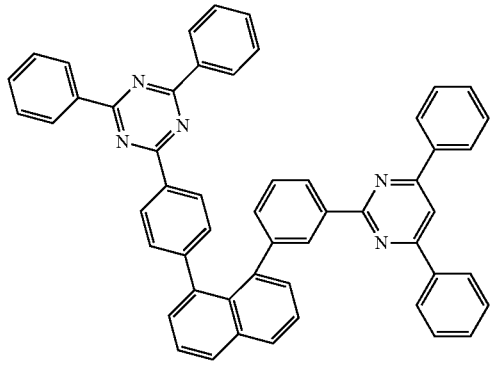
Formula (184)
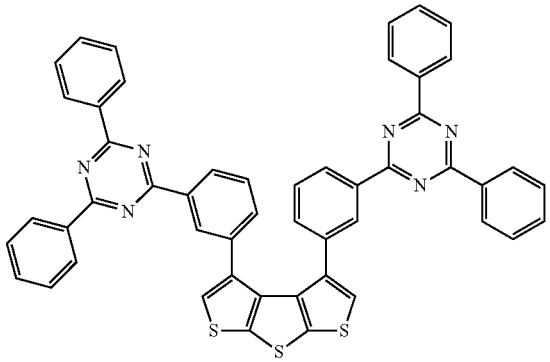
Formula (185)
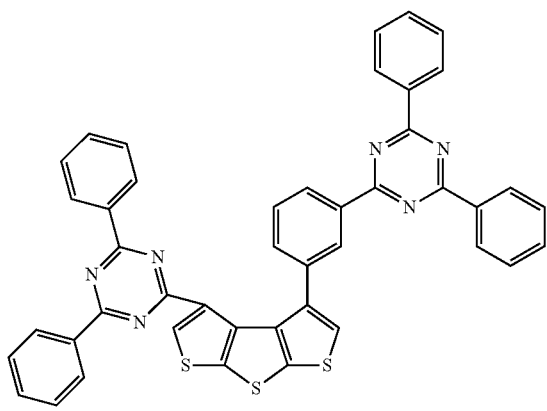
Formula (186)
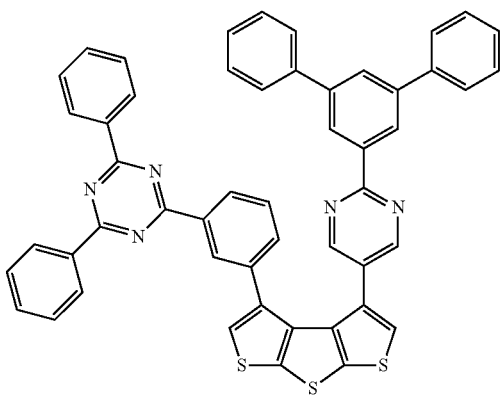
Formula (187)
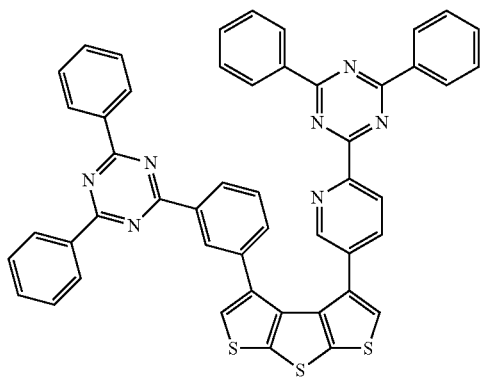
Formula (188)
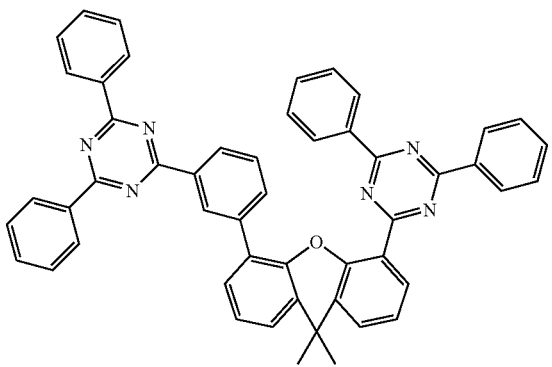
Formula (189)
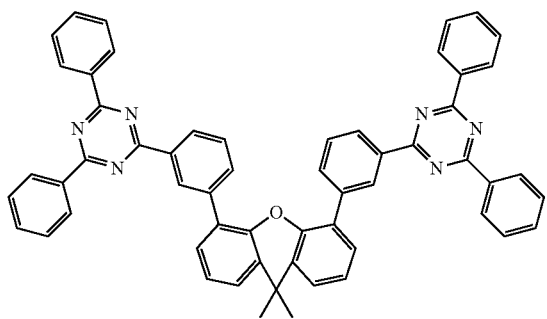
Formula (190)
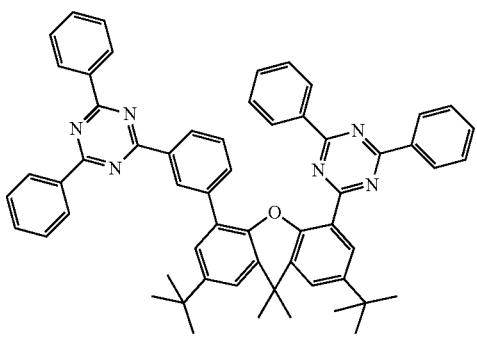

-continued
Formula (191)
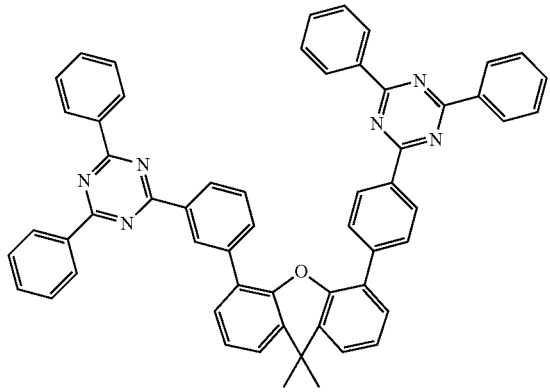
Formula (192)
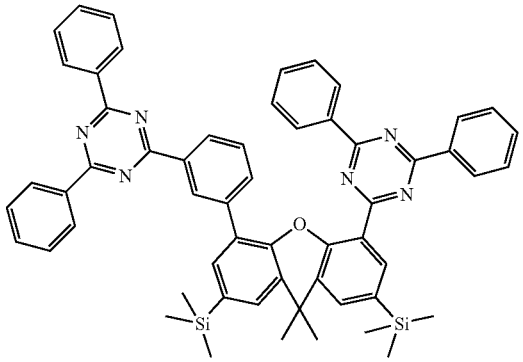
Formula (193)
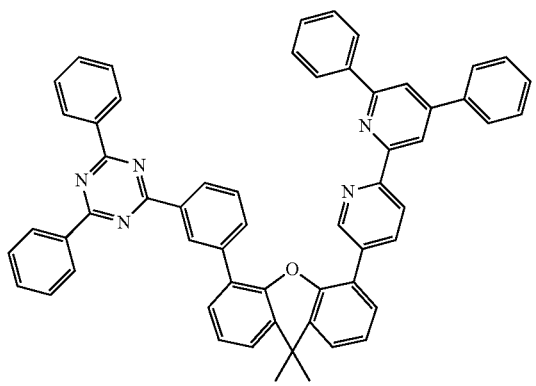
Formula (194)
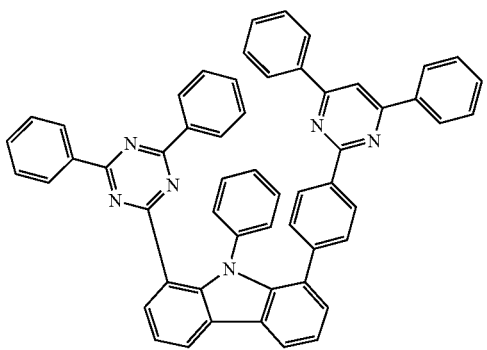
Formula (195)
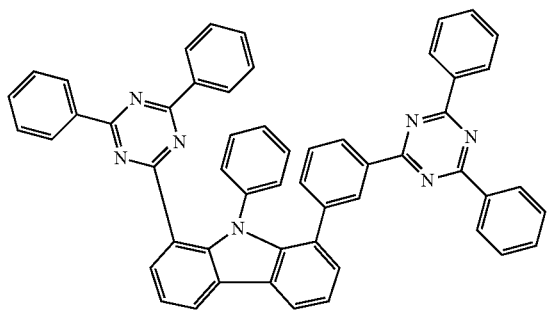
Formula (196)
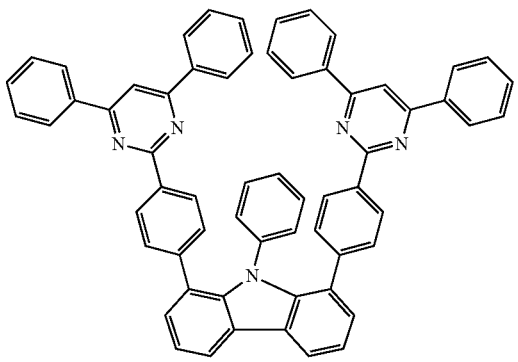
Formula (197)
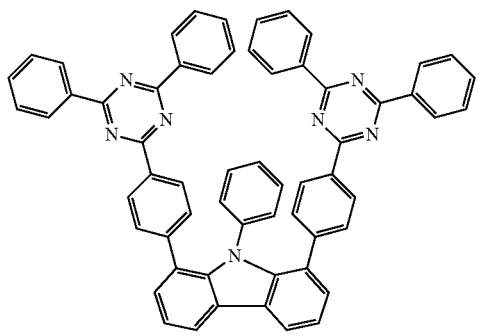
Formula (198)
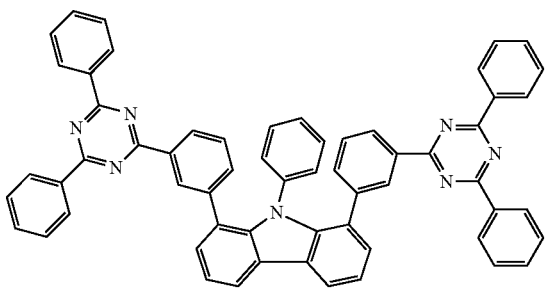

-continued
Formula (199)
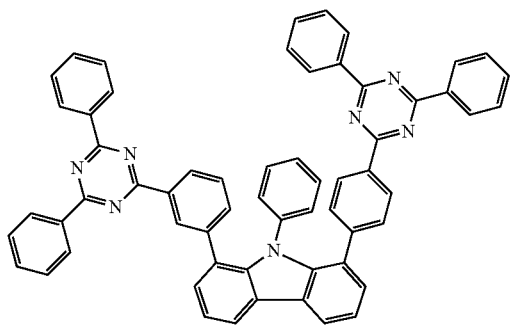
Formula (200)
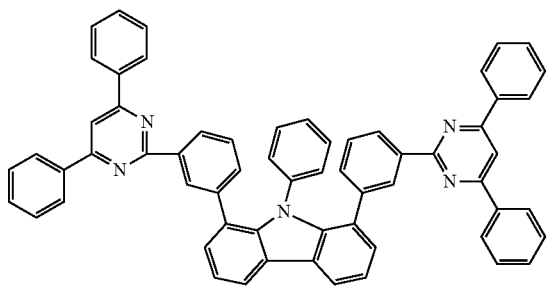
Formula (201)
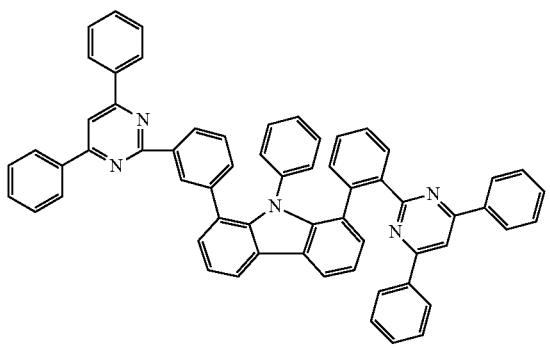
Formula (202)
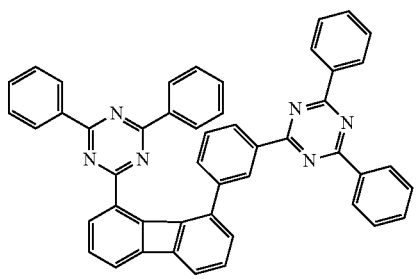
Formula (203)
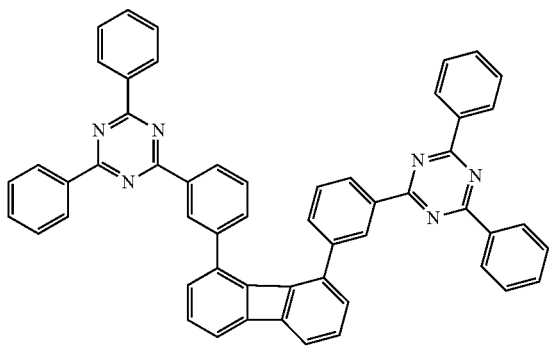
Formula (204)
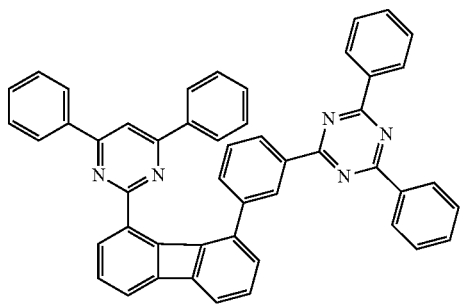
Formula (205)
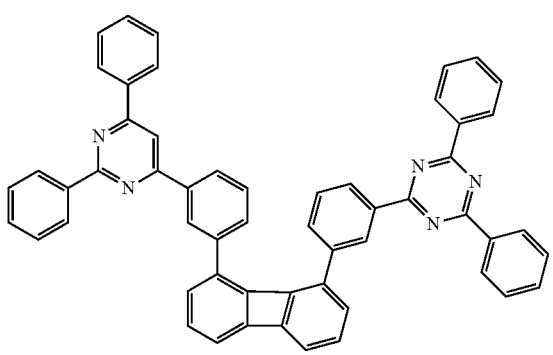
Formula (206)
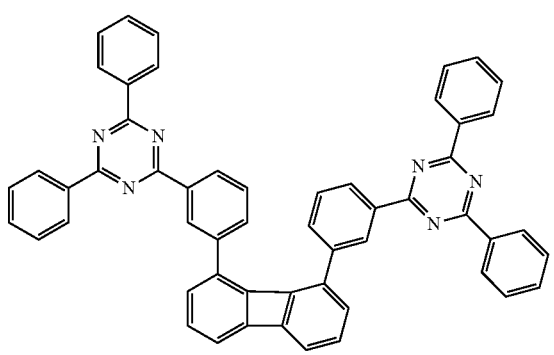

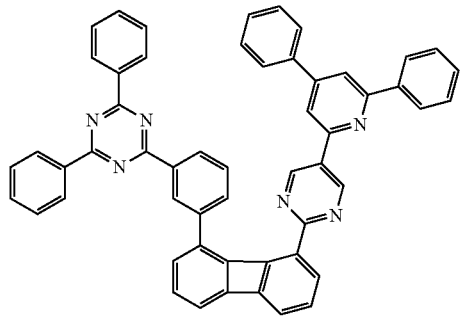
Formula (207)
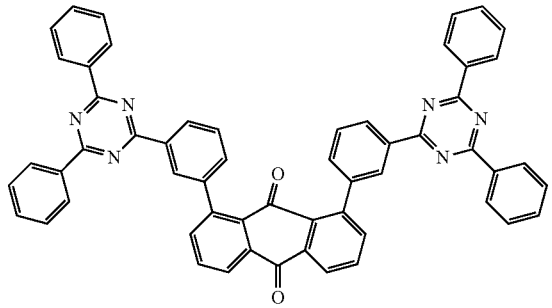
Formula (208)
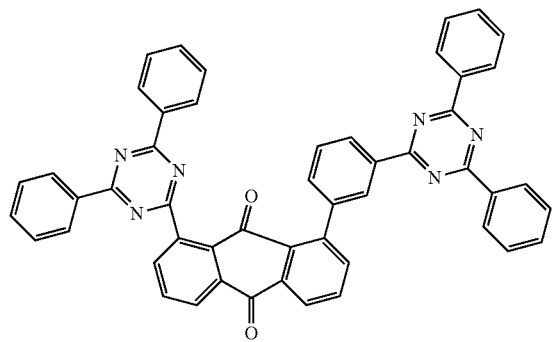
Formula (209)
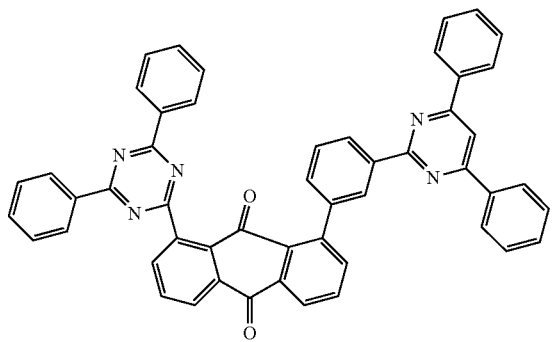
Formula (210)
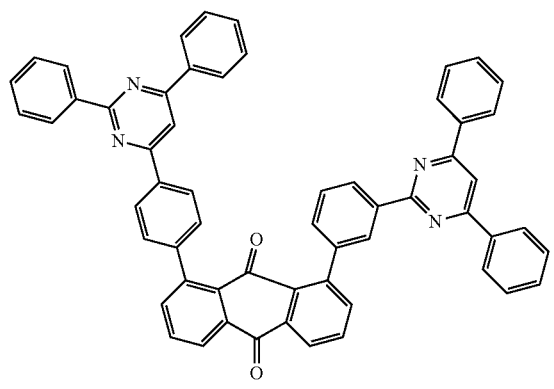
Formula (211)
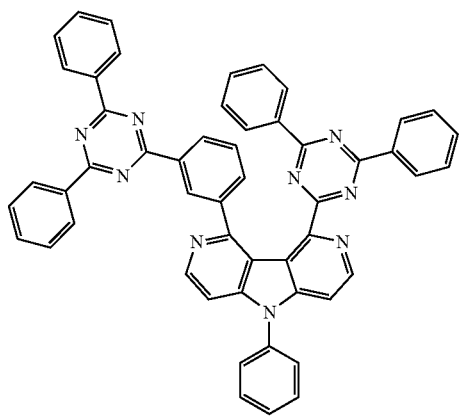
Formula (212)

-continued
Formula (213)
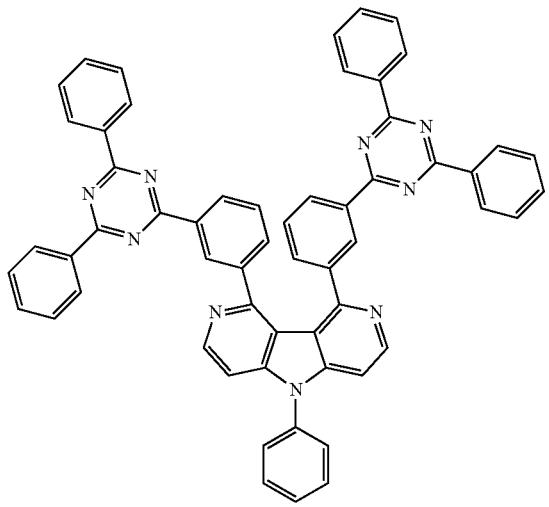
Formula (214)
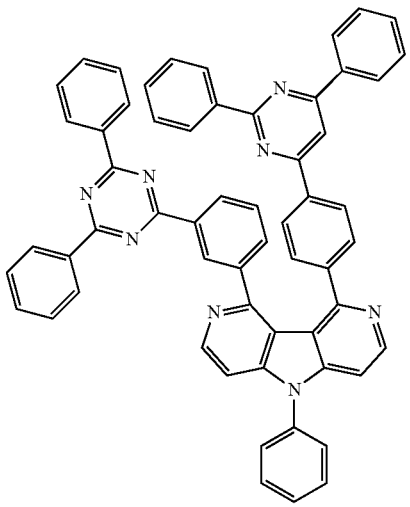
Formula (215)
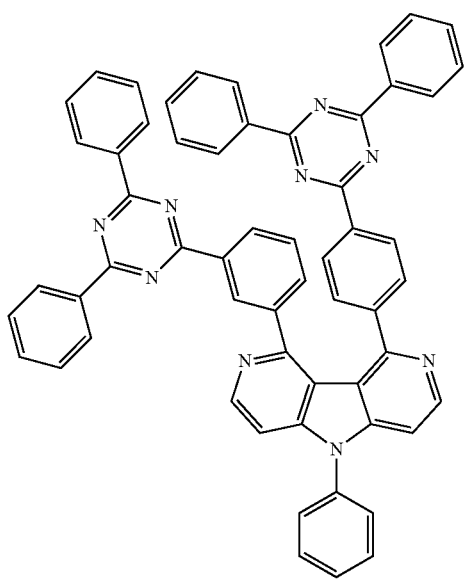
Formula (216)
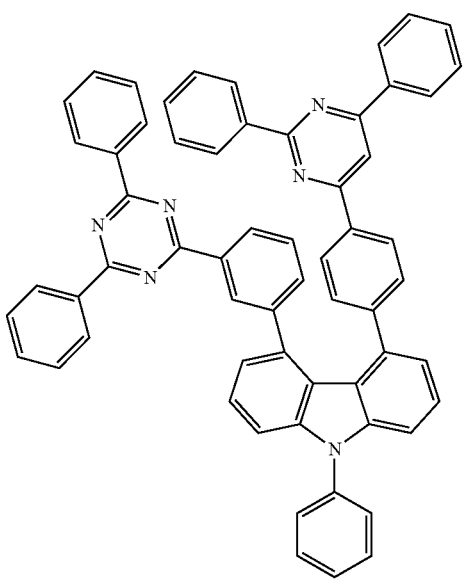
Formula (217)
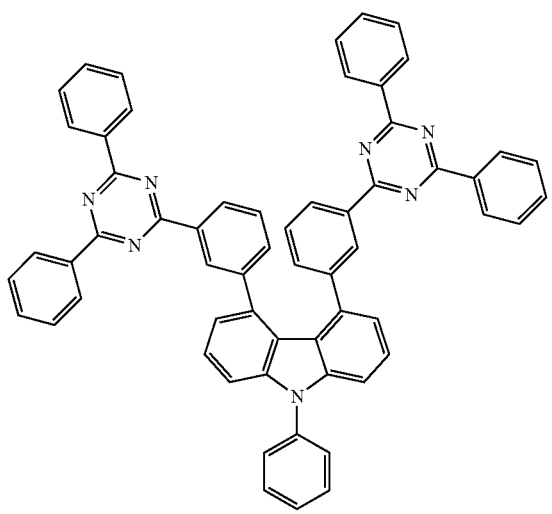
Formula (218)
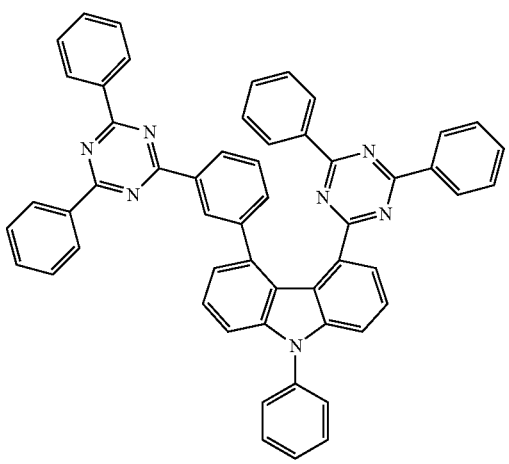

Formula (219)

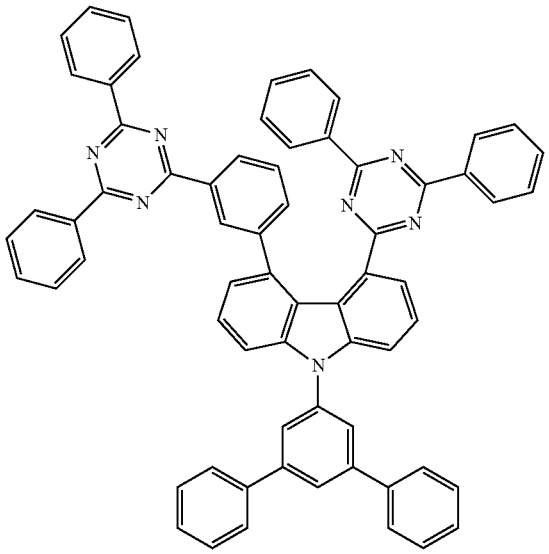

Formula (220)

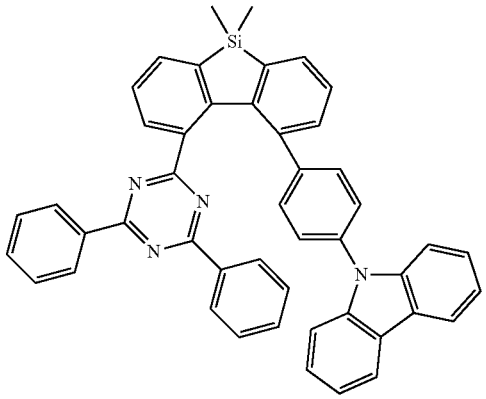

The invention further provides for the use of a compound of the formula (1) in an electronic device, preferably in an electron-transporting layer and/or in an emitting layer.

The electronic device of the invention is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs, LECs or LEECs), organic laser diodes (O-lasers) and organic light-emitting diodes (OLEDs). Particular preference is given to the organic electroluminescent devices, very particular preference to the OLECs and OLEDs and especial preference to the OLEDs.

The organic layer comprising the compound of the formula (1) is preferably a layer having an electron-transporting function. It is more preferably an electron injection layer, electron transport layer, hole blocker layer or emitting layer.

In a very particularly preferred embodiment, both $G^1$ and $G^2$ in the compound of the formula (1) are ETGs and the compounds of the formula (1) in that case are most preferably in a layer of an aforementioned electronic device having an electron-transporting function, and the compound is especially preferably in an electron injection layer (EIL), electron transport layer (ETL), hole blocker layer (HBL) or emitting layer, an EIL and ETL being especially preferable and an ETL even more preferable.

In a further very particularly preferred embodiment, one of the two $G^1$ and $G^2$ groups in the compound of the formula (1) is an LTG and the other group is an ETG and the compound of the formula (1) in that case is most preferably in a layer of an aforementioned electronic device having an electron-transporting function, and the compound is especially preferably in an electron injection layer, electron transport layer, hole blocker layer or emitting layer, it being even more preferable when this compound is present in an emitting layer, especially as matrix material.

A hole transport layer according to the present application is a layer having a hole-transporting function between the anode and emitting layer.

An electron transport layer according to the present application is a layer having an electron-transporting function between the cathode and emitting layer.

Hole injection layers and electron blocker layers are understood in the context of the present application to be specific embodiments of hole transport layers. A hole injection layer, in the case of a plurality of hole transport layers between the anode and emitting layer, is a hole transport layer which directly adjoins the anode or is separated therefrom only by a single coating of the anode. An electron blocker layer, in the case of a plurality of hole transport layers between the anode and emitting layer, is that hole transport layer which directly adjoins the emitting layer on the anode side.

As already mentioned above, the compound of the formula (1), in a preferred embodiment, is used as matrix material in an emission layer of an organic electronic device, especially in an organic electroluminescent device, for example in an OLED or OLEC. In this case, the matrix material of the formula (1) is present in the electronic device in combination with one or more dopants, preferably phosphorescent dopants.

The term "phosphorescent dopants" typically encompasses compounds where the emission of light is effected through a spin-forbidden transition, for example a transition from an excited triplet state or a state having a higher spin quantum number, for example a quintet state.

Suitable phosphorescent dopants are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent dopants, compounds containing copper, molybdenum, tungsten, rhenium, ruthenium, osmium, rhodium, iridium, palladium, platinum, silver, gold or europium, especially compounds containing iridium, platinum or copper.

In the context of the present application, all luminescent iridium, platinum or copper complexes are considered to be phosphorescent compounds. Examples of phosphorescent dopants are adduced in a section which follows.

A dopant in a system comprising a matrix material and a dopant is understood to mean that component having the smaller proportion in the mixture. Correspondingly, a matrix material in a system comprising a matrix material and a dopant is understood to mean that component having the greater proportion in the mixture.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the dopant is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of dopants. In this case too, the dopants are generally those materials having the smaller proportion in the system and the matrix materials are those materials having the greater proportion in the system. In individual cases, however, the proportion of a single matrix material in the system may be less than the proportion of a single dopant.

In a further preferred embodiment of the invention, the compounds of formula (1) are used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The desired electron-transporting and hole-transporting properties of the mixed matrix components may, however, also be combined mainly or entirely in a single mixed matrix component, in which case the further mixed matrix component(s) fulfil(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

Particularly suitable matrix materials which can be used in combination with the inventive compounds as matrix components of a mixed matrix system are selected from the preferred matrix materials specified below for phosphorescent dopants or the preferred matrix materials for fluorescent dopants, according to what type of dopant is used in the mixed matrix system.

The present invention therefore also relates to a composition comprising at least one compound of formula (1) and at least one further matrix material.

The present invention also relates to a composition comprising at least one compound of formula (1) and at least one wide band gap material, a wide band gap material being understood to mean a material in the sense of the disclosure of U.S. Pat. No. 7,294,849. These systems exhibit particularly advantageous performance data in electroluminescent devices.

The present invention further relates to a composition comprising at least one compound of formula (1) and at least one further organic semiconductor material selected from the group consisting of fluorescent emitters, phosphorescent emitters, host materials, matrix materials, electron transport materials, electron injection materials, hole conductor materials, hole injection materials, electron blocker materials and hole blocker materials.

Preferred phosphorescent dopants for use in mixed matrix systems are the preferred phosphorescent dopants specified hereinafter.

Examples of phosphorescent dopants can be found in applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used for phosphorescent OLEDs according to the prior art and as known to those skilled in the art in the field of organic electroluminescent devices are suitable for use in the inventive devices.

Explicit examples of phosphorescent dopants are adduced in the following table:

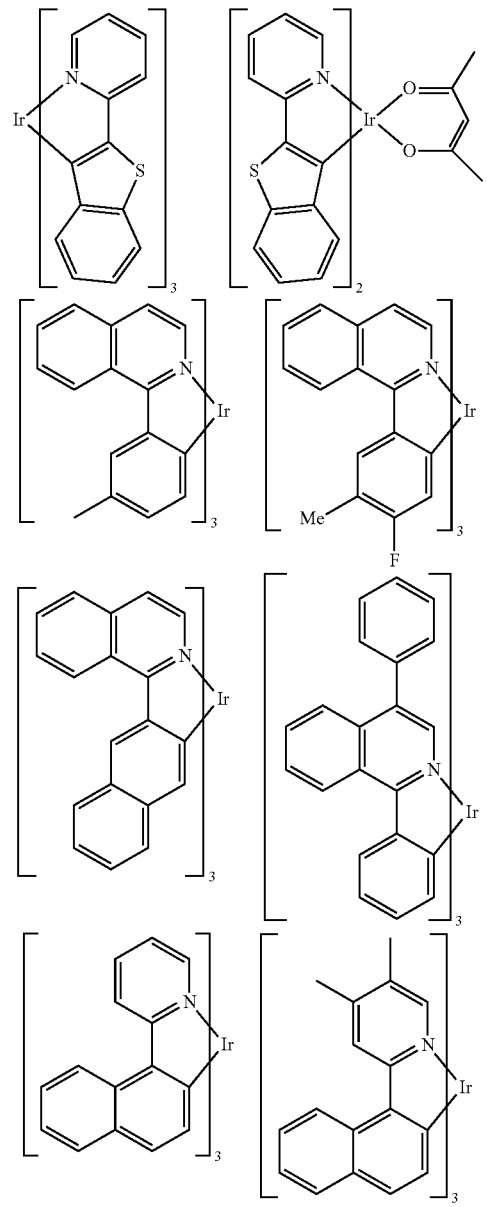

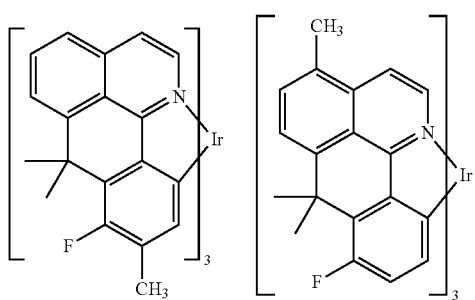
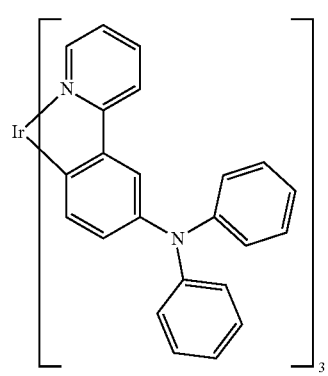
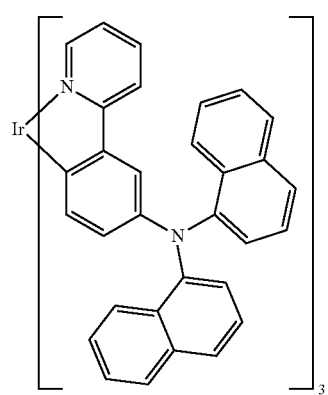
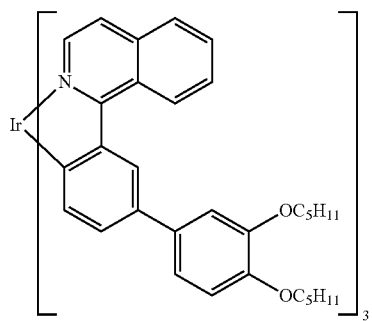
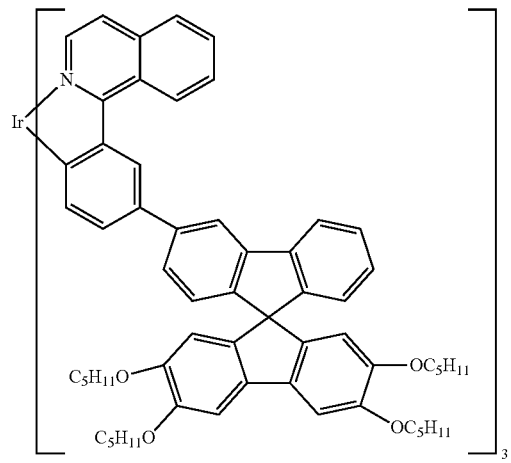
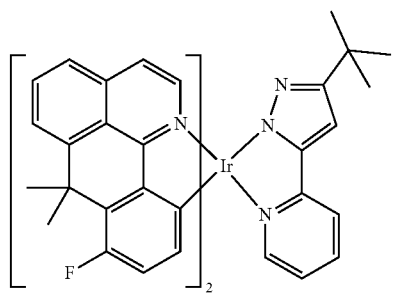
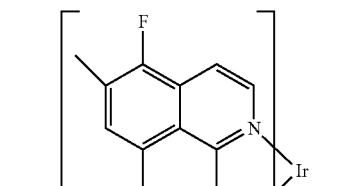
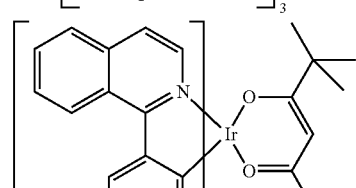
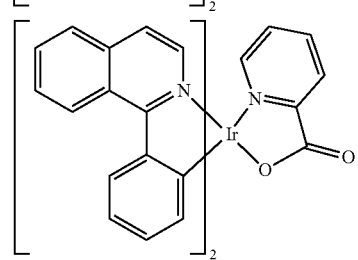

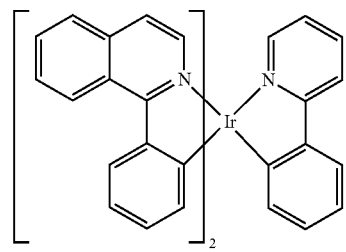
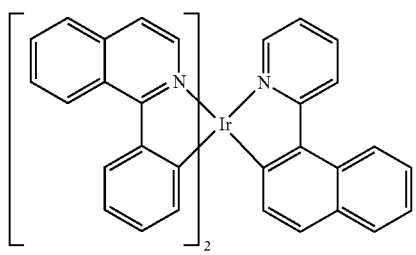
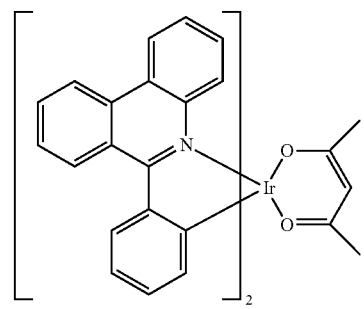
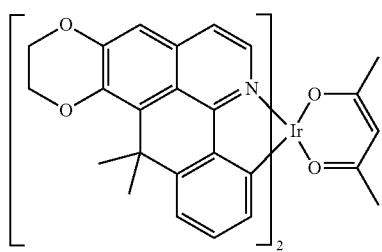
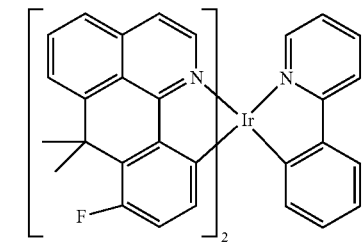
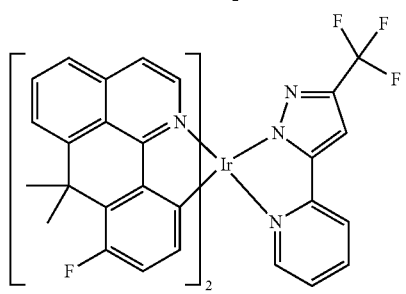
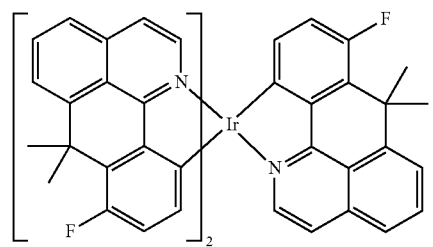
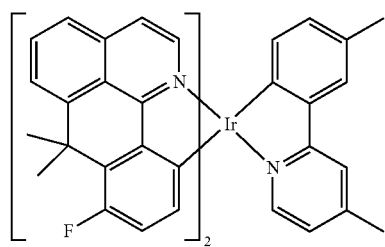
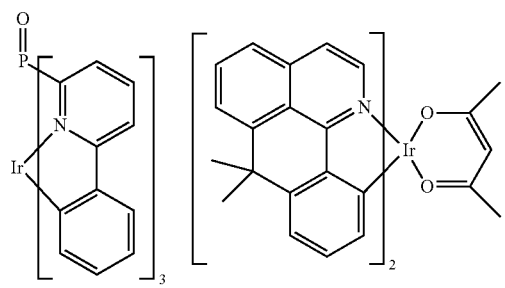
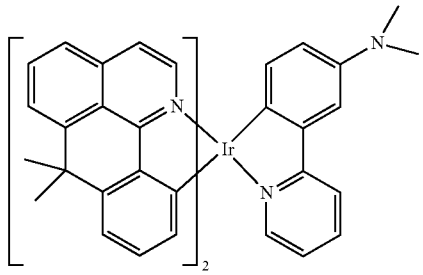
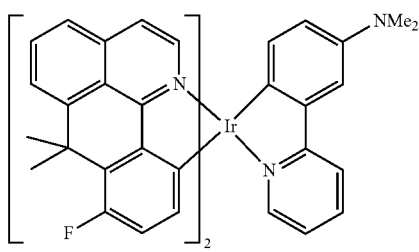

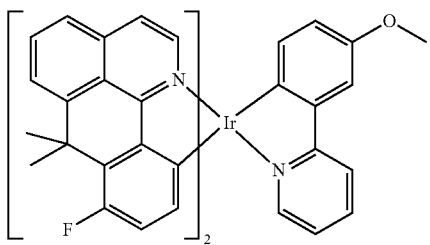
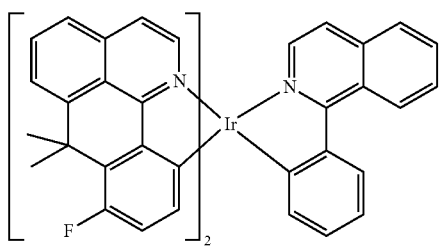
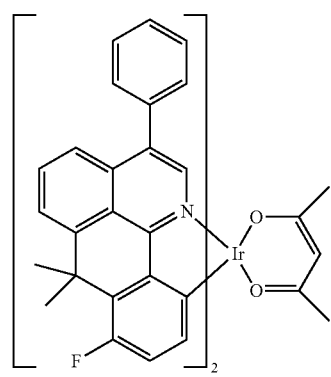
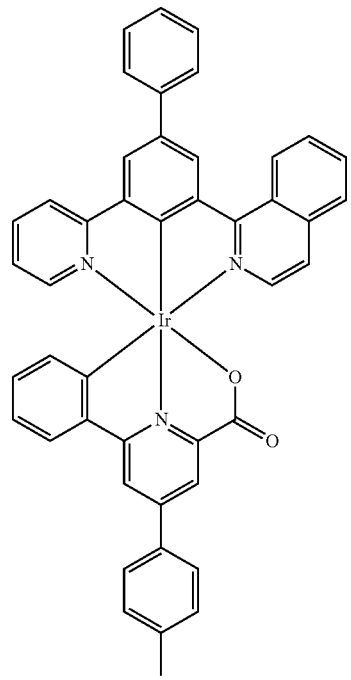
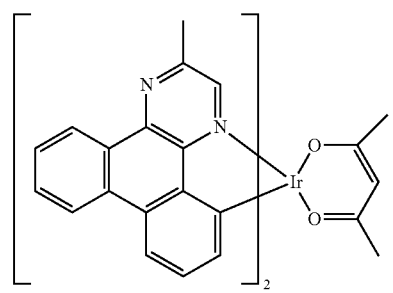
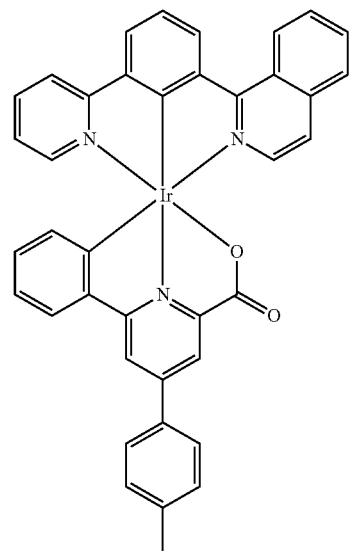
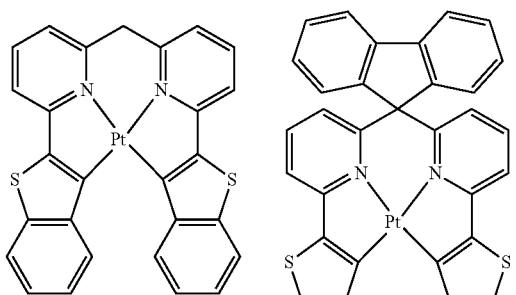
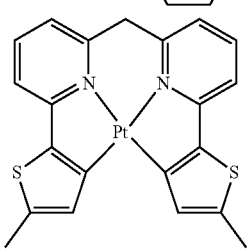

107
-continued
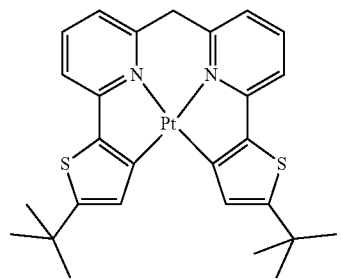
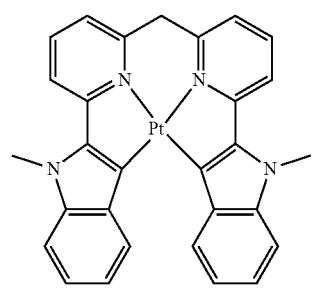
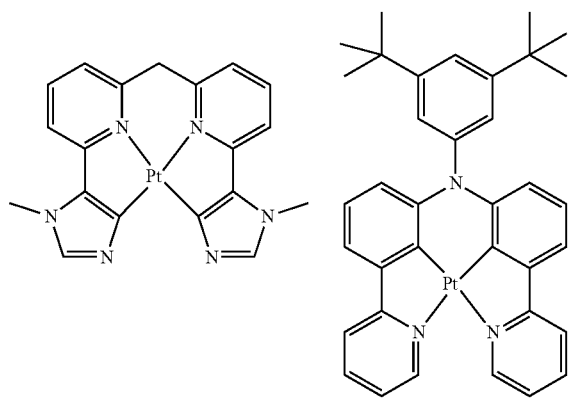
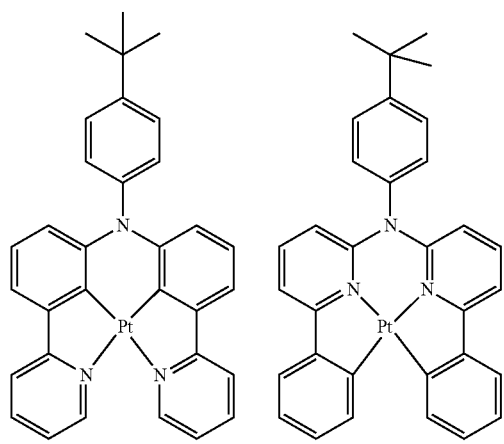
108
-continued
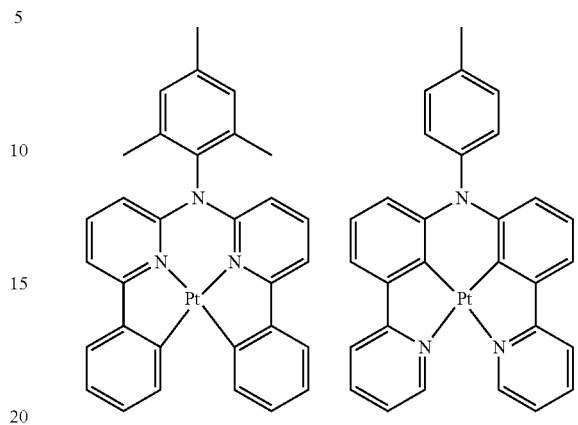
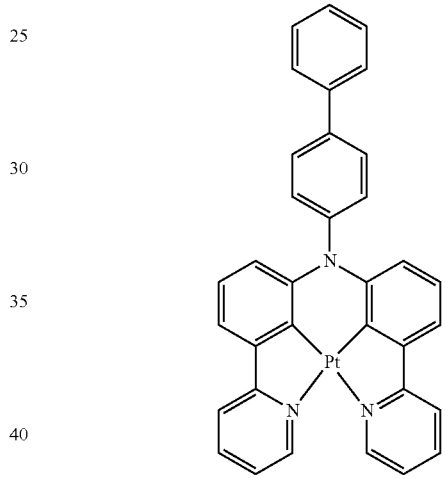
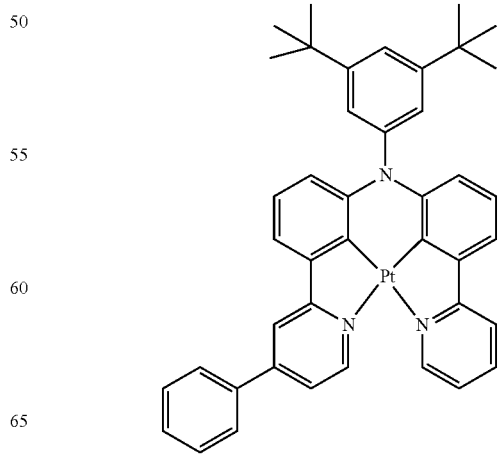

109
-continued
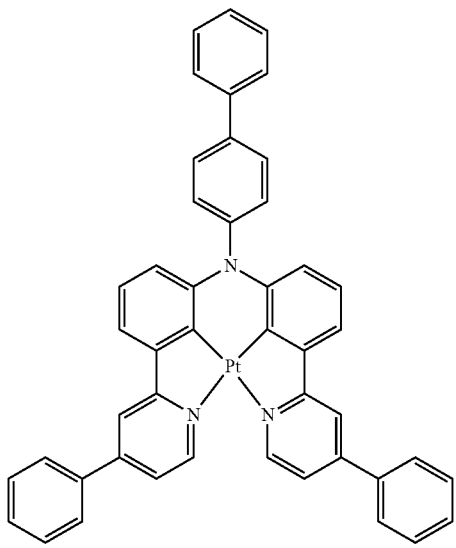
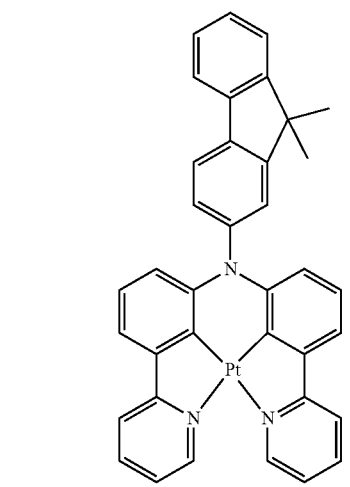
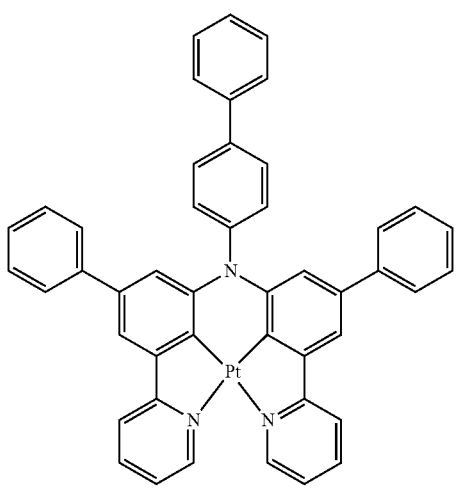
110
-continued
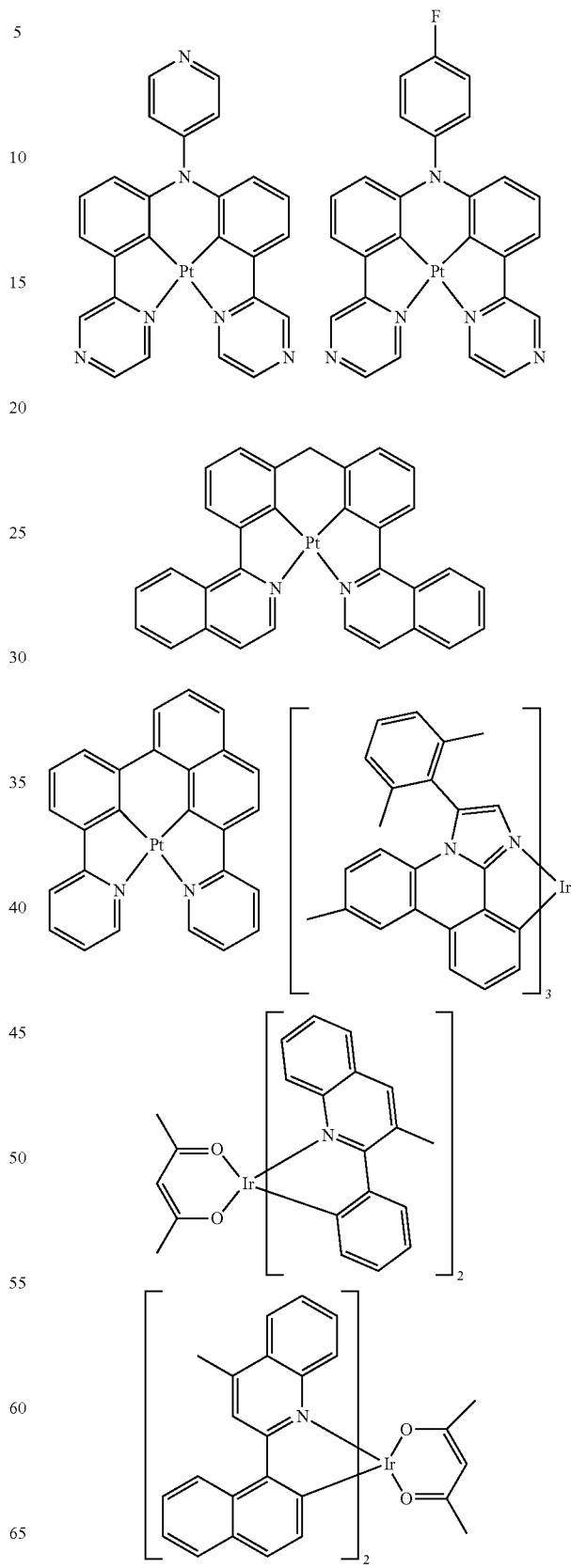

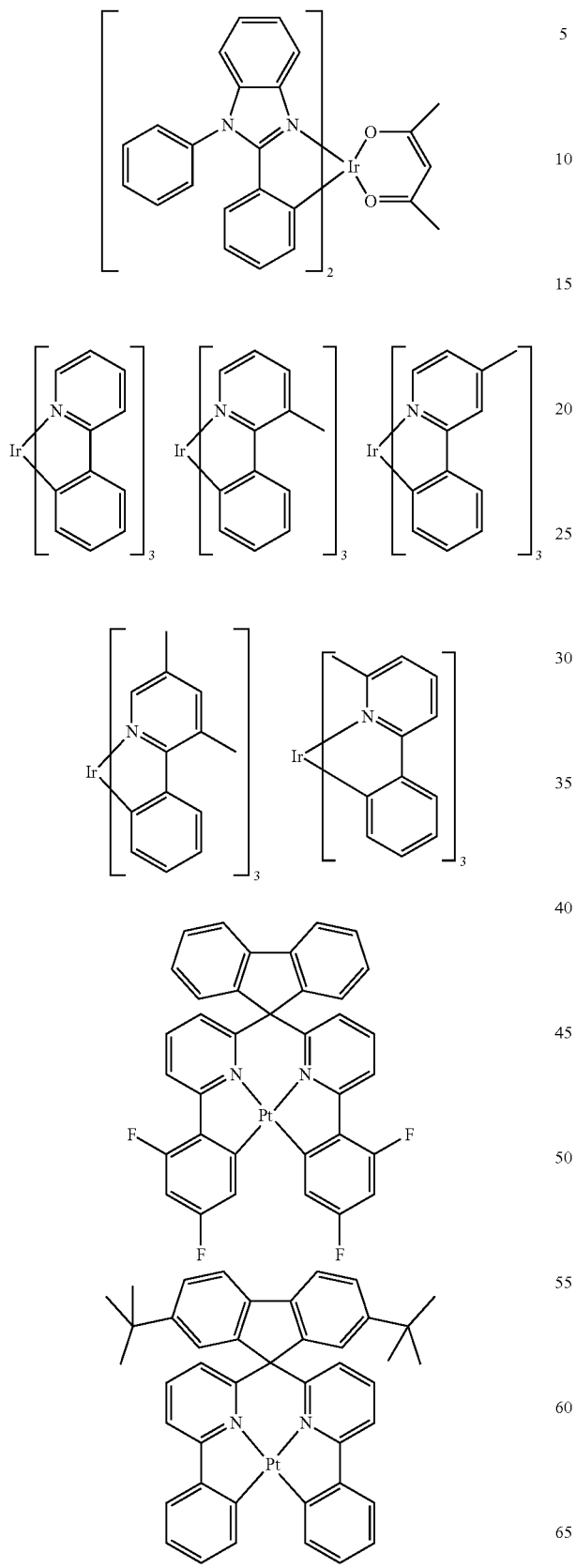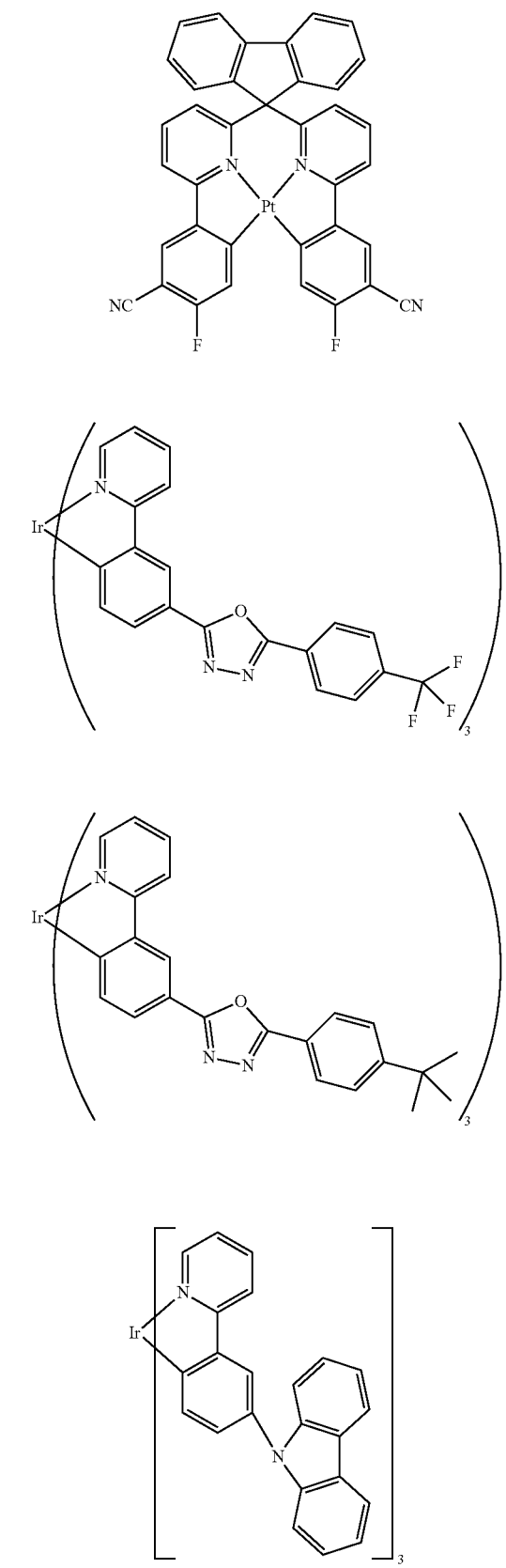

113
-continued
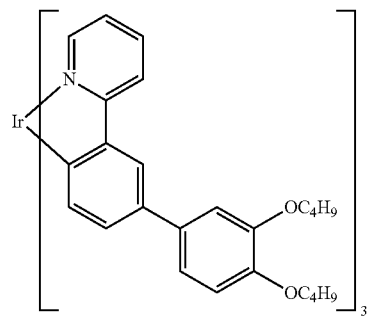
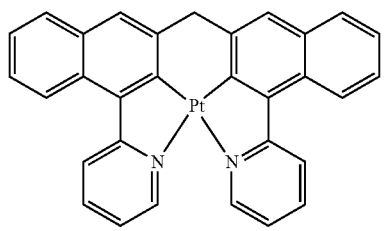
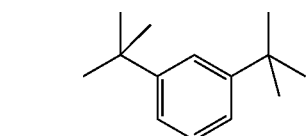
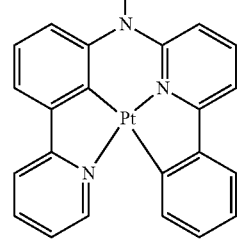
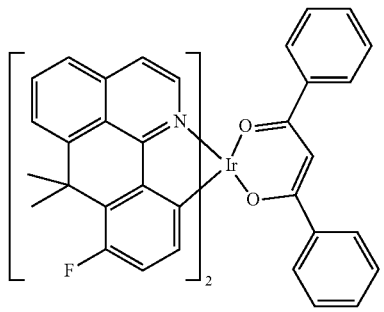
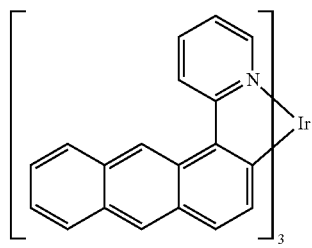
114
-continued
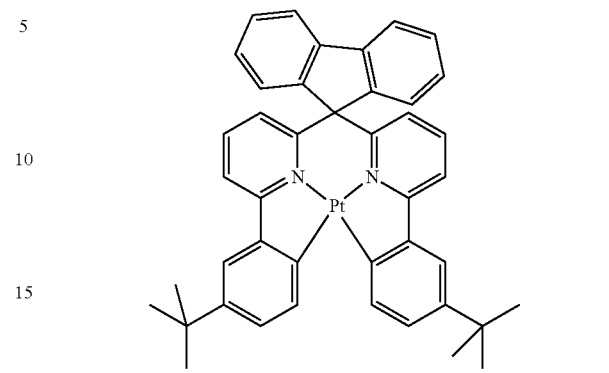
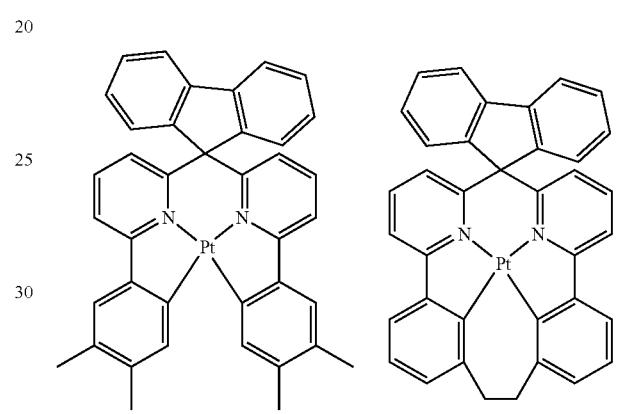
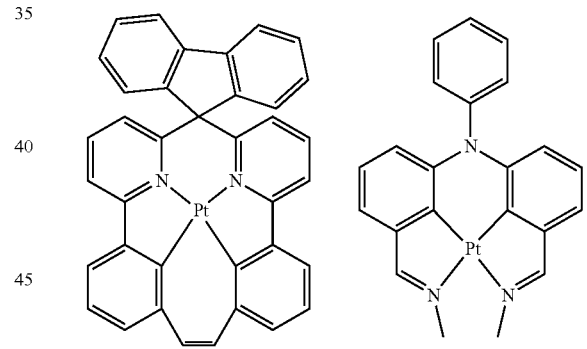
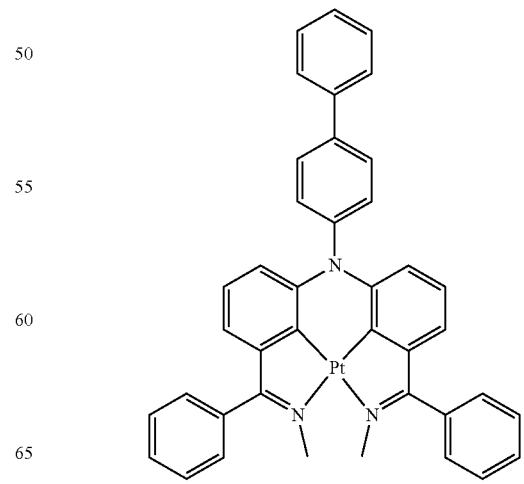

115
-continued
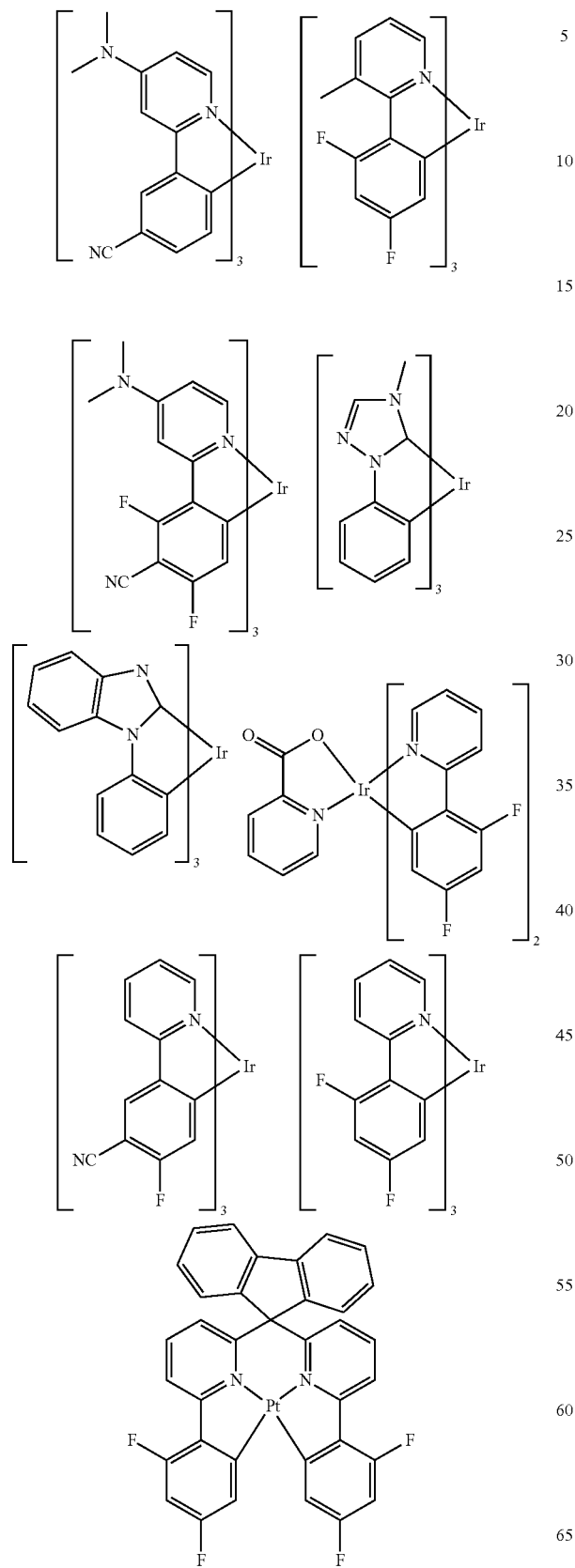
116
-continued
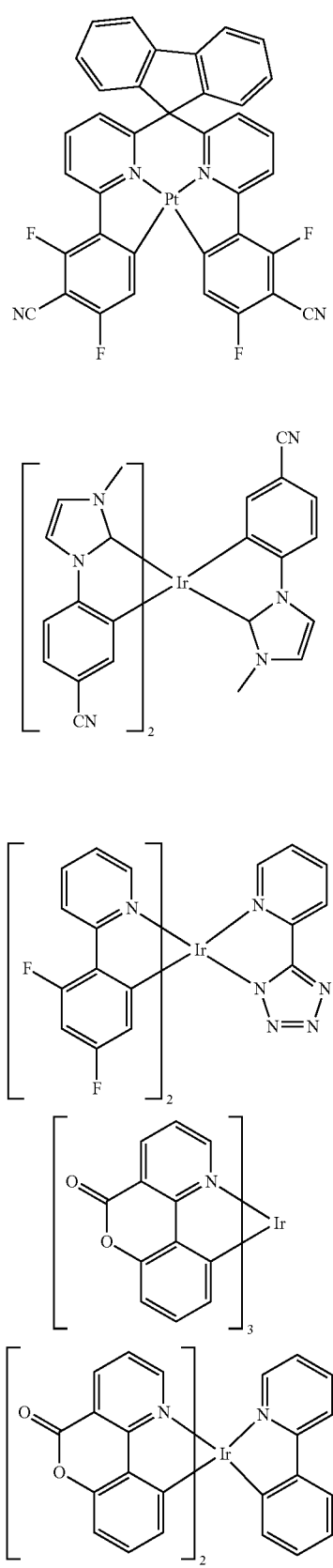

117
-continued
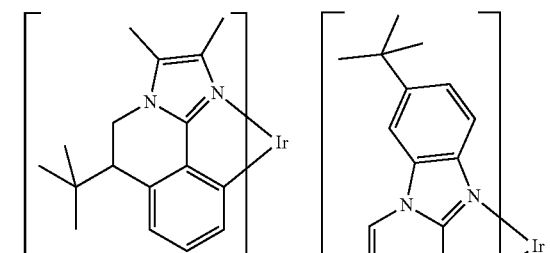
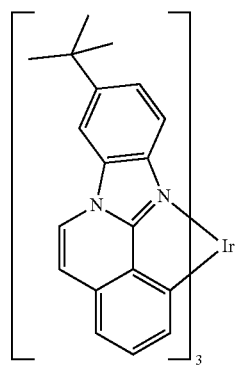
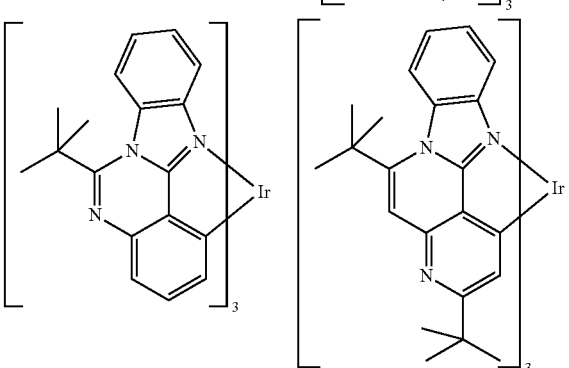
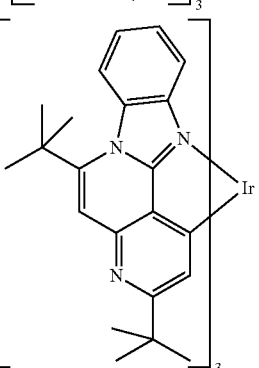
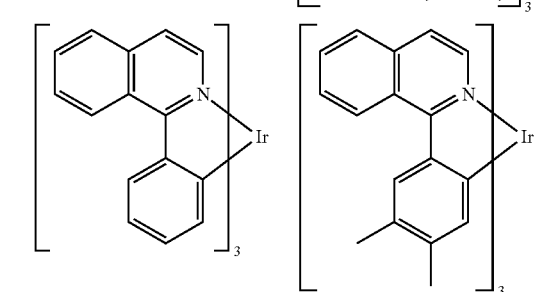
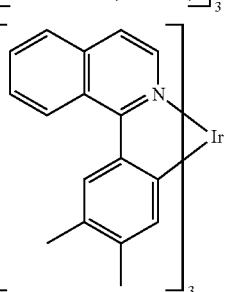
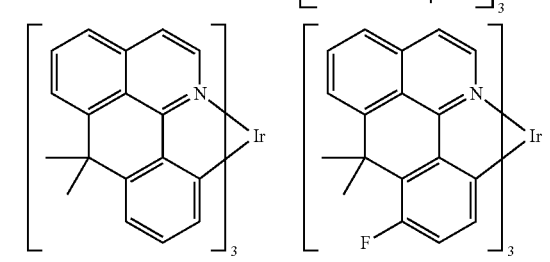
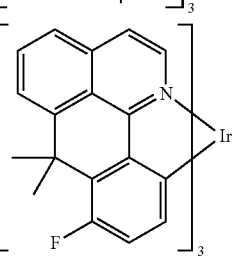
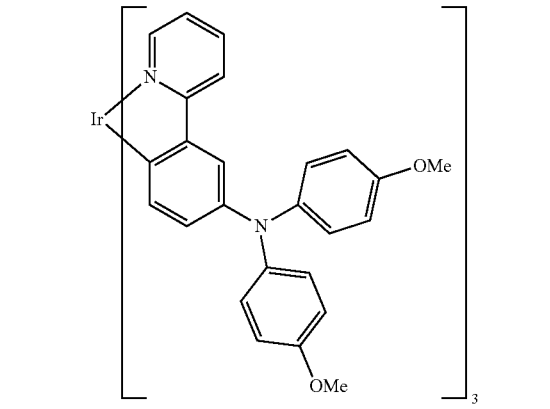
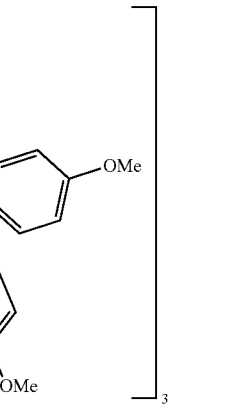
118
-continued
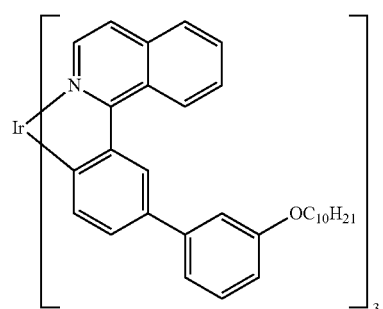
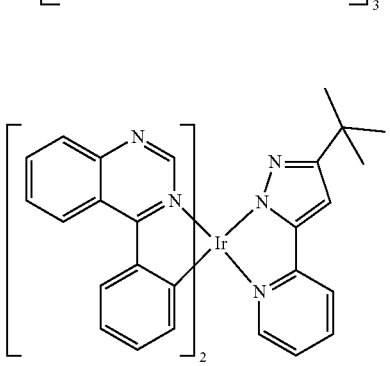
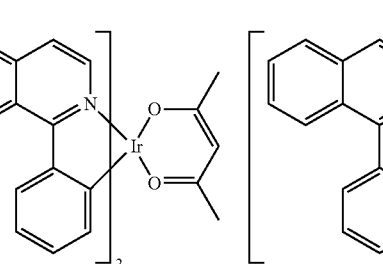
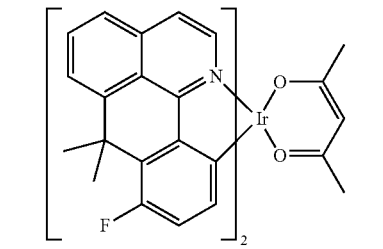
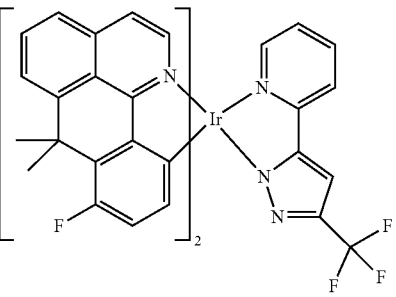

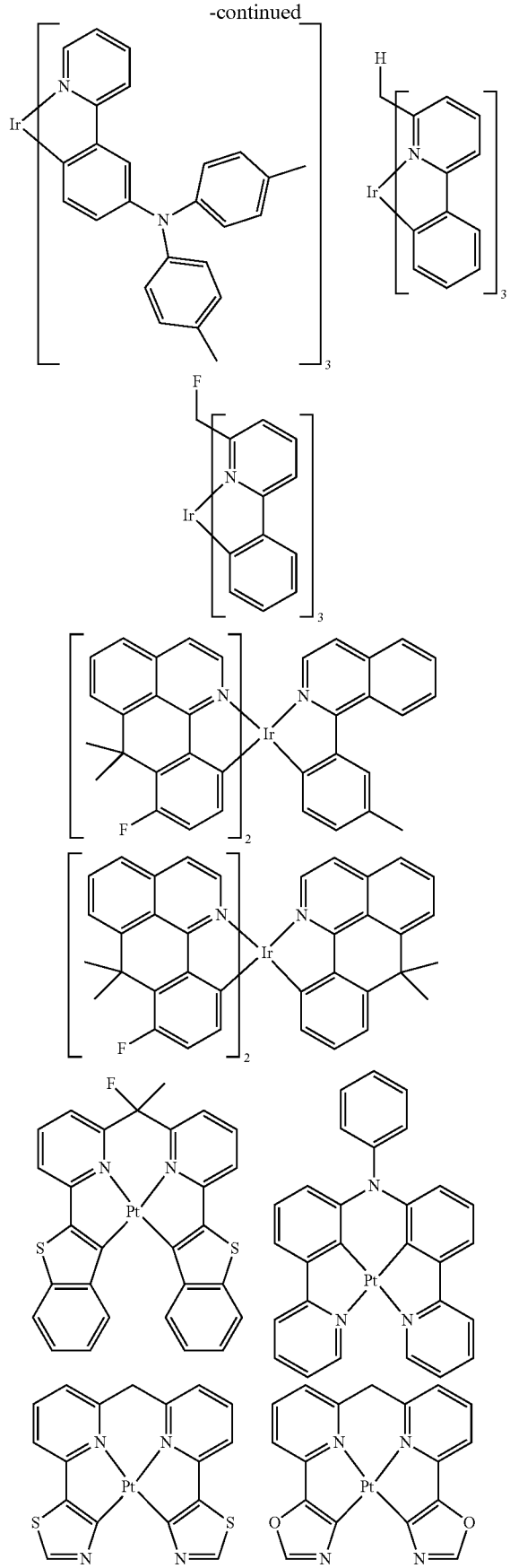
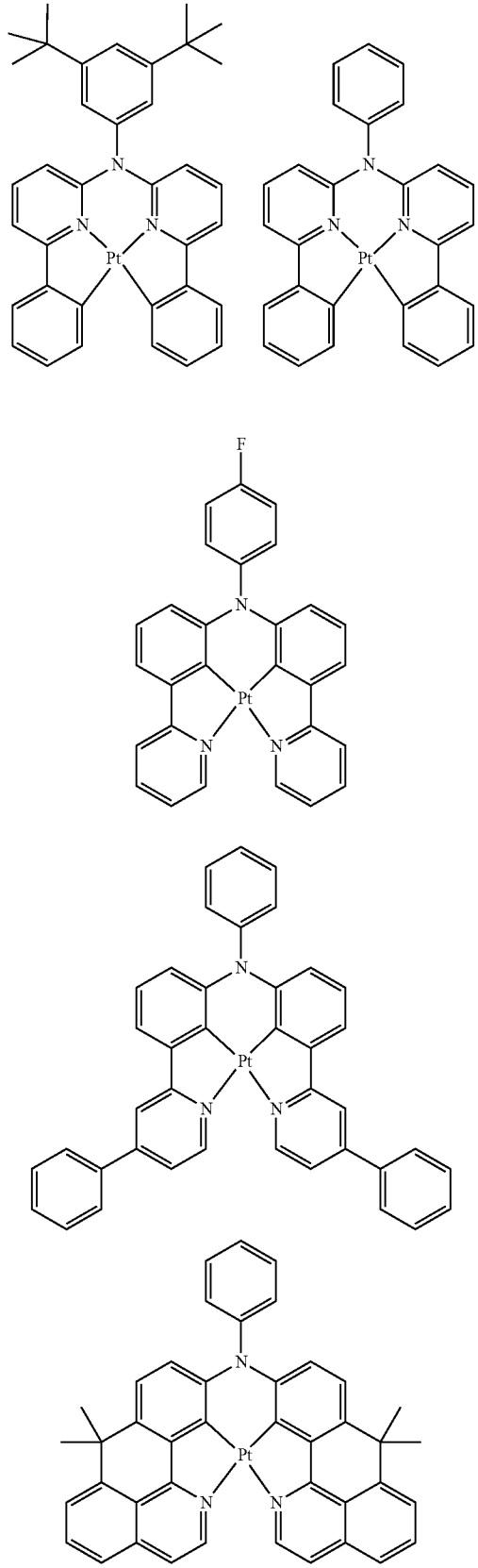

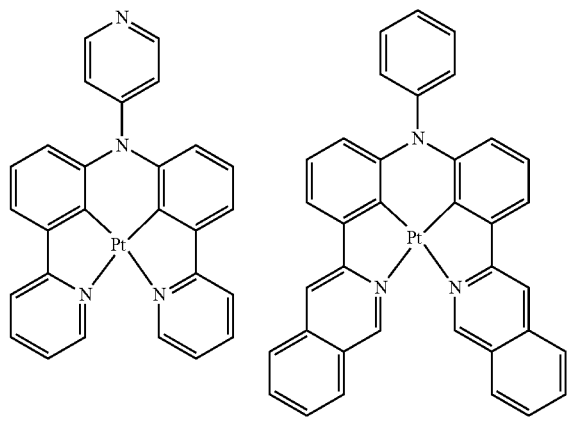
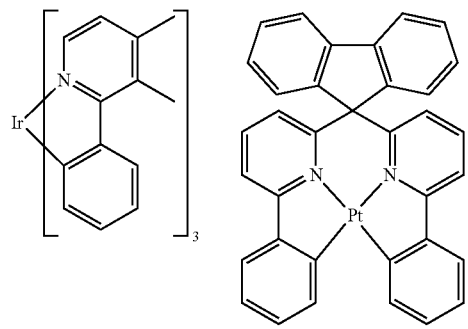
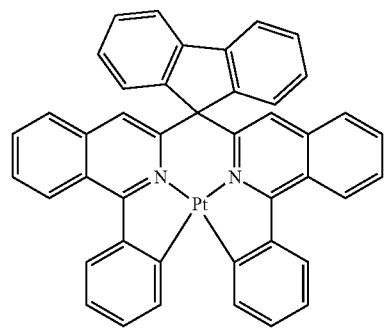
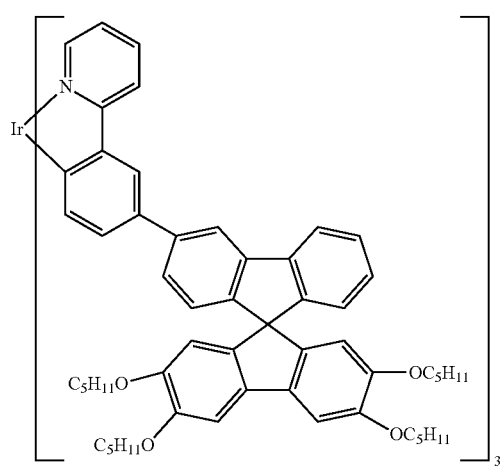
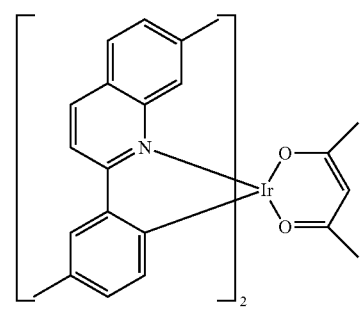
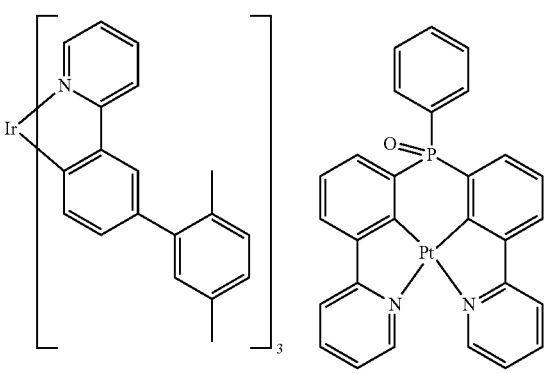
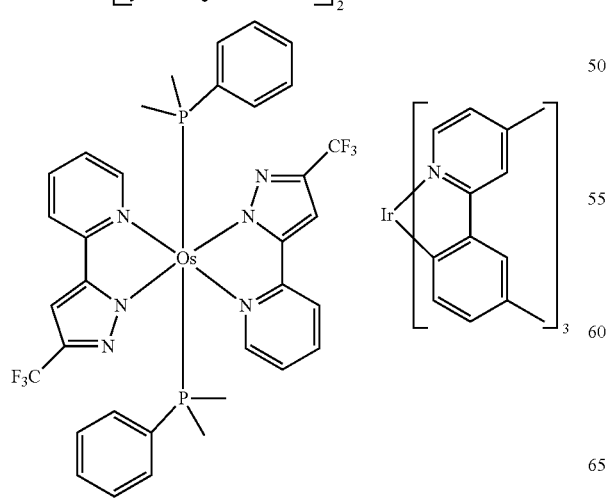
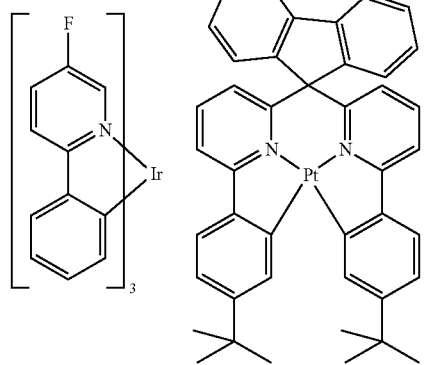

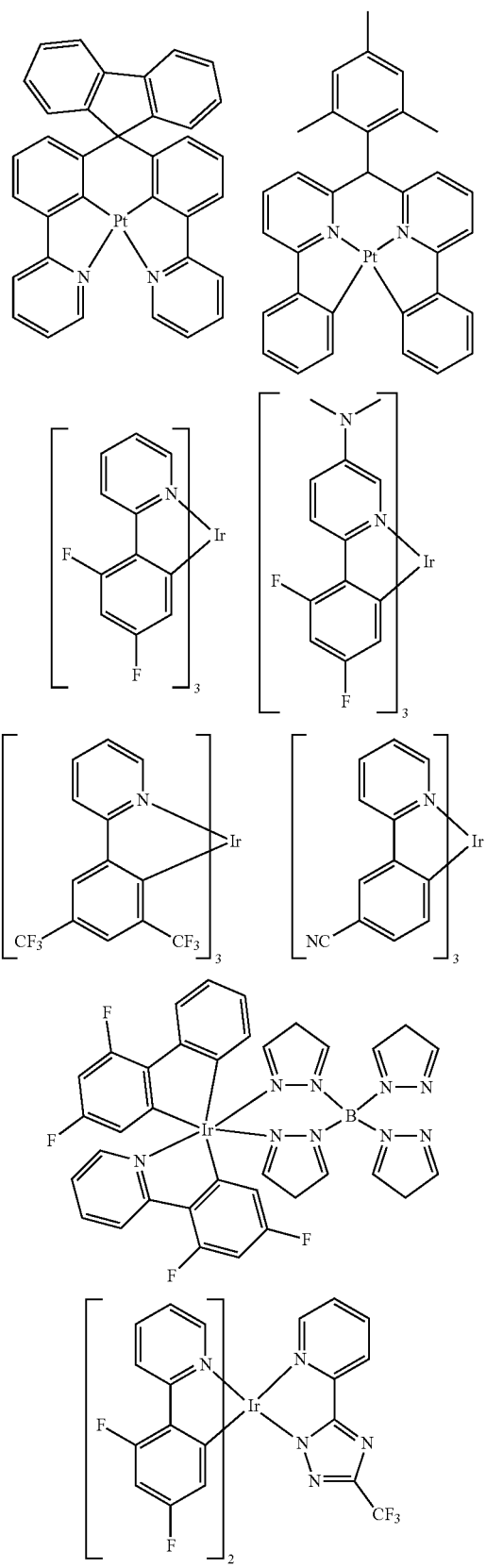
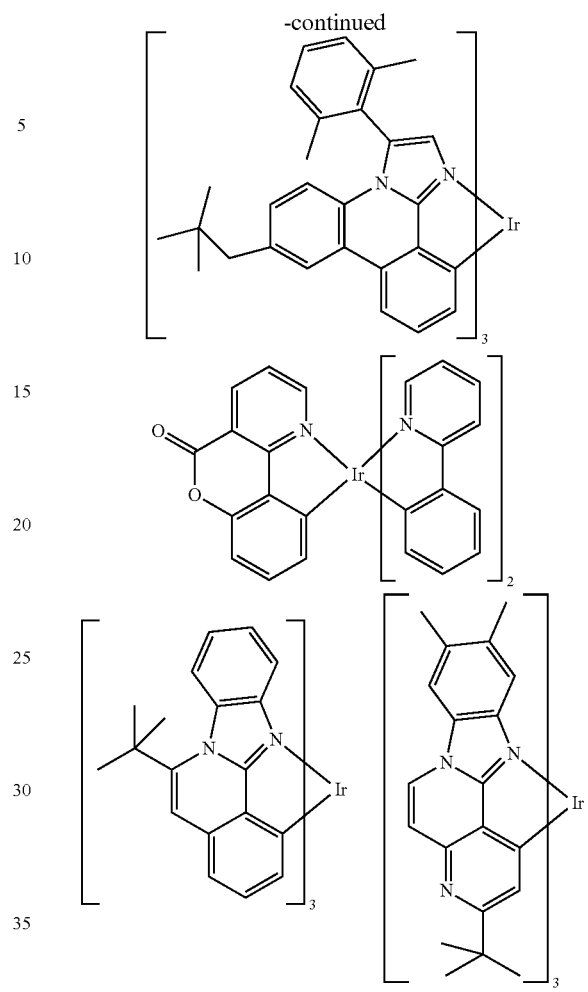

Preferred fluorescent dopants are selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthracenamines, aromatic anthracenediamines, aromatic pyrenamines, aromatic pyrenediamines, aromatic chrysenamines or aromatic chrysenediamines. An aromatic anthracenamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyrenamines, pyrenediamines, chrysenamines and chrysenediamines are defined analogously, where the diarylamino groups in the pyrene are bonded preferably in the 1 position or 1,6 positions. Further preferred dopants are indenofluorenamines or -fluorenediamines, for example according to WO 2006/108497 or WO 2006/122630, benzoindenofluorenamines or -fluorenediamines, for example according to WO 2008/006449, and dibenzoindenofluorenamines or -fluorenediamines, for example according to WO 2007/140847, and the indenofluorene derivatives having fused aryl groups disclosed in WO 2010/012328.

Useful matrix materials, preferably for fluorescent dopants, as well as the compounds of the formula (1), are materials from various substance classes. Preferred matrix materials are selected from the classes of the oligoarylenes (e.g. 2,2',7,7'-tetraphenylspirobifluorene according to EP 676461 or dinaphthylanthracene), especially of the oligoarylenes containing fused aromatic groups, the oligoarylenevinylenes (e.g. DPVBi or spiro-DPVBi according to EP 676461), the polypodal metal complexes (for example according to WO 2004/081017), the hole-conducting compounds (for example according to WO 2004/058911), the electron-conducting compounds, especially ketones, phosphine oxides, sulfoxides, etc. (for example according to WO 2005/084081 and WO 2005/084082), the atropisomers (for example according to WO 2006/048268), the boronic acid derivatives (for example according to WO 2006/117052) or the benzanthracenes (for example according to WO 2008/145239). Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes comprising, anthracene, benzanthracene, benzophenanthrene and/or pyrene or atropisomers of these compounds.

An oligoarylene in the context of this invention shall be understood to mean a compound in which at least three aryl or arylene groups are bonded to one another.

Preferred matrix materials for phosphorescent dopants are, as well as the compounds of the formula (1), aromatic amines, especially triarylamines, for example according to US 2005/0069729, carbazole derivatives (e.g. CBP, N,N-biscarbazolylbiphenyl) or compounds according to WO 2005/039246, US 2005/0069729, JP 2004/288381, EP 1205527 or WO 2008/086851, bridged carbazole derivatives, for example according to WO 2011/088877 and WO 2011/128017, indenocarbazole derivatives, for example according to WO 2010/136109 and WO 2011/000455, azacarbazole derivatives, for example according to EP 1617710, EP 1617711, EP 1731584, JP 2005/347160, indolocarbazole derivatives, for example according to WO 2007/063754 or WO 2008/056746, ketones, for example according to WO 2004/093207 or WO 2010/006680, phosphine oxides, sulfoxides and sulfones, for example according to WO 2005/003253, oligophenylenes, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, aluminum complexes, e.g. BAlq, diazasilole derivatives and tetraazasilole derivatives, for example according to WO 2010/054729, diazaphosphole derivatives, for example according to WO 2010/054730, and aluminum complexes, e.g. BAlQ.

Apart from the cathode, anode and the layer comprising the compound of the formula (1), the electronic device may comprise further layers. These are selected, for example, from in each case one or more hole injection layers, hole transport layers, hole blocker layers, emitting layers, electron transport layers, electron injection layers, electron blocker layers, exciton blocker layers, interlayers, charge generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. However, it should be pointed out that not necessarily every one of these layers need be present.

The sequence of layers in the organic electroluminescent device is preferably as follows:

anode-hole injection layer-hole transport layer-emitting layer-electron transport layer-electron injection layer-cathode.

At the same time, it should be pointed out again that not all the layers mentioned need be present and/or that further layers may additionally be present.

The inventive organic electroluminescent device may contain two or more emitting layers. More preferably, these emission layers in this case have several emission maxima between 380 nm and 750 nm overall, such that the overall result is white emission; in other words, various emitting compounds which may fluoresce or phosphoresce and which emit blue or yellow or orange or red light are used in the emitting layers. Especially preferred are three-layer systems, i.e. systems having three emitting layers, where the three layers show blue, green and orange or red emission (for the basic construction see, for example, WO 2005/011013). It should be noted that, for the production of white light, rather than a plurality of color-emitting emitter compounds, an emitter compound used individually which emits over a broad wavelength range may also be suitable.

Suitable charge transport materials as usable in the hole injection or hole transport layer or electron blocker layer or in the electron transport layer of the organic electroluminescent device of the invention are, for example, the compounds disclosed in Y. Shirota et al., Chem. Rev. 2007, 107(4), 953-1010, or other materials as used in these layers according to the prior art. Materials used for the electron transport layer may be any materials as used according to the prior art as electron transport materials in the electron transport layer. Especially suitable are aluminium complexes, for example $Alq_3$, zirconium complexes, for example $Zrq_4$, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Further suitable materials are derivatives of the abovementioned compounds as disclosed in JP 2000/053957, WO 2003/060956, WO 2004/028217, WO 2004/080975 and WO 2010/072300.

As hole transport materials are especially preferably materials which can be used in a hole transport, hole injection or electron blocker layer, indenofluorenamine derivatives (for example according to WO 06/122630 or WO 06/100896), the amine derivatives disclosed in EP 1661888, hexaazatriphenylene derivatives (for example according to WO 01/049806), amine derivatives having fused aromatic systems (for example according to U.S. Pat. No. 5,061,569), the amine derivatives disclosed in WO 95/09147, monobenzoindenofluorenamines (for example according to WO 08/006449), dibenzoindenofluorenamines (for example according to WO 07/140847), spirobifluorenamines (for example according to WO 2012/034627 or the as yet unpublished EP 12000929.5), fluorenamines (for example according to the as yet unpublished applications EP 12005369.9, EP 12005370.7 and EP 12005371.5), spirodibenzopyranamines (for example according to the as yet unpublished application EP 11009127.9) and dihydroacridine derivatives (for example according to the as yet unpublished EP 11007067.9).

Preferred cathodes of the electronic device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferable. For some applications, at least one of the electrodes has to be transparent or partly transparent in order to enable the irradiation of the organic material (organic solar cell) or the emission of light (OLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

The electronic device, in the course of production, is appropriately (according to the application) structured, contact-connected and finally sealed, since the lifetime of the devices of the invention is shortened in the presence of water and/or air.

In a preferred embodiment, the electronic device of the invention is characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. In this case, however, it is also possible that the initial pressure is even lower, for example less than $10^7$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^5$ mbar and 1 bar. A special case of this method is the OVJP (organic vapour jet printing) method, in which the materials are applied directly by a nozzle and thus structured (for example M. S. Arnold et al., Appl. Phys. Lett. 2008, 92, 053301).

Preference is additionally given to an organic electroluminescent device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds of formula (1) are needed. High solubility can be achieved by suitable substitution of the compounds.

It is further preferable that an organic electroluminescent device of the invention is produced by applying one or more layers from solution and one or more layers by a sublimation method.

The invention thus further provides a process for producing the electronic device of the invention, characterized in that at least one organic layer is applied by gas phase deposition or from solution.

According to the invention, the electronic devices comprising one or more compounds of formula (1) can be used in displays, as light sources in lighting applications and as light sources in medical and/or cosmetic applications (e.g. light therapy).

The present invention also relates to a formulation comprising at least one compound of formula (1) or at least one of the abovementioned compositions and at least one solvent.

Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

Devices comprising the compounds of formula (1) can be used in a wide variety of ways. For example, it is possible to use electroluminescent devices comprising one or more compounds of formula (1) in displays for televisions, mobile phones, computers and cameras. The devices may alternatively be used in lighting applications. In addition, electroluminescent devices can be utilized, for example, in OLEDs or OLECs comprising at least one of the compounds of formula (1) in medicine or cosmetics for phototherapy. It is thus possible to treat a multitude of disorders (psoriasis, atopic dermatitis, inflammation, acne, skin cancer etc.) or to avoid and reduce formation of skin wrinkles, skin reddening and skin aging. In addition, the light-emitting devices can be used to keep drinks or food fresh, or in order to sterilize devices (for example medical devices).

The present invention therefore provides an electronic device, preferably an organic electroluminescent device, very preferably an OLED or OLEC and most preferably an OLED, comprising at least one compound of formula (1) for use in medicine for phototherapy.

The present invention further preferably relates to an electronic device, preferably an organic electroluminescent device, very preferably an OLED or OLEC and most preferably an OLED, comprising at least one compound of formula (1) for use for phototherapeutic treatment of skin diseases.

The present invention further very preferably relates to an electronic device, preferably an organic electroluminescent device, very preferably an OLED or OLEC and most preferably an OLED, comprising at least one compound of formula (1) for use for phototherapeutic treatment of psoriasis, atopic dermatitis, inflammation disorders, vitiligo, wound healing and skin cancer.

The present invention further relates to the use of the electronic device, preferably an organic electroluminescent device, very preferably an OLED or OLEC and most preferably an OLED, comprising at least one compound of formula (1) in cosmetics, preferably for treatment of acne, skin aging and cellulite.

The compounds of the invention and the organic electroluminescent devices of the invention feature the following surprising advantages over the prior art:

1. The compounds of the invention are of very good suitability for use in an emission layer and exhibit improved performance data over compounds from the prior art.
2. The compounds of the invention have a relatively low sublimation temperature and high thermal stability, and can therefore be sublimed without decomposition or residue. In addition, they have high oxidation stability and a high glass transition temperature, which is advantageous for processibility, for example from solution or from the gas phase, and also for use in electronic devices.
3. The use of the compounds of the invention in electronic devices, especially used as electron transport or electron injection material, but also as matrix material, leads to high efficiencies, low operating voltages and long lifetimes.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example from a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

It should also be pointed out that many of the features, and especially those of the preferred embodiments of the present invention, are themselves inventive and should not be regarded merely as some of the embodiments of the present invention. For these features, independent protection may be sought in addition to or as an alternative to any currently claimed invention.

The technical teaching disclosed with the present invention may be abstracted and combined with other examples.

The invention is illustrated in detail by the examples which follow, without any intention of restricting it thereby.

EXAMPLES

The syntheses which follow, unless stated otherwise, are conducted under a protective gas atmosphere in dried solvents. The solvents and reagents can be purchased, for example, from Sigma-ALDRICH or ABCR. The figures in square brackets for chemical compounds known from the literature are the CAS number.

Example 1

Synthesis of 3-dibenzofuran-4-yl-9-phenyl-9H-carbazole

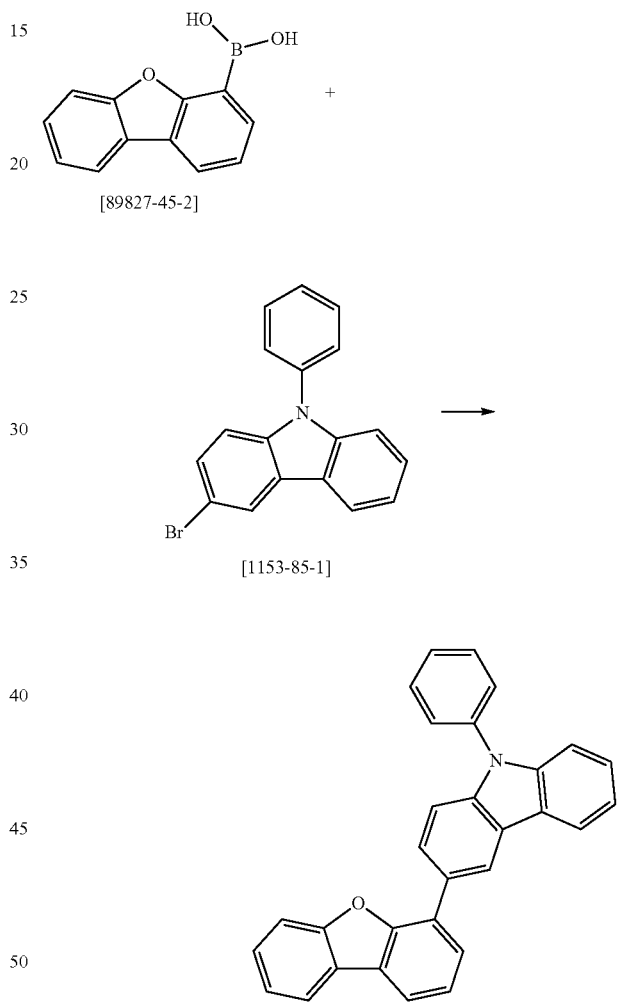

28.9 g (136 mmol) of dibenzofuran-4-boronic acid, 40 g (124.1 mmol) of 3-bromo-9-phenyl-9H-carbazole and 78.9 mL (158 mmol) of $Na_2CO_3$ (2 M solution) are suspended in 120 mL of toluene, 120 mL of ethanol and 100 mL of water. 2.6 g (2.2 mmol) of $Pd(PPh_3)_4$ are added to this suspension, and the reaction mixture is heated under reflux for 16 h. After cooling, the organic phase is removed, filtered through silica gel, washed three times with 200 mL of water and then concentrated to dryness. The residue is recrystallized from toluene. The yield is 49.7 g (121 mmol), corresponding to 97% of theory.

In an analogous manner, it is possible to obtain the following compounds:

| Reactant 1 | Reactant 2 | Product | Yield |
|---|---|---|---|
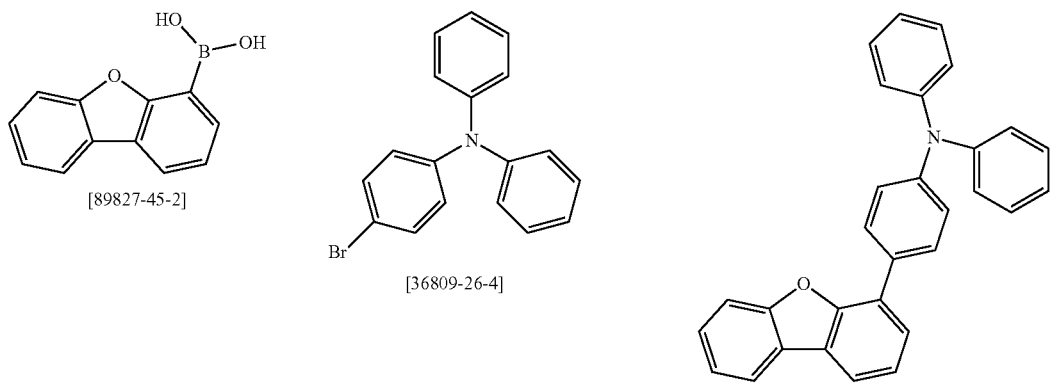
90%
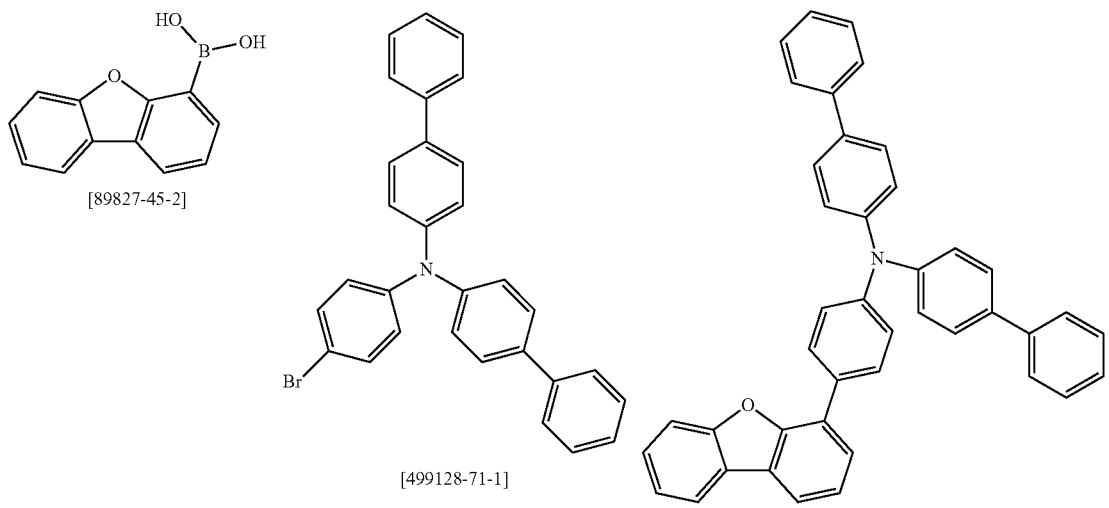
92%
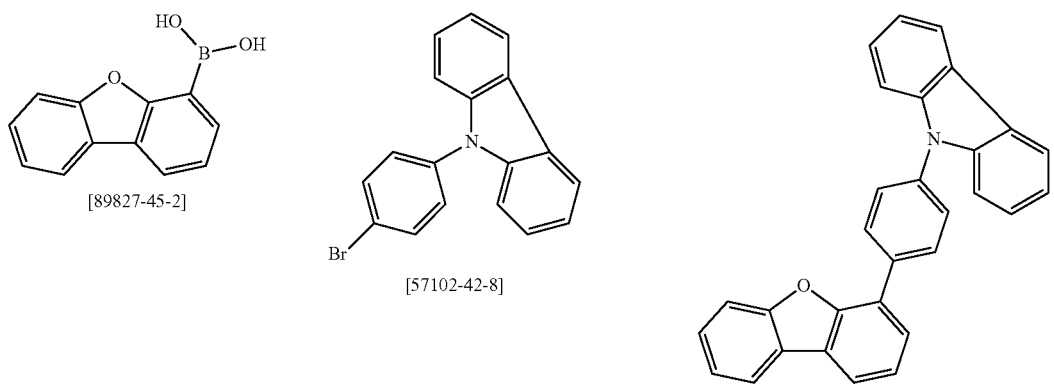
89%

| Reactant 1 | Reactant 2 | Product | Yield |
|---|---|---|---|
| 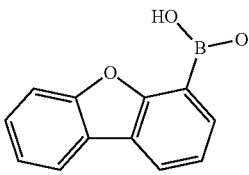 [89827-45-2] | 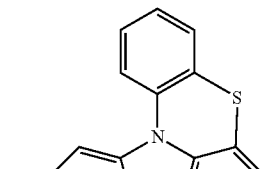 [63524-03-8] | 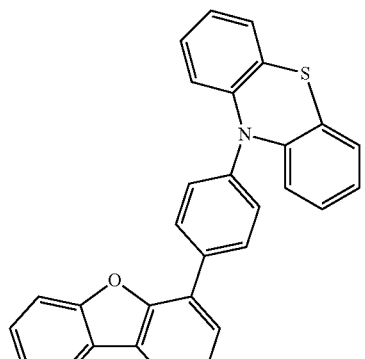 | 92% |
| 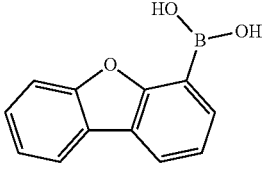 [89827-45-2] | 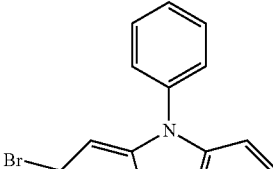 [94994-62-4] | 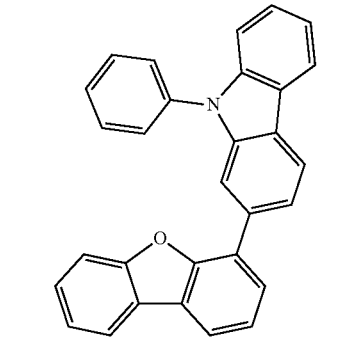 [SMILES: c1ccc(-n2c3ccccc3c3ccc(-c4cccc5c4oc4ccccc45)cc32)cc1] | 86% |
| 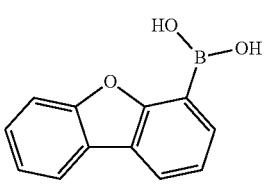 [89827-45-2] | 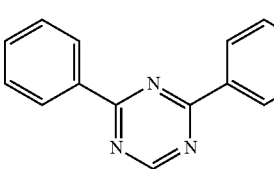 [3842-55-5] | 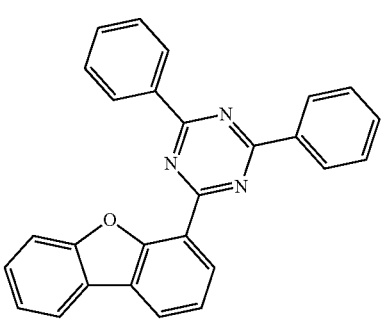 [SMILES: c1ccc(-c2nc(-c3ccccc3)nc(-c3cccc4c3oc3ccccc34)n2)cc1] | 69% |
| 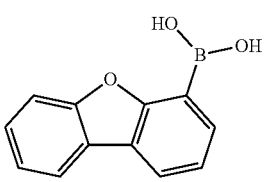 [89827-45-2] | 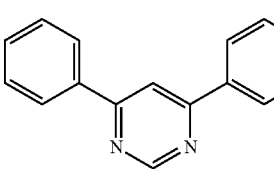 [56181-49-8] | 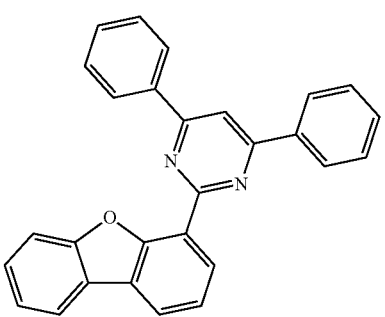 [SMILES: c1ccc(-c2cc(-c3ccccc3)nc(-c3cccc4c3oc3ccccc34)n2)cc1] | 72% |

Example 2

Synthesis of bis(biphenyl-4-yl)dibenzofuran-4-ylamine

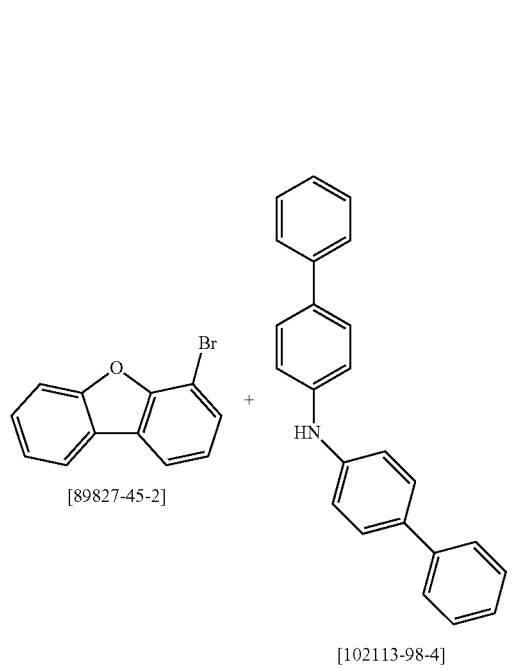

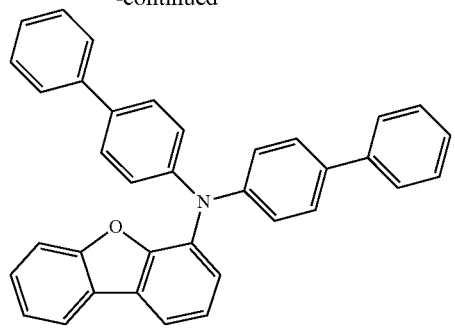

A degassed solution of 36.6 g (147 mmol) of 4-bromodibenzofuran and 39.5 g (123 mmol) of bis(biphenyl-4-yl)amine in 600 mL of toluene is saturated with $N_2$ for 1 h. Added to the solution thereafter are first 2.09 mL (8.6 mmol) of $P(tBu)_3$, then 1.38 g (6.1 mmol) of palladium(II) acetate, and then 17.7 g (185 mmol) of NaOtBu in the solid state. The reaction mixture is heated under reflux for 1 h. After cooling to room temperature, 500 mL of water are added cautiously. The aqueous phase is washed with 3×50 mL of toluene, dried over $M_gSO_4$, and the solvent is removed under reduced pressure. Thereafter, the crude product is purified by chromatography using silica gel with heptane/ethyl acetate (20:1).

The yield is 57.7 g (118 mmol), corresponding to 80% of theory.

In an analogous manner, it is possible to obtain the following compounds:

| Reactant 1 | Reactant 2 | Product | Yield |
|---|---|---|---|
| | | | 90% |

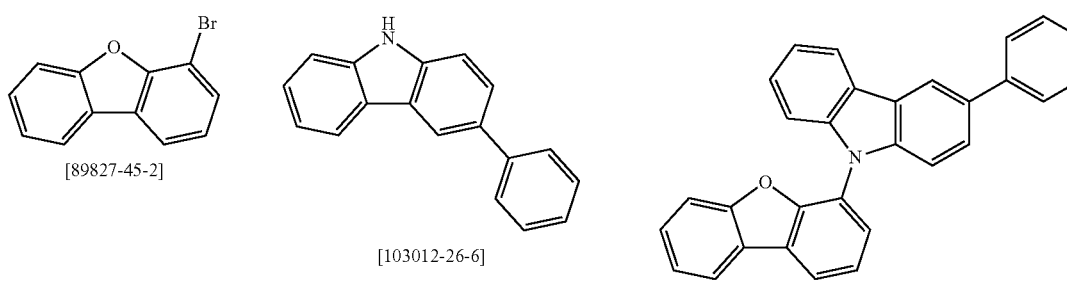

| | | | 87% |

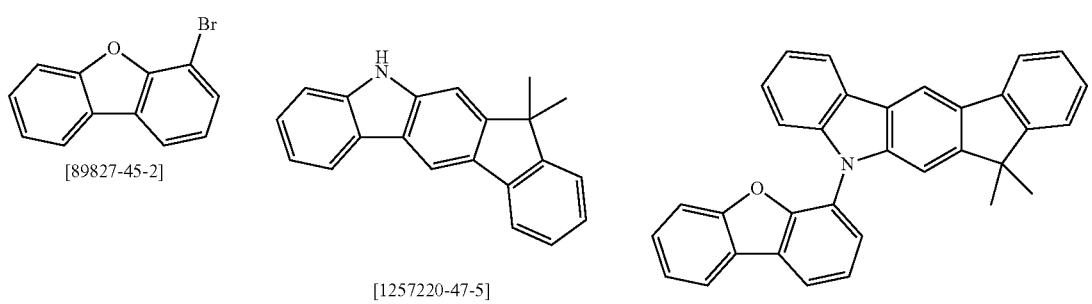

| Reactant 1 | Reactant 2 | Product | Yield |
|---|---|---|---|
| [89827-45-2] | [1060735-14-9] | | 83% |
| [89827-45-2] | [1024598-06-8] | | 57% |
| [89827-45-2] | | | 93% |

Example 3

Synthesis of 9-phenyl-3-(6-trimethylsilanyldibenzofuran-4-yl)-9H-carbazole

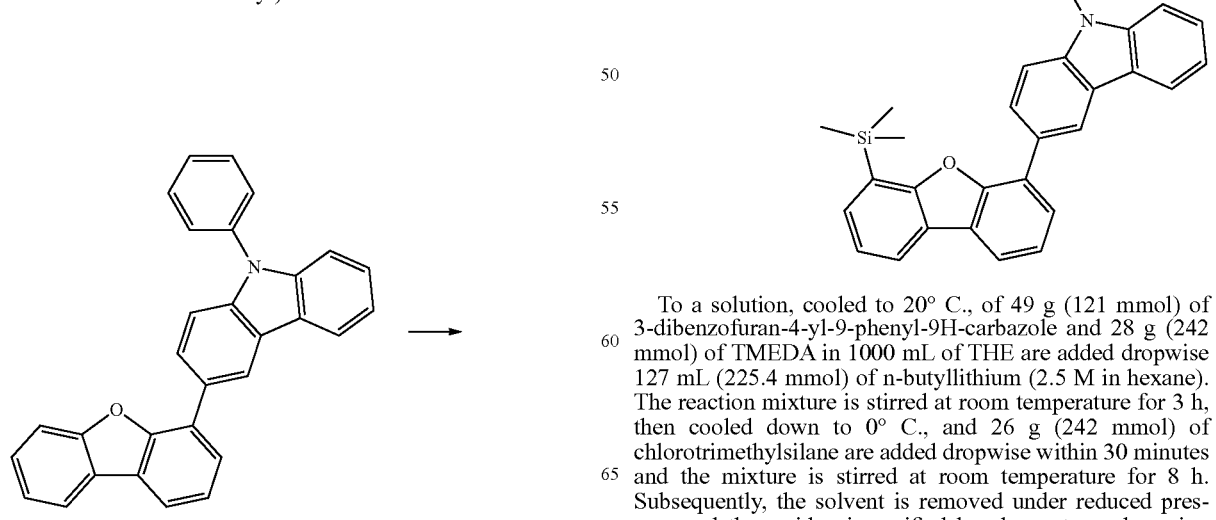

To a solution, cooled to 20° C., of 49 g (121 mmol) of 3-dibenzofuran-4-yl-9-phenyl-9H-carbazole and 28 g (242 mmol) of TMEDA in 1000 mL of THF are added dropwise 127 mL (225.4 mmol) of n-butyllithium (2.5 M in hexane). The reaction mixture is stirred at room temperature for 3 h, then cooled down to 0° C., and 26 g (242 mmol) of chlorotrimethylsilane are added dropwise within 30 minutes and the mixture is stirred at room temperature for 8 h. Subsequently, the solvent is removed under reduced pressure and the residue is purified by chromatography using silica gel with chloroform as eluent. Yield: 34 g (72 mmol), 60% of theory.

In an analogous manner, it is possible to obtain the following compounds:

| Reactant 1 | Product | Yield |
|---|---|---|
| | | 81% |
| | | 83% |
| | | 88% |

-continued

| Reactant 1 | Product | Yield |
|---|---|---|
| | | 84% |
| | | 88% |
| | | 70% |
| | | 86% |
| | | 79% |

-continued

| Reactant 1 | Product | Yield |
|---|---|---|
| | | 75% |
| | | 72% |
| | | 65% |
| | | 64% |
| | | 63% |

Example 4

Synthesis of B-[6-(phenyl-9H-carbazol-3-yl)-4-dibenzofuranyl]boronic acid

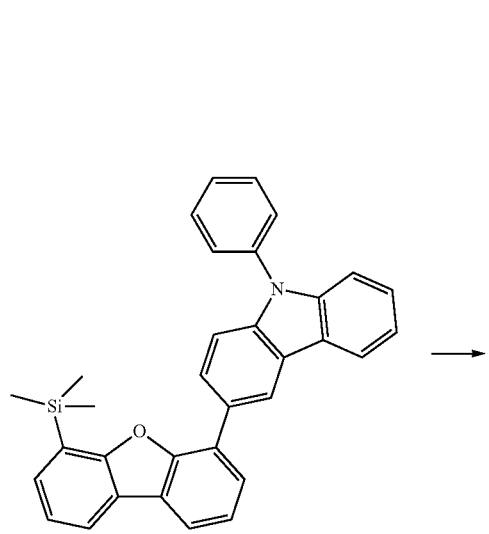 → 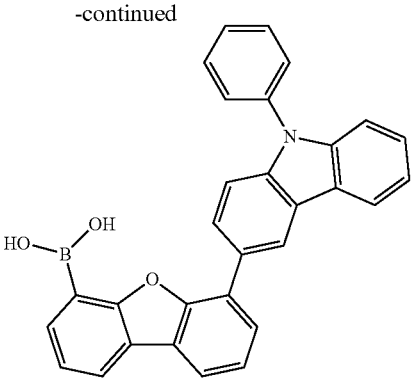

Under protective gas, 21 g (86 mmol) of bromine tribromide are added dropwise to a solution of 34 g (72 mmol) of N-phenyl-3-(6-trimethylsilanyldibenzofuran-4-yl)-9H-carbazole in 500 mL of dichloromethane and the mixture is stirred at room temperature for 10 h. Thereafter, a little water is added gradually to the mixture and the precipitated residue is filtered off and washed with heptane. The yield is 28 g (62 mmol), corresponding to 86% of theory.

In an analogous manner, it is possible to obtain the following compounds:

| Reactant 1 | Product | Yield |
|---|---|---|
|  |  | 84% |
| 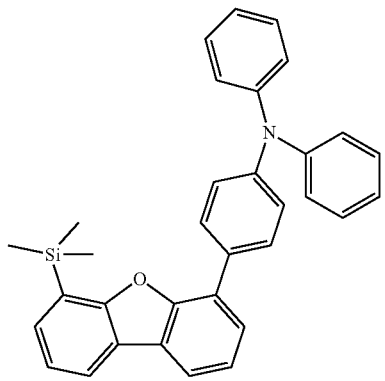 [SMILES: C[Si](C)(C)c1cccc2c1oc1c(-c3ccc(N(c4ccccc4)c4ccccc4)cc3)cccc12] | 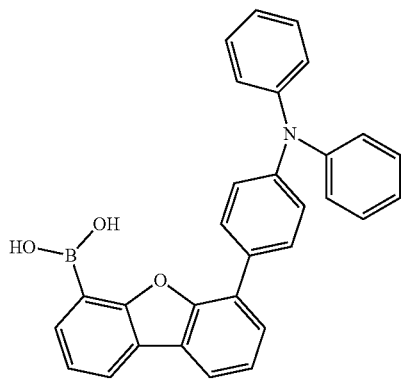 [SMILES: OB(O)c1cccc2c1oc1c(-c3ccc(N(c4ccccc4)c4ccccc4)cc3)cccc12] |  |
|  |  | 84% |
| 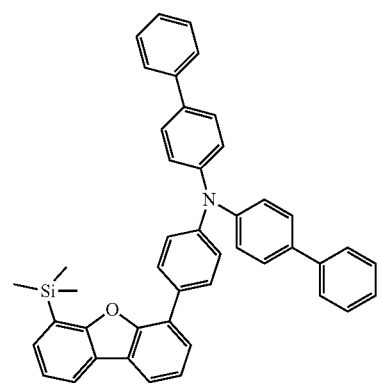 [SMILES: C[Si](C)(C)c1cccc2c1oc1c(-c3ccc(N(c4ccc(-c5ccccc5)cc4)c4ccc(-c5ccccc5)cc4)cc3)cccc12] | 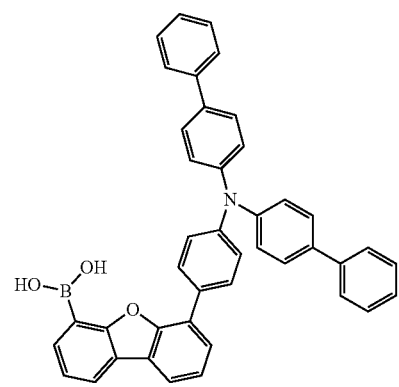 [SMILES: OB(O)c1cccc2c1oc1c(-c3ccc(N(c4ccc(-c5ccccc5)cc4)c4ccc(-c5ccccc5)cc4)cc3)cccc12] |  |

| Reactant 1 | Product | Yield |
|---|---|---|
| | | 81% |
| | | 87% |
| | | 86% |
| | | 79% |
| | | 78% |

-continued

| Reactant 1 | Product | Yield |
|---|---|---|
| | | 83% |
| | | 85% |
| | | 81% |
| | | 78% |
| | | 69% |

| Reactant 1 | Product | Yield |
|---|---|---|
| | | 78% |
| | | 78% |

Example 5

Synthesis of B-[6-(phenyl-9H-carbazol-3-yl)-4-dibenzofuranyl]boronic acid

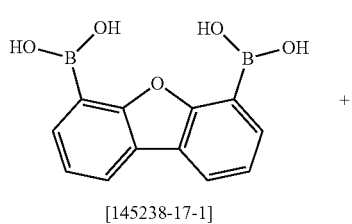

[145238-17-1]

+

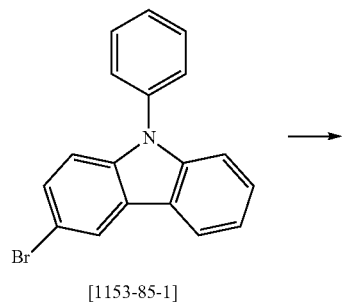

[1153-85-1]

→

-continued

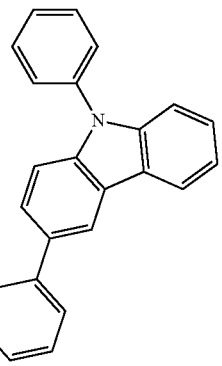

9 g (32 mmol) of B,B'-4,6-dibenzofurandiylbisboronic acid, 15 g (31.6 mmol) of 3-bromo-9-phenyl-9H-carbazole and 31 mL (63 mmol) of $Na_2CO_3$ (2 M solution) are suspended in 120 mL of toluene and 120 mL of ethanol. 0.73 g (0.63 mmol) of $Pd(PPh_3)_4$ are added to this suspension, and the reaction mixture is heated under reflux for 16 h. After cooling, the organic phase is removed, filtered through silica gel, washed three times with 200 mL of water and then concentrated to dryness. The residue is recrystallized from toluene. The yield is 11.1 g (24 mmol), corresponding to 70% of theory.

In an analogous manner, it is possible to obtain the following compounds:

| Reactant 1 | Reactant 2 | Product | Yield |
|---|---|---|---|
| 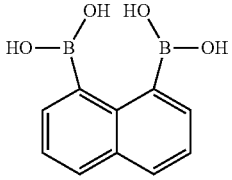 [947617-22-3] | 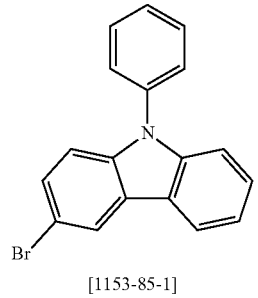 [SMILES: Brc1ccc2c(c1)c1ccccc1n2-c1ccccc1] [1153-85-1] | 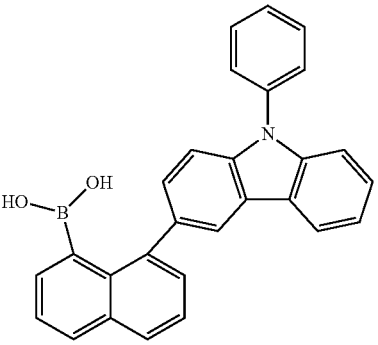 [SMILES: OB(O)c1cccc2cccc(-c3ccc4c(c3)c3ccccc3n4-c3ccccc3)c12] | 85% |
| 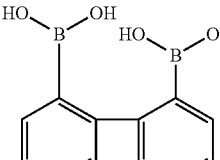 [480438-76-4] | 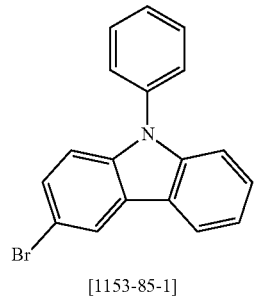 [SMILES: Brc1ccc2c(c1)c1ccccc1n2-c1ccccc1] [1153-85-1] | 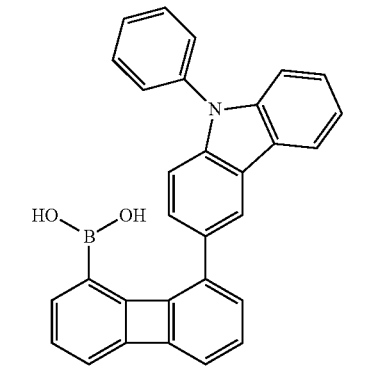 [SMILES: OB(O)c1cccc2c1-c1c(-c3ccc4c(c3)c3ccccc3n4-c3ccccc3)cccc1-2] | 69% |
| 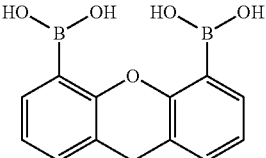 [862159-27-1] | 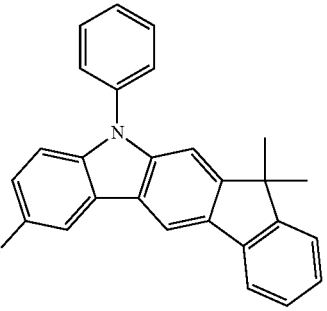 [1257220-44-2] | 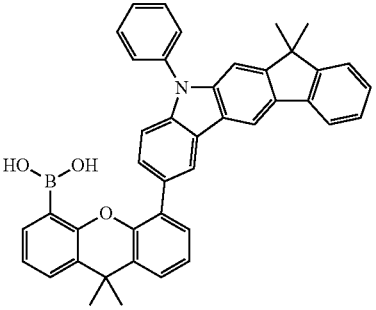 [SMILES: CC1(C)c2ccccc2-c2cc3c4cc(-c5cccc6c5Oc5c(B(O)O)cccc5C6(C)C)ccc4n(-c4ccccc4)c3cc21] | 74% |
Example 6
Synthesis of
3-(6-bromodibenzofuran-4-yl)-9-phenyl-9H-carbazole
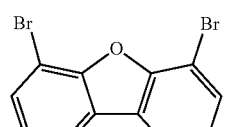
[201138-91-2]
+
-continued
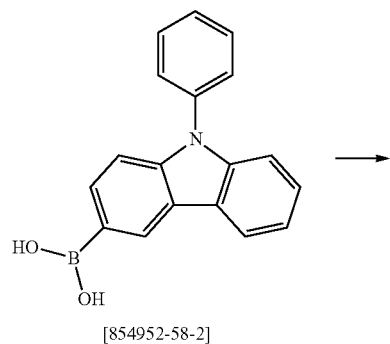
[854952-58-2]
→

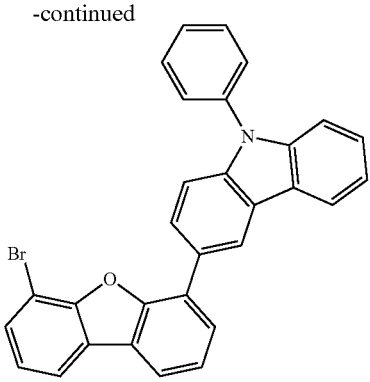

10.43 g (32 mmol) of B-(9-phenyl-9H-carbazol-3-yl) boronic acid, 8.9 g (31.6 mmol) of 4,6-dibromodibenzofuran and 31 mL (63 mmol) of $Na_2CO_3$ (2 M solution) are suspended in 120 mL of toluene and 120 mL of ethanol. 0.73 g (0.63 mmol) of $Pd(PPh_3)_4$ is added to this suspension, and the reaction mixture is heated under reflux for 16 h. After cooling, the organic phase is removed, filtered through silica gel, washed three times with 200 mL of water and then concentrated to dryness. The residue is recrystallized from toluene. The yield is 11.4 g (23 mmol), corresponding to 73% of theory.

In an analogous manner, it is possible to obtain the following compounds:

| Reactant 1 | Reactant 2 | Product | Yield |
|---|---|---|---|
| [669773-34-6] | [1379585-25-7] | | 51% |
| [69414-97-7] | [854952-58-2] | | 65% |
| [1262398-42-4] | [854952-58-2] | | 69% |

-continued
| Reactant 1 | Reactant 2 | Product | Yield |
|---|---|---|---|
| 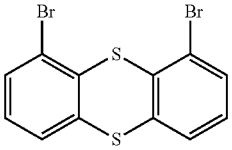 [176646-34-7] | 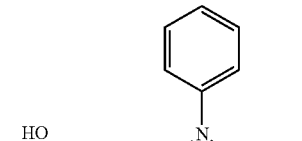 [1001911-63-2] | 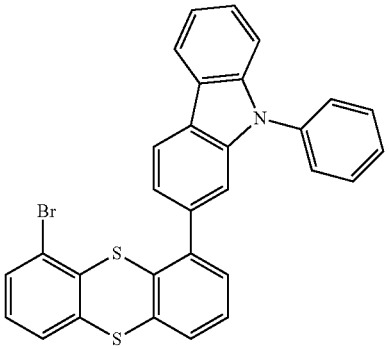 [SMILES: Brc1cccc2c1Sc1c(cccc1-c1ccc3c4ccccc4n(-c4ccccc4)c3c1)S2] | 67% |
| 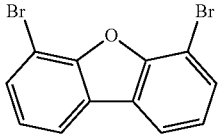 [201138-91-2] | 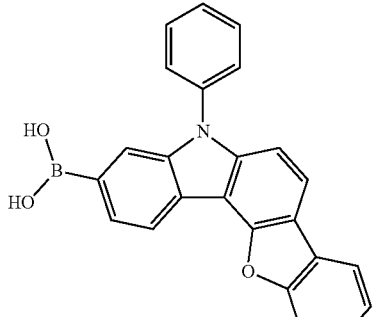 [1391729-62-6] | 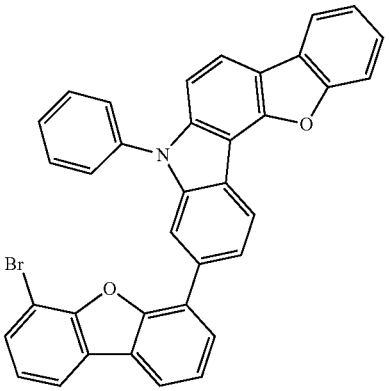 [SMILES: Brc1cccc2c1oc1c(-c3ccc4c5c6oc7ccccc7c6ccc5n(-c5ccccc5)c4c3)cccc12] | 62% |
| 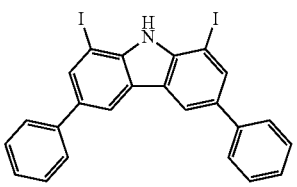 [501330-43-4] | 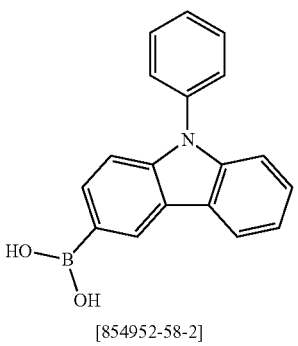 [SMILES: OB(O)c1ccc2c(c1)c1ccccc1n2-c1ccccc1] [854952-58-2] | 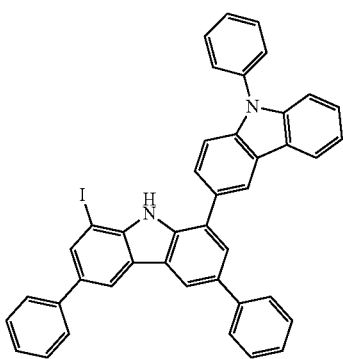 [SMILES: Ic1cc(-c2ccccc2)cc2c1[nH]c1c(-c3ccc4c(c3)c3ccccc3n4-c3ccccc3)cc(-c3ccccc3)cc12] | 62% |
| 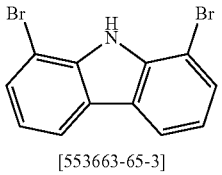 [SMILES: Brc1cccc2c1[nH]c1c(Br)cccc12] [553663-65-3] | 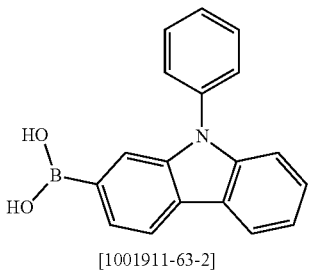 [SMILES: OB(O)c1ccc2c3ccccc3n(-c3ccccc3)c2c1] [1001911-63-2] | 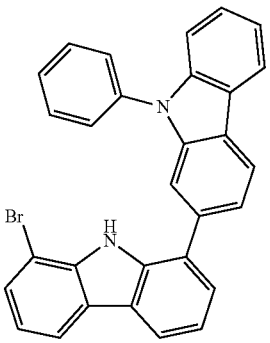 [SMILES: Brc1cccc2c1[nH]c1c(-c3ccc4c5ccccc5n(-c5ccccc5)c4c3)cccc12] | 61% |

-continued

| Reactant 1 | Reactant 2 | Product | Yield |
|---|---|---|---|
| [905702-33-2] | [854952-58-2] | | 64% |
| [502764-54-7] | [854952-58-2] | | 66% |
| [553663-65-3] | [854952-58-2] | | 56% |

In an analogous manner, it is also possible to obtain the following compounds by a second addition with the appropriate boronic acids: The residue is recrystallized from toluene and finally sublimed under high vacuum ($p=5\times10^{-5}$ mbar).

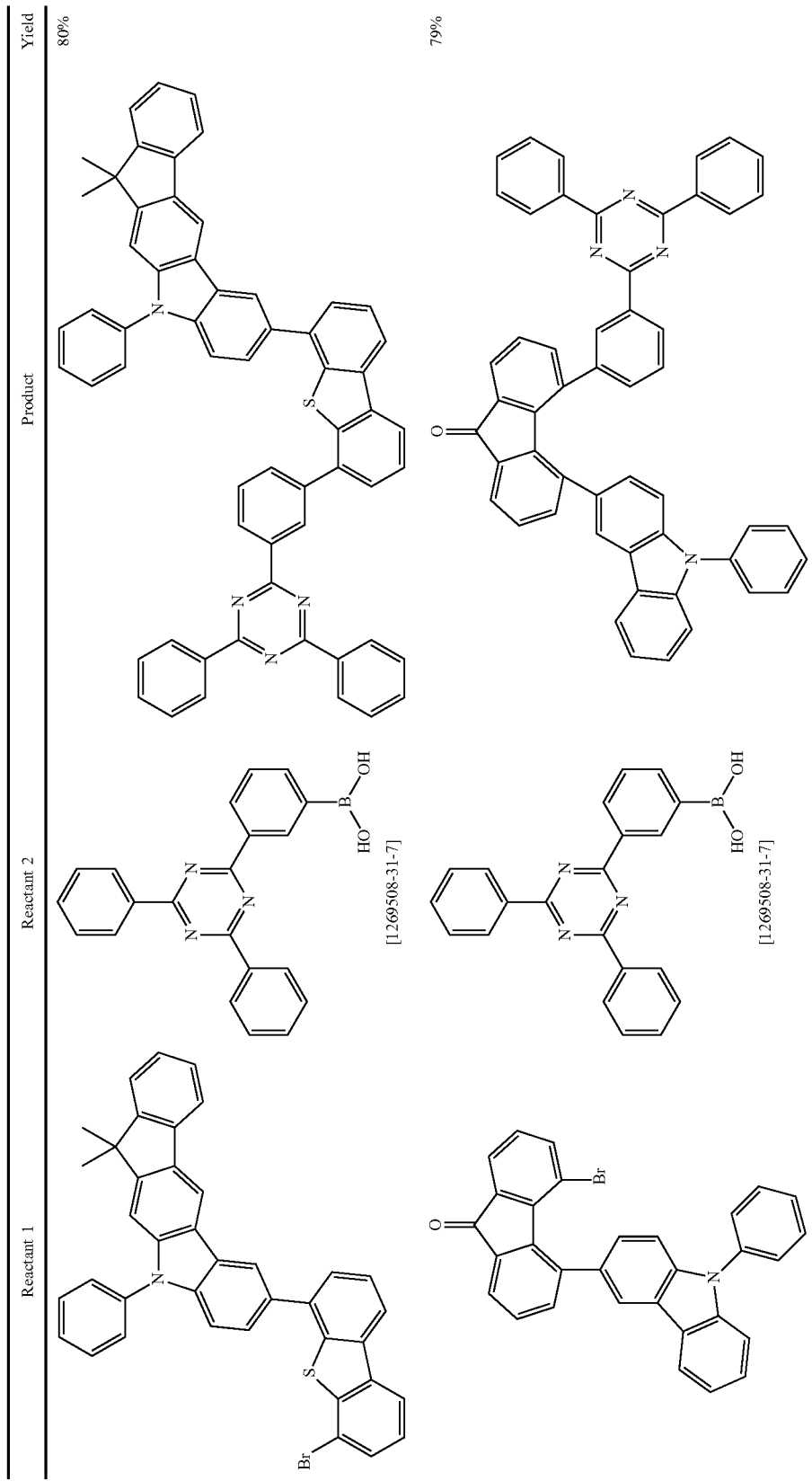

-continued
| Reactant 1 | Reactant 2 | Product | Yield |
|---|---|---|---|
| 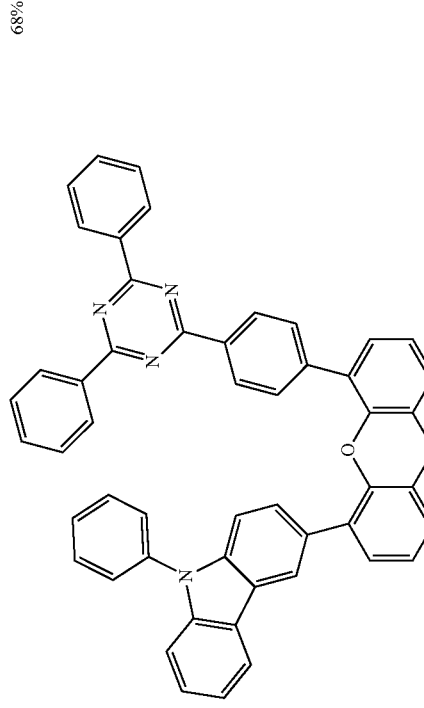 | 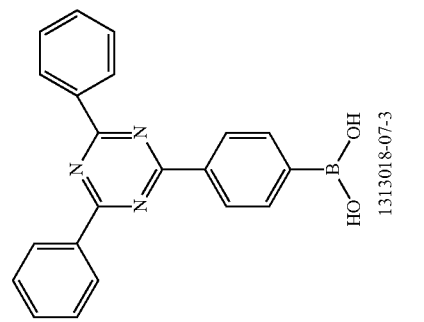 1313018-07-3 | 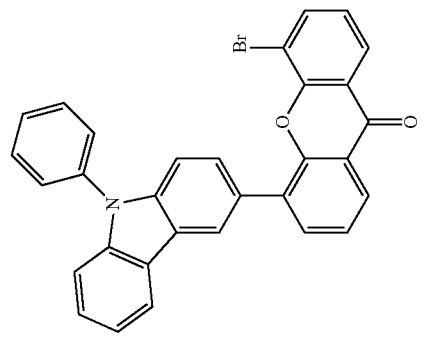 | 68% |
| 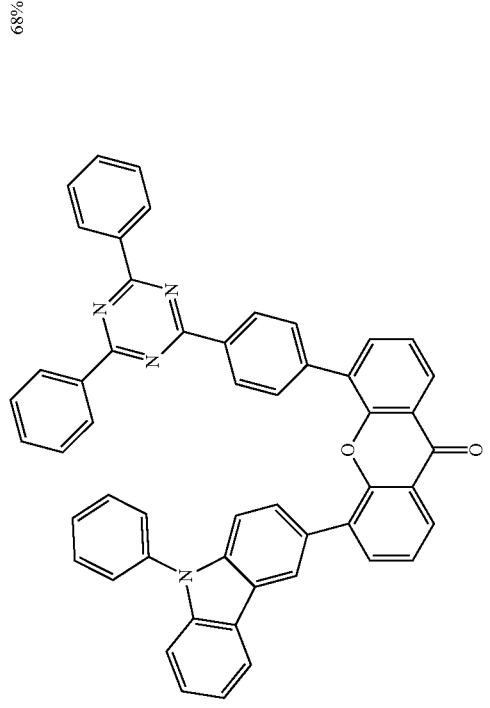 | 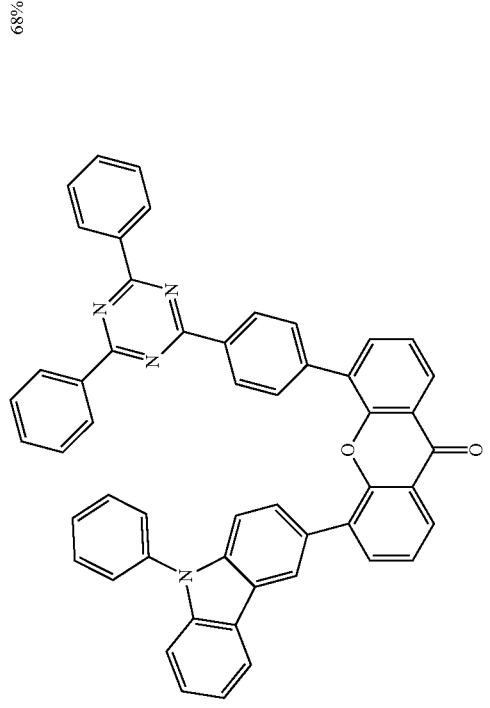 [1269508-31-7] | 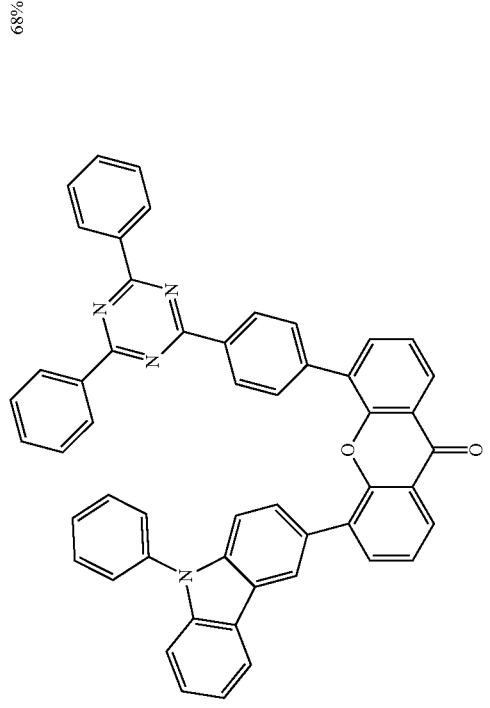 | 78% |

-continued
| Reactant 1 | Reactant 2 | Product | Yield |
|---|---|---|---|
| 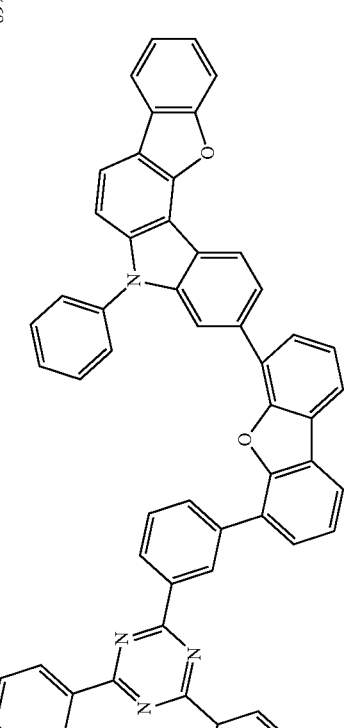 | 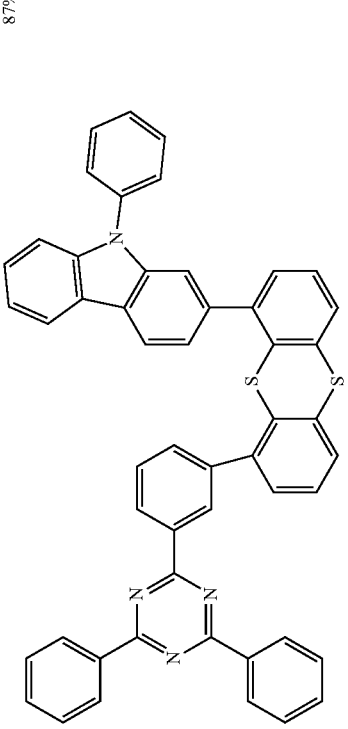 [1269508-31-7] | 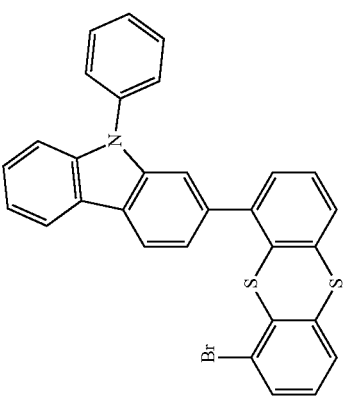 | 87% |
| 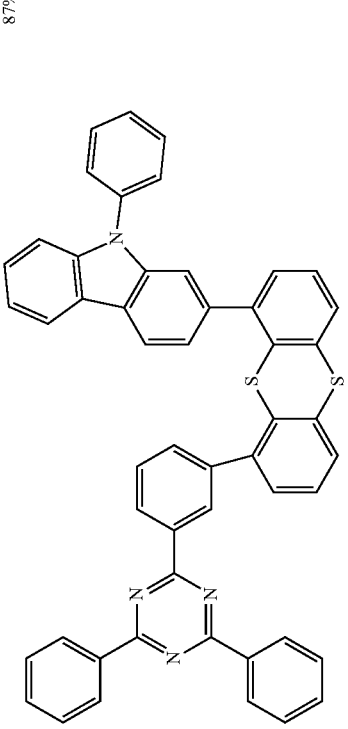 | 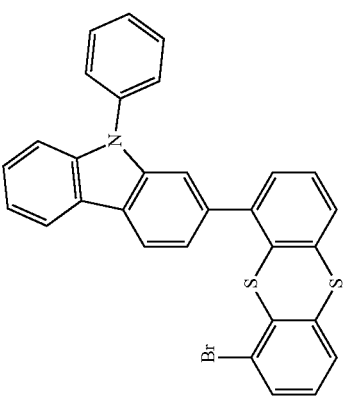 [1381862-91-4] | 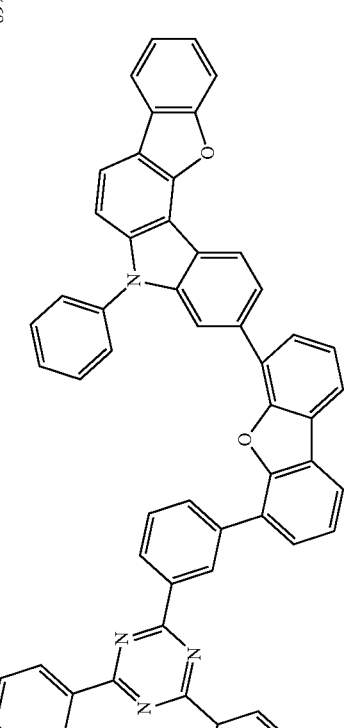 | 89% |

-continued

| Reactant 1 | Reactant 2 | Product | Yield |
|---|---|---|---|
| | [1381862-91-4] | | 87% |
| | [1269508-31-7] | | 83% |

| Reactant 1 | Reactant 2 | Product | Yield |
|---|---|---|---|
| 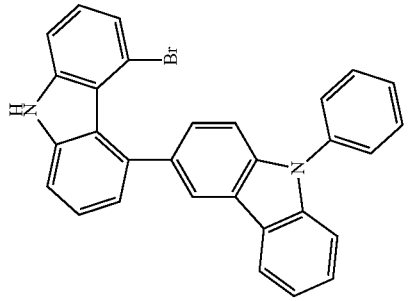 | 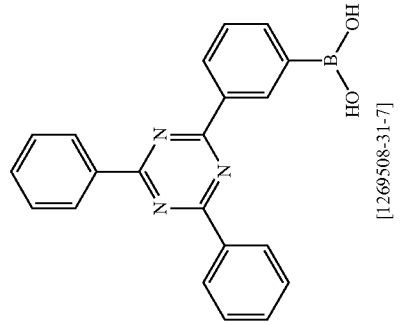 | 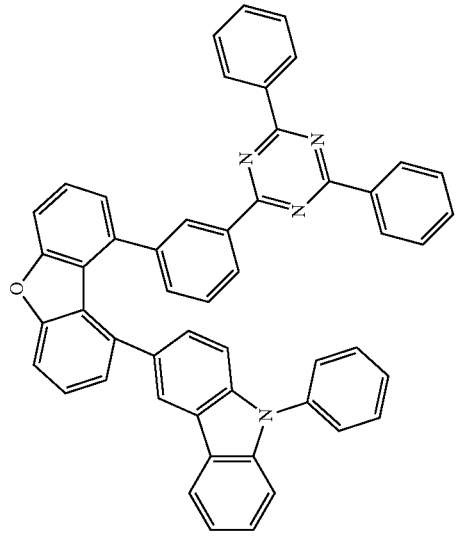 | 80% |
| 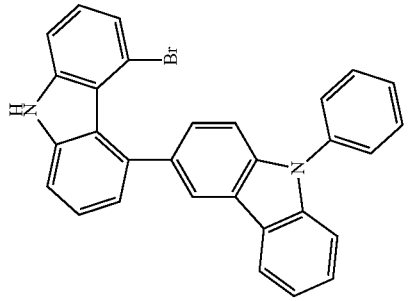 | 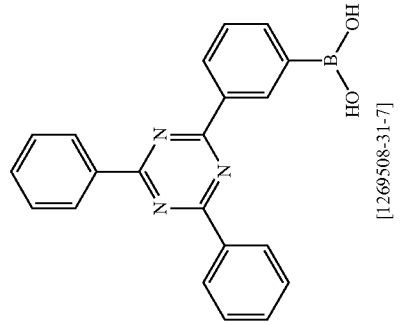 | 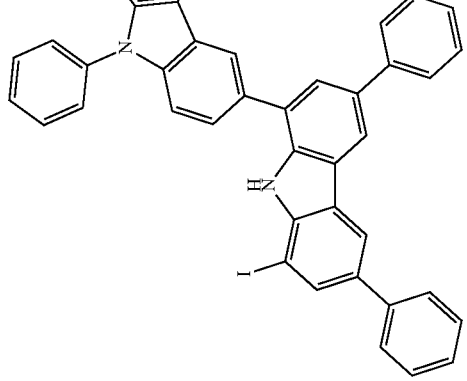 | 79% |

-continued

| Reactant 1 | Reactant 2 | Product | Yield |
|---|---|---|---|
| (9-phenyl-carbazole with Br and carbazole-H substituent) | (4,6-diphenyl-1,3,5-triazin-2-yl)phenylboronic acid, 1313018-07-3 | (macrocyclic product) | 79% |

Example 7
Synthesis of 3-{6-[3-(4,6-diphenyl-[1,3,5]triazin-2-yl)phenyl]dibenzofuran-4-yl}-9-phenyl-9H-carbazole
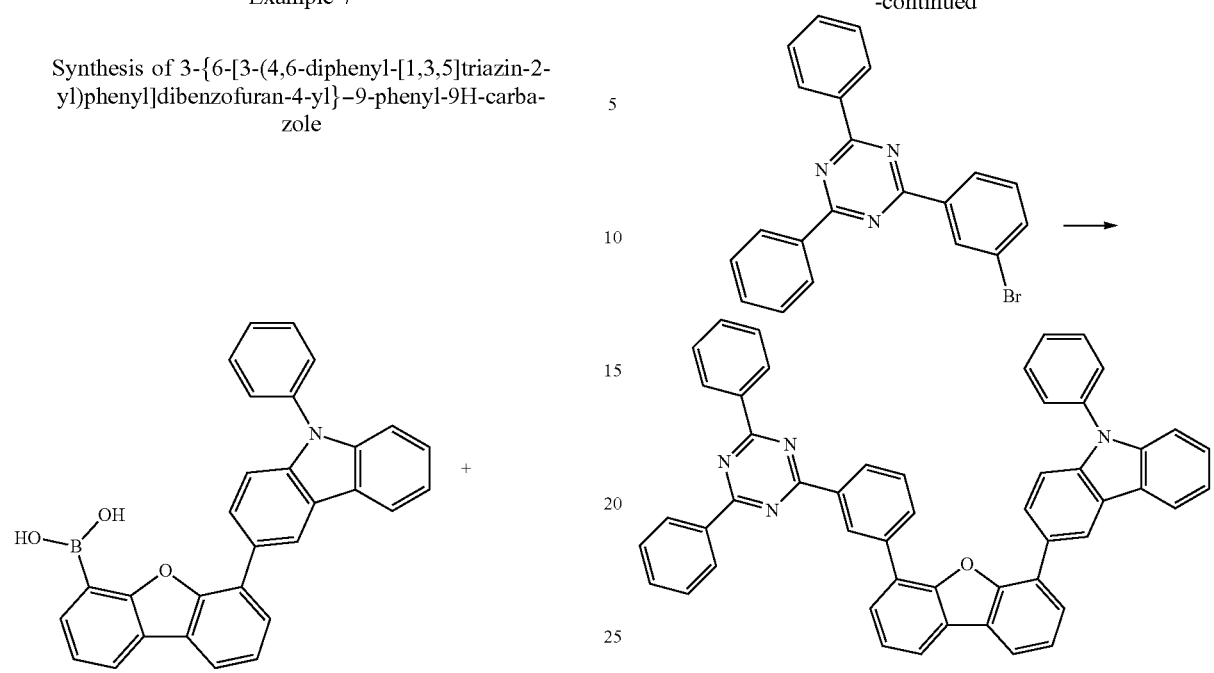

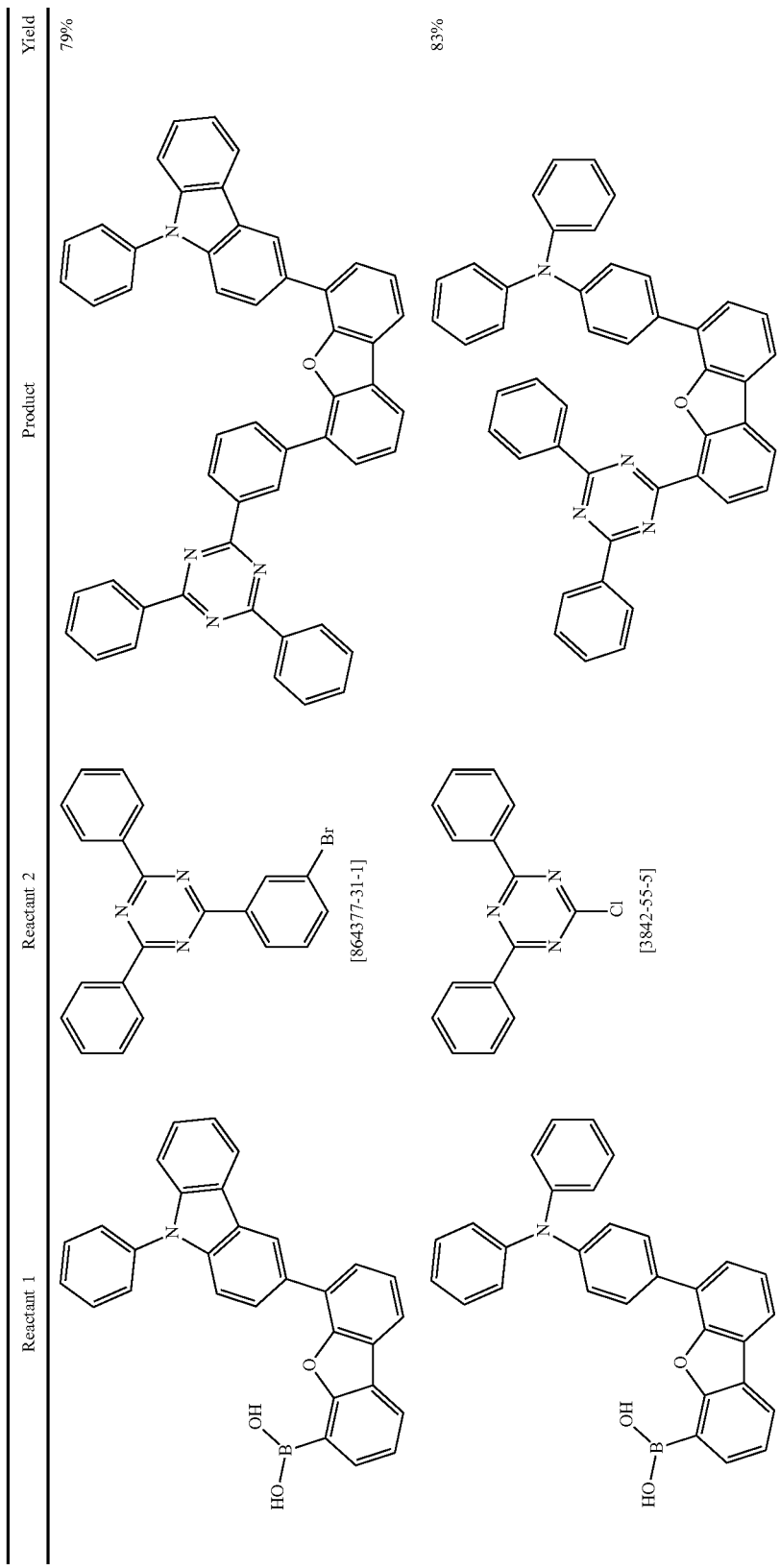

-continued

| Reactant 1 | Reactant 2 | Product | Yield |
|---|---|---|---|
| (dibenzofuran-boronic acid with bis-biphenylamine substituent) | 2-chloro-4,6-diphenylpyrimidine [2915-16-4] | (coupled product) | 86% |
| (dibenzofuran-boronic acid with carbazole substituent) | 2-(3-bromophenyl)-4,6-diphenyl-1,3,5-triazine [864377-31-1] | (coupled product) | 89% |

-continued

| Reactant 1 | Reactant 2 | Product | Yield |
|---|---|---|---|
| (dibenzofuran-phenyl-dibenzothiophene boronic acid) | [3842-55-5] | | 80% |
| (dibenzofuran-carbazole boronic acid) | [864377-22-0] | | 79% |

| Reactant 1 | Reactant 2 | Product | Yield |
|---|---|---|---|
| | [864377-22-0] | | 84% |
| | [864377-31-1] | | 79% |

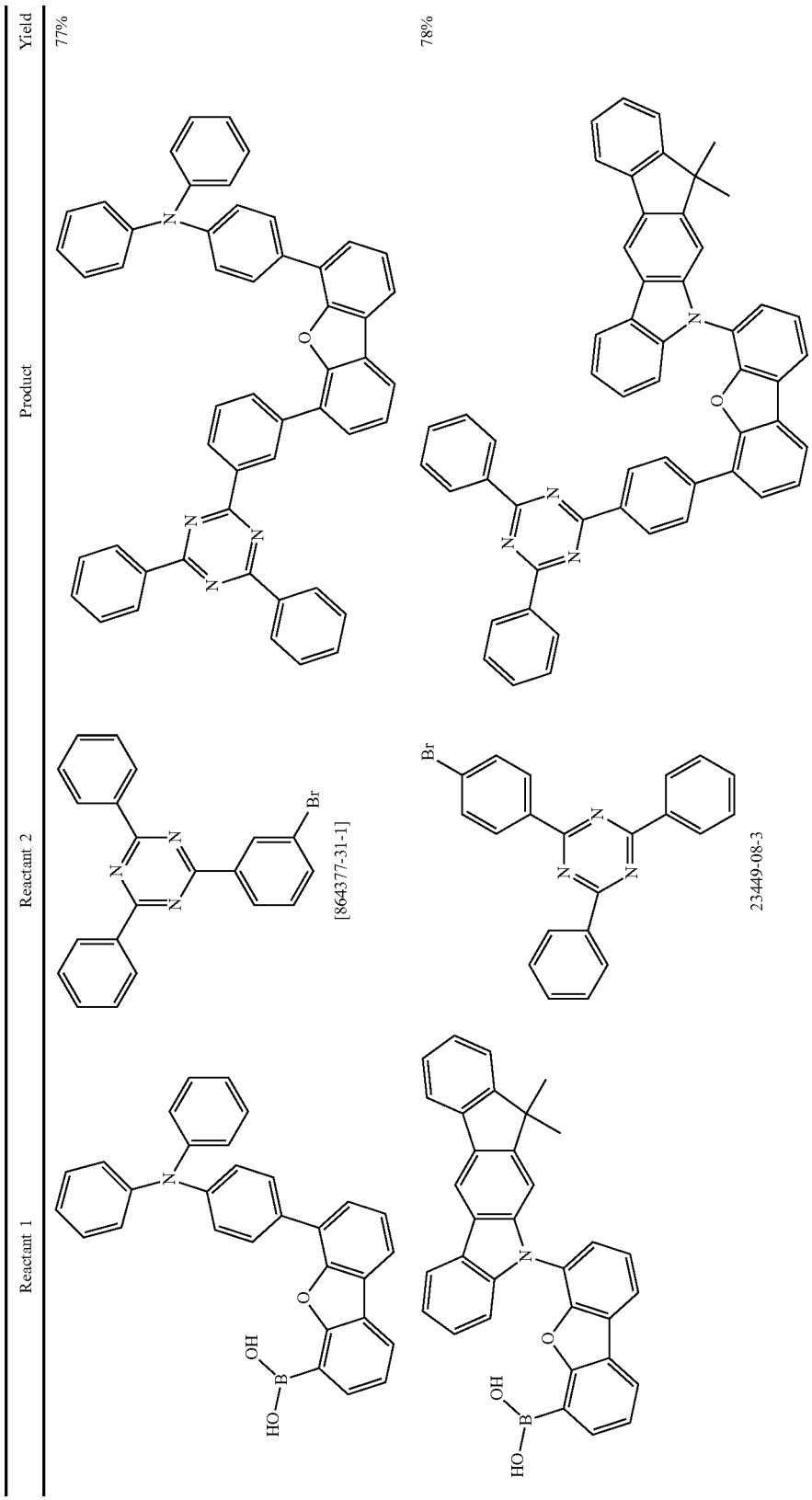

-continued

| Reactant 1 | Reactant 2 | Product | Yield |
|---|---|---|---|
| | [864377-31-1] | | 79% |
| | 77989-15-2 | | 75% |
| | [864377-22-0] | | 74% |

-continued

| Reactant 1 | Reactant 2 | Product | Yield |
|---|---|---|---|
|  | 77989-15-2 |  | 59% |
|  | [864377-31-1] |  | 67% |

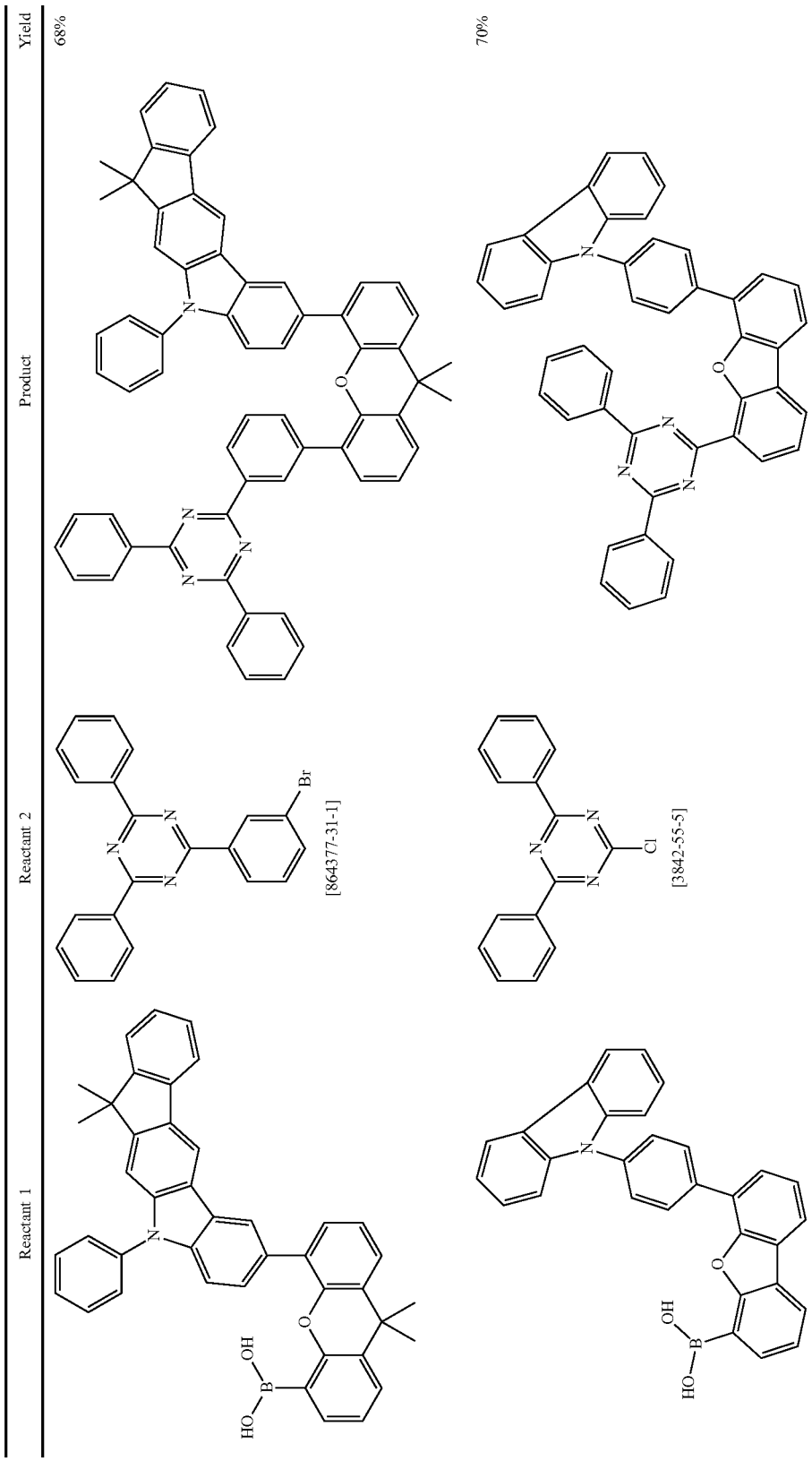

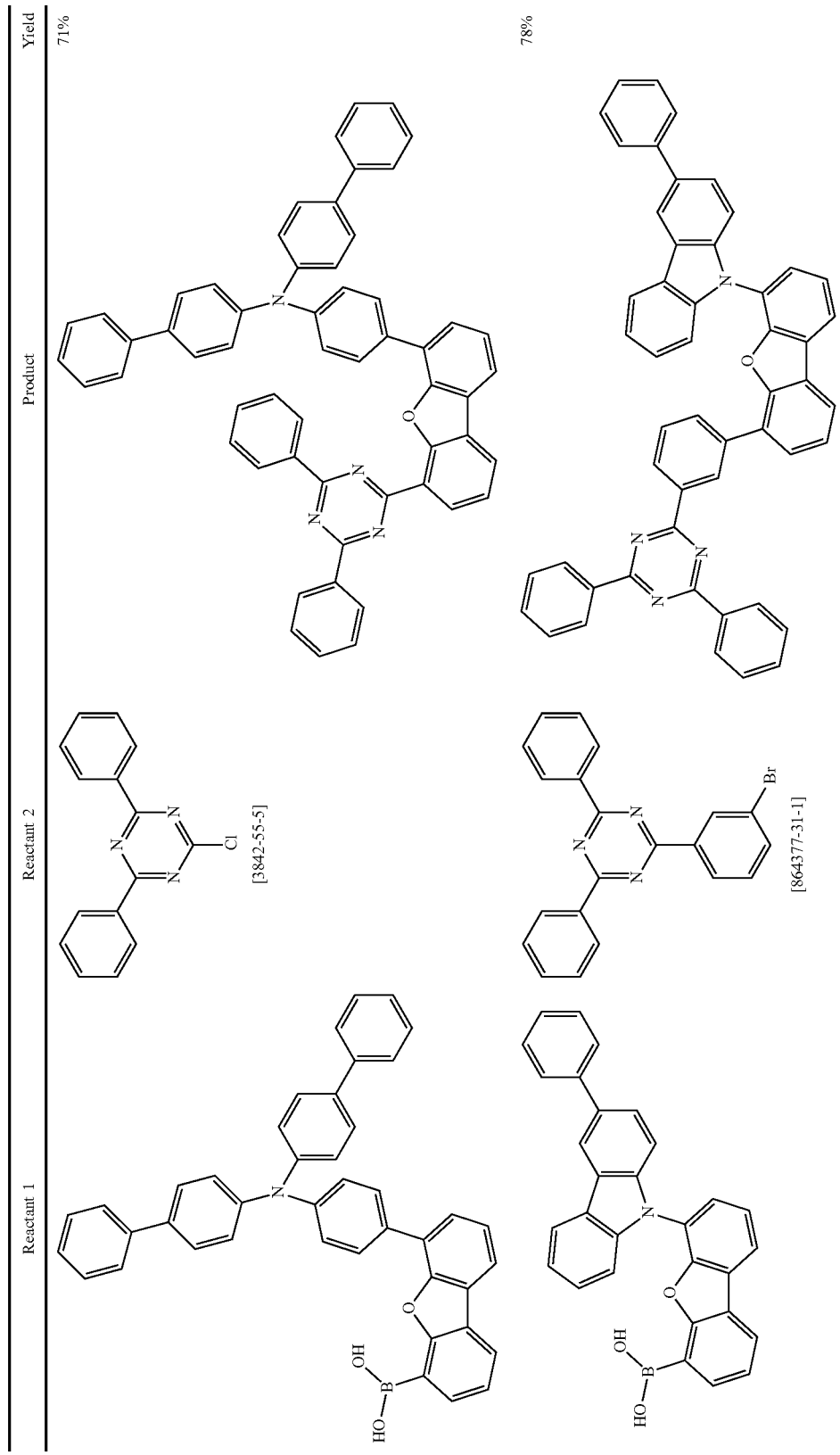

| Reactant 1 | Reactant 2 | Product | Yield |
|---|---|---|---|
| (9-phenylcarbazol-2-yl)-dibenzofuran-6-boronic acid | 2-(4-bromophenyl)-4,6-diphenylpyrimidine [23449-08-3] | | 78% |
| (9H-carbazol-9-yl)-dibenzofuran-6-boronic acid | 2-(4-bromophenyl)-4,6-diphenylpyrimidine [23449-08-3] | | 73% |

| Reactant 1 | Reactant 2 | Product | Yield |
|---|---|---|---|
| (9-phenylcarbazol-2-yl)-dibenzofuran-boronic acid | 2-(3-bromophenyl)-4,6-diphenylpyrimidine [864377-22-0] | coupled product | 79% |

Example 8

Synthesis of 9,9'-diphenyl-8-(3-{4-phenyl-6-[(E)-((Z)-1-propenyl)-buta-1,3-dienyl]-[1,3,5]triazin-2-yl}-phenyl)-9H,9'H-[1,2']bicarbazolyl

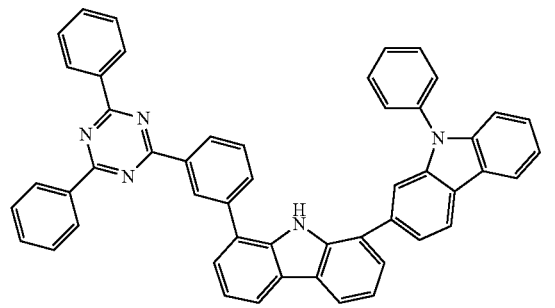

+

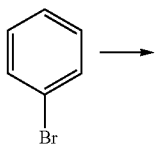

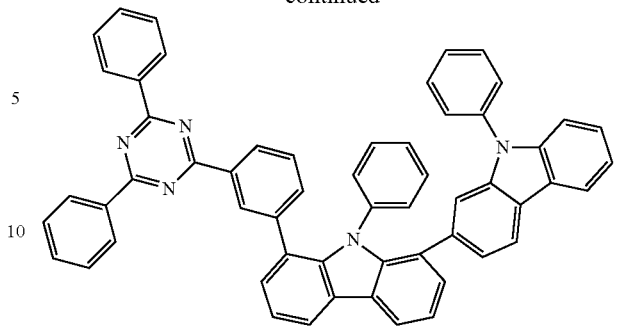

50 g (70.58 mmol) of 8-[3-(4,6-diphenyl-[1,3,5]triazin-2-yl)-phenyl]-9'-phenyl-9H,9'H-[1,2']bicarbazolyl and 16.4 g (105.87 mmol) of bromobenzene are dissolved in toluene and degassed by means of introduction of protective gas. This is followed by addition of 7 mL (7 mmol, 1 M solution in toluene) of tri-tert-butylphosphine, 633.8 mg (2.82 mmol) of Pd(OAc)$_2$ and 10.2 g (105.87 mmol) of NaOtBu. The solids are degassed beforehand, and the reaction mixture is post-degassed and then stirred under reflux for 3 h. The warm reaction solution is filtered through Alox B (activity level 1), washed with water, dried and concentrated. The yield is 42 g (53 mmol), corresponding to 77% of theory. The residue is recrystallized from toluene and finally sublimed under high vacuum (p=5×10$^{-5}$ mbar). The purity is 99.9%.

In an analogous manner, it is possible to obtain the following compounds:

| Reactant 1 | Reactant 2 | Product | Yield |
|---|---|---|---|
| | | | 79% |
| | | | 80% |

-continued

| Reactant 1 | Reactant 2 | Product | Yield |
|---|---|---|---|
| 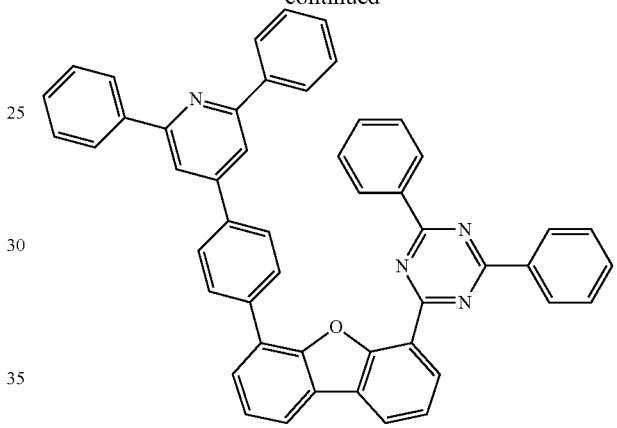 | | | 80% |

Example 9

Synthesis of 2-{6-[4-(2,6-diphenylpyridin-4-yl)phenyl]dibenzofuran-4-yl}-4,6-diphenyl[1,3,5]triazine

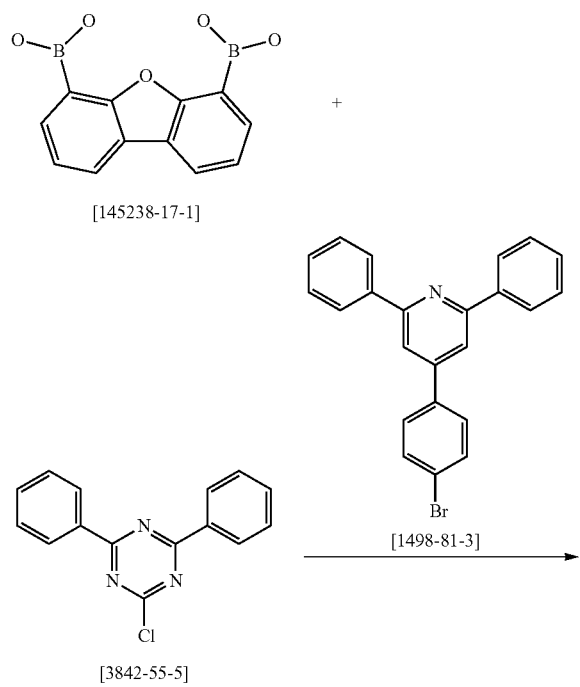

9 g (32 mmol) of B,B'-4,6-dibenzofurandiylbisboronic acid, 6.5 g (31.6 mmol) of 2-chloro-4,6-diphenyl[1,3,5]triazine and 31 mL (63 mmol) of $Na_2CO_3$ (2 M solution) are suspended in 120 mL of toluene and 120 mL of ethanol. 0.73 g (0.63 mmol) of $Pd(PPh_3)_4$ is added to this suspension, and the reaction mixture is heated under reflux for 8 h. Subsequently, 6.5 g (31.6 mmol) of 4-(4-bromophenyl)-2,6-diphenylpyridine are added and the mixture is heated under reflux for a further 8 h. After cooling, the organic phase is removed, filtered through silica gel, washed three times with 200 mL of water and then concentrated to dryness. The residue is recrystallized from toluene. The yield is 19.1 g (26 mmol), corresponding to 77% of theory.

In an analogous manner, it is possible to obtain the following compounds:

In the case of a symmetric compound, first 0.5 eq of reactant 2 and then 0.5 eq of reactant 3 are added.

| Reactant 1<br>1 eq. | Reactant 2<br>0.5 eq. | Reactant 3<br>0.5 eq. | Product | Yield |
|---|---|---|---|---|
| 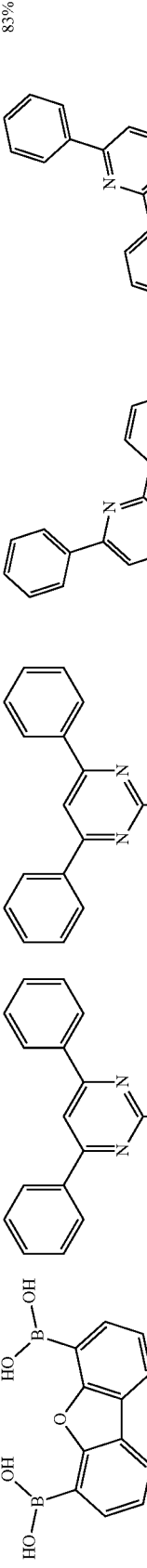 | 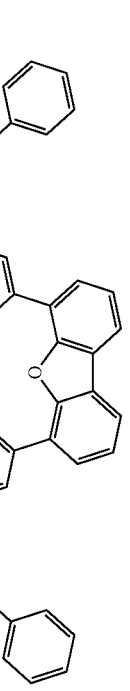 |  | 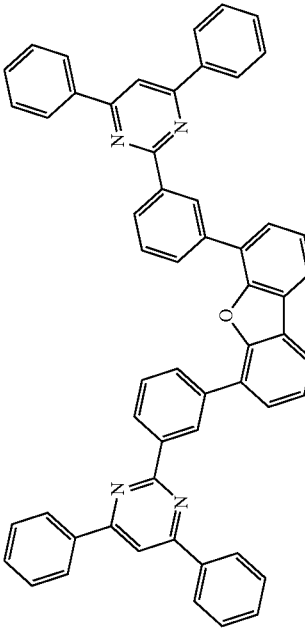 | 83% |
| 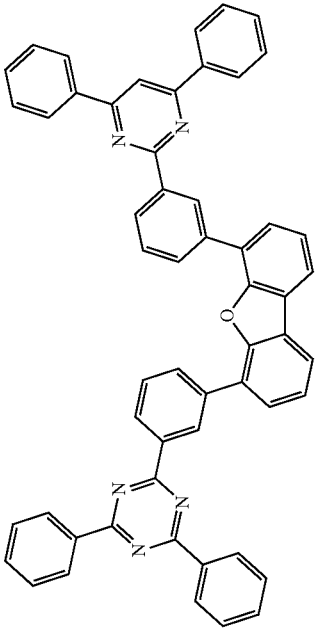 | 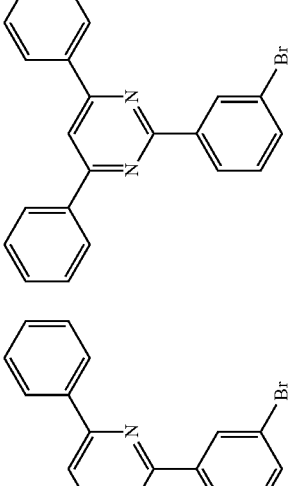 | 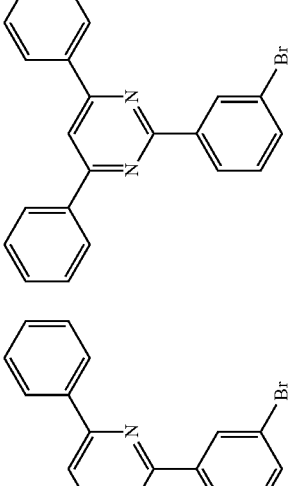 | 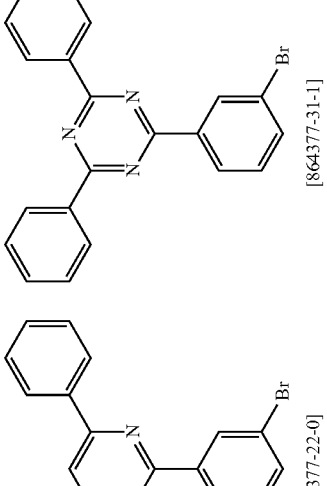 | 79% |

| Reactant 1<br>1 eq. | Reactant 2<br>0.5 eq. | Reactant 3<br>0.5 eq. | Product | Yield |
|---|---|---|---|---|
| 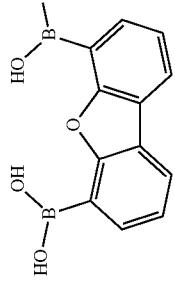 [145238-17-1] | 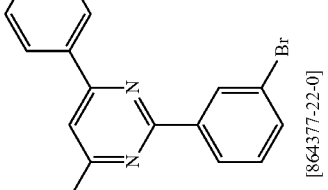 [864377-31-1] | 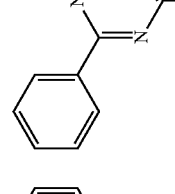 [3842-55-5] | 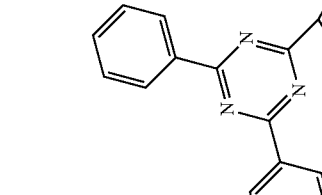 | 69% |
| 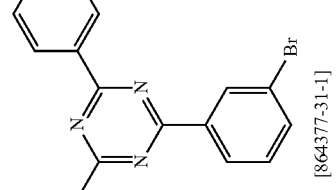 [862159-27-1] | 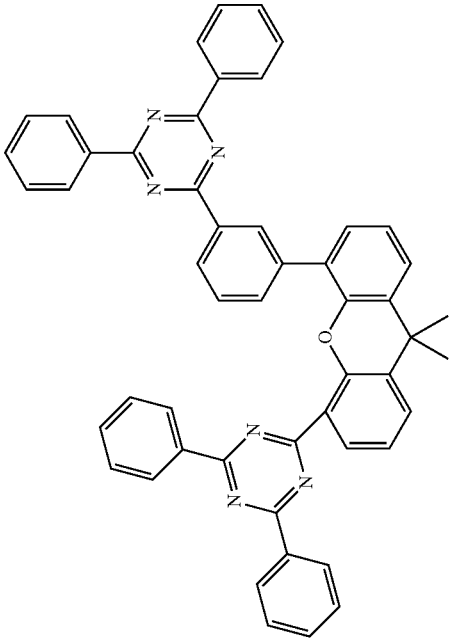 [864377-22-0] | 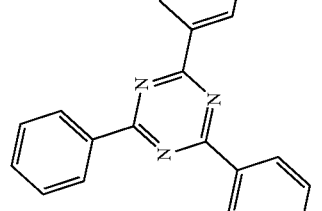 [864377-31-1] | 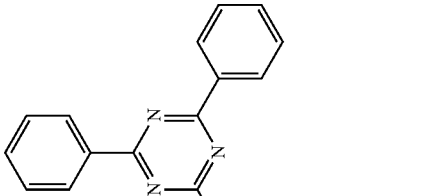 | 71% |

-continued
| Reactant 1<br>1 eq. | Reactant 2<br>0.5 eq. | Reactant 3<br>0.5 eq. | Product | Yield |
|---|---|---|---|---|
| 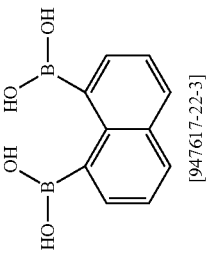 [947617-22-3] | 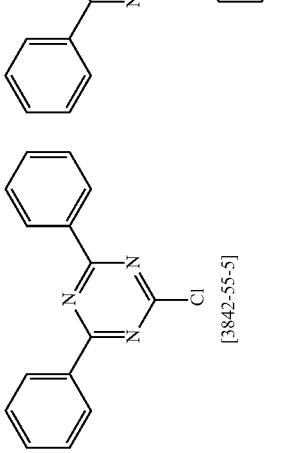 [3842-55-5] | 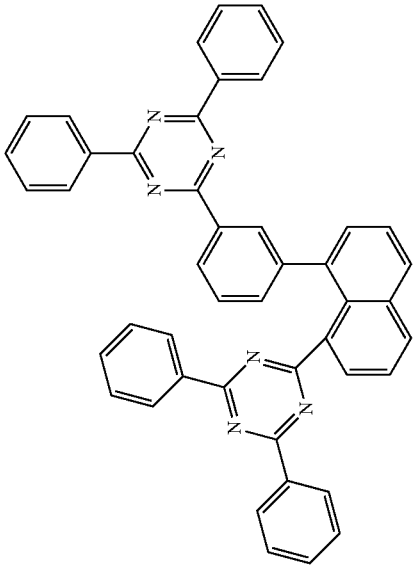 [864377-31-1] | 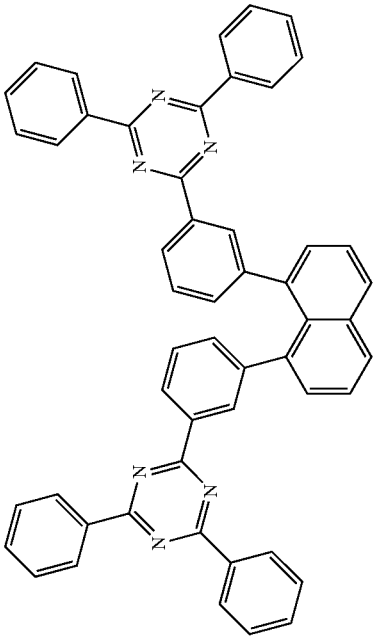 | 60% |
| 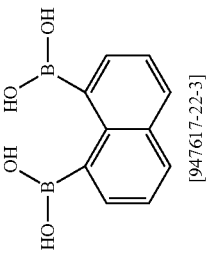 [947617-22-3] | 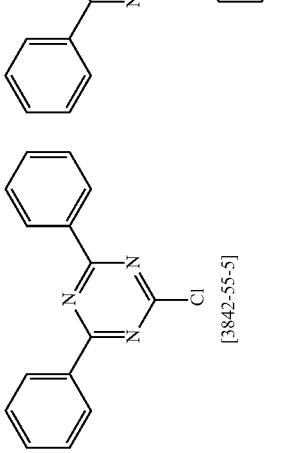 [864377-31-1] | 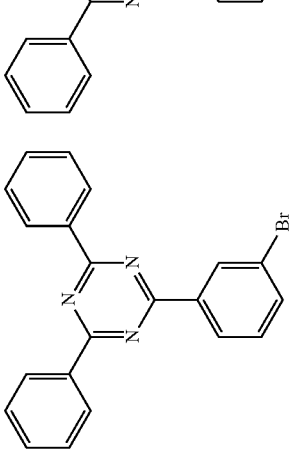 [864377-31-1] | 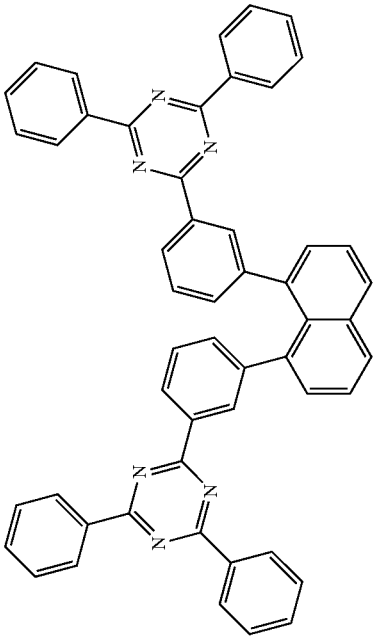 | 59% |

-continued
| Reactant 1 1 eq. | Reactant 2 0.5 eq. | Reactant 3 0.5 eq. | Product | Yield |
|---|---|---|---|---|
| 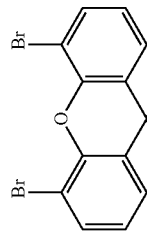 [1262398-42-4] | 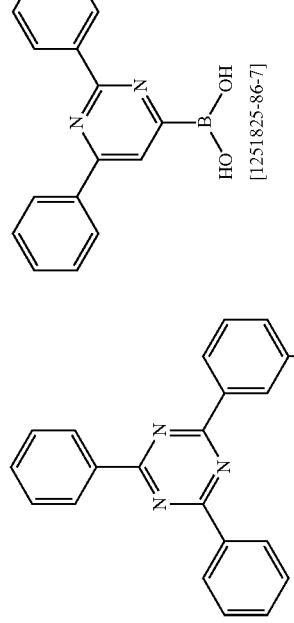 [1269508-31-7] | 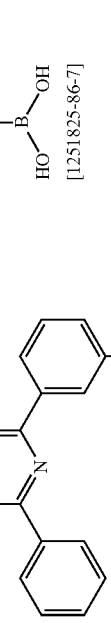 [1251825-86-7] | 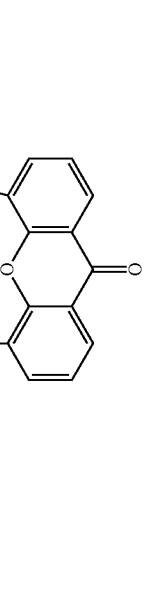 | 65% |
| 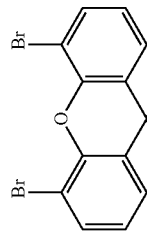 [1262398-42-4] | 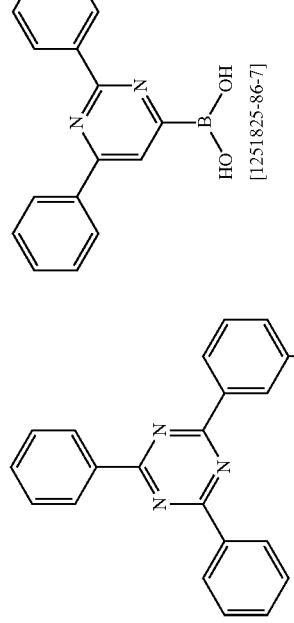 [1269508-31-7] | 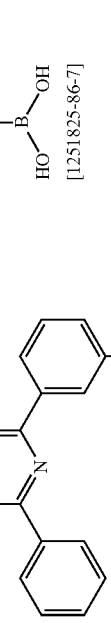 [1269508-31-7] |  | 76% |

-continued
| Reactant 1<br>1 eq. | Reactant 2<br>0.5 eq. | Reactant 3<br>0.5 eq. | Product | Yield |
|---|---|---|---|---|
| 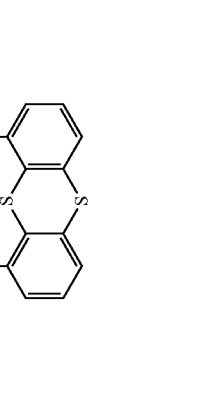 [176646-34-7] | 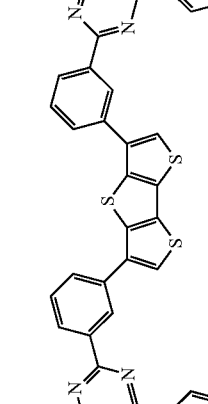 [1269508-31-7] | 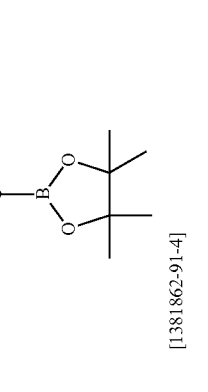 [1381862-91-4] | 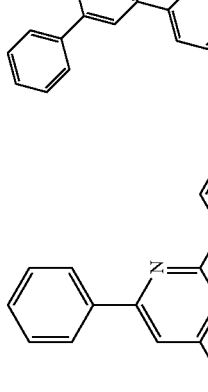 | 65% |
| 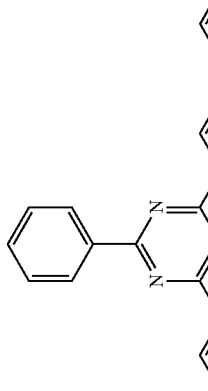 [502764-54-7] |  [1269508-31-7] | 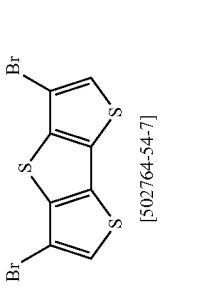 [1381862-91-4] |  | 56% |

-continued
| Reactant 1 1 eq. | Reactant 2 0.5 eq. | Reactant 3 0.5 eq. | Product | Yield |
|---|---|---|---|---|
| 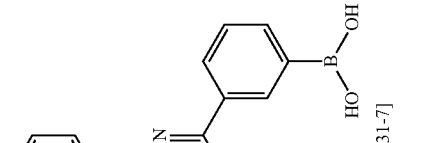 [38313-16-5] | 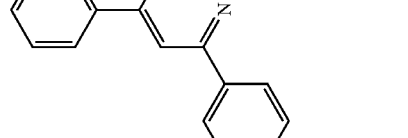 [1269508-31-7] | 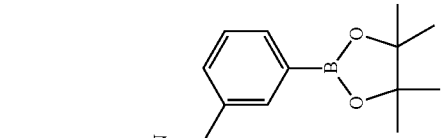 [1381862-91-4] | 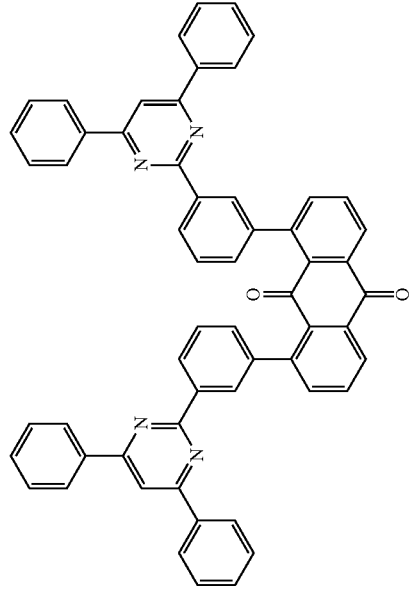 | 61% |

Example 10

Synthesis of 2-{6-[4-(2,6-diphenyl-[1,3,4]triazin-4-yl)phenyl]-dibenzofuran-4-yl}-4,6-diphenyl-[1,3,5]triazine a) Preparation of 2-(6-bromodibenzofuran-4-yl)-4,6-diphenyl-[1,3,5]triazine

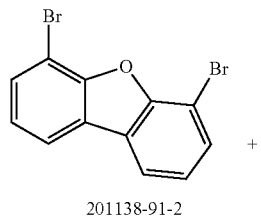

201138-91-2

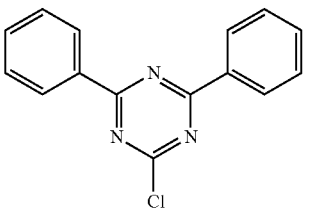

3842-55-5

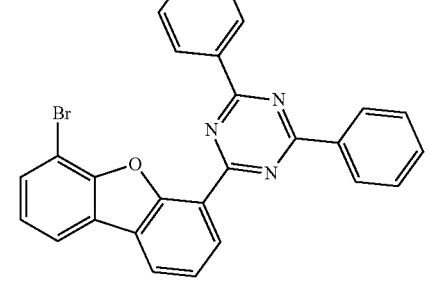

80 g (245 mmol) of 4,6-dibromodibenzofuran are dissolved in a baked-out flask in 500 mL of dried THF. The reaction mixture is cooled to −78° C. At this temperature, 57 mL of a 1.9 M solution of n-phenyllithium in dibutyl ether (115 mmol) are slowly added dropwise. The mixture is stirred at −73° C. for a further 1 hour. Subsequently, 65 g of 2-chloro-4,6-diphenyl-1,3,5-triazine (245 mmol) are dissolved in 150 mL of THF and added dropwise at −70° C. After the addition has ended, the reaction mixture is warmed gradually to room temperature, stirred at room temperature overnight, quenched with water and then concentrated on a rotary evaporator. During this time, a white solid precipitates out. The mixture is then cooled to room temperature, and the precipitated solid is filtered off with suction and washed with methanol. The yield is 40 g (84 mmol), corresponding to 34% of theory.

b) Preparation of 2-{6-[4-(2,6-diphenyl-[1,3,4]triazin-4-yl}phenyl]-dibenzofuran-4-yl)-4,6-diphenyl-[1,3,5]triazine

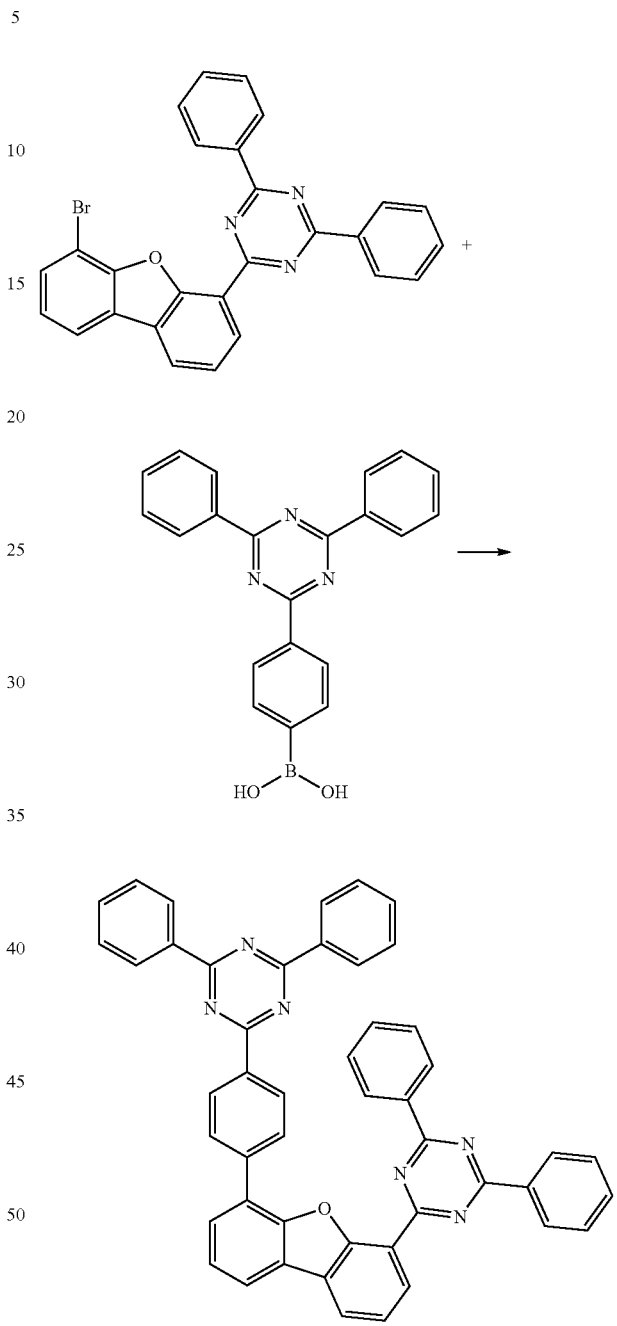

33.4 g (70 mmol) of 2-(6-bromodibenzofuran-4-yl)-4,6-diphenyl-[1,3,5]triazine, 24.7 g (70 mmol) of 4-(4,6-diphenyl-1,3,5-triazin-2-yl)phenylboronic acid and 78.9 mL (158 mmol) of Na$_2$CO$_3$ (2 M solution) are suspended in 120 mL of ethanol and 100 mL of water. 1.3 g (1.1 mmol) of Pd(PPh$_3$)$_4$ are added to this suspension, and the reaction mixture is heated under reflux for 16 h. After cooling, dichloromethane is added to the mixture, and the organic phase is removed, filtered through silica gel and recrystallized from toluene. The yield is 42 g (59 mmol), corresponding to 85% of theory.

Example 11

Preparation of 2-(4-dibenzofuran-3-yl-phenyl)-4,6-diphenyl-[1,3,5]triazine

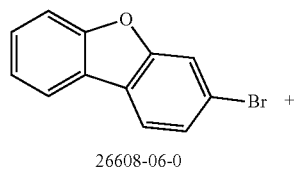

26608-06-0

24 g (70 mmol) of 4-(4,6-diphenyl-1,3,5-triazin-2-ylphenyl)boronic acid, 17.3 g (70 mmol) of 3-bromodibenzofuran and 78.9 mL (158 mmol) of $Na_2CO_3$ (2 M solution) are suspended in 120 mL of ethanol and 100 mL of water. 1.3 g (1.1 mmol) of $Pd(PPh_3)_4$ are added to this suspension, and the reaction mixture is heated under reflux for 16 h. After cooling, dichloromethane is added to the mixture, and the organic phase is removed, filtered through silica gel and recrystallized from toluene. The yield is 28 g (58 mmol), corresponding to 86% of theory.

In an analogous manner, it is possible to prepare the following compound:

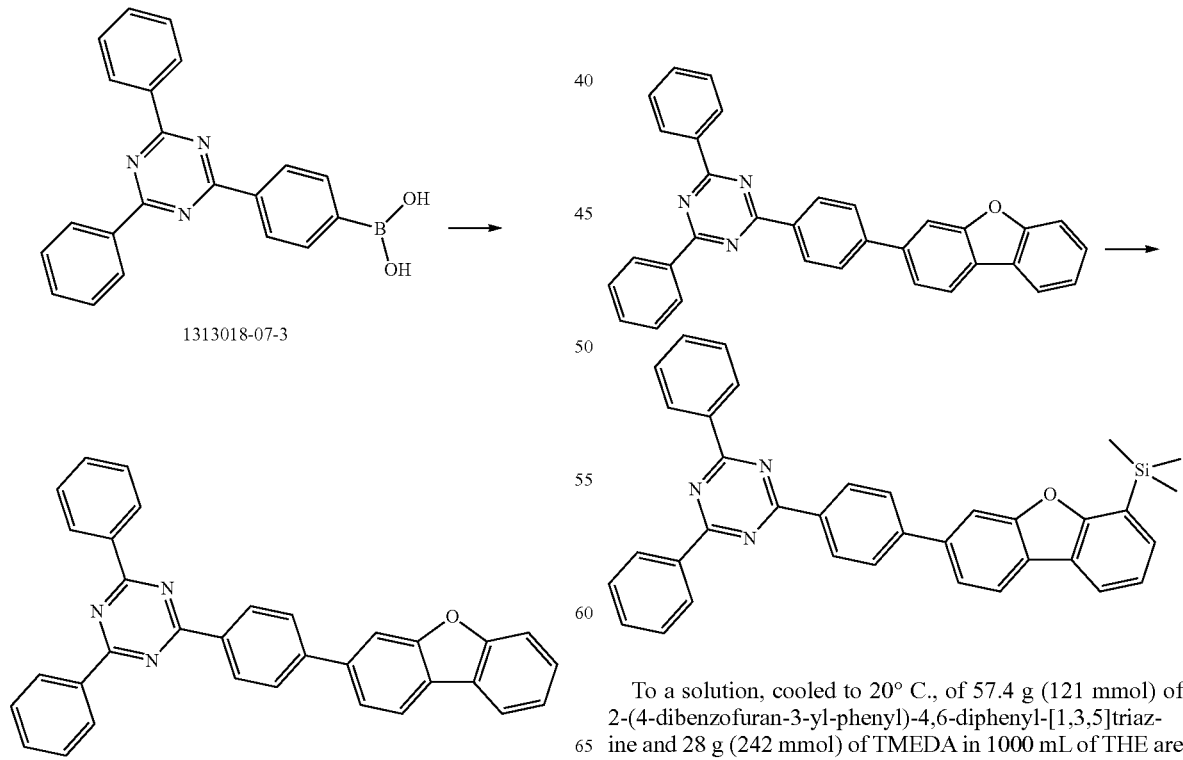

Example 12

Preparation of 2,4-diphenyl-6-[4-(6-trimethylsilanyl-dibenzofuran-3-yl)phenyl]-[1,3,5]triazine To a solution, cooled to 20° C., of 57.4 g (121 mmol) of 2-(4-dibenzofuran-3-yl-phenyl)-4,6-diphenyl-[1,3,5]triazine and 28 g (242 mmol) of TMEDA in 1000 mL of THF are added dropwise 127 mL (225.4 mmol) of n-butyllithium (2.5 M in hexane). The reaction mixture is stirred at room temperature for 3 h, then cooled down to 0° C., and 26 g (242 mmol) of chlorotrimethylsilane are added dropwise within 30 min. The mixture is stirred at room temperature for 8 h. Subsequently, the solvent is removed under reduced pressure and the residue is purified by chromatography using silica gel with chloroform as eluent. Yield: 41 g (74 mmol), 63% of theory.

In an analogous manner, it is possible to prepare the following compound:

| Reactant 1 | Product | Yield |
|---|---|---|
|  |  | 87% |

Example 13

Preparation of 3-[4-(4,6-diphenyl-[1,3,5]triazin-2-yl)phenyl]-dibenzofuran-6-boronic acid

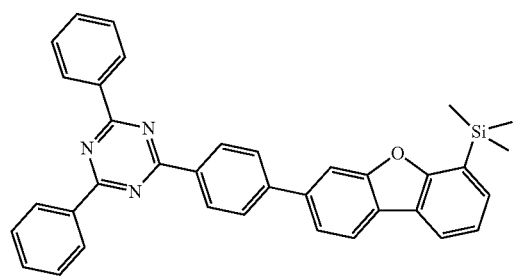

Under protective gas, 21 g (86 mmol) of bromine tribromide are added dropwise to a solution of 39 g of 2,4-diphenyl-6-[4-(6-trimethylsilanyldi-benzofuran-3-yl)phenyl]-[1,3,5]triazine in 500 mL of dichloromethane and the mixture is stirred at room temperature for 10 h. Thereafter, a little water is added gradually to the mixture and the precipitated residue is filtered off and washed with heptane. The yield is 32 g (62 mmol), corresponding to 87% of theory.

In an analogous manner, it is possible to prepare the following compound:

| Reactant 1 | Product | Yield |
|---|---|---|
|  |  | 90% |

Example 14

Preparation of 3-{7-[4-(4,6-diphenyl-[1,3,5]triazin-2-yl)phenyl]dibenzofuran-4-yl}-9-phenyl-9H-carbazole

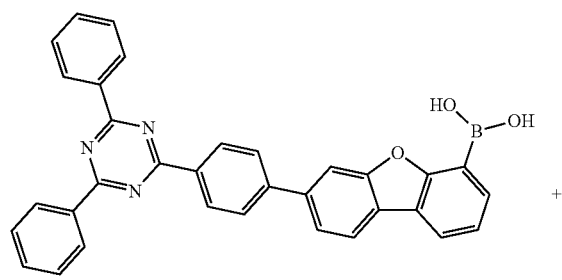

+

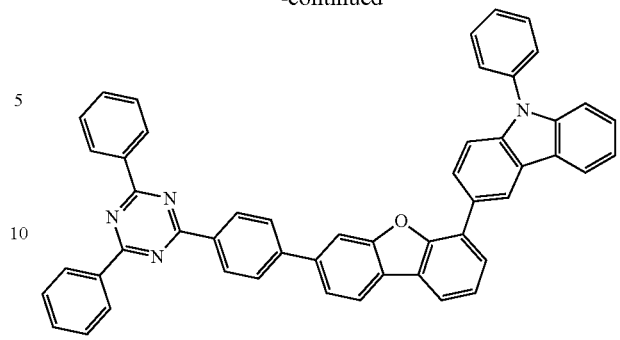

36 g (70 mmol) of 3-[4-(4,6-diphenyl-[1,3,5]triazin-2-yl)phenyl]-dibenzofuran-6 boronic acid, 22.5 g (70 mmol) of 3-bromodibenzofuran and 78.9 mL (158 mmol) of $Na_2CO_3$ (2 M solution) are suspended in 120 mL of ethanol and 100 mL of water. 1.3 g (1.1 mmol) of $Pd(PPh_3)_4$ are added to this suspension, and the reaction mixture is heated under reflux for 16 h. After cooling, dichloromethane is added to the mixture, and the organic phase is removed, filtered through silica gel and recrystallized from toluene. The residue is recrystallized from toluene and finally sublimed under high vacuum ($p=5\times10^{-5}$ mbar). The yield is 39 g (54 mmol), corresponding to 80% of theory.

In an analogous manner, it is possible to prepare the following compound:

| Reactant 1 | Reactant 2 | Product | Yield |
|---|---|---|---|
| 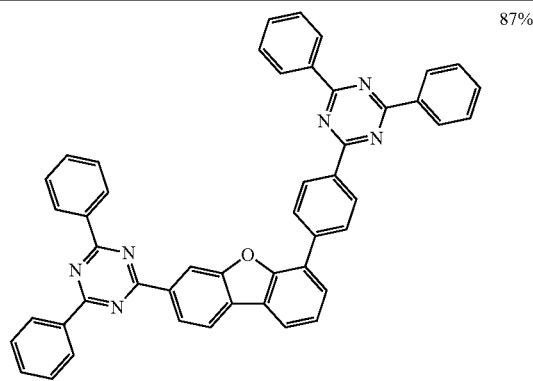 | 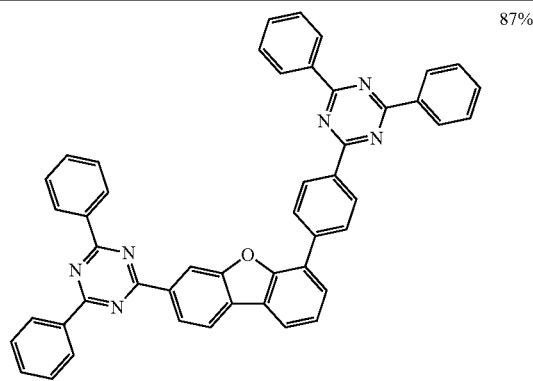 23449-08-3 | 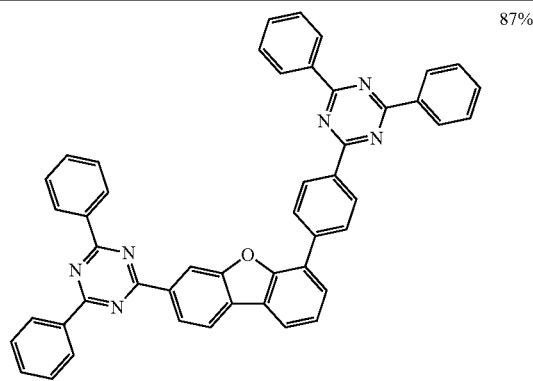 | 87% |

-continued

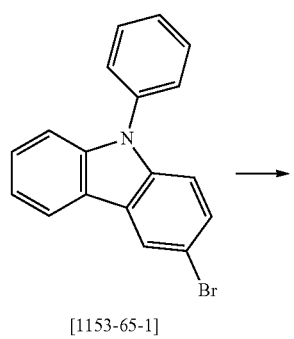

[1153-65-1]

Example 15

Production and Characterization of the OLEDs In examples C1 to I22 which follow (see tables 1 and 2), the data of various OLEDs are presented. Cleaned glass plaques (cleaning in laboratory glass washer, Merck Extran detergent) coated with structured ITO (indium tin oxide) of thickness 50 nm, for improved processing, are coated with 20 nm of PEDOT:PSS (poly(3,4-ethylenedioxythiophene) poly(styrenesulfonate), purchased as CLEVIOS™ P VP Al 4083 from Heraeus Precious Metals GmbH Deutschland, spun on from aqueous solution). These coated glass plaques form the substrates to which the OLEDs are applied.

The OLEDs basically have the following layer structure: substrate/hole transport layer (HTL)/interlayer (IL)/electron blocker layer (EBL)/emission layer (EML)/optional hole blocker layer (HBL)/electron transport layer (ETL)/optional electron injection layer (EIL) and finally a cathode. The cathode is formed by an aluminum layer of thickness 100 nm. The exact structure of the OLEDs can be found in table 1. The materials required for production of the OLEDs are shown in table 3.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as INV-1:IC3:TEG1 (60%:35%:5%) mean here that the material INV-1 is present in the layer in a proportion by volume of 60%, IC3 in a proportion of 35% and TEG1 in a proportion of 5%. Analogously, the electron transport layer may also consist of a mixture of two materials.

The OLEDs are characterized in a standard manner. For this purpose, the electroluminescence spectra, the current efficiency (measured in cd/A), the power efficiency (measured in lm/VW) and the external quantum efficiency (EQE, measured in percent) are determined as a function of luminance, calculated from current-voltage-luminance characteristics (IUL characteristics) assuming Lambertian radiation characteristics. The electroluminescence spectra are determined at a luminance of 1000 cd/m$^2$, and the CIE 1931 x and y color coordinates are calculated therefrom. The parameter U1000 in table 2 refers to the voltage which is required for a luminance of 1000 cd/m$^2$. CE1000 and PE1000 respectively refer to the current and power efficiencies which are achieved at 1000 cd/m$^2$. Finally, EQE1000 refers to the external quantum efficiency at an operating luminance of 1000 cd/m$^2$.

The data for the various OLEDs are collated in table 2. Examples C1-C8 are comparative examples and show OLEDs containing materials according to the prior art. Examples I1-I22 show data for OLEDs comprising materials of the invention.

Some of the examples are elucidated in detail hereinafter, in order to illustrate the advantages of the compounds of the invention. However, it should be pointed out that this is merely a selection of the data shown in table 2. As can be inferred from the table, even when the compounds of the invention that have not been specifically detailed are used, distinct improvement over the prior art are achieved, in some cases in all parameters, but in some cases only an improvement in efficiency or voltage is observed. However, improvement in one of the parameters mentioned is already a significant advance because various applications require optimization with regard to different parameters.

Use of Compounds of the Invention as Electron Transport Materials

Compared to an OLED in which the material VG-6 according to the prior art is used in the ETL, a distinct improvement in voltage and efficiency is observed when the materials INV-5, INV-7, INV-15, INV-21 and INV-20 of the invention are used. Especially when the substance INV-5 is used, a voltage improved by 1.5 V compared to VG-6 is obtained, for instance a 35% better external quantum efficiency and more than double the power efficiency (examples C6, I5).

Use of Compounds of the Invention as Matrix Materials in Phosphorescent OLEDs

By inserting a phenyl ring between pyrimidine and dibenzofuran, it is possible to improve the EQE by 15% and the voltage by 0.1 V (examples C1, I1). This is true in an analogous manner of compounds comprising triazine (examples C2, I2, I3).

In addition, it is advantageous when a triazine or carbazole group is bonded face-to-face with respect to the dibenzofuran (examples C4, I2, I3). This is true in an analogous manner when the connecting group between carbazole and triazine is not a dibenzofuran but a carbazole (examples C5, I4).

TABLE 1

Structure of the OLEDs

| Ex. | HTL thickness | IL thickness | EBL thickness | EML thickness | HBL thickness | ETL thickness | EIL thickness |
|---|---|---|---|---|---|---|---|
| C1 | SpA1 70 nm | HATCN 5 nm | SpMA1 90 nm | VG-1:TEG1 (90%:10%) 30 nm | ST2 10 nm | ST2:LiQ (50%:50%) 30 nm | — |
| C2 | SpA1 70 nm | HATCN 5 nm | SpMA1 90 nm | VG-2:TEG1 (90%:10%) 30 nm | ST2 10 nm | ST2:LiQ (50%:50%) 30 nm | — |
| C3 | SpA1 70 nm | HATCN 5 nm | SpMA1 90 nm | IC1:TEG1 (90%:10%) 30 nm | — | VG-7 40 nm | LiQ 3 nm |
| C4 | SpA1 70 nm | HATCN 5 nm | SpMA1 90 nm | VG-4:TEG1 (90%:10%) 30 nm | ST2 10 nm | ST2:LiQ (50%:50%) 30 nm | — |
| C5 | SpA1 90 nm | HATCN 5 nm | SpMA1 130 nm | VG-5:TER1 (92%:8%) 40 nm | — | ST2:LiQ (50%:50%) 40 nm | — |
| C6 | SpA1 70 nm | HATCN 5 nm | SpMA1 90 nm | IC1:TEG1 (90%:10%) 30 nm | — | VG-6 40 nm | LiQ 3 nm |
| I1 | SpA1 70 nm | HATCN 5 nm | SpMA1 90 nm | INV-1:TEG1 (90%:10%) 30 nm | ST2 10 nm | ST2:LiQ (50%:50%) 30 nm | — |
| I2 | SpA1 70 nm | HATCN 5 nm | SpMA1 90 nm | INV-2:TEG1 (90%:10%) 30 nm | ST2 10 nm | ST2:LiQ (50%:50%) 30 nm | — |
| I3 | SpA1 70 nm | HATCN 5 nm | SpMA1 90 nm | INV-3:TEG1 (90%:10%) 30 nm | ST2 10 nm | ST2:LiQ (50%:50%) 30 nm | — |
| I4 | SpA1 90 nm | HATCN 5 nm | SpMA1 130 nm | INV-4:TER1 (92%:8%) 40 nm | — | ST2:LiQ (50%:50%) 40 nm | — |
| I5 | SpA1 70 nm | HATCN 5 nm | SpMA1 90 nm | IC1:TEG1 (90%:10%) 30 nm | — | INV-5 40 nm | LiQ 3 nm |
| I6 | SpA1 70 nm | HATCN 5 nm | SpMA1 90 nm | INV-10:TEG1 (90%:10%) 30 nm | ST2 10 nm | ST2:LiQ (50%:50%) 30 nm | — |
| I7 | SpA1 70 nm | HATCN 5 nm | SpMA1 90 nm | INV-6:TEG1 (90%:10%) 30 nm | ST2 10 nm | ST2:LiQ (50%:50%) 30 nm | — |
| I8 | SpA1 70 nm | HATCN 5 nm | SpMA1 90 nm | INV-7:TEG1 (90%:10%) 30 nm | ST2 10 nm | ST2:LiQ (50%:50%) 30 nm | — |
| I9 | SpA1 70 nm | HATCN 5 nm | SpMA1 90 nm | IC1:TEG1 (90%:10%) 30 nm | — | INV-7 30 nm | LiQ 3 nm |

TABLE 1-continued

Structure of the OLEDs

| Ex. | HTL thickness | IL thickness | EBL thickness | EML thickness | HBL thickness | ETL thickness | EIL thickness |
|---|---|---|---|---|---|---|---|
| I10 | SpA1 90 nm | HATCN 5 nm | SpMA1 130 nm | INV-8:TER1 (92%:8%) 40 nm | — | ST2:LiQ (50%:50%) 40 nm | — |
| I11 | SpA1 70 nm | HATCN 5 nm | SpMA1 90 nm | INV-9:IC3:TEG1 (60%:35%:5%) 30 nm | IC1 10 nm | ST2:LiQ (50%:50%) 30 nm | — |
| I12 | SpA1 70 nm | HATCN 5 nm | SpMA1 90 nm | INV-11:IC2:TEG1 (45%:45%:10%) 30 nm | IC1 10 nm | ST2:LiQ (50%:50%) 30 nm | — |
| I13 | SpA1 70 nm | HATCN 5 nm | SpMA1 90 nm | INV-12:TEG1 (90%:10%) 30 nm | ST2 10 nm | ST2:LiQ (50%:50%) 30 nm | — |
| I14 | SpA1 70 nm | HATCN 5 nm | SpMA1 90 nm | INV-13:TEG1 (90%:10%) 30 nm | ST2 10 nm | ST2:LiQ (50%:50%) 30 nm | — |
| I15 | SpA1 70 nm | HATCN 5 nm | SpMA1 90 nm | INV-14:TEG1 (90%:10%) 30 nm | ST2 10 nm | ST2:LiQ (50%:50%) 30 nm | — |
| I16 | SpA1 70 nm | HATCN 5 nm | SpMA1 90 nm | IC1:TEG1 (90%:10%) 30 nm | — | INV-15 40 nm | LiQ 3 nm |
| I17 | SpA1 70 nm | HATCN 5 nm | SpMA1 90 nm | INV-16:TEG1 (90%:10%) 30 nm | ST2 10 nm | ST2:LiQ (50%:50%) 30 nm | — |
| I18 | SpA1 70 nm | HATCN 5 nm | SpMA1 90 nm | INV-17:TEG1 (90%:10%) 30 nm | ST2 10 nm | ST2:LiQ (50%:50%) 30 nm | — |
| I19 | SpA1 70 nm | HATCN 5 nm | SpMA1 90 nm | IC1:TEG1 (90%:10%) 30 nm | INV-18 10 nm | ST1:LiQ (50%:50%) 30 nm | — |
| I20 | SpA1 70 nm | HATCN 5 nm | SpMA1 90 nm | IC2:TEG1 (90%:10%) 30 nm | INV-19 10 nm | ST2:LiQ (50%:50%) 30 nm | — |
| I21 | SpA1 70 nm | HATCN 5 nm | SpMA1 90 nm | IC1:TEG1 (90%:10%) 30 nm | — | INV-20 40 nm | LiQ 3 nm |
| I22 | SpA1 70 nm | HATCN 5 nm | SpMA1 90 nm | IC2:TEG1 (90%:10%) 30 nm | — | INV-21 40 nm | LiQ 3 nm |

TABLE 2

Data of the OLEDs

| Ex. | U1000 (V) | CE1000 (cd/A) | PE1000 (lm/W) | EQE 1000 | CIE x/y at 1000 cd/m$^2$ |
|---|---|---|---|---|---|
| C1 | 3.7 | 50 | 43 | 13.7% | 0.33/0.62 |
| C2 | 3.6 | 53 | 45 | 14.4% | 0.34/0.62 |
| C3 | 3.6 | 56 | 49 | 15.5% | 0.34/0.62 |
| C4 | 3.4 | 52 | 49 | 14.1% | 0.33/0.62 |
| C5 | 4.8 | 9.4 | 6.1 | 10.1% | 0.67/0.33 |
| C6 | 4.4 | 45 | 31 | 12.4% | 0.34/0.62 |
| I1 | 3.6 | 58 | 51 | 15.8% | 0.33/0.62 |
| I2 | 3.4 | 61 | 57 | 16.7% | 0.33/0.62 |
| I3 | 3.5 | 57 | 51 | 15.6% | 0.34/0.62 |
| I4 | 4.6 | 10.5 | 7.1 | 11.3% | 0.67/0.33 |
| I5 | 2.9 | 62 | 68 | 16.9% | 0.34/0.63 |
| I6 | 3.7 | 63 | 54 | 17.6% | 0.33/0.63 |
| I7 | 3.1 | 59 | 59 | 16.4% | 0.34/0.62 |
| I8 | 4.3 | 50 | 36 | 14.0% | 0.39/0.59 |
| I9 | 4.0 | 56 | 45 | 15.2% | 0.33/0.62 |
| I10 | 4.2 | 12.3 | 9.1 | 12.4% | 0.67/0.33 |
| I11 | 3.2 | 61 | 60 | 17.1% | 0.34/0.62 |
| I12 | 3.6 | 47 | 41 | 13.1% | 0.32/0.63 |
| I13 | 3.2 | 51 | 50 | 14.4% | 0.33/0.62 |
| I14 | 3.6 | 59 | 52 | 16.6% | 0.34/0.62 |
| I15 | 3.6 | 56 | 49 | 15.8% | 0.33/0.62 |
| I16 | 2.8 | 58 | 65 | 16.2% | 0.32/0.63 |
| I17 | 3.4 | 56 | 51 | 15.5% | 0.34/0.62 |
| I18 | 3.7 | 53 | 46 | 15.0% | 0.33/0.63 |
| I19 | 3.6 | 58 | 51 | 16.1% | 0.32/0.63 |
| I20 | 3.4 | 49 | 46 | 13.7% | 0.35/0.61 |
| I21 | 3.8 | 55 | 45 | 15.5% | 0.35/0.62 |
| I22 | 3.0 | 49 | 51 | 14.5% | 0.35/0.61 |

TABLE 3

Materials used

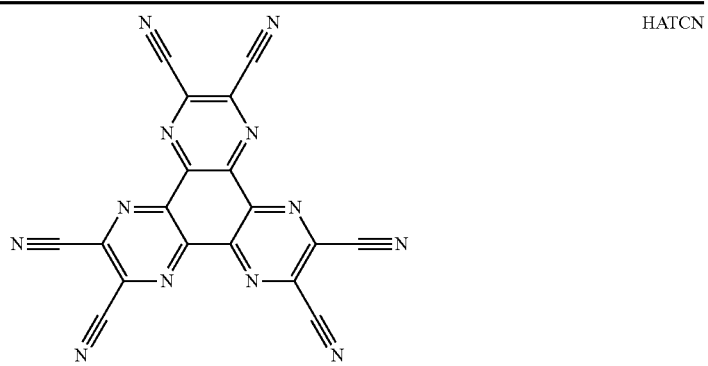

HATCN

TABLE 3-continued
Materials used
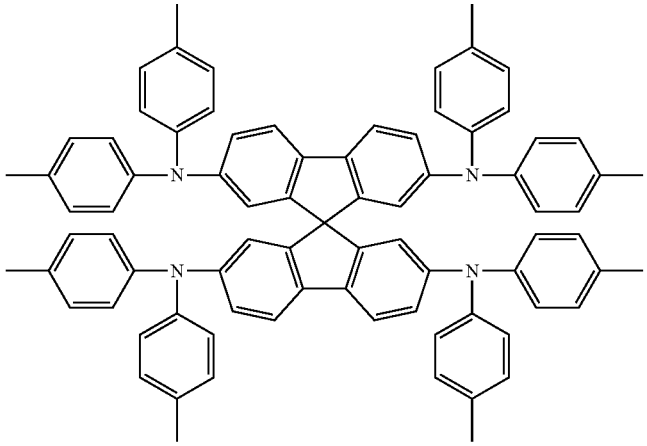
SpA1
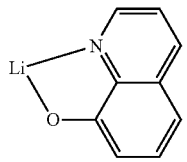
LiQ
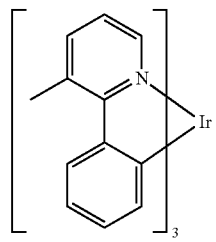
TEG1
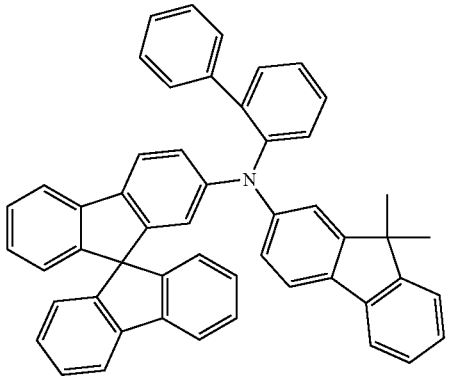 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
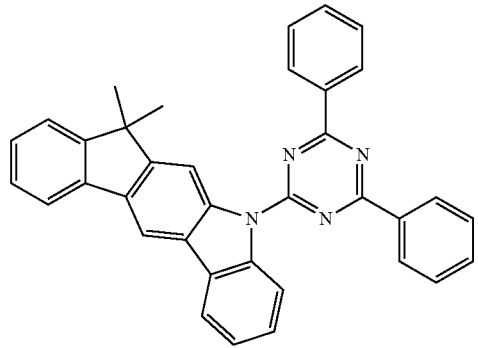 [SMILES: CC1(C)c2ccccc2-c2cc3c4ccccc4n(-c4nc(-c5ccccc5)nc(-c5ccccc5)n4)c3cc21]
IC1

TABLE 3-continued
Materials used
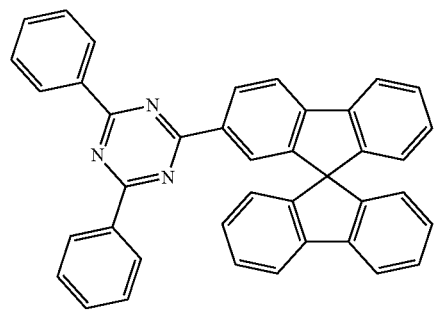 [SMILES: c1ccc(-c2nc(-c3ccccc3)nc(-c3ccc4c(c3)C3(c5ccccc5-c5ccccc53)c3ccccc3-4)n2)cc1]
ST1
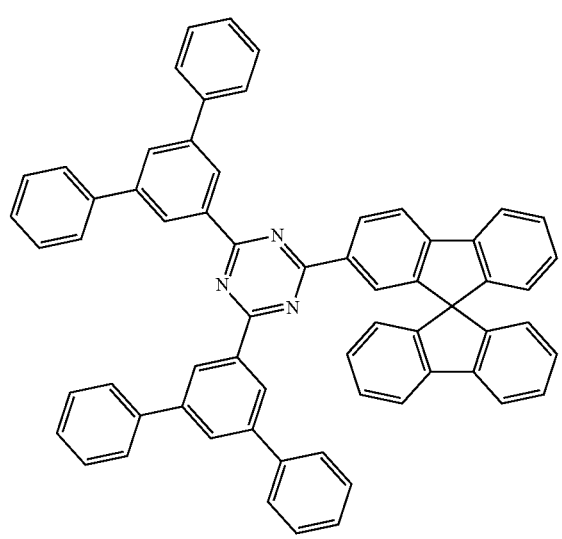 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2
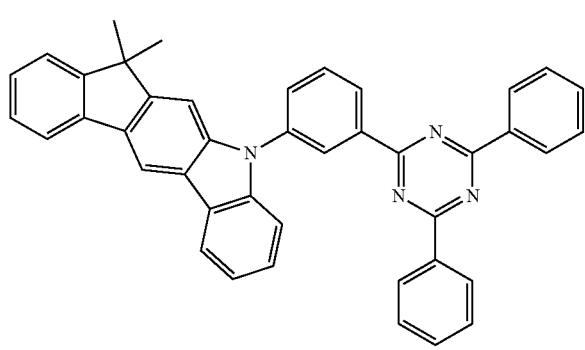 [SMILES: CC1(C)c2ccccc2-c2cc3c4ccccc4n(-c4cccc(-c5nc(-c6ccccc6)nc(-c6ccccc6)n5)c4)c3cc21]
IC2
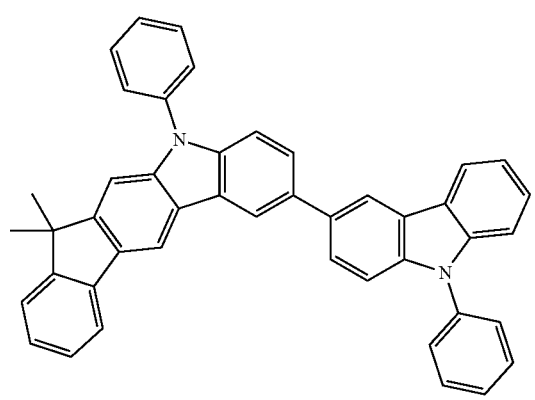 [SMILES: CC1(C)c2ccccc2-c2cc3c4cc(-c5ccc6c(c5)c5ccccc5n6-c5ccccc5)ccc4n(-c4ccccc4)c3cc21]
IC3

TABLE 3-continued
Materials used
TER1
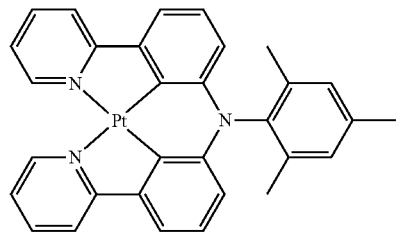
VG-1
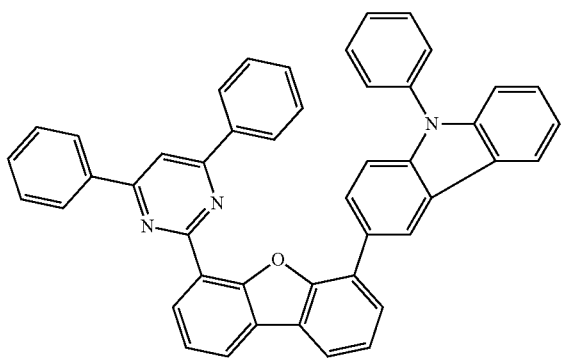
WO 2011/057706
VG-2
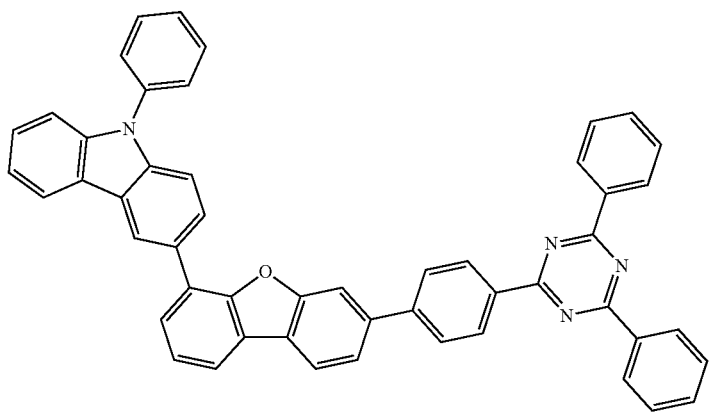 [SMILES: c1ccc(-c2nc(-c3ccccc3)nc(-c3ccc(-c4ccc5c(c4)oc4c(-c6ccc7c(c6)c6ccccc6n7-c6ccccc6)cccc45)cc3)n2)cc1]
VG-3
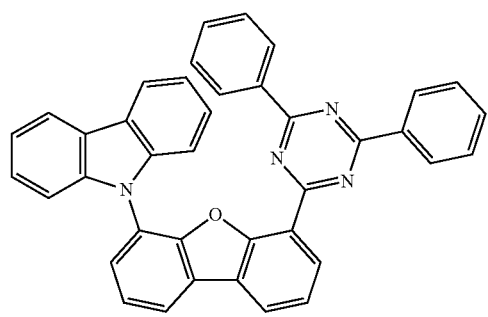 [SMILES: c1ccc(-c2nc(-c3ccccc3)nc(-c3cccc4c3oc3c(-n5c6ccccc6c6ccccc65)cccc34)n2)cc1]

TABLE 3-continued
Materials used
VG-4
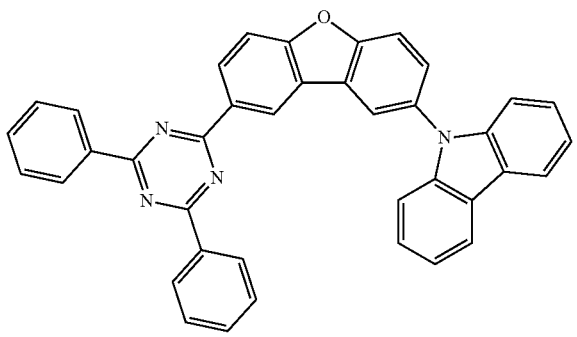
JP 2009/21336
VG-5
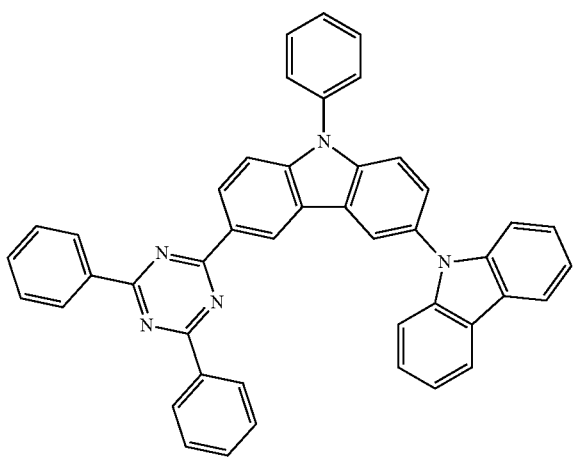
JP 2009/21336
VG-6
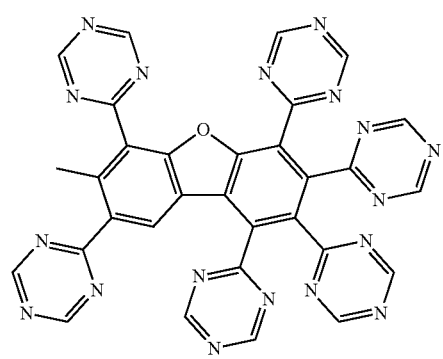
WO 2009/069442

TABLE 3-continued
Materials used
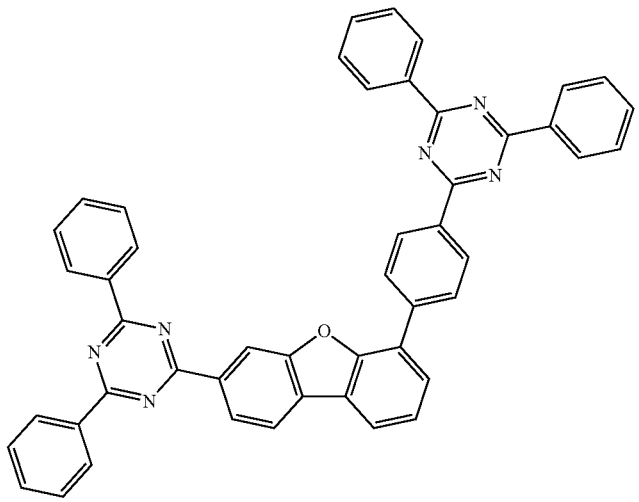 [SMILES: c1ccc(-c2nc(-c3ccccc3)nc(-c3ccc(-c4cccc5c4oc4cc(-c6nc(-c7ccccc7)nc(-c7ccccc7)n6)ccc45)cc3)n2)cc1]
VG-7
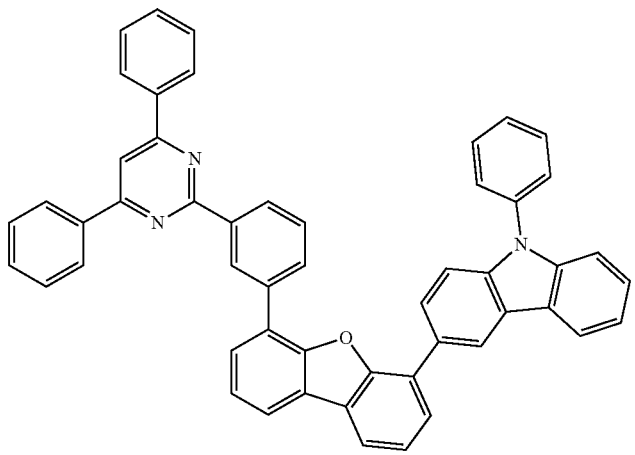 [SMILES: c1ccc(-c2cc(-c3ccccc3)nc(-c3cccc(-c4cccc5c4oc4c(-c6ccc7c(c6)c6ccccc6n7-c6ccccc6)cccc45)c3)n2)cc1]
INV-1
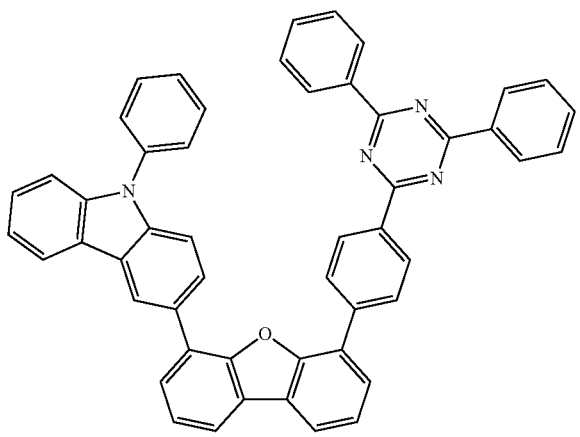 [SMILES: c1ccc(-c2nc(-c3ccccc3)nc(-c3ccc(-c4cccc5c4oc4c(-c6ccc7c(c6)c6ccccc6n7-c6ccccc6)cccc45)cc3)n2)cc1]
INV-2

TABLE 3-continued
Materials used
INV-3
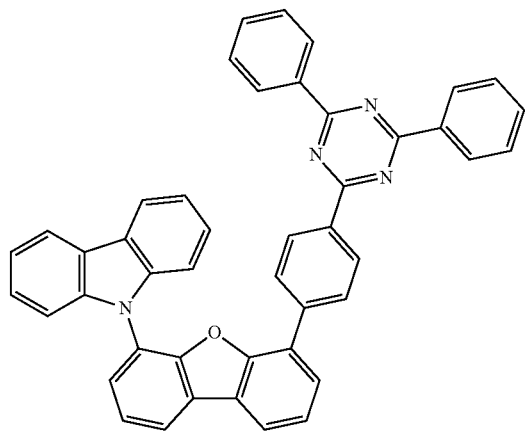 [SMILES: c1ccc(-c2nc(-c3ccccc3)nc(-c3ccc(-c4cccc5c4oc4c(-n6c7ccccc7c7ccccc76)cccc45)cc3)n2)cc1]
INV-4
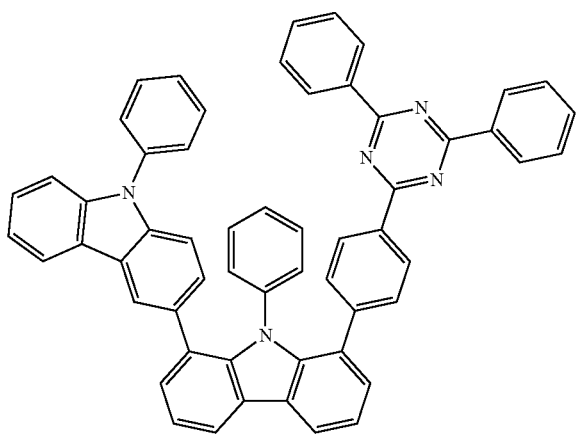 [SMILES: c1ccc(-c2nc(-c3ccccc3)nc(-c3ccc(-c4cccc5c6cccc(-c7ccc8c(c7)c7ccccc7n8-c7ccccc7)c6n(-c6ccccc6)c45)cc3)n2)cc1]
INV-5
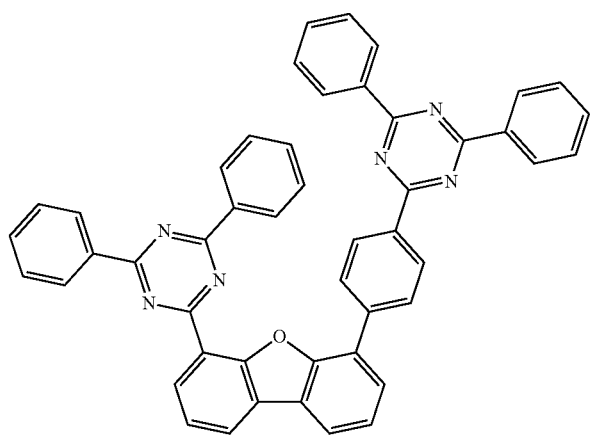 [SMILES: c1ccc(-c2nc(-c3ccccc3)nc(-c3ccc(-c4cccc5c4oc4c(-c6nc(-c7ccccc7)nc(-c7ccccc7)n6)cccc45)cc3)n2)cc1]

TABLE 3-continued

Materials used

INV-6

INV-7

INV-8

INV-9

TABLE 3-continued
Materials used
INV-10
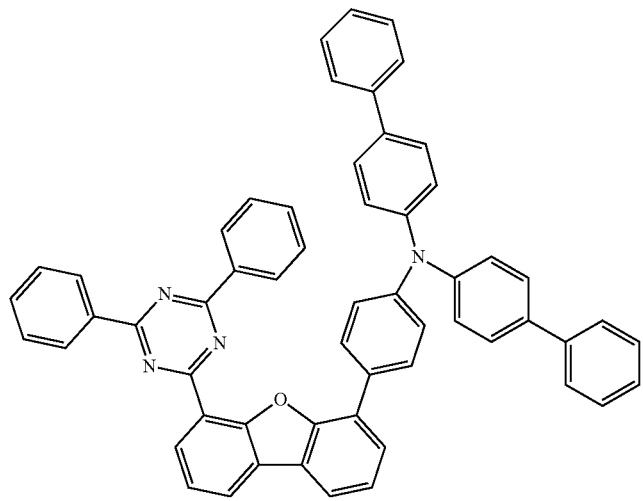 [SMILES: c1ccc(-c2ccc(N(c3ccc(-c4ccccc4)cc3)c3ccc(-c4cccc5c4oc4c(-c6nc(-c7ccccc7)nc(-c7ccccc7)n6)cccc45)cc3)cc2)cc1]
INV-11
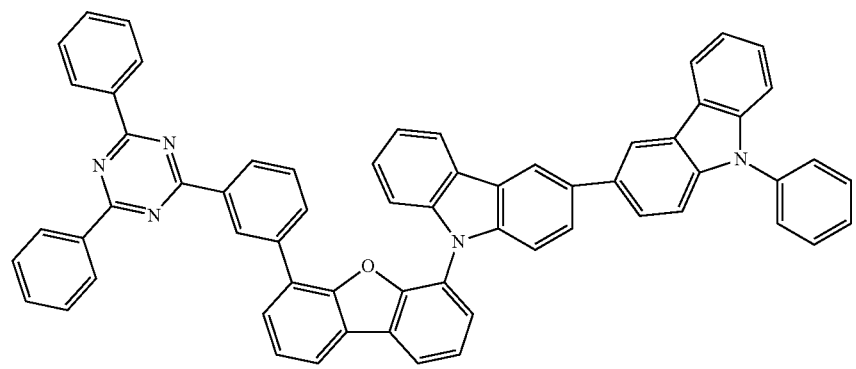 [SMILES: c1ccc(-c2nc(-c3ccccc3)nc(-c3cccc(-c4cccc5c4oc4c(-n6c7ccccc7c7cc(-c8ccc9c(c8)c8ccccc8n9-c8ccccc8)ccc76)cccc45)c3)n2)cc1]
INV-12
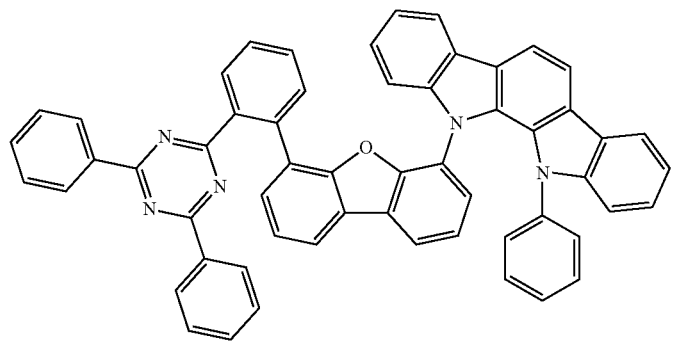 [SMILES: c1ccc(-c2nc(-c3ccccc3)nc(-c3ccccc3-c3cccc4c3oc3c(-n5c6ccccc6c6ccc7c8ccccc8n(-c8ccccc8)c7c65)cccc34)n2)cc1]

TABLE 3-continued
Materials used
INV-13
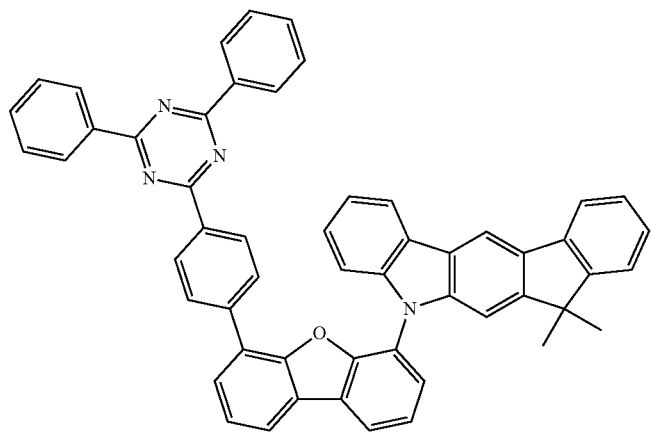 [SMILES: CC1(C)c2ccccc2-c2cc3c4ccccc4n(-c4cccc5c4oc4c(-c6ccc(-c7nc(-c8ccccc8)nc(-c8ccccc8)n7)cc6)cccc45)c3cc21]
INV-14
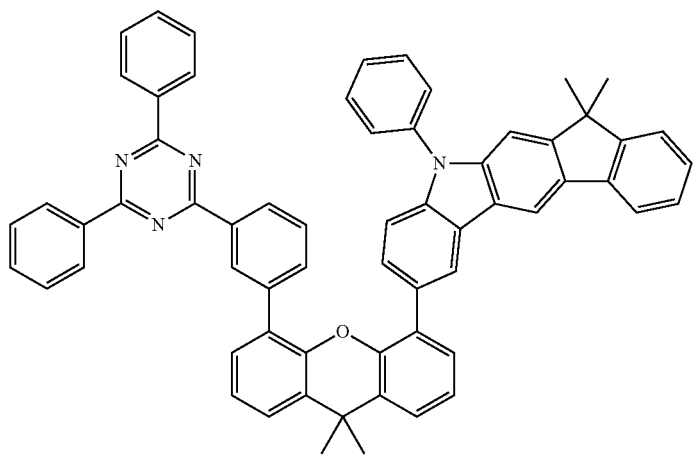 [SMILES: CC1(C)c2ccccc2-c2cc3c4cc(-c5cccc6c5Oc5c(-c7cccc(-c8nc(-c9ccccc9)nc(-c9ccccc9)n8)c7)cccc5C6(C)C)ccc4n(-c4ccccc4)c3cc21]
INV-15
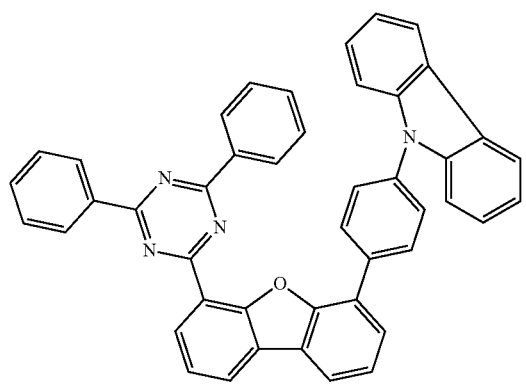 [SMILES: c1ccc(-c2nc(-c3ccccc3)nc(-c3cccc4c3oc3c(-c5ccc(-n6c7ccccc7c7ccccc76)cc5)cccc34)n2)cc1]

TABLE 3-continued
Materials used
INV-16
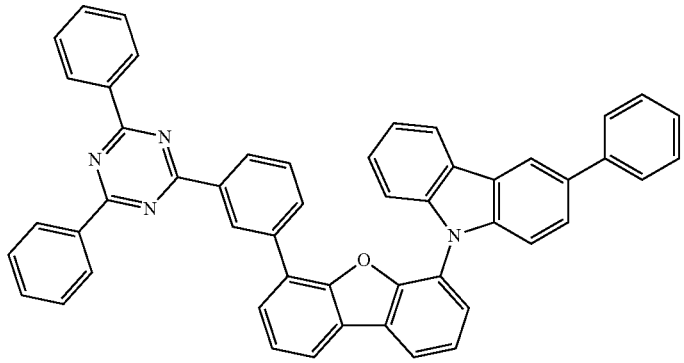 [SMILES: c1ccc(-c2ccc3c(c2)c2ccccc2n3-c2cccc3c2oc2c(-c4cccc(-c5nc(-c6ccccc6)nc(-c6ccccc6)n5)c4)cccc23)cc1]
INV-17
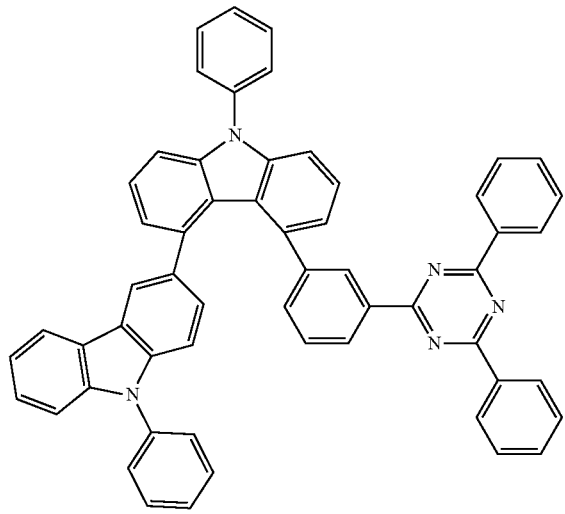 [SMILES: c1ccc(-c2nc(-c3ccccc3)nc(-c3cccc(-c4cccc5c4c4c(-c6ccc7c(c6)c6ccccc6n7-c6ccccc6)cccc4n5-c4ccccc4)c3)n2)cc1]
INV-18
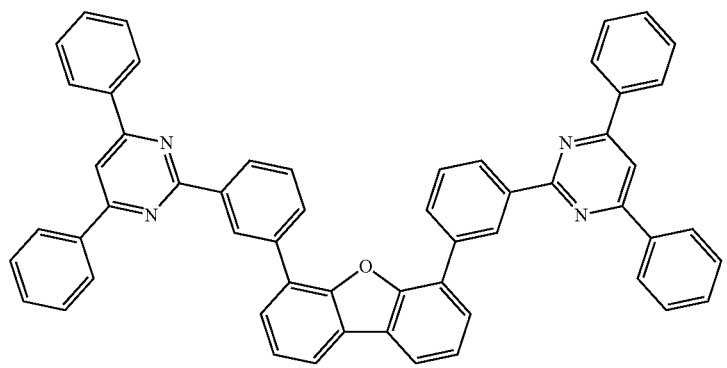 [SMILES: c1ccc(-c2cc(-c3ccccc3)nc(-c3cccc(-c4cccc5c4oc4c(-c6cccc(-c7nc(-c8ccccc8)cc(-c8ccccc8)n7)c6)cccc45)c3)n2)cc1]

TABLE 3-continued

Materials used

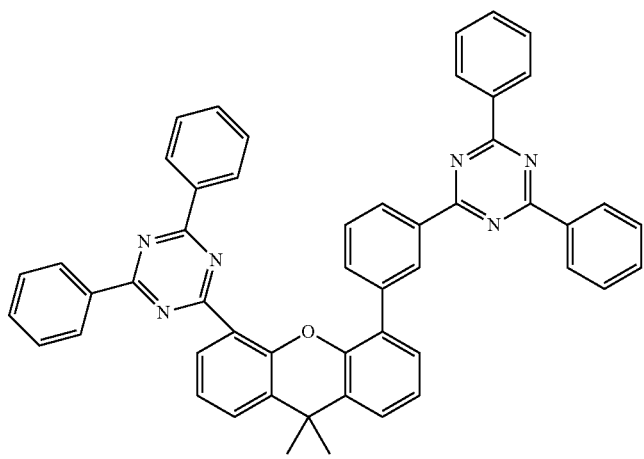 [SMILES: CC1(C)c2cccc(-c3cccc(-c4nc(-c5ccccc5)nc(-c5ccccc5)n4)c3)c2Oc2c(-c3nc(-c4ccccc4)nc(-c4ccccc4)n3)cccc21]

INV-19

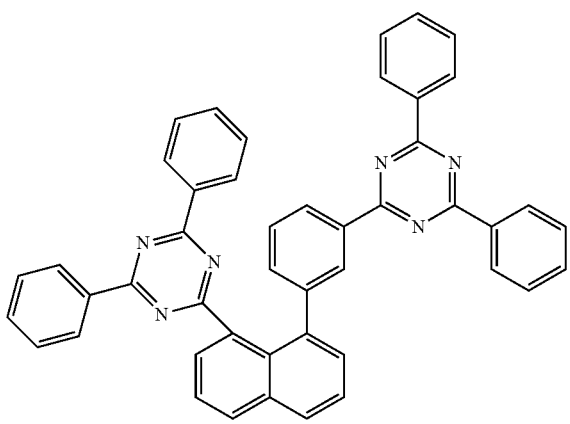 [SMILES: c1ccc(-c2nc(-c3ccccc3)nc(-c3cccc(-c4cccc5cccc(-c6nc(-c7ccccc7)nc(-c7ccccc7)n6)c45)c3)n2)cc1]

INV-20

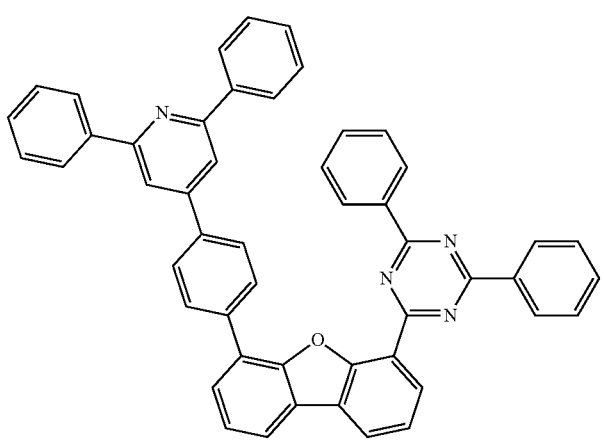 [SMILES: c1ccc(-c2cc(-c3ccc(-c4cccc5c4oc4c(-c6nc(-c7ccccc7)nc(-c7ccccc7)n6)cccc45)cc3)cc(-c3ccccc3)n2)cc1]

INV-20

Example 2

Synthesis of bis(biphenyl-4-yl)dibenzofuran-4-ylamnine

A degassed solution of 36.6 g (147 mmol) of 4-bromodibenzofuran and 39.5 g (123 mmol) of bis(biphenyl-4-yl)amine in 600 mL of toluene is saturated with $N_2$ for 1 h. Added to the solution thereafter are first 2.09 mL (8.6 mmol) of $P(tBu)_3$, then 1.38 g (6.1 mmol) of palladium(II) acetate, and then 17.7 g (185 mmol) of NaOtBu in the solid state. The reaction mixture is heated under reflux for 1 h. After cooling to room temperature, 500 mL of water are added cautiously The aqueous phase is washed with 3×50 mL of toluene, dried over $M_gSO_4$, and the solvent is removed under reduced pressure. Thereafter, the crude product is purified by chromatography using silica gel with heptane/ethyl acetate (20:1)

The yield is 57.7 g (118 mmol), corresponding to 80% of theory.

In an analogous manner, it is possible to obtain the following compounds:

Example 3

Synthesis of 9-phenyl-3-(6-trimethylsilanyldibenzofuran-4-yl)-9H-carbazole

To a solution, cooled to 20° C., of 49 g (121 mmol) of 3-dibenzofuran-4-yl-9-phenyl-9H-carbazole and 28 g (242 mmol) of TMEDA in 1000 mL of THF are added dropwise 127 mL (225.4 mmol) of n-butyllithium (2.5 M in hexane). The reaction mixture is stirred at room temperature for 3 h, then cooled down to 0° C., and 26 g (242 mmol) of chlorotrimethylsilane are added dropwise within 30 minutes and the mixture is stirred at room temperature for 8 h. Subsequently, the solvent is removed under reduced pressure and the residue is purified by chromatography using silica gel with chloroform as eluent. Yield: 34 g (72 mmol), 60% of theory.

In an analogous manner, it is possible to obtain the following compounds:

Example 4

Synthesis of B-[6-(phenyl-9H-carbazol-3-yl)-4-dibenzofuranyl]boronic acid

Under protective gas, 21 g (86 mmol) of bromine tribromide are added dropwise to a solution of 34 g (72 mmol) of N-phenyl-3-(6-trimethylsilanyldibenzofuran-4-yl)-9H-carbazole in 500 mL of dichloromethane and the mixture is stirred at room temperature for 10 h. Thereafter, a little water is added gradually to the mixture and the precipitated residue is filtered off and washed with heptane. The yield is 28 g (62 mmol), corresponding to 86% of theory.

In an analogous manner, it is possible to obtain the following compounds:

Example 5

Synthesis of B-[6-(phenyl-9H-carbazol-3-yl)-4-dibenzofuranyl]boronic acid 9 g (32 mmol) of B,B'-4,6-dibenzofurandiylbisboronic acid, 15 g (31.6 mmol) of 3-bromo-9-phenyl-9H-carbazole and 31 mL (63 mmol) of $Na_2CO_3$ (2 M solution) are suspended in 120 mL of toluene and 120 mL of ethanol. 0.73 g (0.63 mmol) of $Pd(PPh_3)_4$ are added to this suspension, and the reaction mixture is heated under reflux for 16 h. After cooling, the organic phase is removed, filtered through silica gel, washed three times with 200 mL of water and then concentrated to dryness. The residue is recrystallized from toluene. The yield is 11.1 g (24 mmol), corresponding to 70% of theory.

In an analogous manner, it is possible to obtain the following compounds:

Example 6

Synthesis of 3-(6-bromodibenzofuran-4-yl)-9-phenyl-9H-carbazole 10.43 g (32 mmol) of B-(9-phenyl-9H-carbazol-3-yl) boronic acid, 8.9 g (31.6 mmol) of 4,6-dibromodibenzofuran and 31 mL (63 mmol) of $Na_2CO_3$ (2 M solution) are suspended in 120 mL of toluene and 120 mL of ethanol. 0.73 g (0.63 mmol) of $Pd(PPh_3)_4$ is added to this suspension, and the reaction mixture is heated under reflux for 16 h. After cooling, the organic phase is removed, filtered through silica gel, washed three times with 200 mL of water and then concentrated to dryness. The residue is recrystallized from toluene. The yield is 11.4 g (23 mmol), corresponding to 73% of theory.

In an analogous manner, it is possible to obtain the following compounds:

In an analogous manner, it is also possible to obtain the following compounds by a second addition with the appropriate boronic acids: The residue is recrystallized from toluene and finally sublimed under high vacuum ($p=5\times10^{-5}$ mbar).

Example 7

Synthesis of 3-{6-[3-(4,6-diphenyl-[1,3,5]triazin-2-yl)phenyl]dibenzofuran-4-yl}-9-phenyl-9H-carbazole

Example 8

Synthesis of 9,9'-diphenyl-8-(3-{4-phenyl-6-[(E)-((Z)-1-propenyl)-buta-1,3-dienyl]-[1,3,5]triazin-2-yl}-phenyl)-9H,9'H-[1,2']bicarbazolyl 50 g (70.58 mmol) of 8-[3-(4,6-diphenyl-[1,3,5]triazin-2-yl)-phenyl]-9'-phenyl-9H,9'H-[1,2']bicarbazolyl and 16.4 g (105.87 mmol) of bromobenzene are dissolved in toluene and degassed by means of introduction of protective gas. This is followed by addition of 7 mL (7 mmol, 1 M solution in toluene) of tri-tert-butylphosphine, 633.8 mg (2.82 mmol) of $Pd(OAc)_2$ and 10.2 g (105.87 mmol) of NaOtBu. The solids are degassed beforehand, and the reaction mixture is post-degassed and then stirred under reflux for 3 h. The warm reaction solution is filtered through Alox B (activity level 1), washed with water, dried and concentrated. The yield is 42 g (53 mmol), corresponding to 77% of theory. The residue is recrystallized from toluene and finally sublimed under high vacuum ($p=5\times10^{-5}$ mbar). The purity is 99.9%.

In an analogous manner, it is possible to obtain the following compounds:

The invention claimed is:
1. A compound of the general formula (16a)

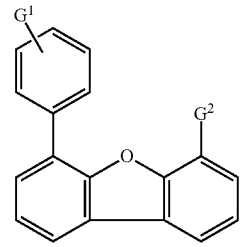

Formula (16a)

where the symbols and indices used are as follows:
$G^1$ is an organic electron-transporting group (ETG) of the formula E-11

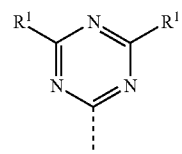

Formula (E-11), where the dotted bond indicates the binding positions to the structure of formula (16a); G² is an electron-rich organic group selected from the a group of the formula (L-18)-(L-30) and L(34)-L(36):
Formula (L-18)
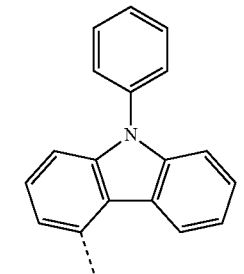
Formula (L-19)
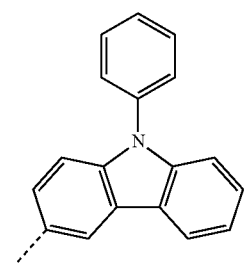
Formula (L-20)
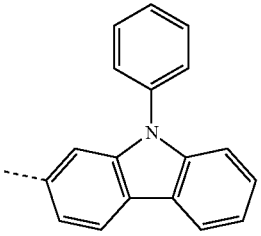
Formula (L-21)
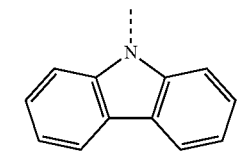
Formula (L-22)
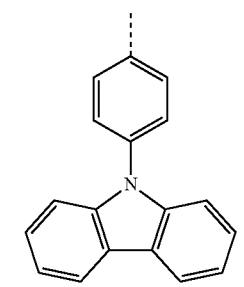
Fomrula (L-23)
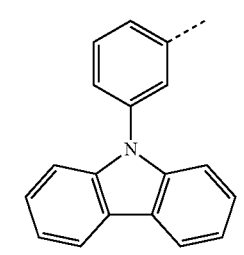
Formula (L-24)
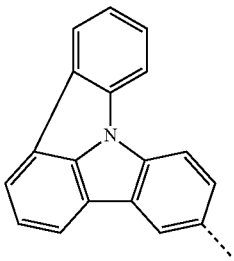
Formula (L-25)
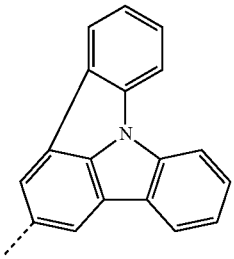
Formula (L-26)
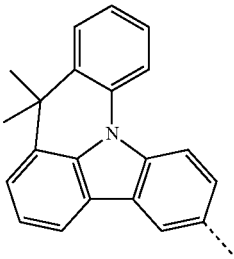
Formula (L-27)
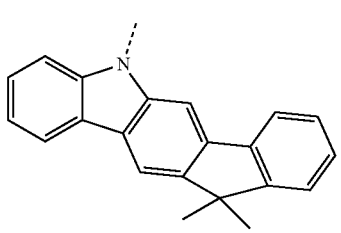
Formula (L-28)
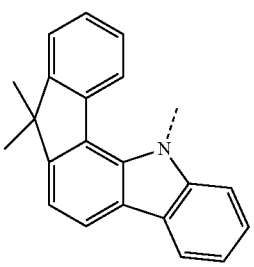
Formula (L-29)
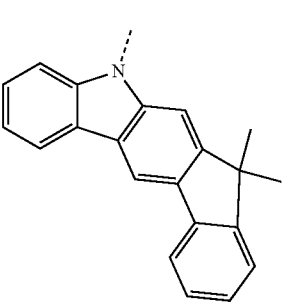

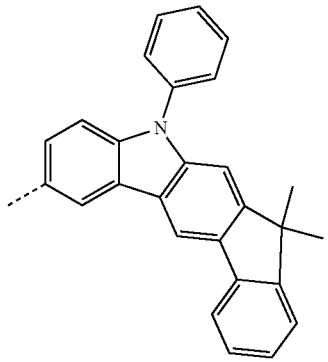

Formula (L-30)

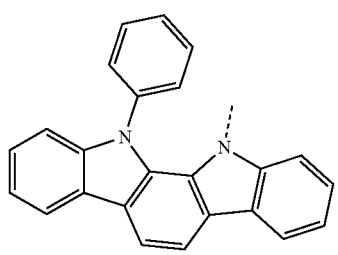

Formula (L-34)

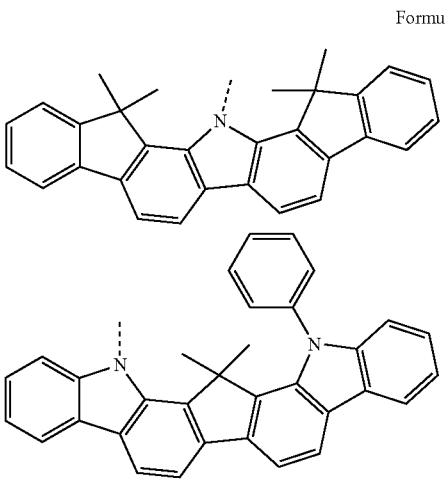

Formula (L-35)

Formula (L-36)

where dotted bonds indicate the binding positions to the structure of formula (16a), which may be substituted by one or more independent $R^2$ radicals;

$R^1$ is the same or different at each instance and is H, D, F, Cl, Br, I, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 carbon atoms or a straight-chain alkenyl or alkynyl group having 2 to 40 carbon atoms or a branched or cyclic alkyl, alkenyl, alkynyl, alkoxy, alkylalkoxy or thioalkoxy group having 3 to 40 carbon atoms, which is optionally substituted by one or more $R^2$ radicals; where one or more nonadjacent $CH_2$ groups is optionally replaced by $R^2C=CR^2$, C≡C, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more hydrogen atoms is optionally replaced by D, F, Cl, Br, I, CN or $NO_2$, or an aromatic or heteroaromatic ring system which has 5 to 60 aromatic ring atoms which is optionally substituted by one or more $R^2$ radicals; or an aryloxy, arylalkoxy or heteroaryloxy group which has 5 to 60 aromatic ring atoms which is optionally substituted by one or more $R^2$ radicals; or a diarylamino group, diheteroarylamino group or arylheteroarylamino group which has 10 to 40 aromatic ring atoms which is optionally substituted by one or more $R^2$ radicals, or a combination of two or more of these groups or a crosslinkable Q group;

$R^2$ is the same or different at each instance and is H, D, F, Cl, Br, I, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy or thioalkoxy group having 1 to 40 carbon atoms or a straight-chain alkenyl or alkynyl group having 2 to 40 carbon atoms or a branched or cyclic alkyl, alkenyl, alkynyl, alkoxy, alkylalkoxy or thioalkoxy group having 3 to 40 carbon atoms, which is optionally substituted by one or more $R^3$ radicals, where one or more nonadjacent $CH_2$ groups is optionally replaced by $R^3C=CR^3$, C≡C, $Si(R^3)_2$, $Ge(R^3)_2$, $Sn(R^3)_2$, C=O, C=S, C=Se, $C=NR^3$, $P(=O)(R^3)$, SO, $SO_2$, $NR^3$, O, S or $CONR^3$ and where one or more hydrogen atoms is optionally replaced by D, F, Cl, Br, I, CN or $NO_2$; or an aromatic ring system which has 6 to 60 aromatic ring atoms which is optionally substituted by one or more $R^3$ radicals; or an aryloxy, arylalkoxy or heteroaryloxy group which has 5 to 60 aromatic ring atoms which is optionally substituted by one or more $R^3$ radicals; or a diarylamino group, diheteroarylamino group or arylheteroarylamino group which has 10 to 40 aromatic ring atoms which is optionally substituted by one or more $R^3$ radicals; or a combination of two or more of these groups; at the same time, two or more adjacent $R^2$ radicals together may form a mono- or polycyclic, aliphatic or aromatic ring system;

$R^3$ is the same or different at each instance and is H, D, F or an aliphatic, or aromatic radical having 1 to 20 carbon atoms, in which one or more hydrogen atoms may also be replaced by F; at the same time, two or more $R^3$ substituents together may also form a mono- or polycyclic aliphatic or aromatic ring system.

2. A formulation comprising at least one compound as claimed in claim 1 and at least one solvent.

3. The compound as claimed in claim 1, wherein $G^1$ is selected from the formula E-17, E-22, E-24, E-25, E-26, E-27, E-28, or E-29:

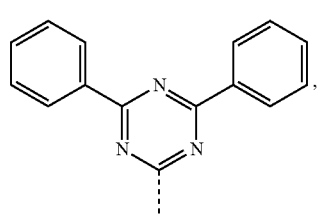

Formula (E-17)

Formula (E-22)

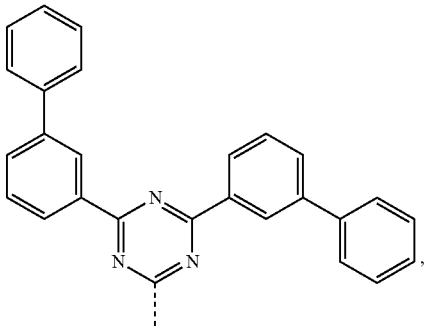

Formula (E-24)

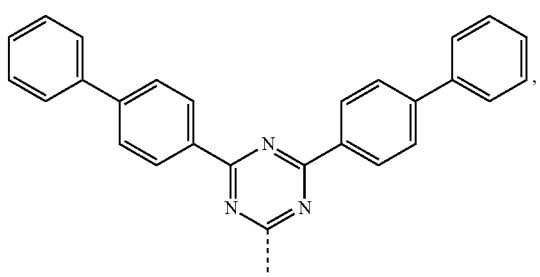

Formula (E-25)

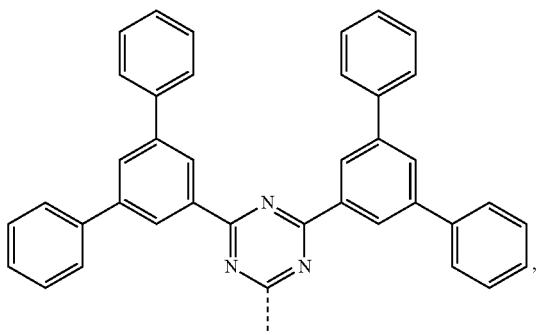

Formula (E-26)

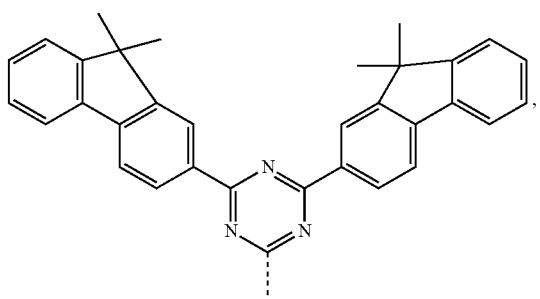

Formula (E-27)

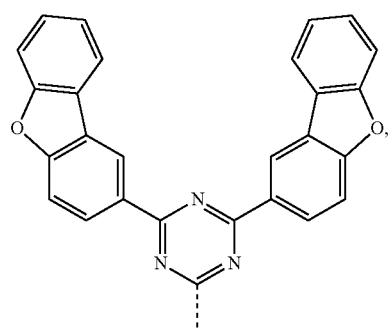

Formula (E-28)

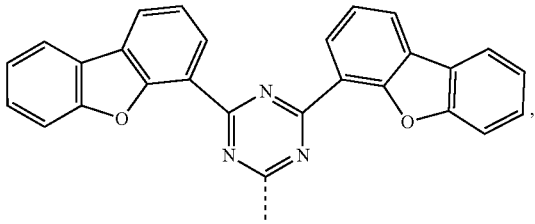

Formula (E-29)

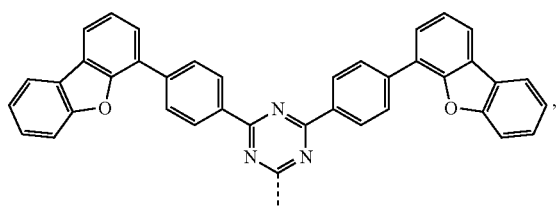

which may be substituted by one or more independent $R^2$ radicals.

4. The compound as claimed in claim 1, wherein each $R^1$ is independently selected from the group consisting of H and an aromatic or heteroaromatic ring system having 5 to 60 aromatic ring atoms, each of which is optionally substituted by one or more $R^2$ radicals.

5. An electronic device comprising at least one compound as claimed in claim 1 in an emission layer (EML), electron transport layer (ETL) or in a hole blocker layer (HBL).

6. The electronic device as claimed in claim 5, wherein the device is an organic electroluminescent device which is selected from the group consisting of organic light-emitting transistors (OLETs), organic field quench devices (OFQDs), organic light-emitting electrochemical cells (OLECs, LECs, LEECs), organic laser diodes (O-lasers) and organic light-emitting diodes (OLEDs).

7. An electronic device comprising at least one compound as claimed in claim 1.

8. The electronic device as claimed in claim 7, wherein the device is an organic integrated circuit (OIC), an organic field-effect transistor (OFET), an organic thin-film transistor (OTFT), an organic electroluminescent device (OLED), an organic light-emitting electrochemical cell (OLEC, LEEC, LEC), an organic solar cell (OSC), an organic optical detector, or an organic photoreceptor.

9. A process for producing an electronic device as claimed in claim 7, which comprises applying at least one organic layer by gas phase deposition or from solution.

10. The electronic device as claimed in claim 9, for use in medicine for phototherapy.

11. A composition comprising at least one additional compound as claimed in claim 1 and at least one further compound selected from the group consisting of fluorescent emitters, phosphorescent emitters, host materials, matrix materials, electron transport materials, electron injection materials, hole conductor materials, hole injection materials, electron blocker materials and hole blocker materials.

12. The composition as claimed in claim 11, wherein the additional compound is a host or matrix material.

13. The composition as claimed in claim 11, wherein the additional compound has a band gap of 2.5 eV or more.

* * * * *